(12) United States Patent
Chaudhary

(10) Patent No.: US 12,196,759 B2
(45) Date of Patent: Jan. 14, 2025

(54) NON-RADIOACTIVE CYTOTOXICITY ASSAYS

(71) Applicant: University of Southern California, Los Angeles, CA (US)

(72) Inventor: Preet M. Chaudhary, Toluca Lake, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 17/723,284

(22) Filed: Apr. 18, 2022

(65) Prior Publication Data

US 2022/0252606 A1 Aug. 11, 2022

Related U.S. Application Data

(63) Continuation of application No. 16/333,980, filed as application No. PCT/US2017/052344 on Sep. 19, 2017, now Pat. No. 11,307,205.

(60) Provisional application No. 62/396,650, filed on Sep. 19, 2016.

(51) Int. Cl.
| | |
|---|---|
| G01N 33/58 | (2006.01) |
| C12Q 1/44 | (2006.01) |
| C12Q 1/66 | (2006.01) |
| G01N 33/50 | (2006.01) |

(52) U.S. Cl.
CPC .............. *G01N 33/581* (2013.01); *C12Q 1/44* (2013.01); *C12Q 1/66* (2013.01); *G01N 33/5014* (2013.01); *G01N 33/5017* (2013.01); *G01N 33/502* (2013.01); *G01N 33/582* (2013.01)

(58) Field of Classification Search
CPC ........ C12Q 1/44; C12Q 1/66; G01N 353/581; G01N 33/5014; G01N 33/5017; G01N 33/502; G01N 33/582
See application file for complete search history.

(56) References Cited

U.S. PATENT DOCUMENTS

| | | | |
|---|---|---|---|
| 5,298,429 | A | 3/1994 | Evans et al. |
| 5,350,674 | A | 9/1994 | Boenisch et al. |
| 5,585,089 | A | 12/1996 | Queen et al. |
| 5,585,362 | A | 12/1996 | Wilson et al. |
| 6,326,193 | B1 | 12/2001 | Liu et al. |
| 7,939,286 | B2 | 5/2011 | Walia |
| 8,557,970 | B2 | 10/2013 | Encell et al. |
| 2012/0060646 | A1 | 3/2012 | Arnold |
| 2012/0122182 | A1 | 5/2012 | Tannous et al. |
| 2014/0302512 | A1 | 10/2014 | Rabinowitz et al. |

FOREIGN PATENT DOCUMENTS

| | | |
|---|---|---|
| WO | 01/020002 A1 | 3/2001 |
| WO | WO 2001-20002 A1 * | 3/2001 |
| WO | 01/29058 A1 | 4/2001 |
| WO | 01/96584 A2 | 12/2001 |
| WO | 2011/144749 A1 | 11/2011 |
| WO | 2013/059343 A1 | 4/2013 |
| WO | 2015/142675 A2 | 9/2015 |
| WO | 2015/143033 A1 | 9/2015 |
| WO | 2016/187349 A1 | 11/2016 |
| WO | 2017/070608 A1 | 4/2017 |
| WO | 2017/172981 A2 | 10/2017 |
| WO | 2018/102795 A2 | 6/2018 |

OTHER PUBLICATIONS

Whisstock et al. Quaterly Reviews of Biophysics, 2003, "Prediction of protein function from protein sequence and structure", 36(3): 307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
Aden et al., "Controlled synthesis of HBsAg in a differentiated human liver carcinoma-derived cell line," Nature: 282:615-617, 1979.
Gaur, Shuchi et al., "Engineering Intracellularly Retained Gaussia Luciferase Reporters for Improved Biosensing and Molecular Imaging Applications", ACS Chemical Biology, vol. 12, No. 9, Aug. 10, 2017, pp. 2345-2353.
Heise, Kerstin et al., "Dual Luciferase Assay for Secreted Luciferases Based on Gaussia and Nanoluc", Assay and drug development technologies, vol. 11, No. 4, May 1, 2013, pp. 244-252.
Jacques, Patrice, Search Report, European Patent Office, Application No. 17851811.4, May 29, 2020.
Matta, Hittu et al., "Development and characterization of a novel luciferase based cytotoxicity assay", Scientific Reports, vol. 8, No. 1, Jan. 9, 2018.
Schafer, H. et al., "A highly sensitive cytotoxicity assay based on the release of reporter enzymes, from stably transfected cell lines—I. In vitro immunization of allogeneic and syngeneic mouse spleen cell suspensions against DBA mastocytoma cells", Journal of Immunological Methods, Elsevier Science Publishers B.V., Amsterdam, NL, vol. 204, No. 1, May 12, 1997, pp. 89-98.
Tsuji et al., "A cytoplasmic Form of Gaussia luciferase Provides a Highly Sensitive Test for Cytotoxicity," PLoS ONE, 11(5):e0156202, pp. 1-14, May 26, 2016.
Wadee et al., "HLA expression in hepatocellular carcinoma cell lines," Clin. Exp. Immunol., 97:328-333, 1994.

(Continued)

*Primary Examiner* — Iqbal H Chowdhury
(74) *Attorney, Agent, or Firm* — IPath PLC; Steven J. Miller

(57) ABSTRACT

Described herein are methods for assessing cytotoxicity of an agent. The methods include providing a target cell that has been engineered to express intracellularly a reporter that is not expressed endogenously by the target cell, exposing the target cell to an agent capable of modulating cytotoxicity and assaying the activity of the reporter, wherein a change in reporter activity relative to a reference value is indicative of the agent being able to modulate cytotoxicity of the target cell.

19 Claims, 28 Drawing Sheets

Specification includes a Sequence Listing.

(56) References Cited

OTHER PUBLICATIONS

Wittmann-Regis, Agnes, International Preliminary Report on Patentability and Written Opinion, The International Bureau of WIPO, PCT/US2017/052344, Mar. 28, 2019.
Xinping, Fu et al., "A Simple and Sensitive Method for Measuring Tumor-Specific T Cell Cytotoxicity", PLoS ONE, vol. 5, No. 7, Jul. 29, 2010, p. e11867.
Young, Lee W., International Search Report, U.S. Patent & Trademark Office, PCT/US2017/052344, Feb. 13, 2018.
Young, Lee W., Written Opinion of the International Searching Authority, U.S. Patent & Trademark Office, PCT/US2017/052344, Jan. 24, 2018.
Bovenberg et al., "Enhanced Gaussia Luciferase Blood Assay for Monitoring of in Vivo Biological Processes", Analytical Chemistry vol. 84, No. 2, pp. 1189-1192, 2012.
Brown et al., "Biophotonic Cytotoxicity Assay for High-throughput Screening of Cytolytic Killing", Journal of Immunological Methods, vol. 297, pp. 39-52, 2005.
Degeling et al., "Directed Molecular Evolution Reveals Gaussia Luciferase Variants with Enhanced Light Output Stability", Analytical Chemistry, vol. 85, No. 5, 12 pages, Mar. 5, 2013.
Eshhar et al., "Specific Activation and Targeting of Cytotoxic Lymphocytes Through Chimeric Single Chains Consisting of Antibody-binding Domains and the Gamma or Zeta Subunits of the Immunoglobulin and T-cell Receptors", Proceedings of the National Academy of Sciences USA, vol. 90, pp. 720-724, Jan. 1993.
Fu et al., "A Simple and Sensitive Method for Measuring Tumor-Specific T Cell Cytotoxicity", Plos One, vol. 5, No. 7, e11867, pp. 1-6, Jul. 2010.
Green et al., "Molecular Cloning: a Laboratory Manual", 4 Edition, vols. 1, Cold Spring Harbor Lanoratory Press, 34 pages, 2012.
Gross et al., "Expression of Immunoglobulin-T-Cell Receptor Chimeric Molecules as Functional Receptors with Antibody-Type Specificity", Proceedings of the National Academy of Sciences USA, vol. 86, pp. 10024-10028, Dec. 1989.
Gross et al., "Therapeutic Potential of T Cell Chimeric Antigen Receptors (CARs) in Cancer Treatment: Counteracting Off-Tumor Toxicities for Safe CAR T Cell Therapy", vol. 56, pp. 59-83, 2016.
Hall et al., "Engineered Luciferase Reporter from a Deep Sea Shrimp Utilizing a Novel Imidazopyrazinone Substrate", ACS Chemical Biology, vol. 7, pp. 1848-1857, Aug. 15, 2012.
June et al., "Engineering Lymphocyte Subsets: Tools, Trials and Tribulations", Nature Reviews Immunology, vol. 9, No. 10, 29 pages, 2009.
Matta et al., "Use of Lentiviral Vectors for Delivery of Small Interfering RNA", Cancer Biology & Therapy, vol. 2, No. 2, pp. 206-210, Mar./Apr. 2003.
Nacheva et al., "Preventing Nondesired RNA-Primed RNA Extension Catalyzed by T7 RNA Polymerase", European Journal of Biochemistry, vol. 270, pp. 1458-1465, 2003.
Riechmann et al., "Reshaping Human Antibodies for Therapy", Nature, vol. 332, pp. 323-327, Mar. 24, 1988.
Roybal et al., "Precision Tumor Recognition by T Cells With Combinatorial Antigen-Sensing Circuits", Cell, vol. 164, pp. 770-779, Feb. 11, 2016.
Schenborn et al., "A Novel Transcription Property of Sp6 and T7 RNA Polymerases: Dependence on Template Structure", Nucleic Acids Research, vol. 13, No. 17, pp. 6223-6236, 1985.
Singleton et al., "Dictionary of Microbiology and Molecular Biology 3rd Edition", Wiley & Sons Ltd., 904 pages, 2006.
Stepinski et al., "Synthesis and properties of mRNAs containing the novel "anti-reverse" cap analogs 7-methyl(3'-O-methyl)GpppG and 7-methyl (3'-deoxy)GpppG", RNA, vol. 7, pp. 1486-1495, 2001.
Takenaka et al., "Evolution of Bioluminescence in Marine Planktonic Copepods", Molecular Biology and Evolution, vol. 29, No. 6, pp. 1669-1681, Jan. 12, 2012.

* cited by examiner

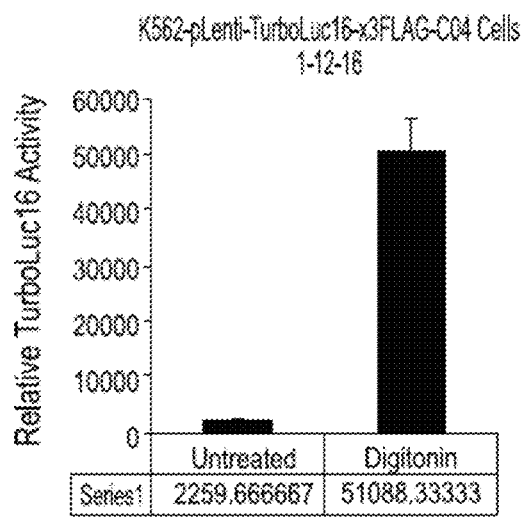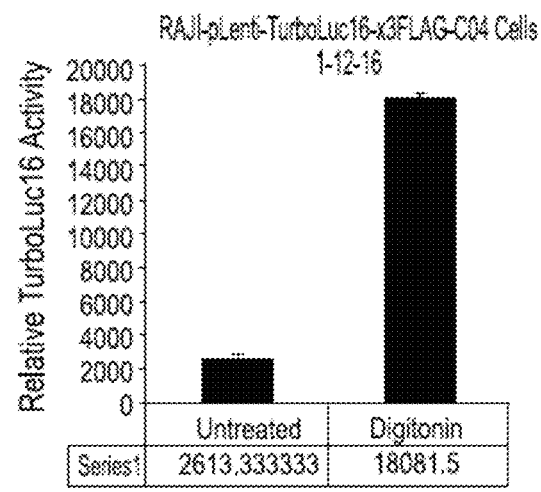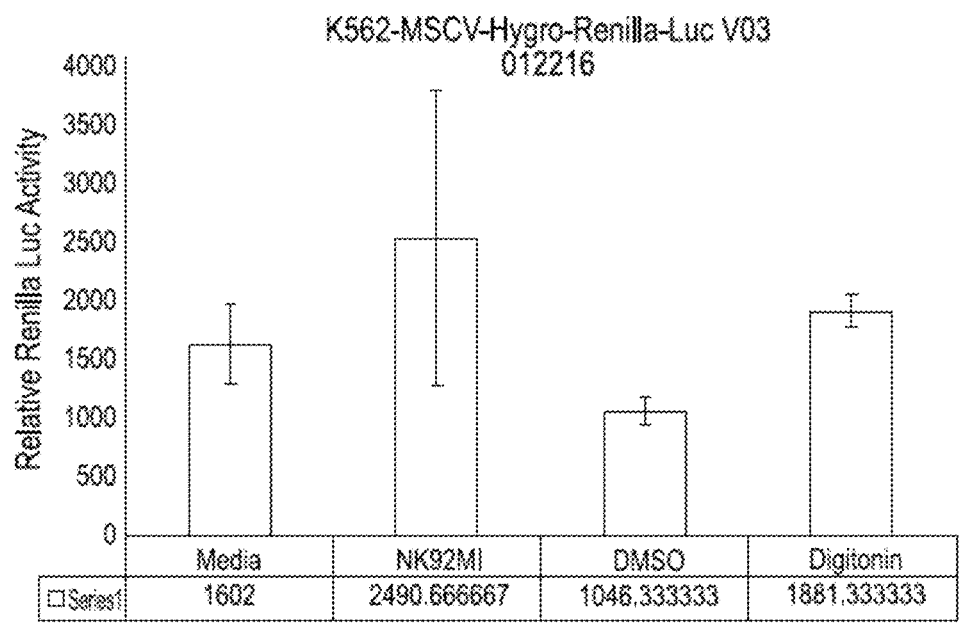

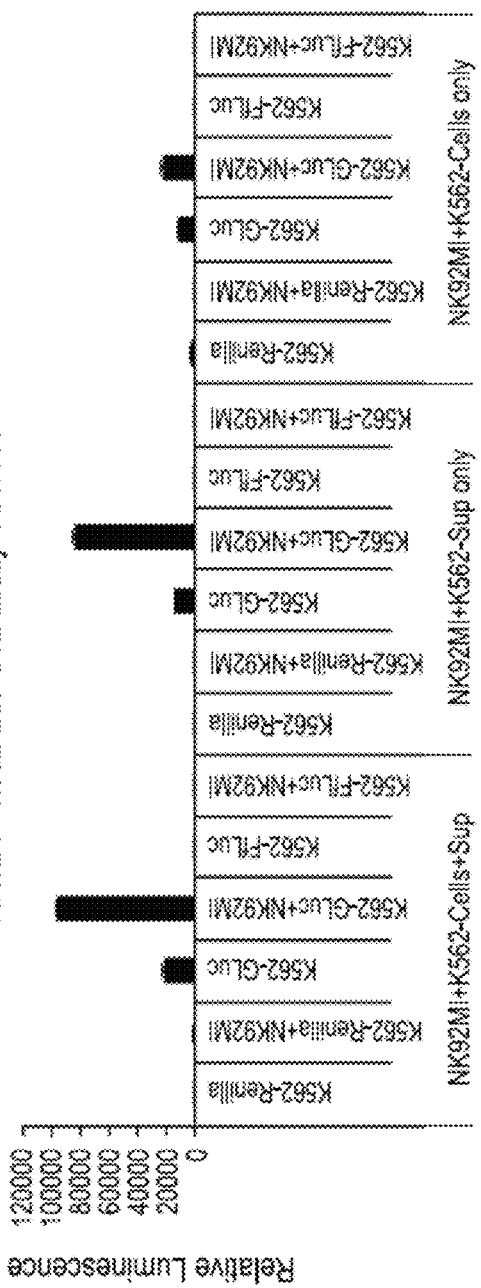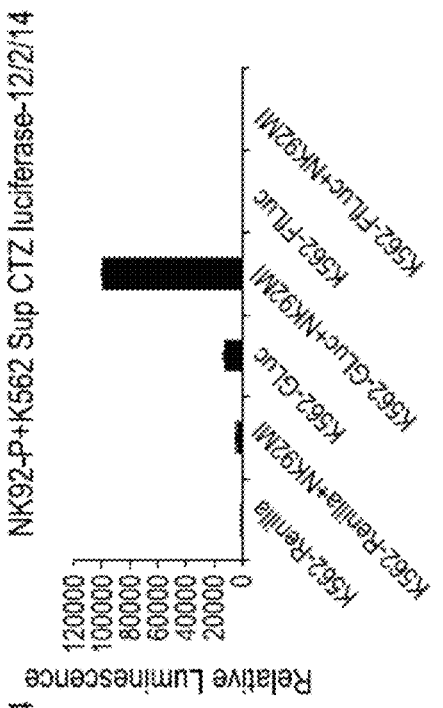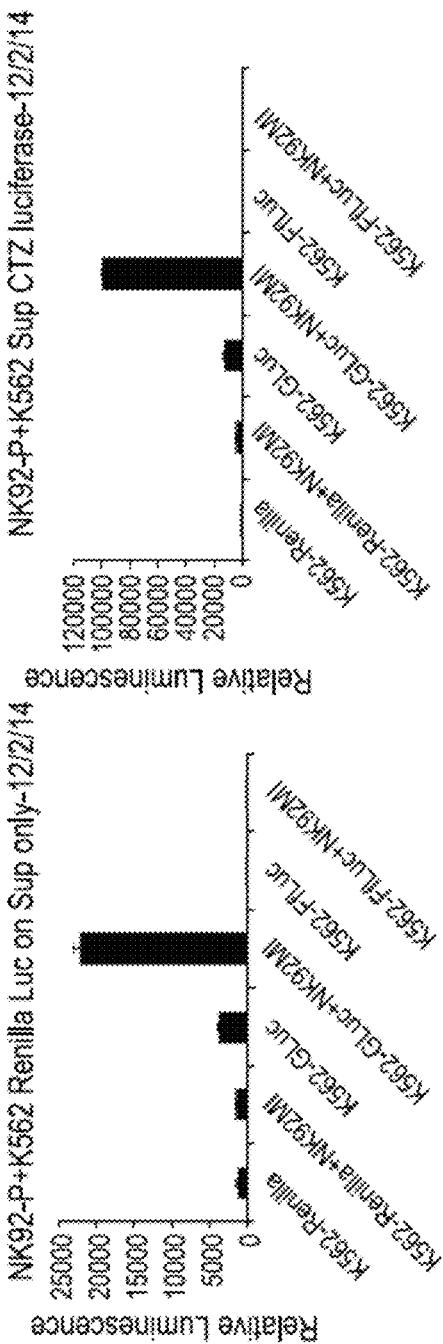

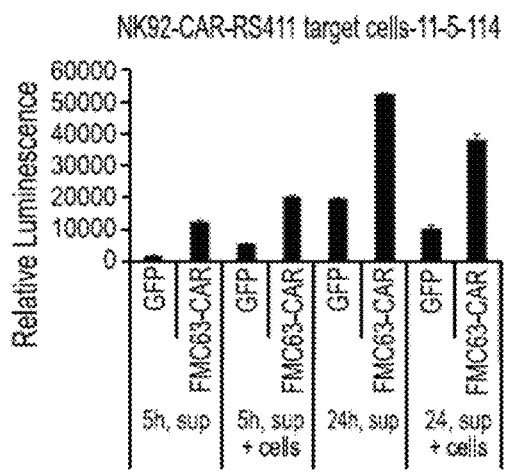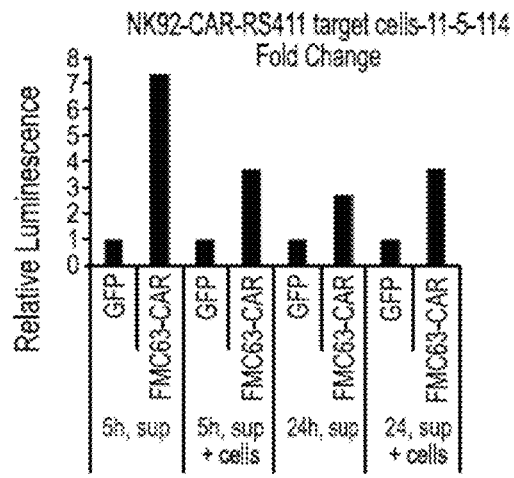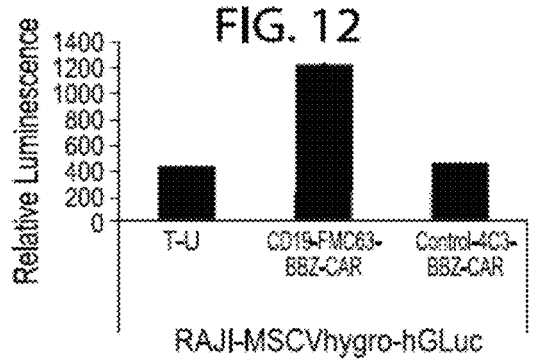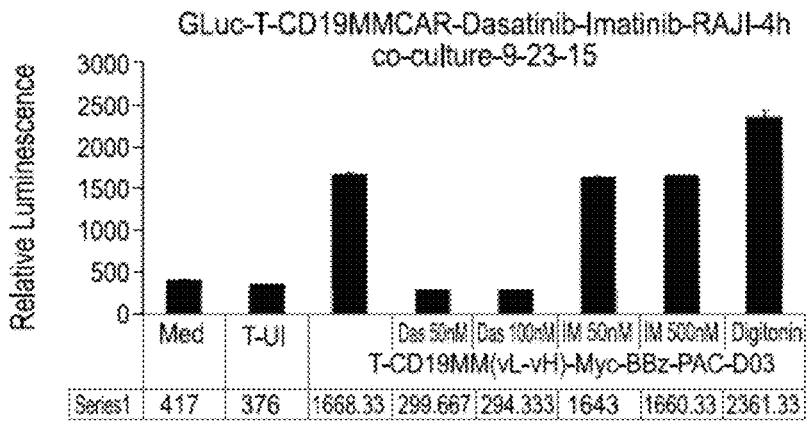

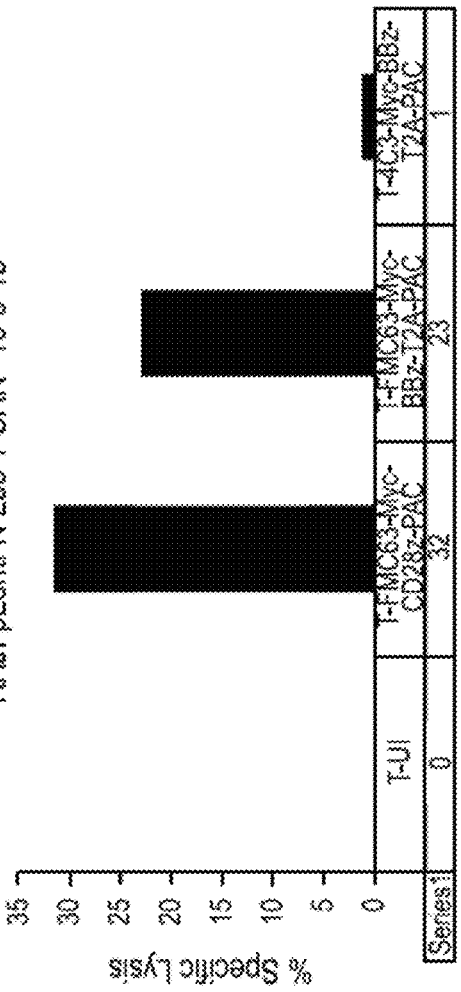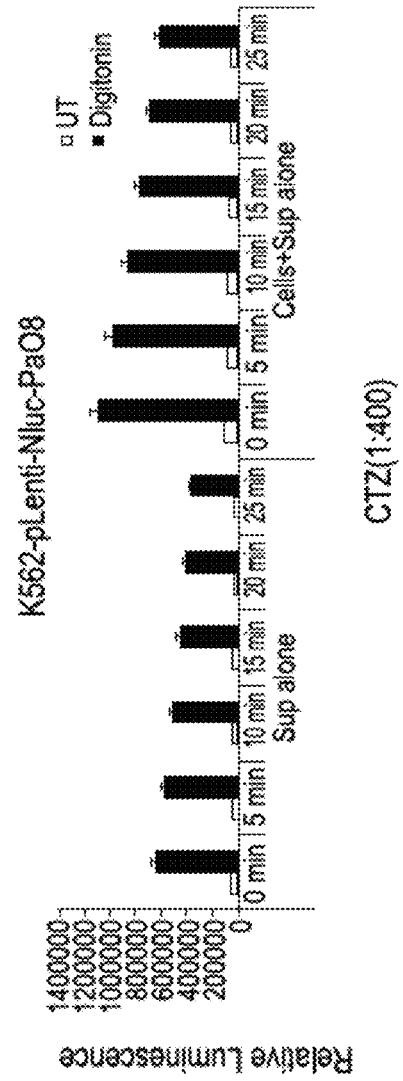

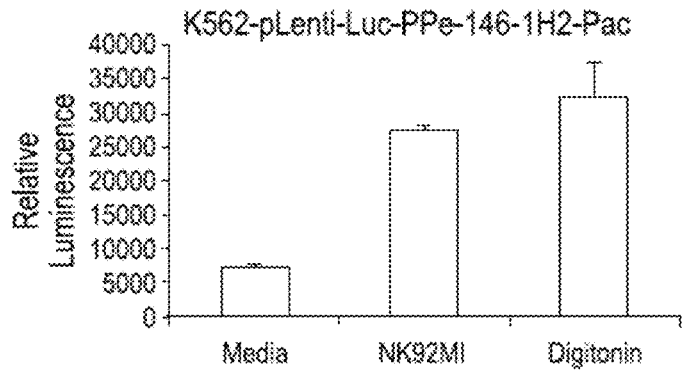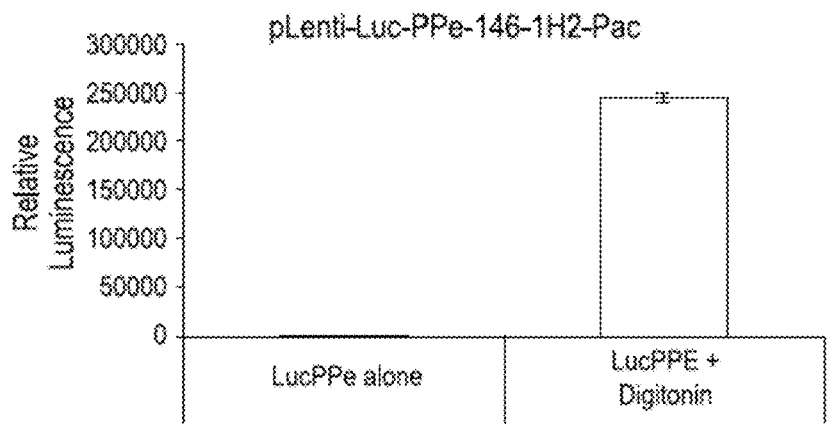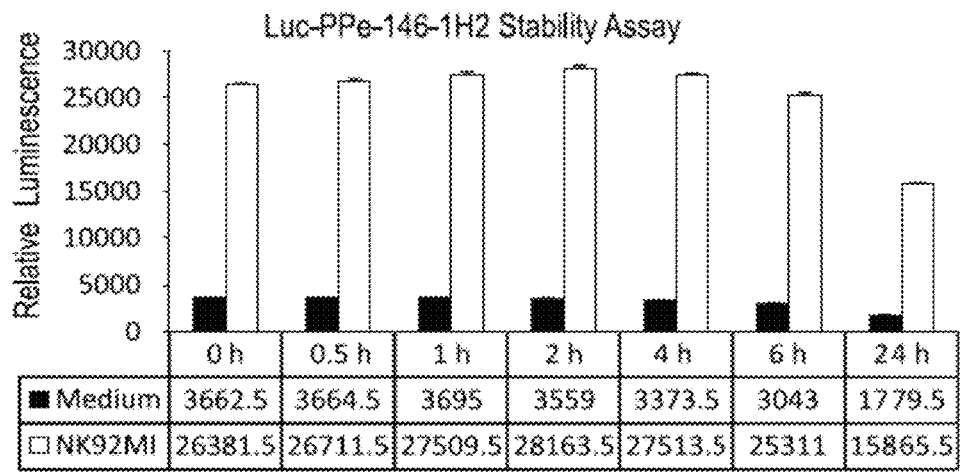

D-Luciferin Assay buffer
(LucPPe)

CTZ Assay buffer
(NLuc)

DLR Assay- 1st Reading
(LucPPe)

DLR Assay- 2nd Reading
(NLuc)

SEQUENCE LISTING

<160> NUMBER OF SEQ ID NOS: 103

<210> SEQ ID NO 1
<211> LENGTH: 507
<212> TYPE: DNA
<213> ORGANISM: Artificial Sequence
<220> FEATURE:
<223> OTHER INFORMATION: GLuc (Gaussia princeps Luc)

<400> SEQUENCE: 1

```
atgaagccca ccgagaacaa cgaagacttc aacatcgtgg ccgtgccag caacttcgcg      60 accacggatc tcgatgctga ccgcgggaag ttgcccggca agaagctgcc gctggaggtg    120
ctcaaagaga tggaagccaa tgcccggaaa gctggctgca ccaggggctg tctgatctgc    180
ctgtcccaca tcaagtgcac gcccaagatg aagaagttca tcccaggacg ctgccacacc    240
tacgaaggcg acaaagagtc cgcacagggc ggcataggca ggcgatcgt cgacattcct    300 gagattcctg ggttcaagga cttggagccc atggagcagt tcatcgcaca ggtcgatctg    360
tgtgtggact gcacaactgg ctgcctcaaa gggcttgcca acgtgcagtg ttctgacctg    420
ctcaagaagt ggctgccgca acgctgtgcg acctttgcca gcaagatcca gggccaggtg    480
gacaagatca aggggccgg tggtgac                                          507
```

<210> SEQ ID NO 2
<211> LENGTH: 513
<212> TYPE: DNA
<213> ORGANISM: Artificial Sequence
<220> FEATURE:
<223> OTHER INFORMATION: NLuc (NanoLuc)

<400> SEQUENCE: 2

```
atggtcttca cactcgaaga tttcgttggg gactggcgac agacagccgg ctacaacctg      60
gaccaagtcc ttgaacaggg aggtgtgtcc agtttgtttc agaatctcgg ggtgtccgta     120
actccgatcc aaaggattgt cctgagcggt gaaaatgggc tgaagatcga catccatgtc     180
atcatcccgt atgaaggtct gagcggcgac caaatgggcc agatcgaaaa aattttaag     240
gtggtgtacc ctgtggatga tcatcacttt aaggtgatcc tgcactatgg cacactggta     300
atcgacgggg ttacgccgaa catgatcgac tatttcggac ggccctatga aggcatcgcc     360
gtgttcgacg gcaaaaagat cactgtaaca gggaccctgt ggaacggcaa caaaattatc     420
gacgagcgcc tgatcaaccc cgacggctcc ctgctgttcc gagtaaccat caacggagtg     480
accggctggc ggctgtgcga acgcattctg gcg                                  513
```

<210> SEQ ID NO 3
<211> LENGTH: 444
<212> TYPE: DNA
<213> ORGANISM: Artificial Sequence
<220> FEATURE:
<223> OTHER INFORMATION: TLuc (TurboLuc16)

<400> SEQUENCE: 3

```
atggaagccg aggccgagag aggcaagctg cccggcaaaa agctgccct ggaagtgctg       60
atcgagctgg aagccaacgc cagaaaggcc ggctgcacca gaggctgcct gatctgcctg     120
agcaagatca gtgcaccgc caagatgaag aagtacatcc ccggcagatg cgccgactac     180
ggcggcgata agaaaacagg ccaggccggc atcgtgggag ccatcgtgga tatccctgag     240
atcagcggct tcaaagaaat ggaacccatg aacagtttta tcgcccaggt ggaccgctgc     300
gccgattgca caacaggctg tctgaagggc ctggctaacg tgaagtgcag cgacctgctg     360
aagaagtggc tgcctggcag atgtgccacc ttcgccgaca gatccagag cgaggtggac      420
aacatcaagg gactggccgg cgac                                            444
```

<210> SEQ ID NO 4
<211> LENGTH: 459
<212> TYPE: DNA
<213> ORGANISM: Artificial Sequence
<220> FEATURE:
<223> OTHER INFORMATION: MLuc7 (Metrida longa Luc7) M43L/M110L variant

<400> SEQUENCE: 4

```
atgaacccca ccgtgaacaa cgacgtgaac cggggcaaga tgcccggcaa gaaactgccc       60
ctggaagtgc tgatcgagct ggaagccaac gccttcaagg ccggctgcac cagaggctgc     120
ctgatctgcc tgagcaagat caagtgtacc gccaagatga agcagtacat ccccggcaga     180
tgccacgact acggcggcga caagaaaaca ggccaggccg gaatcgtggg agccatcgtg     240
gacatccctg agatcagcgg cttcaaagag atggaacccc tggaacagtt tatcgcccag     300
gtggacctgt gcgccgattg cacaaccggc tgtctgaagg gcctggctaa cgtgaagtgc     360
agcgagctgc tgaagaagtg gctgcccgac agatgcgcca gcttcgccga caagatccag     420
aaagaggccc acaacatcaa gggactggcc ggcgacaga                            459
```

<210> SEQ ID NO 5
<211> LENGTH: 618
<212> TYPE: DNA
<213> ORGANISM: Artificial Sequence
<220> FEATURE:
<223> OTHER INFORMATION: LoLuc (Lucicutia ovaliformis Luc)

<400> SEQUENCE: 5

```
atgctgcctg ccagccccac cgacagatcc atcgtgctgg acaacggcta cgtgtgcagc      60
tgggagggca tccccgacga cctgagagac tgccccaaga ccgaggacat gagcaagcag     120
catggcgctg ccctgaagct gccccccgat gtgctggacg agatggaatg caacgccaag     180
aaaagcggct gcgtgcgggg ctgcctccag tgtctggccc tgattaagtg caccgccaag     240
atgcggaagt acatccccgg cagatgccac agctacgagg cgacaaggga cattgcccag     300
ggcggcatcg gcaaagagct gaccatcgac atccccgaga tccccggctt cctggacctg     360
gcccctatgg atcagttcgt ggcccaggtg gacctgtgcg tggactgctc cagcagatgc     420
ctgaagggcc tggctaacgt gcagtgctcc tgcaagctgt ataagtggct gcccaccaga     480
tgcaccggct ccaggccaa gatcaagaaa gaggccgaca ccgtgatcgg actggaagat     540
gccctggccc tgggcttcga caccatccag gcttgtgtgg ccgctggcaa gtgcaaggac     600
accgtgggca gatacagc                                                   618
```

<210> SEQ ID NO 6
<211> LENGTH: 507
<212> TYPE: DNA
<213> ORGANISM: Artificial Sequence
<220> FEATURE:
<223> OTHER INFORMATION: HtLuc (Heterorhabdus tanneri Luc)

<400> SEQUENCE: 6

```
atggccgcct ctgaagaggc cgatgacgat cacgtgtccc tcgtgaagaa ctactggcgg      60
atcggcgtgg gcaacgagcg ggatgtgtct ctggatagag gcggccctcc caagctgagc     120
aaagaactgc tggccgagat gcacgccatt gccagcaatg ccggctgctc cagagtgtgc     180
ctgatcggcc tgagcaagat caagtgcacc cccaagatga agaccttcct gcccggcaga     240
tgcaacacct tcgcccctaa acctgccacc ggcgacggac cttttgccgc cgctgctgcc     300
atccctggct tcagcgatct gaccgctatg aacagtaca aggcccaggt ggcccagtgc     360
gactgctcca acagatgcct cgtgggcctg gctaacatca agtgttctgc cgccctgaag     420
gccgccctgc ctcagagatg taccacctt gccaccaaca tccagaaaga gggcgaggtg     480
gacagcatca agggctacgg cagaaag                                         507
```

<210> SEQ ID NO 7
<211> LENGTH: 585
<212> TYPE: DNA
<213> ORGANISM: Artificial Sequence
<220> FEATURE:
<223> OTHER INFORMATION: PaLuc1 (Pleuromamma abdominalis Luc1)

<400> SEQUENCE: 7

```
atgcagccca ccgagaacaa gcaggaaagc cagatcgagg acatcgacag aagcaccagc      60
ctgggcctga tgtgctacga gcagtgtaca ggccagagcg gcctggatct gaagtgctac     120
aaagagtgcg ccgacttcac cggcgaccgg aacagaggca aaagctgcc cggcaagaaa     180
ctgcccctga agtgctgaa gatcatggaa gccaacgcca agggccggc tgcaccaga     240
ggctgcctga tctgcctgag caagatcaag tgcaccgcca agatgaagca gtacatcccc     300
```

```
ggcagatgcc acacctacga gggcgacaag tctatcggcc agggcggcat cggaggcccc    360
atcgtggata tccctgagat catcggcttc cagaacatgg aacctatgga acagtttatc    420
gcccaggtgg aactgtgcgc cgattgcaca accggctgtc tgaagggcct ggctaacgtg    480
cggtgcaacg acctgctgaa gaagtggctg cccgacagat cgccggcttc gccaacaag     540 atccagagcg aggtggacaa catcaaggga ctggccggcg acaga                    585
```

```
<210> SEQ ID NO 8
<211> LENGTH: 510
<212> TYPE: DNA
<213> ORGANISM: Artificial Sequence
<220> FEATURE:
<223> OTHER INFORMATION: PaLuc2 (Pleuromamma abdominalis Luc2)

<400> SEQUENCE: 8
```

```
atgaagagca tagacagcta cgaaaatatt gatatagtgg ctgttgcggg caacttcgct     60
gctgttgacc aggacgctaa ccgcggagga aacctgccgg gtaagaaaat gccaatagag    120
gttcttaaag aaatggaagc taacgccaag cgagcagggt gtgttcgggg ctgtttgata    180
tgcttgtccc acatcaaatg cacagctaaa atgaaaaaat cataccagg tcggtgtcat     240 agctatcatg gagatgcaga tacgaagcaa ggggcacttg aagaagtggt tgacatgccc    300
gagataccgg gatttgtgga catggagccc atgaacagt ttatagccca ggtggataaa     360
tgcgaggact gtaccactgg ttgtttgaaa ggtctcgcca acgtccactg cagcgatctc    420
ctcaagaaat ggctgccgca aagatgctca cagtttgcgg ataagatcca atccgaggtg    480
gacacaataa agggcctggc aggggaccgg                                     510
```

```
<210> SEQ ID NO 9
<211> LENGTH: 579
<212> TYPE: DNA
<213> ORGANISM: Artificial Sequence
<220> FEATURE:
<223> OTHER INFORMATION: MpLuc1[Metridia pacifica Luc1]

<400> SEQUENCE: 9
```

```
atgaacccga cggagaacaa ggacgatatt gatattgtgg gagtggaagg caaattcggg     60
actacggatc ttgaaactga tctctttacg attgttgagg acatgaacgt aatctcaagg    120
gatacgaacc tggcaaatag tgacgcagac cgaggcaaaa tgccgggaaa aaaacttccg    180
ttggaagtac tgatcgagat ggaagcgaat gcacgcaagg cagggtgtac acggggatgc    240
ttgatctgtc tgagtaagat taaatgcacc gctaaaatga agtttatat accccggtcg     300 tgccacgatt atggggcga taagaaaacc ggtcaggcag ggatcgtcgg agcaatcgtg     360
gatattcctg aaatttcagg attcaaagaa cttggaccaa tggagcaatt tatagcacaa    420
gtggacctct cgctgactg cacgacggga tgtctgaaag tcttgcaaa tgtaaagtgt       480 tcagcactcc ttaagaaatg gcttcccgac cgatgtgcct cttttgctga caagattcag    540
tctgaagttg ataacataaa gggtcttgcg ggtgatcgg                          579
```

```
<210> SEQ ID NO 10
<211> LENGTH: 510
<212> TYPE: DNA
<213> ORGANISM: Artificial Sequence
<220> FEATURE:
<223> OTHER INFORMATION: McLuc1 [Metridia curticauda Luc1]

<400> SEQUENCE: 10
```

```
atgaagccta ccgaaaataa tgatgatatt gatatagttg ggatcgcaag tacatttatc    60
acgacaaaca ccgacgcgga ccggggcaag atgccgggaa agaaacttcc cttggcagtc   120
ctcaaggaaa tggaggcgaa cgctgcaaag gcagggtgtt ccagaggttg tctgatctgc   180
ttgtctaaaa tcaagtgtac agctaagatg aagcagttta ttccggggcg ctgtcacgac   240
tacggtggtg ataaaaaaac gggccaggcg gcgctggtcg agcaatatt cgacatccct    300 gaaatcttcg gatttctcga tatggaacct atcgagcagt tcatagcaca agtagatttg   360
tgtgctggct gcacaacagg ctgcttgaaa ggactcgcaa atattaagtg ttctgaactc   420
ttgaagaagt ggcttccgaa aagatgtacc tccttcgcgt ataaaatgca aaaggaaatg   480
cacaatataa aaggcatggc aggagatcgg                                    510
```

<210> SEQ ID NO 11
<211> LENGTH: 510
<212> TYPE: DNA
<213> ORGANISM: Artificial Sequence
<220> FEATURE:
<223> OTHER INFORMATION: MaLuc1 [Metridia asymmetrica Luc1]

<400> SEQUENCE: 11

```
atgaaagcga ccgaaaacaa tgacgacata gacatagttg gaatcgcgtc aaccttcata    60
acgacaaaca cggacgccga ccgaggcaaa atgccgggga aaagattgcc actggcggtg   120
ttgaaagaga tggaagcgaa cgcagtcaaa gcgggatgta gcaggggctg ccttatatgt   180
ctgagtaaga ttaaatgcac cgcgaagatg aagcaataca tccccggcag gtgccacgat   240
tacggaggag acaagaagac cgggcaggcg gctatagagg gcgcgataga tgatattcct   300
gaaatctctg gctttaagga gatggcgcct atggagcaat tcattgcgca ggttgacttg   360
tgcgcagact gcacgacagg atgcctcaag ggcttggcaa atgtaaaatg ttccgaactt   420
ctgaaaaaat ggctgcccaa gaggtgtacc tccttcgcca cgaagatgca aaggagatc    480 cataacatca aaggcatggg gggggaccgc                                    510
```

<210> SEQ ID NO 12
<211> LENGTH: 588
<212> TYPE: DNA
<213> ORGANISM: Artificial Sequence
<220> FEATURE:
<223> OTHER INFORMATION: MoLuc1 [Metridia okhotensis Luc1]

<400> SEQUENCE: 12

```
atgaaccta cggagaccca ggacggagtg gacattctcg gcgtggaagg gaaattcggg     60
acagaaacca acttggagac tgatctgttt accatttggg agataaatgg aataattaaa   120
tctgatcgcg acacaaatag ggcaaatgca gacgctgatc gaggaaaaat gcccggcaag   180
aaacttcctt tggcggtgct catagagatg gaggcaaacg cattcaaagc gggttgcact   240
cgcggttgtc tcatttgttt gtccaaaatc aaatgcacgg ctaagatgaa agagtatatc   300
ccaggacggt gccatgatta cggtggggat aaaaaaacgg acaagcagg tatagtaggt    360 gctatcgtgg acattccaga aatctcagga tttaaagagc ttggccccat ggagcaattc   420
atagcgcaag tagacctttg cgctgattgc actactggct gtcttaaggg actggcgaat   480
gttaagtgca gcgccctgtt gaagaagtgg ctgccagacc gatgcgcatc attcgcggat   540
aagatacagt ccgaagtcca taatataaaa ggtctcgcag gtgatcgc                588
```

<210> SEQ ID NO 13
<211> LENGTH: 522

```
<212> TYPE: DNA
<213> ORGANISM: Artificial Sequence
<220> FEATURE:
<223> OTHER INFORMATION: MoLuc2 [Metridia okhotensis Luc2]

<400> SEQUENCE: 13
atggccacaa tcaatgaaaa tttcgaagac atcgaccttg tcgcgattgg aggctcattt      60
gctacagatg tggacgccaa caggggtggt catggtggac atccgggcaa aaagatgcct     120
aaagaggtct tgttggaaat ggaagcgaac gcaaaacgag ccggatgtca taggggttgt     180
ttgatttgtc tttctcacat caaatgtacg cagaagatga agaaattcat accgggacgg     240
tgtcactcct atgctggtga caaggatagc gctcagggcg gcataacaga ggaggagact     300
gttgacatgc ccgagatcgc tgggttcaag gatcttgaac ctatggagca gtttattgca     360
caggtagact tgtgcgttga ctgcacaact ggttgtttga agggctggc caacgtccac      420 tgttctgact tgctcaaaaa gtggctgcct cccggtgca agacttttgc ctcaaaaatt      480
cagagtcagg ttgacaccat caaggggttg gctggtgaca gg                        522

<210> SEQ ID NO 14
<211> LENGTH: 579
<212> TYPE: DNA
<213> ORGANISM: Artificial Sequence
<220> FEATURE:
<223> OTHER INFORMATION: MLuc39 [Metridia longa Luc39]

<400> SEQUENCE: 14
atgaatccta cagagaacaa tgatcatatc aatattgtcg ggatcgaggg taaattcgga      60
atcacagact tggagacgga tctcttcact atctgggaga caaatcgcat gatttctacc     120
gataacgaac aggcaaatac agacagtaat agagggaaga tgccaggtaa gaaactgcca     180
ttggcagttc ttatagagat ggaagccaac gctttcaagg cgggttgtac aagaggctgt     240
ctcatttgct tgtctaaaat caagtgtact gctaagatga agaaatacat accgggaaga     300
tgccatgact acggaggtga taagaagact gggcaggcag gaatcgtggg cgcgattgtc     360
gacatacccg acatatccgg gttcaaggaa atgggaccga tggagcaatt catcgcccaa     420
gtggatcgat gcaccgactg cacaacggga tgtttgaagg gtcttgcaaa tgttaagtgc     480
tccgagctgt tgaagaagtg gttgccggac cgctgcgcga gtttcgccga taaaattcaa     540
agtgaggtgc ataatattaa aggtctggcg ggagatcgc                            579

<210> SEQ ID NO 15
<211> LENGTH: 498
<212> TYPE: DNA
<213> ORGANISM: Artificial Sequence
<220> FEATURE:
<223> OTHER INFORMATION: PsLuc1 [Pleuromamma scutullata Luc1]

<400> SEQUENCE: 15
atgcaaccca ctgagaataa aaaggaatcc tataccgaag acacagacgt aaacggggac      60
catgatcgag gcaggaagct tccggggaag aaacttccac tggaagttct gaaaatcatg     120
gaagctaacg caaggagagc aggttgcacg cgaggctgtt tgatatgtct tagcaagata     180
aaatgtactg caaaaatgaa gcaatacata ccgggaagat gccatactta tgaggggac      240 aaaagcatag ggcaggcagg cataggaggc ccaatcattg atataccgga aattataggg     300
tttaagaaca tggaaccaat ggaacagttc atcgcacagg tggatcctg tgcggactgc     360 actactggat gcctcaaagg tctcgcaat gtaagatgca acgatctttt gaaaaatgg      420
```

```
ttgccagatc gatgcgcggg gttcgcactc aagatacaag gtgaagtgga aaacataaag    480
gggatggccg gggatcga                                                  498
```

<210> SEQ ID NO 16
<211> LENGTH: 618
<212> TYPE: DNA
<213> ORGANISM: Artificial Sequence
<220> FEATURE:
<223> OTHER INFORMATION: LoLuc1-3 [Lucicutia ovaliformis Luc1-3]

<400> SEQUENCE: 16

```
atgcttccag cgtcacccac cgataggtca atagtccttg acaacggcta tgtgtgttcc     60
tgggagggta tcccagacga cctgcgggac tgtccgaaga cagaggatat gtctaagcag    120
cacggagctg ctctcaaact gccgccagat gtgttggatg agatggaatg taatgctaaa    180
aagagtggat gcgtgcgagg atgtcttcag tgtctggcac tcataaaatg tactgcaaaa    240
atgagaaagt atatcccccgg acgctgtcat agctacgagg gtgacaagga cattgctcag    300 gggggatcg gaaaggaact gacaattgac atccctgaga ttcctggctt cttggatctt    360
gcaccaatgg accagttcgt ggcgcaggtc gacctctgcg tggactgcag cagtcggtgc    420
ctgaagggct tggctaatgt ccaatgcagt tgtaagctct acaaatggtt gccaaccccgg    480 tgtaccggct ccaagcgaa aataaagaaa gaagctgaca cggtaattgg gctggaagat    540
gcgctcgcac tcggattcga caccatccag gcatgcgtag cggccggtaa atgcaaggat    600
acggttggcc ggtactct                                                 618
```

<210> SEQ ID NO 17
<211> LENGTH: 534
<212> TYPE: DNA
<213> ORGANISM: Artificial Sequence
<220> FEATURE:
<223> OTHER INFORMATION: HtLuc2 [Heterorhabdus tanneri Luc 2]

<400> SEQUENCE: 17

```
atgtgggcgg cctccgagga ggccgatgac gacctcgtat ctttggtcaa aaactactgg     60
ggcgtaggcg taagcaatga acgcgatgta tctctcgaca ggggggggcca tggcaagctg    120 ccgaaaaagc ttagcgttga gattctcgct gaaatggaag caaacgccca gaagagtaat    180
tgctctcggg ggtgtctgat agggcttttct aaaattaaat gcacgcccaa aatgaaaaaa    240
ttcctccctg gcaggtgcca cgaatactct ggtgatccca aaactggaca gggtccgctt    300
actgcggctg cggttatacc agggtatagt gatcttacag ctatggagca gttcaagctc    360
caagtagaca agtgtgactg ttcaactcaa tgtcttaagg gtcttgcaaa tgtcaagtgc    420
tcagcggccc tcaaagcggt gttgccaaca agatgctcac aattcgcaac tcagatccaa    480
gctgaagtag gcaccataaa agggaagggg aagaaaccga ctccaccgat aggt          534
```

<210> SEQ ID NO 18
<211> LENGTH: 579
<212> TYPE: DNA
<213> ORGANISM: Artificial Sequence
<220> FEATURE:
<223> OTHER INFORMATION: Lucia-Luc

<400> SEQUENCE: 18

```
atgaaaccca ctgaaatcaa tgaagacctc aatatagctg ctgtggcctc caactttgcc     60
accacagatc ttgagactga cctgttcacc aactgggaga ccatgaatgt gattagcact    120
gacacagagc aggtgaacac agatgctgac aggggcaagc tgcctggcaa aaaactcccc    180
```

```
ccagatgtcc tgagggagct ggaggccaat gccagaaggg ctggttgcac aagaggctgc    240
ctcatttgcc tctcccacat taagtgcacc cctaagatga agaaatttat ccctggcagg    300
tgccacactt atgaaggtga aaaggagtct gctcagggag ggattggaga ggcaattgtt    360
gatatcccag agattcctgg cttcaaggat aaggagccac tggaccagtt tattgctcaa    420
gtggacctct gtgctgattg caccactggc tgtctgaagg ccttgccaa tgtccagtgc     480 tctgacctcc tgaagaagtg gcttccccag aggtgtacca cttttgccag caagattcag    540
ggtagggtgg acaaaatcaa gggtctggct ggggacaga                           579
```

```
<210> SEQ ID NO 19
<211> LENGTH: 933
<212> TYPE: DNA
<213> ORGANISM: Artificial Sequence
<220> FEATURE:
<223> OTHER INFORMATION: RLuc (Renilla Luc)

<400> SEQUENCE: 19
atggcttcca aggtgtacga ccccgagcaa cgcaaacgca tgatcactgg gcctcagtgg     60
tgggctcgct gcaagcaaat gaacgtgctg gactccttca tcaactacta tgattccgag    120
aagcacgccg agaacgccgt gattttctg catggtaacg ctgcctccag ctacctgtgg     180
aggcacgtcg tgcctcacat cgagcccgtg gctagatgca tcatccctga tctgatcgga    240
atgggtaagt ccggcaagag cgggaatggc tcatatcgcc tcctggatca ctacaagtac    300
ctcaccgctt ggttcgagct gctgaacctt ccaaagaaaa tcatctttgt gggccacgac    360 tgggggggctt gtctggcctt tcactactcc tacgagcacc aagacaagat caaggccatc    420
gtccatgctg agagtgtcgt ggacgtgatc gagtcctggg acgagtggcc tgacatcgag    480
gaggatatcg ccctgatcaa gagcgaagag ggcgagaaaa tggtgcttga ataacttc      540 ttcgtcgaga ccatgctccc aagcaagatc atgcggaaac tggagcctga ggagttcgct    600
gcctacctgg agccattcaa ggagaagggc gaggttagac ggcctaccct ctcctggcct    660
cgcgagatcc ctctcgttaa gggaggcaag cccgacgtcg tccagattgt ccgcaactac    720
aacgcctacc ttcgggccag cgacgatctg cctaagatgt tcatcgagtc cgaccctggg    780
ttcttttcca cgctattgt cgagggagct aagaagttcc ctaacaccga gttcgtgaag    840
gtgaagggcc tccacttcag ccaggaggac gctccagatg aaatgggtaa gtacatcaag    900
agcttcgtgg agcgcgtgct gaagaacgag cag                                 933
```

```
<210> SEQ ID NO 20
<211> LENGTH: 1650
<212> TYPE: DNA
<213> ORGANISM: Artificial Sequence
<220> FEATURE:
<223> OTHER INFORMATION: Fluc or FfLuc (Firefly Luc)

<400> SEQUENCE: 20
atggaagacg ccaaaaacat aaagaaaggc ccggcgccat tctatccgct ggaagatgga     60
accgctggag agcaactgca taaggctatg aagagatacg ccctggttcc tggaacaatt    120
gcttttacag atgcacatat cgaggtggac atcacttacg ctgagtactt cgaaatgtcc    180
gttcggttgg cagaagctat gaaacgatat gggctgaata caaatcacag aatcgtcgta    240
tgcagtgaaa actctcttca attctttatg ccggtgttgg cgcgttatt tatcggagtt    300 gcagttgcgc ccgcgaacga catttataat gaacgtgaat tgctcaacag tatgggcatt    360
```

| | |
|---|---|
| tcgcagccta ccgtggtgtt cgtttccaaa aaggggttgc aaaaaatttt gaacgtgcaa | 420 |
| aaaaagctcc caatcatcca aaaaattatt atcatggatt ctaaaacgga ttaccaggga | 480 |
| tttcagtcga tgtacacgtt cgtcacatct catctacctc ccggttttaa tgaatacgat | 540 |
| tttgtgccag agtccttcga tagggacaag acaattgcac tgatcatgaa ctcctctgga | 600 |
| tctactggtc tgcctaaagg tgtcgctctg cctcatagaa ctgcctgcgt gagattctcg | 660 |
| catgccagag atcctatttt tggcaatcaa atcattccgg atactgcgat tttaagtgtt | 720 |
| gttccattcc atcacggttt tggaatgttt actacactcg atatttgat atgtggattt | 780 |
| cgagtcgtct taatgtatag atttgaagaa gagctgtttc tgaggagcct tcaggattac | 840 |
| aagattcaaa gtgcgctgct ggtgccaacc ctattctcct tcttcgccaa agcactctg | 900 |
| attgacaaat cgatttatc taatttacac gaaattgctt ctggtggcgc tcccctctct | 960 |
| aaggaagtcg gggaagcggt tgccaagagg ttccatctgc caggtatcag gcaaggatat | 1020 |
| gggctcactg agactacatc agctattctg attacacccg aggggatga taaaccgggc | 1080 |
| gcggtcggta aagttgttcc attttttgaa gcgaaggttg tggatctgga taccgggaaa | 1140 |
| acgctgggcg ttaatcaaag aggcgaactg tgtgtgagag gtcctatgat tatgtccggt | 1200 |
| tatgtaaaca atccggaagc gaccaacgcc ttgattgaca aggatggatg ctacattct | 1260 |
| ggagacatag cttactggga cgaagacgaa cacttcttca tcgttgaccg cctgaagtct | 1320 |
| ctgattaagt acaaaggcta tcaggtggct cccgctgaat ggaatccat cttgctccaa | 1380 |
| caccccaaca tcttcgacgc aggtgtcgca ggtcttcccg acgatgacgc cggtgaactt | 1440 |
| cccgccgccg ttgttgtttt ggagcacgga agacgatga cggaaaaaga gatcgtggat | 1500 |
| tacgtcgcca gtcaagtaac aaccgcgaaa aagttgcgcg gaggagttgt gtttgtggac | 1560 |
| gaagtaccga aaggtcttac cggaaaaactc gacgcaagaa aaatcagaga gatcctcata | 1620 |
| aaggccaaga agggcggaaa gatcgccgtg | 1650 |

<210> SEQ ID NO 21
<211> LENGTH: 1632
<212> TYPE: DNA
<213> ORGANISM: Artificial Sequence
<220> FEATURE:
<223> OTHER INFORMATION: LucPPe-146-1H2

<400> SEQUENCE: 21

| | |
|---|---|
| atggccgaca agaacatcct gtacggcccc gagccttcct accctctgga agatggaaca | 60 |
| gccggcgagc agatgttcga cgccctgagc agatatgccg ccattcctgg atgtatcgcc | 120 |
| ctgacaaacg cccacaccaa agaaaacgtg ctgtacgaag agttcctgaa gctgagctgt | 180 |
| cggctggccg agagcttcaa gaagtacggc ctgaagcaga acgacacaat cgccgtgtgc | 240 |
| agcgagaaca gcctccagtt cttcctgcct gtgatcgcca gcctgtacct gggcattatt | 300 |
| gtggcccctg tgaacgacaa gtacatcgag agagagctga ccacagcct gggcatcgtg | 360 |
| aagccccgga tcgtgttctg ctccaagaac accttccaga aggtgctgaa cgtcaagagc | 420 |
| aagctgaagt ccatcgagac aatcatcatc ctggacctga cgaggacct cggcggctac | 480 |
| cagtgcctga caacttcat cagccagaac agcgacagca acctggacgt gaagaagttc | 540 |
| aagccctaca gcttcaaccg ggacgaccag gtggcctcca tcatgtttag cagcggcacc | 600 |
| accggactgc ccaaaggcgt tatgctgacc cacaagaata tcgtggcccg gttctctatc | 660 |
| gctaaggacc ccaccttcgg caacgccatc aatcctacaa gcgctatcct gacagtgatc | 720 |
| cccttccacc acggcttcgg catgatgacc acactgggct acttcacctg tggcttcaga | 780 |

```
gtggtgctga tgcacacctt cgaggaaaag ctgtttctcc agagcctcca ggactacaag    840
gtggaaagca ccctgctggt gcctactctg atggccttcc tggctaagtc tgccctggtc    900
gagaagtacg atctgagcca cctgaaagag atcgcctctg gcggagcccc tctgagcaaa    960
gaaatcggcg agatggtcaa gaagcggttc aagctgaact tcgtgcggca aggctatggc   1020
ctgaccgaga caacaagcgc cgtgctgatt acccctaagg cgacgccaa gcctggcagc   1080 acaggcaaaa ttgtgcctct gcacgccgtg aaggtggtgg accctaccac aggcaagatc   1140
ctgggaccta atgagcccgg cgagctgtac ttcaagggac ccatgattat gaagggctac   1200
tacaacaacg aggaagccac caaggccatt atcgacaacg acggctggct gcggagcggc   1260
gatattgcct actacgacaa tgacggccac ttctacatcg tggacagact gaagtccctc   1320
atcaagtaca agggctatca ggtggcccca gccgagatcg agggtatcct gctgcaacac   1380
ccctatatcg tggatgccgg cgtgacaggc atccctgatg aagctgctgg cgaacttcca   1440
gcagctggcg tggtggttca gaccggcaag tacctgaatg agcagatcgt gcaggactac   1500
gtggcctctc aggtgtccac agccaaatgg ctgagaggcg gcgtgaagtt cctggacgag   1560
atcccaaagg gctctaccgg caagatcgac agaaaggtgc tgcggcagat gctggaaaag   1620
cacaccaatg gc                                                        1632

<210> SEQ ID NO 22
<211> LENGTH: 1632
<212> TYPE: DNA
<213> ORGANISM: Artificial Sequence
<220> FEATURE:
<223> OTHER INFORMATION: LucPPe-133-1B2

<400> SEQUENCE: 22
atggccgaca agaacatcct gtacggcccc gagccttcct accctctgga agatggaaca     60
gccggcgagc agatgttcga cgccctgagc agatacgccg acattcctgg atgtatcgcc    120
ctgacaaacg cccacaccaa agaaaacgtg ctgtacgaag agttcctgaa gctgagctgt    180
cggctggccg agagcttcaa gaagtacggc ctgaagcaga acgacacaat cgccgtgtgc    240
agcgagaaca gcctccagtt cttcctgcct gtgatcgcca gcctgtacct gggcattatt    300
gtggcccctg tgaacgacaa gtacatcgag agagagctga tccacagcct gggcatcgtg    360 aagcccccgga tcgtgttctg ctccaagaac accttccaga ggtgctgaa cgtcaagagc    420 aagctgaagt ccatcgagac aatcatcatc ctggacctga cgacgacct cggcggctac    480 cagtgcctga caacttcat cagccagaac agcgacagca cctggacgt gaagaagttc    540 aagcccctaca gcttcaaccg ggacgaccag gtggccctga ttatgtttag cagcggcacc    600
accggactgc ccaaaggcgt tatgctgacc cacaagaata tcgtggcccg gttctctatc    660
gctaaggacc ccaccttcgg caacgccatc aatcctacaa gcgctatcct gacagtgatc    720
cccttccacc acggcttcgg catgatgacc acactgggct acttcacctg tggcttcaga    780
gtggtgctga tgcacacctt cgaggaaaag ctgtttctcc agagcctcca ggactacaag    840
gtggaaagca ccctgctggt gcctactctg atggccttcc tggctaagtc tgccctggtc    900
gagaagtacg atctgagcca cctgaaagag atcgcctctg gcggagcccc tctgagcaaa    960
gaaatcggcg agatggtcaa gaagcggttc aagctgaact tcgtgcggca aggctatggc   1020
ctgaccgaga caacaagcgc cgtgctgatt acccctaagg cgacgccaa gcctggcagc   1080 acaggcaaga ttgtgccttt ccacgccgtg aaggtggtgg accctaccac cggaaagatc   1140
```

| | |
|---|---|
| ctgggaccta atgagcccgg cgagctgtac ttcaagggac ccatgattat gaagggctac | 1200 |
| tacaacaacg aggaagccac caaggccatt atcgacaacg acggctggct gcggagcggc | 1260 |
| gatattgcct actacgacaa tgacggccac ttctacatcg tggacagact gaagtccctc | 1320 |
| atcaagtaca agggctacca ggtcgcccct gccgagattg agggtatcct gctgcaacac | 1380 |
| ccctatatcg tggatgccgg cgtgacaggc atccctgatg aagctgctgg cgaacttcca | 1440 |
| gcagctggcg tggtggttca gaccggcaag tacctgaatg agcagatcgt gcaggactac | 1500 |
| gtggcctctc aggtgtccac agccaaatgg ctgagaggcg gcgtgatctt cctggacgag | 1560 |
| atcccaaagg ctctaccgg caagatcgac agaaaggtgc tgcggcagat gctggaaaag | 1620 |
| cacaccaatg gc | 1632 |

<210> SEQ ID NO 23
<211> LENGTH: 1632
<212> TYPE: DNA
<213> ORGANISM: Artificial Sequence
<220> FEATURE:
<223> OTHER INFORMATION: LucPPe-78-0B10

<400> SEQUENCE: 23

| | |
|---|---|
| atggccgaca gaacatcct gtacggcccc gagcctttct accctctggc tgatggaaca | 60 |
| gccggcgagc agatgttcga tgccctgagc agatacgccg acatcagcgg atgtatcgcc | 120 |
| ctgacaaacg cccacaccaa agaaaacgtg ctgtacgaag agttcctgaa gctgagctgt | 180 |
| cggctggccg agagcttcaa gaagtacggc ctgaagcaga acgacacaat cgccgtgtgc | 240 |
| agcgagaacg gcctccagtt ctttctgcct gtgatcgcca gcctgtacct gggcattatc | 300 |
| gctgcccctg tgtccgataa gtacatcgag agagagctga tccacagcct gggcatcgtg | 360 |
| aagcccggga tcatcttctg ctccaagaac accttccaga aggtgctgaa cgtcaagagc | 420 |
| aagctgaagt ccgtggaaac catcatcatc ctggacctga cgaggaccct cggcggctac | 480 |
| cagtgcctga caacttcat ctctcagaac agcgacagca acctggacgt gaagaagttc | 540 |
| aagcccctaca gcttcaaccg ggacgaccag gtggccctgg tcatgtttag ctctggcaca | 600 |
| accggcgtgc caagggcgt tatgctgacc cacaagaata tcgtggcccg gttcagcctg | 660 |
| gctaaggacc ctaccttcgg caacgccatc aatcccacca ccgctatcct gacagtgatc | 720 |
| cccttccacc acggcttcgg catgatgacc acactgggct acttcacctg tggcttcaga | 780 |
| gtggtgctga tgcacacctt cgaggaaaag ctgtttctcc agagcctcca ggactacaag | 840 |
| gtggaaagca ccctgctggt gcctactctg atggcctttc tggccaagtc tgccctggtc | 900 |
| gagaagtacg atctgagcca cctgaaagag atcgcctctg gcggagcccc tctgagcaaa | 960 |
| gaaatcggcg agatggtcaa gaagcggttc aagctgaact tcgtgcggca aggctatggc | 1020 |
| ctgaccgaga caacaagcgc cgtgctgatt accccctaagg gcgacgctag acctggcagc | 1080 |
| acaggcaaga tcgtgccttt ccacgccgtg aaggtggtgg accctacaac cggcaagatc | 1140 |
| ctgggaccta atgagcccgg cgagctgtac tttaagggcg ccatgattat gaagggctac | 1200 |
| tacaacaacg aggaagccac caaggccatt atcgacaacg acggctggct gcggagcggc | 1260 |
| gatattgcct actacgacaa tgacggccac ttctacatcg tggacagact gaagtccctc | 1320 |
| atcaagtaca agggctacca ggtcgcccct gccgagattg agggtatcct gctgcaacac | 1380 |
| ccctatatcg tggatgccgg cgtgacaggc atccctgatg aagctgctgg cgaacttcca | 1440 |
| gcagcaggcg tggtggttca gaccggcaag tacctgaatg agcagatcgt gcaggacttc | 1500 |
| gtgtccagcc aggtgtccac agccaaatgg ctgagaggcg gcgtgaagtt cctggacgag | 1560 |

```
atcccaaagg gctccaccgg aaagatcgac agaaaggtgc tgcggcagat gtttgagaag    1620
cacaccaacg gc                                                       1632
```

<210> SEQ ID NO 24
<211> LENGTH: 1632
<212> TYPE: DNA
<213> ORGANISM: Artificial Sequence
<220> FEATURE:
<223> OTHER INFORMATION: LucPPe49-7C6A

<400> SEQUENCE: 24

```
atggccgaca agaacatcct gtacggcccc gagcctttct accctctggc tgatggaaca     60
gccggcgagc agatgttcta cgccctgagc agatacgccg acatcagcgg atgtatcgcc    120
ctgacaaacg cccacaccaa agaaaacgtg ctgtacgaag agttcctgaa gctgagctgt    180
cggctggccg agagcttcaa gaagtacggc ctgaagcaga cgacacaat cgccgtgtgc     240
agcgagaacg gcctccagtt cttcctgcct atcattgcca gcctgtacct gggcatcatt    300
gctgcccctg tgtccgataa gtacatcgag agagagctga tccactctct gggcatcgtg    360
aagcccggga tcatcttctg ctccaagaac accttccaga aggtgctgaa cgtcaagagc    420
aagctgaaat acgtggaaac catcatcatc ctggacctga cgaggacct cggcggctac    480
cagtgcctga caacttcat ctctcagaac agcgacatca acctggacgt caagaagttc     540
aagccctaca gcttcaaccg ggacgaccag gtggccctgg tcatgtttag ctctggcaca    600
accggcgtgt ccaagggcgt gatgctgacc cacaagaata tcgtggcccg gttcagcctg    660
gctaaggacc ctaccttcgg caacgccatc aatcccacca ccgctatcct gacagtgatc    720
cccttccacc acggcttcgg catgatgacc acactgggct acttcacctg tggcttcaga    780
gtggtgctga tgcacacctt cgaggaaaag ctgtttctcc agagcctcca ggactacaag    840
gtggaaagca ccctgctggt gcctactctg atggcctttc tggctaagag cgccctggtc    900
gagaagtacg atctgagcca cctgaaagag atcgcctctg gcggagcccc tctgagcaaa    960
gaaatcggcg agatggtcaa gaagcggttc aagctgaact tcgtgcggca aggctatggc   1020
ctgaccgaga caacaagcgc cgtgctgatt acccctaaca acgatgtgcg gctggcagc   1080
acaggcaaga tcgtgccttt tcacgccgtg aaggtggtgg accctacaac cggcaagatc   1140
ctgggaccta tgagcccgg cgagctgtac ttcaagggcg acatgattat gaagggctac   1200
tacaacaacg aggaagccac caaggccatt atcaacaagg acggctggct gcggagcggc   1260
gacattgcct actatgacaa cgacggccac ttctacatcg tggaccggct gaagtccctg   1320
attaagtaca agggctacca ggtcgcccct gccgagattg agggtatcct gctgcaacac   1380
ccctatatcg tggatgccgg cgtgacaggc atccctgatg aagctgctgg cgaacttcca   1440
gcagctggcg tggtggttca gaccggcaag tacctgaatg agcagatcgt gcagaatttc   1500
gtgtccagcc aggtgtccac cgccaagtgg cttagaggcg gcgtgaagtt cctggacgag   1560
atccctaaag gctccaccgg aaagatcgac agaaaggtgc tgcgccagat gttcgagaag   1620
cacaccaatg gc                                                       1632
```

<210> SEQ ID NO 25
<211> LENGTH: 1626
<212> TYPE: DNA
<213> ORGANISM: Artificial Sequence
<220> FEATURE:
<223> OTHER INFORMATION: LucPpL-81-6G1

<400> SEQUENCE: 25

```
atgatgaagc gcgagaagaa cgtgatctac ggccccgaac ctctgcaccc tcttgaggat       60
cttacagccg gcgagatgct gttcagagcc ctgcggaaac acagccatct gcctcaggct      120
ctggtggatg tcgtgggaga tgagagcctg tcctacaaag agttcttcga ggccaccgtg      180
ctgctggccc agtctctgca taattgcggc tacaagatga cgacgtggt gtccatctgc       240
gccgagaaca cacccggtt cttcatccct gtgatcgccg cctggtacat cggcatgatt       300
gtggcccctg tgaacgagag ctacatcccc gacgagctgt gcaaagtgat gggcatcagc      360
aagccccaga tcgtgttcac caccaagaac atcctgaaca aggtgctgga agtgcagagc      420
cggaccaact tcatcaagcg gatcatcatc ctggacaccg tggaaaacat ccacggctgc      480
gagagcctgc aaacggcat ctccagatac agcgacggca atatcgccaa cttcaagccc       540
ctgcacttcg accccgtgga acaggtggca gccatcctgt gtagcagcgg cacaacagga      600
ctgcccaaag gcgtgatgca gacccaccag aatatctgcg tgcggctgat ccacgctctg      660
gaccctagag ctggaaccca gctgattcct ggcgtgaccg tgctggtgta cctgcctttc      720
tttcacgcct tcggcttcag catcacccty ggctacttca tggtcggact gagagtgatt      780
atgtttcggc gcttcgacca agaagccttc ctgaaggcca tccaggacta cgaagtgcgc      840
tccgtgatta acgtgcccag cgtgatcctg ttcctgagca agagcccact ggtggataag      900
tacgacctga gcagcctgag agagctgtgt gcggagctg cccctctggc taagaggtg       960
gcagaagttg ccgccaagcg gctgaatctg cctggcatca gatgtggctt tggcctgacc     1020
gagagcacca cgccaatat ccacagcctg cgggacgagt ttaagagcgg ctctctgggc     1080
agagtgaccc ctctgatggc cgccaagatc gccgatagag agacaggcaa agccctggga     1140
cctaatcaag tgggcgagct gtgtatcaag ggacctatgg tgtccaaggg ctacgtgaac     1200
aacgtggaag ccaccaaaga ggccatcgac gacgacggct ggctgcactc tggcgatttc     1260
ggctactacg acgaggacga gcacttctac gtggtggaca gatacaaaga gctgattaag     1320
tacaagggca gccaggtggc cccagccgag ctggaagaaa tcctgctgaa gaaccctgc      1380
atccgcgacg tggcagttgt gggcattcct gatctggaag ccggcgaact gcctagcgcc     1440
tttgtggtta agcagcccgg caaagagatc accgccaaag aggtgtacga ctacctggcc     1500
gagagagtgt cccacaccaa gtatctgaga ggcggcgtca gattcgtgga cagcatcccc     1560
agaaacgtga ccggcaagat cacccggaaa gagctgctga acagctgct ggaaaaggct      1620
ggcgga                                                                1626
```

<210> SEQ ID NO 26
<211> LENGTH: 1626
<212> TYPE: DNA
<213> ORGANISM: Artificial Sequence
<220> FEATURE:
<223> OTHER INFORMATION: CBGRluc

<400> SEQUENCE: 26

```
atggtaaagc gtgagaaaaa tgtcatctat ggccctgagc ctctccatcc tttggaggat       60
ttgactgccg cgaaatgct gtttcgtgct ctccgcaaga actctcattt gcctcaagcc       120
ttggtcgatg tggtcggcga tgaatctttg agctacaagg agtttttga ggcaaccgtc       180
ttgctggctc agtccctcca caattgtggc tacaagatga cgacgtcgt tagtatctgt       240
gctgaaaaca tacccgtttt cttcattcca gtcatcgccg catggtatat cggtatgatc       300
gtggctccag tcaacgagag ctacattccc gacgaactgt gtaaagtcat gggtatctct       360
```

```
aagccacaga ttgtcttcac cactaagaat attctgaaca aagtcctgga agtccaaagc    420
cgcaccaact ttattaagcg tatcatcatc ttggacactg tggagaatat tcacggttgc    480
gaatctttgc ctaatttcat ctctcgctat tcagacggca acatcgcaaa ctttaaacca    540
ctccacttcg accctgtgga acaagttgca gccattctgt gtagcagcgg tactactgga    600
ctcccaaagg gagtcatgca gacccatcaa acatttgcg tgcgtctgat ccatgctctc    660
gatccacgct acggcactca gctgattcct ggtgtcaccg tcttggtcta cttgcctttc    720
ttccatgctt tcggctttca tattactttg ggttacttta tggtcggtct ccgcgtgatt    780
atgttccgcc gttttgatca ggaggctttc ttgaaagcca tccaagatta tgaagtccgc    840
agtgtcatca acgtgcctag cgtgatcctg tttttgtcta agagcccact cgtggacaag    900
tacgacttgt cttcactgcg tgaattgtgt tgcggtgccg ctccactggc taaggaggtc    960
gctgaagtgg ccgccaaacg cttgaatctt ccagggattc gttgtggctt cggcctcacc   1020
gaatctacca gtgcgattat ccagactctc ggggatgagt ttaagagcgg ctctttgggc   1080
cgtgtcactc cactcatggc tgctaagatc gctgatcgcg aaactggtaa ggctttgggc   1140
ccgaaccaag tgggcgagct gtgtatcaaa ggccctatgg tgagcaaggg ttatgtcaat   1200
aacgttgaag ctaccaagga ggccatcgac gacgacggct ggttgcattc tggtgatttt   1260
ggatattacg acgaagatga gcattttac gtcgtggatc gttacaagga gctgatcaaa   1320
tacaagggta gccaggttgc tccagctgag ttggaggaga ttctgttgaa aaatccatgc   1380
attcgcgatg tcgctgtggt cggcattcct gatctggagg ccggcgaact gccttctgct   1440
ttcgttgtca agcagcctgg tacagaaatt accgccaaag aagtgtatga ttacctggct   1500
gaacgtgtga gccatactaa gtacttgcgt ggcggcgtgc gttttgttga ctccatccct   1560
cgtaacgtaa caggcaaaat tacccgcaag gagctgttga acaattgtt ggtgaaggcc   1620 ggcggt                                                             1626

<210> SEQ ID NO 27
<211> LENGTH: 1470
<212> TYPE: DNA
<213> ORGANISM: Artificial Sequence
<220> FEATURE:
<223> OTHER INFORMATION: Embryonic Alkaline Phosphatase (EAP)

<400> SEQUENCE: 27
atgatcatcc cagttgagga ggagaacccg gacttctgga accgcgaggc agccgaggcc     60
ctgggtgccg ccaagaagct gcagcctgca cagacagccg ccaagaacct catcatcttc    120
ctgggcgatg ggatgggggt gtctacggtg acagctgcca ggatcctaaa agggcagaag    180
aaggacaaac tggggcctga gatacccctg gccatggacc gcttcccata tgtggctctg    240
tccaagacat acaatgtaga caaacatgtg ccagacagtg agccacagc cacggcctac    300 ctgtgcgggg tcaagggcaa cttccagacc attggcttga gtcagccgc cgctttaaac    360 cagtgcaaca cgacacgcgg caacgaggtc atctccgtga tgaatcgggc caagaaagca    420
gggaagtcag tgggagtggt aaccaccaca cgagtgcagc acgcctcgcc agccggcacc    480
tacgcccaca cggtgaaccg caactggtac tcggacgccc acgtgcctgc ctcggcccgc    540
caggaggggt gccaggacat cgctacgcag ctcatctcca acatggacat tgacgtgatc    600
ctaggtggag gccgaaagta catgtttcgc atgggaaccc cagaccctga gtacccagat    660
gactacagcc aaggtgggac caggctggac gggaagaatc tggtgcagga atggctggcg    720
```

| | |
|---|---|
| aagcgccagg gtgcccggta tgtgtggaac cgcactgagc tcatgcaggc ttccctggac | 780 |
| ccgtctgtga cccatctcat gggtctcttt gagcctggag acatgaaata cgagatccac | 840 |
| cgagactcca cactggaccc ctccctgatg gagatgacag aggctgccct gcgcctgctg | 900 |
| agcaggaacc cccgcggctt cttcctcttc gtggagggtg gtcgcatcga ccatggtcat | 960 |
| catgaaagca gggcttaccg ggcactgact gagacgatca tgttcgacga cgccattgag | 1020 |
| agggcgggcc agctcaccag cgaggaggac acgctgagcc tcgtcactgc cgaccactcc | 1080 |
| cacgtcttct ccttcggagg ctaccccctg cgagggagct ccatcttcgg gctggcccct | 1140 |
| ggcaaggccc gggacaggaa ggcctacacg gtcctcctat acggaaacgg tccaggctat | 1200 |
| gtgctcaagg acggcgcccg gccggatgtt accgagagcg agagcgggag ccccgagtat | 1260 |
| cggcagcagt cagcagtgcc cctggacgaa gagacccacg caggcgagga cgtggcggtg | 1320 |
| ttcgcgcgcg gcccgcaggc gcacctggtt cacggcgtgc aggagcagac cttcatagcg | 1380 |
| cacgtcatgg ccttcgccgc ctgcctggag ccctacaccg cctgcgacct ggcgcccccc | 1440 |
| gccggcacca ccgacgccgc gcacccgggt | 1470 |

<210> SEQ ID NO 28
<211> LENGTH: 708
<212> TYPE: DNA
<213> ORGANISM: Artificial Sequence
<220> FEATURE:
<223> OTHER INFORMATION: mCherry

<400> SEQUENCE: 28

| | |
|---|---|
| atggtgagca agggcgagga ggataacatg gccatcatca aggagttcat gcgcttcaag | 60 |
| gtgcacatgg agggctccgt gaacggccac gagttcgaga tcgagggcga gggcgagggc | 120 |
| cgcccctacg agggcaccca gaccgccaag ctgaaggtga ccaagggtgg ccccctgccc | 180 |
| ttcgcctggg acatcctgtc ccctcagttc atgtacggct ccaaggccta cgtgaagcac | 240 |
| cccgccgaca tccccgacta cttgaagctg tccttcccccg agggcttcaa gtgggagcgc | 300 |
| gtgatgaact tcgaggacgg cggcgtggtg accgtgaccc aggactcctc cctgcaggac | 360 |
| ggcgagttca tctacaaggt gaagctgcgc ggcaccaact cccctccga cggccccgta | 420 |
| atgcagaaga agaccatggg ctgggaggcc tcctccgagc ggatgtaccc cgaggacggc | 480 |
| gccctgaagg gcgagatcaa gcagaggctg aagctgaagg acggcggcca ctacgacgct | 540 |
| gaggtcaaga ccacctacaa ggccaagaag cccgtgcagc tgcccggcgc ctacaacgtc | 600 |
| aacatcaagt tggacatcac ctcccacaac gaggactaca ccatcgtgga acagtacgaa | 660 |
| cgcgccgagg gccgccactc caccggcggc atggacgagc tgtacaag | 708 |

<210> SEQ ID NO 29
<211> LENGTH: 717
<212> TYPE: DNA
<213> ORGANISM: Artificial Sequence
<220> FEATURE:
<223> OTHER INFORMATION: EGFP (Enhanced Green Fluorescent Protein)

<400> SEQUENCE: 29

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |

```
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaag      717

<210> SEQ ID NO 30
<211> LENGTH: 522
<212> TYPE: DNA
<213> ORGANISM: Artificial Sequence
<220> FEATURE:
<223> OTHER INFORMATION: MYR-GGS-GLuc (M60L/M127L variant)

<400> SEQUENCE: 30
atggggagta gcaagagcaa gcctaaggac cccagccagc gcagaagggg cggatctggg     60
gatcccaagc ccaccgagaa caacgaagac gccgacagag gcaagctgcc cggcaagaaa    120
ctgcccctgg aagtgctgaa agagctggaa gccaacgccc ggaaggccgg ctgtacaaga    180
ggctgcctga tctgcctgag ccacatcaag tgcacgccca agatgaagaa gttcatcccc    240
ggcagatgcc acacctacga gggcgacaaa gagtctgccc agggcggaat cggcgaggct    300
atcgtggaca ttcctgagat tcctgggttc aaggacctgg aacccctgga acagtttatc    360
gcccaggtgg acctgtgcgt ggactgcacc acaggctgtc tgaagggcct ggctaacgtg    420
cagtgcagcg acctgctgaa gaagtggctg ccccagagat gcgccacctt cgcctctaag    480
atccagggac aggtggacaa gatcaagggg gccggtggtg ac                       522

<210> SEQ ID NO 31
<211> LENGTH: 169
<212> TYPE: PRT
<213> ORGANISM: Artificial Sequence
<220> FEATURE:
<223> OTHER INFORMATION: GLuc (Gaussia princeps Luc)

<400> SEQUENCE: 31

Met Lys Pro Thr Glu Asn Asn Glu Asp Phe Asn Ile Val Ala Val Ala
1               5                   10                  15

Ser Asn Phe Ala Thr Thr Asp Leu Asp Ala Asp Arg Gly Lys Leu Pro
            20                  25                  30

Gly Lys Lys Leu Pro Leu Glu Val Leu Lys Glu Met Glu Ala Asn Ala
        35                  40                  45

Arg Lys Ala Gly Cys Thr Arg Gly Cys Leu Ile Cys Leu Ser His Ile
    50                  55                  60

Lys Cys Thr Pro Lys Met Lys Lys Phe Ile Pro Gly Arg Cys His Thr
65                  70                  75                  80

Tyr Glu Gly Asp Lys Glu Ser Ala Gln Gly Gly Ile Gly Glu Ala Ile
                85                  90                  95

Val Asp Ile Pro Glu Ile Pro Gly Phe Lys Asp Leu Glu Pro Met Glu
            100                 105                 110

Gln Phe Ile Ala Gln Val Asp Leu Cys Val Asp Cys Thr Thr Gly Cys
        115                 120                 125

Leu Lys Gly Leu Ala Asn Val Gln Cys Ser Asp Leu Leu Lys Lys Trp
    130                 135                 140
```

-continued

```
Leu Pro Gln Arg Cys Ala Thr Phe Ala Ser Lys Ile Gln Gly Gln Val
145                 150                 155                 160

Asp Lys Ile Lys Gly Ala Gly Gly Asp
                165

<210> SEQ ID NO 32
<211> LENGTH: 171
<212> TYPE: PRT
<213> ORGANISM: Artificial Sequence
<220> FEATURE:
<223> OTHER INFORMATION: NLuc (NanoLuc)

<400> SEQUENCE: 32

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 33
<211> LENGTH: 148
<212> TYPE: PRT
<213> ORGANISM: Artificial Sequence
<220> FEATURE:
<223> OTHER INFORMATION: TLuc (TurboLuc16)

<400> SEQUENCE: 33

Met Glu Ala Glu Ala Glu Arg Gly Lys Leu Pro Gly Lys Lys Leu Pro
1               5                   10                  15

Leu Glu Val Leu Ile Glu Leu Glu Ala Asn Ala Arg Lys Ala Gly Cys
            20                  25                  30

Thr Arg Gly Cys Leu Ile Cys Leu Ser Lys Ile Lys Cys Thr Ala Lys
        35                  40                  45

Met Lys Lys Tyr Ile Pro Gly Arg Cys Ala Asp Tyr Gly Gly Asp Lys
    50                  55                  60

Lys Thr Gly Gln Ala Gly Ile Val Gly Ala Ile Val Asp Ile Pro Glu
65                  70                  75                  80

Ile Ser Gly Phe Lys Glu Met Glu Pro Met Glu Gln Phe Ile Ala Gln
                85                  90                  95

Val Asp Arg Cys Ala Asp Cys Thr Thr Gly Cys Leu Lys Gly Leu Ala
```

100                 105                 110

Asn Val Lys Cys Ser Asp Leu Leu Lys Lys Trp Leu Pro Gly Arg Cys
        115                 120                 125

Ala Thr Phe Ala Asp Lys Ile Gln Ser Glu Val Asp Asn Ile Lys Gly
        130                 135                 140

Leu Ala Gly Asp
145

<210> SEQ ID NO 34
<211> LENGTH: 153
<212> TYPE: PRT
<213> ORGANISM: Artificial Sequence
<220> FEATURE:
<223> OTHER INFORMATION: MLuc7 (Metrida longa Luc7) M43L/M110L variant

<400> SEQUENCE: 34

Met Asn Pro Thr Val Asn Asn Asp Val Asn Arg Gly Lys Met Pro Gly
1               5                   10                  15

Lys Lys Leu Pro Leu Glu Val Leu Ile Glu Leu Glu Ala Asn Ala Phe
            20                  25                  30

Lys Ala Gly Cys Thr Arg Gly Cys Leu Ile Cys Leu Ser Lys Ile Lys
        35                  40                  45

Cys Thr Ala Lys Met Lys Gln Tyr Ile Pro Gly Arg Cys His Asp Tyr
    50                  55                  60

Gly Gly Asp Lys Lys Thr Gly Gln Ala Gly Ile Val Gly Ala Ile Val
65                  70                  75                  80

Asp Ile Pro Glu Ile Ser Gly Phe Lys Glu Met Glu Pro Leu Glu Gln
                85                  90                  95

Phe Ile Ala Gln Val Asp Leu Cys Ala Asp Cys Thr Thr Gly Cys Leu
            100                 105                 110

Lys Gly Leu Ala Asn Val Lys Cys Ser Glu Leu Leu Lys Lys Trp Leu
        115                 120                 125

Pro Asp Arg Cys Ala Ser Phe Ala Asp Lys Ile Gln Lys Glu Ala His
    130                 135                 140

Asn Ile Lys Gly Leu Ala Gly Asp Arg
145                 150

<210> SEQ ID NO 35
<211> LENGTH: 206
<212> TYPE: PRT
<213> ORGANISM: Artificial Sequence
<220> FEATURE:
<223> OTHER INFORMATION: LoLuc (Lucicutia ovaliformis Luc)

<400> SEQUENCE: 35

Met Leu Pro Ala Ser Pro Thr Asp Arg Ser Ile Val Leu Asp Asn Gly
1               5                   10                  15

Tyr Val Cys Ser Trp Glu Gly Ile Pro Asp Asp Leu Arg Asp Cys Pro
            20                  25                  30

Lys Thr Glu Asp Met Ser Lys Gln His Gly Ala Ala Leu Lys Leu Pro
        35                  40                  45

Pro Asp Val Leu Asp Glu Met Glu Cys Asn Ala Lys Lys Ser Gly Cys
    50                  55                  60

Val Arg Gly Cys Leu Gln Cys Leu Ala Leu Ile Lys Cys Thr Ala Lys
65                  70                  75                  80

Met Arg Lys Tyr Ile Pro Gly Arg Cys His Ser Tyr Glu Gly Asp Lys
                85                  90                  95

Asp Ile Ala Gln Gly Gly Ile Gly Lys Glu Leu Thr Ile Asp Ile Pro
            100                 105                 110

Glu Ile Pro Gly Phe Leu Asp Leu Ala Pro Met Asp Gln Phe Val Ala
        115                 120                 125

Gln Val Asp Leu Cys Val Asp Cys Ser Ser Arg Cys Leu Lys Gly Leu
    130                 135                 140

Ala Asn Val Gln Cys Ser Cys Lys Leu Tyr Lys Trp Leu Pro Thr Arg
145                 150                 155                 160

Cys Thr Gly Phe Gln Ala Lys Ile Lys Lys Glu Ala Asp Thr Val Ile
                165                 170                 175

Gly Leu Glu Asp Ala Leu Ala Leu Gly Phe Asp Thr Ile Gln Ala Cys
            180                 185                 190

Val Ala Ala Gly Lys Cys Lys Asp Thr Val Gly Arg Tyr Ser
        195                 200                 205

<210> SEQ ID NO 36
<211> LENGTH: 169
<212> TYPE: PRT
<213> ORGANISM: Artificial Sequence
<220> FEATURE:
<223> OTHER INFORMATION: HtLuc (Heterorhabdus tanneri Luc)

<400> SEQUENCE: 36

Met Ala Ala Ser Glu Glu Ala Asp Asp Asp His Val Ser Leu Val Lys
1               5                   10                  15

Asn Tyr Trp Arg Ile Gly Val Gly Asn Glu Arg Asp Val Ser Leu Asp
            20                  25                  30

Arg Gly Gly Pro Pro Lys Leu Ser Lys Glu Leu Leu Ala Glu Met His
        35                  40                  45

Ala Ile Ala Ser Asn Ala Gly Cys Ser Arg Val Cys Leu Ile Gly Leu
    50                  55                  60

Ser Lys Ile Lys Cys Thr Pro Lys Met Lys Thr Phe Leu Pro Gly Arg
65                  70                  75                  80

Cys Asn Thr Phe Ala Pro Lys Pro Ala Thr Gly Asp Gly Pro Phe Ala
                85                  90                  95

Ala Ala Ala Ala Ile Pro Gly Phe Ser Asp Leu Thr Ala Met Glu Gln
            100                 105                 110

Tyr Lys Ala Gln Val Ala Gln Cys Asp Cys Ser Asn Arg Cys Leu Val
        115                 120                 125

Gly Leu Ala Asn Ile Lys Cys Ser Ala Ala Leu Lys Ala Leu Pro
    130                 135                 140

Gln Arg Cys Thr Thr Phe Ala Thr Asn Ile Gln Lys Glu Gly Glu Val
145                 150                 155                 160

Asp Ser Ile Lys Gly Tyr Gly Arg Lys
                165

<210> SEQ ID NO 37
<211> LENGTH: 195
<212> TYPE: PRT
<213> ORGANISM: Artificial Sequence
<220> FEATURE:
<223> OTHER INFORMATION: PaLuc1 (Pleuromamma abdominalis Luc1)

<400> SEQUENCE: 37

Met Gln Pro Thr Glu Asn Lys Gln Glu Ser Gln Ile Glu Asp Ile Asp
1               5                   10                  15

Arg Ser Thr Ser Leu Gly Leu Met Cys Tyr Glu Gln Cys Thr Gly Gln
            20                  25                  30

```
Ser Gly Leu Asp Leu Lys Cys Tyr Lys Glu Cys Ala Asp Phe Thr Gly
        35                  40                  45

Asp Arg Asn Arg Gly Arg Lys Leu Pro Gly Lys Lys Leu Pro Leu Glu
    50                  55                  60

Val Leu Lys Ile Met Glu Ala Asn Ala Arg Arg Ala Gly Cys Thr Arg
65                  70                  75                  80

Gly Cys Leu Ile Cys Leu Ser Lys Ile Lys Cys Thr Ala Lys Met Lys
                85                  90                  95

Gln Tyr Ile Pro Gly Arg Cys His Thr Tyr Glu Gly Asp Lys Ser Ile
            100                 105                 110

Gly Gln Gly Gly Ile Gly Gly Pro Ile Val Asp Ile Pro Glu Ile Ile
        115                 120                 125

Gly Phe Gln Asn Met Glu Pro Met Glu Gln Phe Ile Ala Gln Val Asp
    130                 135                 140

Leu Cys Ala Asp Cys Thr Thr Gly Cys Leu Lys Gly Leu Ala Asn Val
145                 150                 155                 160

Arg Cys Asn Asp Leu Leu Lys Lys Trp Leu Pro Asp Arg Cys Ala Gly
                165                 170                 175

Phe Ala Asn Lys Ile Gln Ser Glu Val Asp Asn Ile Lys Gly Leu Ala
            180                 185                 190

Gly Asp Arg
        195

<210> SEQ ID NO 38
<211> LENGTH: 170
<212> TYPE: PRT
<213> ORGANISM: Artificial Sequence
<220> FEATURE:
<223> OTHER INFORMATION: PaLuc2 (Pleuromamma abdominalis Luc2)

<400> SEQUENCE: 38

Met Lys Ser Ile Asp Ser Tyr Glu Asn Ile Asp Ile Val Ala Val Ala
1               5                   10                  15

Gly Asn Phe Ala Ala Val Asp Gln Asp Ala Asn Arg Gly Gly Asn Leu
            20                  25                  30

Pro Gly Lys Lys Met Pro Ile Glu Val Leu Lys Glu Met Glu Ala Asn
        35                  40                  45

Ala Lys Arg Ala Gly Cys Val Arg Gly Cys Leu Ile Cys Leu Ser His
    50                  55                  60

Ile Lys Cys Thr Ala Lys Met Lys Lys Phe Ile Pro Gly Arg Cys His
65                  70                  75                  80

Ser Tyr His Gly Asp Ala Asp Thr Lys Gln Gly Ala Leu Glu Glu Val
                85                  90                  95

Val Asp Met Pro Glu Ile Pro Gly Phe Val Asp Met Glu Pro Met Glu
            100                 105                 110

Gln Phe Ile Ala Gln Val Asp Lys Cys Glu Asp Cys Thr Thr Gly Cys
        115                 120                 125

Leu Lys Gly Leu Ala Asn Val His Cys Ser Asp Leu Leu Lys Lys Trp
    130                 135                 140

Leu Pro Gln Arg Cys Ser Gln Phe Ala Asp Lys Ile Gln Ser Glu Val
145                 150                 155                 160

Asp Thr Ile Lys Gly Leu Ala Gly Asp Arg
                165                 170

<210> SEQ ID NO 39
```

```
<211> LENGTH: 193
<212> TYPE: PRT
<213> ORGANISM: Artificial Sequence
<220> FEATURE:
<223> OTHER INFORMATION: MpLuc1[Metridia pacifica Luc1]

<400> SEQUENCE: 39

Met Asn Pro Thr Glu Asn Lys Asp Asp Ile Asp Ile Val Gly Val Glu
1               5                   10                  15

Gly Lys Phe Gly Thr Thr Asp Leu Glu Thr Asp Leu Phe Thr Ile Val
            20                  25                  30

Glu Asp Met Asn Val Ile Ser Arg Asp Thr Asn Leu Ala Asn Ser Asp
        35                  40                  45

Ala Asp Arg Gly Lys Met Pro Gly Lys Lys Leu Pro Leu Glu Val Leu
    50                  55                  60

Ile Glu Met Glu Ala Asn Ala Arg Lys Ala Gly Cys Thr Arg Gly Cys
65                  70                  75                  80

Leu Ile Cys Leu Ser Lys Ile Lys Cys Thr Ala Lys Met Lys Val Tyr
                85                  90                  95

Ile Pro Gly Arg Cys His Asp Tyr Gly Gly Asp Lys Lys Thr Gly Gln
            100                 105                 110

Ala Gly Ile Val Gly Ala Ile Val Asp Ile Pro Glu Ile Ser Gly Phe
        115                 120                 125

Lys Glu Leu Gly Pro Met Glu Gln Phe Ile Ala Gln Val Asp Leu Cys
    130                 135                 140

Ala Asp Cys Thr Thr Gly Cys Leu Lys Gly Leu Ala Asn Val Lys Cys
145                 150                 155                 160

Ser Ala Leu Leu Lys Lys Trp Leu Pro Asp Arg Cys Ala Ser Phe Ala
                165                 170                 175

Asp Lys Ile Gln Ser Glu Val Asp Asn Ile Lys Gly Leu Ala Gly Asp
            180                 185                 190

Arg

<210> SEQ ID NO 40
<211> LENGTH: 170
<212> TYPE: PRT
<213> ORGANISM: Artificial Sequence
<220> FEATURE:
<223> OTHER INFORMATION: McLuc1 [Metridia curticauda Luc1]

<400> SEQUENCE: 40

Met Lys Pro Thr Glu Asn Asn Asp Asp Ile Asp Ile Val Gly Ile Ala
1               5                   10                  15

Ser Thr Phe Ile Thr Thr Asn Thr Asp Ala Asp Arg Gly Lys Met Pro
            20                  25                  30

Gly Lys Lys Leu Pro Leu Ala Val Leu Lys Glu Met Glu Ala Asn Ala
            35                  40                  45

Ala Lys Ala Gly Cys Ser Arg Gly Cys Leu Ile Cys Leu Ser Lys Ile
    50                  55                  60

Lys Cys Thr Ala Lys Met Lys Gln Phe Ile Pro Gly Arg Cys His Asp
65                  70                  75                  80

Tyr Gly Gly Asp Lys Lys Thr Gly Gln Ala Ala Leu Val Gly Ala Ile
                85                  90                  95

Phe Asp Ile Pro Glu Ile Phe Gly Phe Leu Asp Met Glu Pro Ile Glu
            100                 105                 110

Gln Phe Ile Ala Gln Val Asp Leu Cys Ala Gly Cys Thr Thr Gly Cys
        115                 120                 125
```

Leu Lys Gly Leu Ala Asn Ile Lys Cys Ser Glu Leu Leu Lys Lys Trp
        130                 135                 140

Leu Pro Lys Arg Cys Thr Ser Phe Ala Tyr Lys Met Gln Lys Glu Met
145                 150                 155                 160

His Asn Ile Lys Gly Met Ala Gly Asp Arg
                165                 170

<210> SEQ ID NO 41
<211> LENGTH: 170
<212> TYPE: PRT
<213> ORGANISM: Artificial Sequence
<220> FEATURE:
<223> OTHER INFORMATION: MaLuc1 [Metridia asymmetrica Luc1]

<400> SEQUENCE: 41

Met Lys Ala Thr Glu Asn Asn Asp Asp Ile Asp Ile Val Gly Ile Ala
1               5                   10                  15

Ser Thr Phe Ile Thr Thr Asn Thr Asp Ala Asp Arg Gly Lys Met Pro
            20                  25                  30

Gly Lys Arg Leu Pro Leu Ala Val Leu Lys Glu Met Glu Ala Asn Ala
        35                  40                  45

Val Lys Ala Gly Cys Ser Arg Gly Cys Leu Ile Cys Leu Ser Lys Ile
    50                  55                  60

Lys Cys Thr Ala Lys Met Lys Gln Tyr Ile Pro Gly Arg Cys His Asp
65                  70                  75                  80

Tyr Gly Gly Asp Lys Lys Thr Gly Gln Ala Ala Ile Glu Gly Ala Ile
                85                  90                  95

Asp Asp Ile Pro Glu Ile Ser Gly Phe Lys Glu Met Ala Pro Met Glu
            100                 105                 110

Gln Phe Ile Ala Gln Val Asp Leu Cys Ala Asp Cys Thr Thr Gly Cys
        115                 120                 125

Leu Lys Gly Leu Ala Asn Val Lys Cys Ser Glu Leu Leu Lys Lys Trp
    130                 135                 140

Leu Pro Lys Arg Cys Thr Ser Phe Ala Thr Lys Met Gln Lys Glu Ile
145                 150                 155                 160

His Asn Ile Lys Gly Met Gly Gly Asp Arg
                165                 170

<210> SEQ ID NO 42
<211> LENGTH: 196
<212> TYPE: PRT
<213> ORGANISM: Artificial Sequence
<220> FEATURE:
<223> OTHER INFORMATION: MoLuc1 [Metridia okhotensis Luc1]

<400> SEQUENCE: 42

Met Asn Pro Thr Glu Thr Gln Asp Gly Val Asp Ile Leu Gly Val Glu
1               5                   10                  15

Gly Lys Phe Gly Thr Glu Thr Asn Leu Glu Thr Asp Leu Phe Thr Ile
            20                  25                  30

Trp Glu Ile Asn Gly Ile Ile Lys Ser Asp Arg Asp Thr Asn Arg Ala
        35                  40                  45

Asn Ala Asp Ala Asp Arg Gly Lys Met Pro Gly Lys Lys Leu Pro Leu
    50                  55                  60

Ala Val Leu Ile Glu Met Glu Ala Asn Ala Phe Lys Ala Gly Cys Thr
65                  70                  75                  80

Arg Gly Cys Leu Ile Cys Leu Ser Lys Ile Lys Cys Thr Ala Lys Met

```
                    85                  90                  95
Lys Glu Tyr Ile Pro Gly Arg Cys His Asp Tyr Gly Gly Asp Lys Lys
                100                 105                 110

Thr Gly Gln Ala Gly Ile Val Gly Ala Ile Val Asp Ile Pro Glu Ile
            115                 120                 125

Ser Gly Phe Lys Glu Leu Gly Pro Met Glu Gln Phe Ile Ala Gln Val
        130                 135                 140

Asp Leu Cys Ala Asp Cys Thr Thr Gly Cys Leu Lys Gly Leu Ala Asn
145                 150                 155                 160

Val Lys Cys Ser Ala Leu Leu Lys Lys Trp Leu Pro Asp Arg Cys Ala
                165                 170                 175

Ser Phe Ala Asp Lys Ile Gln Ser Glu Val His Asn Ile Lys Gly Leu
                180                 185                 190

Ala Gly Asp Arg
        195

<210> SEQ ID NO 43
<211> LENGTH: 174
<212> TYPE: PRT
<213> ORGANISM: Artificial Sequence
<220> FEATURE:
<223> OTHER INFORMATION: MoLuc2 [Metridia okhotensis Luc2]

<400> SEQUENCE: 43

Met Ala Thr Ile Asn Glu Asn Phe Glu Asp Ile Asp Leu Val Ala Ile
1               5                   10                  15

Gly Gly Ser Phe Ala Thr Asp Val Asp Ala Asn Arg Gly Gly His Gly
            20                  25                  30

Gly His Pro Gly Lys Lys Met Pro Lys Glu Val Leu Leu Glu Met Glu
        35                  40                  45

Ala Asn Ala Lys Arg Ala Gly Cys His Arg Gly Cys Leu Ile Cys Leu
    50                  55                  60

Ser His Ile Lys Cys Thr Gln Lys Met Lys Lys Phe Ile Pro Gly Arg
65                  70                  75                  80

Cys His Ser Tyr Ala Gly Asp Lys Asp Ser Ala Gln Gly Gly Ile Thr
                85                  90                  95

Glu Glu Glu Thr Val Asp Met Pro Gly Ile Ala Gly Phe Lys Asp Leu
            100                 105                 110

Glu Pro Met Glu Gln Phe Ile Ala Gln Val Asp Leu Cys Val Asp Cys
        115                 120                 125

Thr Thr Gly Cys Leu Lys Gly Leu Ala Asn Val His Cys Ser Asp Leu
    130                 135                 140

Leu Lys Lys Trp Leu Pro Ser Arg Cys Lys Thr Phe Ala Ser Lys Ile
145                 150                 155                 160

Gln Ser Gln Val Asp Thr Ile Lys Gly Leu Ala Gly Asp Arg
                165                 170

<210> SEQ ID NO 44
<211> LENGTH: 193
<212> TYPE: PRT
<213> ORGANISM: Artificial Sequence
<220> FEATURE:
<223> OTHER INFORMATION: MLuc39 [Metridia longa Luc39]

<400> SEQUENCE: 44

Met Asn Pro Thr Glu Asn Asn Asp His Ile Asn Ile Val Gly Ile Glu
1               5                   10                  15
```

Gly Lys Phe Gly Ile Thr Asp Leu Glu Thr Asp Leu Phe Thr Ile Trp
                20                  25                  30

Glu Thr Asn Arg Met Ile Ser Thr Asp Asn Glu Gln Ala Asn Thr Asp
            35                  40                  45

Ser Asn Arg Gly Lys Met Pro Gly Lys Lys Leu Pro Leu Ala Val Leu
        50                  55                  60

Ile Glu Met Glu Ala Asn Ala Phe Lys Ala Gly Cys Thr Arg Gly Cys
65                  70                  75                  80

Leu Ile Cys Leu Ser Lys Ile Lys Cys Thr Ala Lys Met Lys Lys Tyr
                85                  90                  95

Ile Pro Gly Arg Cys His Asp Tyr Gly Gly Asp Lys Lys Thr Gly Gln
            100                 105                 110

Ala Gly Ile Val Gly Ala Ile Val Asp Ile Pro Asp Ile Ser Gly Phe
        115                 120                 125

Lys Glu Met Gly Pro Met Glu Gln Phe Ile Ala Gln Val Asp Arg Cys
130                 135                 140

Thr Asp Cys Thr Thr Gly Cys Leu Lys Gly Leu Ala Asn Val Lys Cys
145                 150                 155                 160

Ser Glu Leu Leu Lys Lys Trp Leu Pro Asp Arg Cys Ala Ser Phe Ala
                165                 170                 175

Asp Lys Ile Gln Ser Glu Val His Asn Ile Lys Gly Leu Ala Gly Asp
            180                 185                 190

Arg

<210> SEQ ID NO 45
<211> LENGTH: 166
<212> TYPE: PRT
<213> ORGANISM: Artificial Sequence
<220> FEATURE:
<223> OTHER INFORMATION: PsLuc1 [Pleuromamma scutullata Luc1]

<400> SEQUENCE: 45

Met Gln Pro Thr Glu Asn Lys Lys Glu Ser Tyr Thr Glu Asp Thr Asp
1               5                   10                  15

Val Asn Gly Asp His Asp Arg Gly Arg Lys Leu Pro Gly Lys Lys Leu
            20                  25                  30

Pro Leu Glu Val Leu Lys Ile Met Glu Ala Asn Ala Arg Arg Ala Gly
        35                  40                  45

Cys Thr Arg Gly Cys Leu Ile Cys Leu Ser Lys Ile Lys Cys Thr Ala
    50                  55                  60

Lys Met Lys Gln Tyr Ile Pro Gly Arg Cys His Thr Tyr Glu Gly Asp
65                  70                  75                  80

Lys Ser Ile Gly Gln Ala Gly Ile Gly Gly Pro Ile Ile Asp Ile Pro
                85                  90                  95

Glu Ile Ile Gly Phe Lys Asn Met Glu Pro Met Glu Gln Phe Ile Ala
            100                 105                 110

Gln Val Asp Leu Cys Ala Asp Cys Thr Thr Gly Cys Leu Lys Gly Leu
        115                 120                 125

Ala Asn Val Arg Cys Asn Asp Leu Leu Lys Lys Trp Leu Pro Asp Arg
    130                 135                 140

Cys Ala Gly Phe Ala Leu Lys Ile Gln Gly Glu Val Glu Asn Ile Lys
145                 150                 155                 160

Gly Met Ala Gly Asp Arg
            165

```
<210> SEQ ID NO 46
<211> LENGTH: 206
<212> TYPE: PRT
<213> ORGANISM: Artificial Sequence
<220> FEATURE:
<223> OTHER INFORMATION: LoLuc1-3 [Lucicutia ovaliformis Luc1-3]

<400> SEQUENCE: 46
```

Met Leu Pro Ala Ser Pro Thr Asp Arg Ser Ile Val Leu Asp Asn Gly
1               5                   10                  15

Tyr Val Cys Ser Trp Glu Gly Ile Pro Asp Asp Leu Arg Asp Cys Pro
                20                  25                  30

Lys Thr Glu Asp Met Ser Lys Gln His Gly Ala Ala Leu Lys Leu Pro
            35                  40                  45

Pro Asp Val Leu Asp Glu Met Glu Cys Asn Ala Lys Lys Ser Gly Cys
    50                  55                  60

Val Arg Gly Cys Leu Gln Cys Leu Ala Leu Ile Lys Cys Thr Ala Lys
65                  70                  75                  80

Met Arg Lys Tyr Ile Pro Gly Arg Cys His Ser Tyr Glu Gly Asp Lys
                85                  90                  95

Asp Ile Ala Gln Gly Gly Ile Gly Lys Glu Leu Thr Ile Asp Ile Pro
            100                 105                 110

Glu Ile Pro Gly Phe Leu Asp Leu Ala Pro Met Asp Gln Phe Val Ala
        115                 120                 125

Gln Val Asp Leu Cys Val Asp Cys Ser Ser Arg Cys Leu Lys Gly Leu
    130                 135                 140

Ala Asn Val Gln Cys Ser Cys Lys Leu Tyr Lys Trp Leu Pro Thr Arg
145                 150                 155                 160

Cys Thr Gly Phe Gln Ala Lys Ile Lys Lys Glu Ala Asp Thr Val Ile
                165                 170                 175

Gly Leu Glu Asp Ala Leu Ala Leu Gly Phe Asp Thr Ile Gln Ala Cys
            180                 185                 190

Val Ala Ala Gly Lys Cys Lys Asp Thr Val Gly Arg Tyr Ser
        195                 200                 205

```
<210> SEQ ID NO 47
<211> LENGTH: 178
<212> TYPE: PRT
<213> ORGANISM: Artificial Sequence
<220> FEATURE:
<223> OTHER INFORMATION: HtLuc2 [Heterorhabdus tanneri Luc 2]

<400> SEQUENCE: 47
```

Met Trp Ala Ala Ser Glu Glu Ala Asp Asp Asp Leu Val Ser Leu Val
1               5                   10                  15

Lys Asn Tyr Trp Gly Val Gly Val Ser Asn Glu Arg Asp Val Ser Leu
                20                  25                  30

Asp Arg Gly Gly His Gly Lys Leu Pro Lys Lys Leu Ser Val Glu Ile
            35                  40                  45

Leu Ala Glu Met Glu Ala Asn Ala Gln Lys Ser Asn Cys Ser Arg Gly
        50                  55                  60

Cys Leu Ile Gly Leu Ser Lys Ile Lys Cys Thr Pro Lys Met Lys Lys
65                  70                  75                  80

Phe Leu Pro Gly Arg Cys His Glu Tyr Ser Gly Asp Pro Lys Thr Gly
                85                  90                  95

Gln Gly Pro Leu Thr Ala Ala Val Ile Pro Gly Tyr Ser Asp Leu
            100                 105                 110

```
Thr Ala Met Glu Gln Phe Lys Leu Gln Val Asp Lys Cys Asp Cys Ser
            115                 120                 125

Thr Gln Cys Leu Lys Gly Leu Ala Asn Val Lys Cys Ser Ala Ala Leu
        130                 135                 140

Lys Ala Val Leu Pro Thr Arg Cys Ser Gln Phe Ala Thr Gln Ile Gln
145                 150                 155                 160

Ala Glu Val Gly Thr Ile Lys Gly Lys Gly Lys Lys Pro Thr Pro Pro
                165                 170                 175

Ile Gly

<210> SEQ ID NO 48
<211> LENGTH: 193
<212> TYPE: PRT
<213> ORGANISM: Artificial Sequence
<220> FEATURE:
<223> OTHER INFORMATION: Lucia-Luc

<400> SEQUENCE: 48

Met Lys Pro Thr Glu Ile Asn Glu Asp Leu Asn Ile Ala Ala Val Ala
1               5                   10                  15

Ser Asn Phe Ala Thr Thr Asp Leu Glu Thr Asp Leu Phe Thr Asn Trp
            20                  25                  30

Glu Thr Met Asn Val Ile Ser Thr Asp Thr Glu Gln Val Asn Thr Asp
        35                  40                  45

Ala Asp Arg Gly Lys Leu Pro Gly Lys Lys Leu Pro Pro Asp Val Leu
    50                  55                  60

Arg Glu Leu Glu Ala Asn Ala Arg Arg Ala Gly Cys Thr Arg Gly Cys
65                  70                  75                  80

Leu Ile Cys Leu Ser His Ile Lys Cys Thr Pro Lys Met Lys Lys Phe
                85                  90                  95

Ile Pro Gly Arg Cys His Thr Tyr Glu Gly Glu Lys Glu Ser Ala Gln
            100                 105                 110

Gly Gly Ile Gly Glu Ala Ile Val Asp Ile Pro Glu Ile Pro Gly Phe
        115                 120                 125

Lys Asp Lys Glu Pro Leu Asp Gln Phe Ile Ala Gln Val Asp Leu Cys
    130                 135                 140

Ala Asp Cys Thr Thr Gly Cys Leu Lys Gly Leu Ala Asn Val Gln Cys
145                 150                 155                 160

Ser Asp Leu Leu Lys Lys Trp Leu Pro Gln Arg Cys Thr Thr Phe Ala
                165                 170                 175

Ser Lys Ile Gln Gly Arg Val Asp Lys Ile Lys Gly Leu Ala Gly Asp
            180                 185                 190

Arg

<210> SEQ ID NO 49
<211> LENGTH: 311
<212> TYPE: PRT
<213> ORGANISM: Artificial Sequence
<220> FEATURE:
<223> OTHER INFORMATION: RLuc (Renilla Luc)

<400> SEQUENCE: 49

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
```

```
                 35                  40                  45
Phe Leu His Gly Asn Ala Ala Ser Ser Tyr Leu Trp Arg His Val Val
 50                  55                  60

Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
                100                 105                 110

Lys Ile Ile Phe Val Gly His Asp Trp Gly Ala Cys Leu Ala Phe His
                115                 120                 125

Tyr Ser Tyr Glu His Gln Asp Lys Ile Lys Ala Ile Val His Ala Glu
130                 135                 140

Ser Val Val Asp Val Ile Glu Ser Trp Asp Trp Pro Asp Ile Glu
145                 150                 155                 160

Glu Asp Ile Ala Leu Ile Lys Ser Glu Gly Glu Lys Met Val Leu
                165                 170                 175

Glu Asn Asn Phe Phe Val Glu Thr Met Leu Pro Ser Lys Ile Met Arg
                180                 185                 190

Lys Leu Glu Pro Glu Glu Phe Ala Ala Tyr Leu Glu Pro Phe Lys Glu
                195                 200                 205

Lys Gly Glu Val Arg Arg Pro Thr Leu Ser Trp Pro Arg Glu Ile Pro
210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
                260                 265                 270

Phe Pro Asn Thr Glu Phe Val Lys Val Lys Gly Leu His Phe Ser Gln
                275                 280                 285

Glu Asp Ala Pro Asp Glu Met Gly Lys Tyr Ile Lys Ser Phe Val Glu
                290                 295                 300

Arg Val Leu Lys Asn Glu Gln
305                 310

<210> SEQ ID NO 50
<211> LENGTH: 550
<212> TYPE: PRT
<213> ORGANISM: Artificial Sequence
<220> FEATURE:
<223> OTHER INFORMATION: Fluc or FfLuc (Firefly Luc)

<400> SEQUENCE: 50

Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
                35                  40                  45

Val Asp Ile Thr Tyr Ala Glu Tyr Phe Glu Met Ser Val Arg Leu Ala
                50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
```

```
            85                  90                  95
Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
            115                 120                 125

Ser Lys Lys Gly Leu Gln Lys Ile Leu Asn Val Gln Lys Lys Leu Pro
            130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
                180                 185                 190

Ala Leu Ile Met Asn Ser Ser Gly Ser Thr Gly Leu Pro Lys Gly Val
                195                 200                 205

Ala Leu Pro His Arg Thr Ala Cys Val Arg Phe Ser His Ala Arg Asp
                210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
                275                 280                 285

Pro Thr Leu Phe Ser Phe Phe Ala Lys Ser Thr Leu Ile Asp Lys Tyr
                290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
                340                 345                 350

Pro Glu Gly Asp Asp Lys Pro Gly Ala Val Gly Lys Val Val Pro Phe
                355                 360                 365

Phe Glu Ala Lys Val Val Asp Leu Asp Thr Gly Lys Thr Leu Gly Val
                370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
                420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
                450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510
```

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
    530                 535                 540

Gly Gly Lys Ile Ala Val
545                 550

<210> SEQ ID NO 51
<211> LENGTH: 544
<212> TYPE: PRT
<213> ORGANISM: Artificial Sequence
<220> FEATURE:
<223> OTHER INFORMATION: LucPPe-146-1H2

<400> SEQUENCE: 51

Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
            20                  25                  30

Ala Ala Ile Pro Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
            85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
        115                 120                 125

Lys Asn Thr Phe Gln Lys Val Leu Asn Val Lys Ser Lys Leu Lys Ser
    130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
            165                 170                 175

Val Lys Lys Phe Lys Pro Tyr Ser Phe Asn Arg Asp Asp Gln Val Ala
            180                 185                 190

Ser Ile Met Phe Ser Ser Gly Thr Thr Gly Leu Pro Lys Gly Val Met
        195                 200                 205

Leu Thr His Lys Asn Ile Val Ala Arg Phe Ser Ile Ala Lys Asp Pro
    210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
            245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

-continued

```
Glu Ile Gly Glu Met Val Lys Arg Phe Lys Leu Asn Phe Val Arg
            325                 330                 335
Gln Gly Tyr Gly Leu Thr Glu Thr Thr Ser Ala Val Leu Ile Thr Pro
        340                 345                 350
Lys Gly Asp Ala Lys Pro Gly Ser Thr Gly Lys Ile Val Pro Leu His
        355                 360                 365
Ala Val Lys Val Val Asp Pro Thr Thr Gly Lys Ile Leu Gly Pro Asn
    370                 375                 380
Glu Pro Gly Glu Leu Tyr Phe Lys Gly Pro Met Ile Met Lys Gly Tyr
385                 390                 395                 400
Tyr Asn Asn Glu Glu Ala Thr Lys Ala Ile Ile Asp Asn Asp Gly Trp
            405                 410                 415
Leu Arg Ser Gly Asp Ile Ala Tyr Tyr Asp Asn Asp Gly His Phe Tyr
        420                 425                 430
Ile Val Asp Arg Leu Lys Ser Leu Ile Lys Tyr Lys Gly Tyr Gln Val
        435                 440                 445
Ala Pro Ala Glu Ile Glu Gly Ile Leu Leu Gln His Pro Tyr Ile Val
    450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
            485                 490                 495
Val Gln Asp Tyr Val Ala Ser Gln Val Ser Thr Ala Lys Trp Leu Arg
        500                 505                 510
Gly Gly Val Lys Phe Leu Asp Glu Ile Pro Lys Gly Ser Thr Gly Lys
        515                 520                 525
Ile Asp Arg Lys Val Leu Arg Gln Met Leu Glu Lys His Thr Asn Gly
    530                 535                 540
```

<210> SEQ ID NO 52
<211> LENGTH: 544
<212> TYPE: PRT
<213> ORGANISM: Artificial Sequence
<220> FEATURE:
<223> OTHER INFORMATION: LucPPe-133-1B2

<400> SEQUENCE: 52

```
Met Ala Asp Lys Asn Ile Leu Tyr Gly Pro Glu Pro Phe Tyr Pro Leu
1               5                   10                  15
Glu Asp Gly Thr Ala Gly Glu Gln Met Phe Asp Ala Leu Ser Arg Tyr
            20                  25                  30
Ala Asp Ile Pro Gly Cys Ile Ala Leu Thr Asn Ala His Thr Lys Glu
        35                  40                  45
Asn Val Leu Tyr Glu Glu Phe Leu Lys Leu Ser Cys Arg Leu Ala Glu
    50                  55                  60
Ser Phe Lys Lys Tyr Gly Leu Lys Gln Asn Asp Thr Ile Ala Val Cys
65                  70                  75                  80
Ser Glu Asn Ser Leu Gln Phe Phe Leu Pro Val Ile Ala Ser Leu Tyr
            85                  90                  95
Leu Gly Ile Ile Val Ala Pro Val Asn Asp Lys Tyr Ile Glu Arg Glu
        100                 105                 110
Leu Ile His Ser Leu Gly Ile Val Lys Pro Arg Ile Val Phe Cys Ser
    115                 120                 125
Lys Asn Thr Phe Gln Lys Val Leu Asn Val Lys Ser Lys Leu Lys Ser
130                 135                 140
```

```
Ile Glu Thr Ile Ile Ile Leu Asp Leu Asn Asp Asp Leu Gly Gly Tyr
145                 150                 155                 160

Gln Cys Leu Asn Asn Phe Ile Ser Gln Asn Ser Asp Ser Asn Leu Asp
            165                 170                 175

Val Lys Lys Phe Lys Pro Tyr Ser Phe Asn Arg Asp Asp Gln Val Ala
        180                 185                 190

Leu Ile Met Phe Ser Ser Gly Thr Thr Gly Leu Pro Lys Gly Val Met
    195                 200                 205

Leu Thr His Lys Asn Ile Val Ala Arg Phe Ser Ile Ala Lys Asp Pro
210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Gly Asp Ala Lys Pro Gly Ser Thr Gly Lys Ile Val Pro Phe His
        355                 360                 365

Ala Val Lys Val Val Asp Pro Thr Thr Gly Lys Ile Leu Gly Pro Asn
    370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
            500                 505                 510

Gly Gly Val Ile Phe Leu Asp Glu Ile Pro Lys Gly Ser Thr Gly Lys
        515                 520                 525

Ile Asp Arg Lys Val Leu Arg Gln Met Leu Glu Lys His Thr Asn Gly
    530                 535                 540

<210> SEQ ID NO 53
<211> LENGTH: 544
```

<212> TYPE: PRT
<213> ORGANISM: Artificial Sequence
<220> FEATURE:
<223> OTHER INFORMATION: LucPPe-78-0B10

<400> SEQUENCE: 53

```
Met Ala Asp Lys Asn Ile Leu Tyr Gly Pro Glu Pro Phe Tyr Pro Leu
1               5                   10                  15

Ala Asp Gly Thr Ala Gly Glu Gln Met Phe Asp Ala Leu Ser Arg Tyr
            20                  25                  30

Ala Asp Ile Ser Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Val Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
        115                 120                 125

Lys Asn Thr Phe Gln Lys Val Leu Asn Val Lys Ser Lys Leu Lys Ser
    130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Leu Val Met Phe Ser Ser Gly Thr Thr Gly Val Pro Lys Gly Val Met
        195                 200                 205

Leu Thr His Lys Asn Ile Val Ala Arg Phe Ser Leu Ala Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Gly Asp Ala Arg Pro Gly Ser Thr Gly Lys Ile Val Pro Phe His
        355                 360                 365

Ala Val Lys Val Val Asp Pro Thr Thr Gly Lys Ile Leu Gly Pro Asn
    370                 375                 380
```

Glu Pro Gly Glu Leu Tyr Phe Lys Gly Ala Met Ile Met Lys Gly Tyr
385                 390                 395                 400

Tyr Asn Asn Glu Glu Ala Thr Lys Ala Ile Ile Asp Asn Asp Gly Trp
            405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
            435                 440                 445

Ala Pro Ala Glu Ile Glu Gly Ile Leu Leu Gln His Pro Tyr Ile Val
            450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
            485                 490                 495

Val Gln Asp Phe Val Ser Ser Gln Val Ser Thr Ala Lys Trp Leu Arg
            500                 505                 510

Gly Gly Val Lys Phe Leu Asp Glu Ile Pro Lys Gly Ser Thr Gly Lys
            515                 520                 525

Ile Asp Arg Lys Val Leu Arg Gln Met Phe Glu Lys His Thr Asn Gly
530                 535                 540

<210> SEQ ID NO 54
<211> LENGTH: 544
<212> TYPE: PRT
<213> ORGANISM: Artificial Sequence
<220> FEATURE:
<223> OTHER INFORMATION: LucPPe49-7C6A

<400> SEQUENCE: 54

Met Ala Asp Lys Asn Ile Leu Tyr Gly Pro Glu Pro Phe Tyr Pro Leu
1               5                   10                  15

Ala Asp Gly Thr Ala Gly Glu Gln Met Phe Tyr Ala Leu Ser Arg Tyr
            20                  25                  30

Ala Asp Ile Ser Gly Cys Ile Ala Leu Thr Asn Ala His Thr Lys Glu
            35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65              70                  75                  80

Ser Glu Asn Gly Leu Gln Phe Phe Leu Pro Ile Ile Ala Ser Leu Tyr
            85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
            115                 120                 125

Lys Asn Thr Phe Gln Lys Val Leu Asn Val Lys Ser Lys Leu Lys Tyr
130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
            165                 170                 175

Val Lys Lys Phe Lys Pro Tyr Ser Phe Asn Arg Asp Asp Gln Val Ala
            180                 185                 190

Leu Val Met Phe Ser Ser Gly Thr Thr Gly Val Ser Lys Gly Val Met
            195                 200                 205

Leu Thr His Lys Asn Ile Val Ala Arg Phe Ser Leu Ala Lys Asp Pro
        210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Asn Asn Asp Val Arg Pro Gly Ser Thr Gly Lys Ile Val Pro Phe His
        355                 360                 365

Ala Val Lys Val Val Asp Pro Thr Thr Gly Lys Ile Leu Gly Pro Asn
370                 375                 380

Glu Pro Gly Glu Leu Tyr Phe Lys Gly Asp Met Ile Met Lys Gly Tyr
385                 390                 395                 400

Tyr Asn Asn Glu Glu Ala Thr Lys Ala Ile Ile Asn Lys Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asn Phe Val Ser Ser Gln Val Ser Thr Ala Lys Trp Leu Arg
            500                 505                 510

Gly Gly Val Lys Phe Leu Asp Glu Ile Pro Lys Gly Ser Thr Gly Lys
        515                 520                 525

Ile Asp Arg Lys Val Leu Arg Gln Met Phe Glu Lys His Thr Asn Gly
530                 535                 540

<210> SEQ ID NO 55
<211> LENGTH: 542
<212> TYPE: PRT
<213> ORGANISM: Artificial Sequence
<220> FEATURE:
<223> OTHER INFORMATION: LucPpL-81-6G1

<400> SEQUENCE: 55

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

-continued

```
Lys His Ser His Leu Pro Gln Ala Leu Val Asp Val Gly Asp Glu
         35                  40                  45
Ser Leu Ser Tyr Lys Glu Phe Glu Ala Thr Val Leu Leu Ala Gln
 50                  55                  60
Ser Leu His Asn Cys Gly Tyr Lys Met Asn Asp Val Val Ser Ile Cys
 65                  70                  75                  80
Ala Glu Asn Asn Thr Arg Phe Phe Ile Pro Val Ile Ala Ala Trp Tyr
                 85                  90                  95
Ile Gly Met Ile Val Ala Pro Val Asn Glu Ser Tyr Ile Pro Asp Glu
             100                 105                 110
Leu Cys Lys Val Met Gly Ile Ser Lys Pro Gln Ile Val Phe Thr Thr
             115                 120                 125
Lys Asn Ile Leu Asn Lys Val Leu Glu Val Gln Ser Arg Thr Asn Phe
130                 135                 140
Ile Lys Arg Ile Ile Ile Leu Asp Thr Val Glu Asn Ile His Gly Cys
145                 150                 155                 160
Glu Ser Leu Pro Asn Gly Ile Ser Arg Tyr Ser Asp Gly Asn Ile Ala
                 165                 170                 175
Asn Phe Lys Pro Leu His Phe Asp Pro Val Glu Gln Val Ala Ala Ile
             180                 185                 190
Leu Cys Ser Ser Gly Thr Thr Gly Leu Pro Lys Gly Val Met Gln Thr
             195                 200                 205
His Gln Asn Ile Cys Val Arg Leu Ile His Ala Leu Asp Pro Arg Ala
             210                 215                 220
Gly Thr Gln Leu Ile Pro Gly Val Thr Val Leu Val Tyr Leu Pro Phe
225                 230                 235                 240
Phe His Ala Phe Gly Phe Ser Ile Thr Leu Gly Tyr Phe Met Val Gly
                 245                 250                 255
Leu Arg Val Ile Met Phe Arg Arg Phe Asp Gln Glu Ala Phe Leu Lys
             260                 265                 270
Ala Ile Gln Asp Tyr Glu Val Arg Ser Val Ile Asn Val Pro Ser Val
             275                 280                 285
Ile Leu Phe Leu Ser Lys Ser Pro Leu Val Asp Lys Tyr Asp Leu Ser
             290                 295                 300
Ser Leu Arg Glu Leu Cys Cys Gly Ala Ala Pro Leu Ala Lys Glu Val
305                 310                 315                 320
Ala Glu Val Ala Ala Lys Arg Leu Asn Leu Pro Gly Ile Arg Cys Gly
                 325                 330                 335
Phe Gly Leu Thr Glu Ser Thr Ser Ala Asn Ile His Ser Leu Arg Asp
             340                 345                 350
Glu Phe Lys Ser Gly Ser Leu Gly Arg Val Thr Pro Leu Met Ala Ala
             355                 360                 365
Lys Ile Ala Asp Arg Glu Thr Gly Lys Ala Leu Gly Pro Asn Gln Val
             370                 375                 380
Gly Glu Leu Cys Ile Lys Gly Pro Met Val Ser Lys Gly Tyr Val Asn
385                 390                 395                 400
Asn Val Glu Ala Thr Lys Glu Ala Ile Asp Asp Gly Trp Leu His
                 405                 410                 415
Ser Gly Asp Phe Gly Tyr Tyr Asp Glu Asp Glu His Phe Tyr Val Val
             420                 425                 430
Asp Arg Tyr Lys Glu Leu Ile Lys Tyr Lys Gly Ser Gln Val Ala Pro
             435                 440                 445
Ala Glu Leu Glu Glu Ile Leu Leu Lys Asn Pro Cys Ile Arg Asp Val
```

-continued

```
                450                 455                 460
Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
                500                 505                 510

Val Arg Phe Val Asp Ser Ile Pro Arg Asn Val Thr Gly Lys Ile Thr
                515                 520                 525

Arg Lys Glu Leu Leu Lys Gln Leu Leu Glu Lys Ala Gly Gly
                530                 535                 540

<210> SEQ ID NO 56
<211> LENGTH: 542
<212> TYPE: PRT
<213> ORGANISM: Artificial Sequence
<220> FEATURE:
<223> OTHER INFORMATION: CBGRluc

<400> SEQUENCE: 56

Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
                20                  25                  30

Lys His Ser His Leu Pro Gln Ala Leu Val Asp Val Val Gly Asp Glu
                35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
                100                 105                 110

Leu Cys Lys Val Met Gly Ile Ser Lys Pro Gln Ile Val Phe Thr Thr
                115                 120                 125

Lys Asn Ile Leu Asn Lys Val Leu Glu Val Gln Ser Arg Thr Asn Phe
130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
                180                 185                 190

Leu Cys Ser Ser Gly Thr Thr Gly Leu Pro Lys Gly Val Met Gln Thr
                195                 200                 205

His Gln Asn Ile Cys Val Arg Leu Ile His Ala Leu Asp Pro Arg Tyr
                210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
                260                 265                 270

Ala Ile Gln Asp Tyr Glu Val Arg Ser Val Ile Asn Val Pro Ser Val
```

```
                275                 280                 285
Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Thr Leu Gly Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Thr Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Val Lys Ala Gly Gly
    530                 535                 540

<210> SEQ ID NO 57
<211> LENGTH: 490
<212> TYPE: PRT
<213> ORGANISM: Artificial Sequence
<220> FEATURE:
<223> OTHER INFORMATION: Embryonic Alkaline Phosphatase (EAP)

<400> SEQUENCE: 57

Met Ile Ile Pro Val Glu Glu Glu Asn Pro Asp Phe Trp Asn Arg Glu
1               5                   10                  15

Ala Ala Glu Ala Leu Gly Ala Ala Lys Lys Leu Gln Pro Ala Gln Thr
                20                  25                  30

Ala Ala Lys Asn Leu Ile Ile Phe Leu Gly Asp Gly Met Gly Val Ser
            35                  40                  45

Thr Val Thr Ala Ala Arg Ile Leu Lys Gly Gln Lys Lys Asp Lys Leu
        50                  55                  60

Gly Pro Glu Ile Pro Leu Ala Met Asp Arg Phe Pro Tyr Val Ala Leu
65                  70                  75                  80

Ser Lys Thr Tyr Asn Val Asp Lys His Val Pro Asp Ser Gly Ala Thr
                85                  90                  95

Ala Thr Ala Tyr Leu Cys Gly Val Lys Gly Asn Phe Gln Thr Ile Gly
```

```
            100                 105                 110
Leu Ser Ala Ala Ala Arg Phe Asn Gln Cys Asn Thr Thr Arg Gly Asn
        115                 120                 125

Glu Val Ile Ser Val Met Asn Arg Ala Lys Lys Ala Gly Lys Ser Val
    130                 135                 140

Gly Val Val Thr Thr Thr Arg Val Gln His Ala Ser Pro Ala Gly Thr
145                 150                 155                 160

Tyr Ala His Thr Val Asn Arg Asn Trp Tyr Ser Asp Ala Asp Val Pro
                165                 170                 175

Ala Ser Ala Arg Gln Glu Gly Cys Gln Asp Ile Ala Thr Gln Leu Ile
            180                 185                 190

Ser Asn Met Asp Ile Asp Val Ile Leu Gly Gly Arg Lys Tyr Met
        195                 200                 205

Phe Arg Met Gly Thr Pro Asp Pro Glu Tyr Pro Asp Asp Tyr Ser Gln
    210                 215                 220

Gly Gly Thr Arg Leu Asp Gly Lys Asn Leu Val Gln Glu Trp Leu Ala
225                 230                 235                 240

Lys Arg Gln Gly Ala Arg Tyr Val Trp Asn Arg Thr Glu Leu Met Gln
                245                 250                 255

Ala Ser Leu Asp Pro Ser Val Thr His Leu Met Gly Leu Phe Glu Pro
            260                 265                 270

Gly Asp Met Lys Tyr Glu Ile His Arg Asp Ser Thr Leu Asp Pro Ser
        275                 280                 285

Leu Met Glu Met Thr Glu Ala Ala Leu Arg Leu Leu Ser Arg Asn Pro
    290                 295                 300

Arg Gly Phe Phe Leu Phe Val Glu Gly Gly Arg Ile Asp His Gly His
305                 310                 315                 320

His Glu Ser Arg Ala Tyr Arg Ala Leu Thr Glu Thr Ile Met Phe Asp
                325                 330                 335

Asp Ala Ile Glu Arg Ala Gly Gln Leu Thr Ser Glu Glu Asp Thr Leu
            340                 345                 350

Ser Leu Val Thr Ala Asp His Ser His Val Phe Ser Phe Gly Gly Tyr
        355                 360                 365

Pro Leu Arg Gly Ser Ser Ile Phe Gly Leu Ala Pro Gly Lys Ala Arg
    370                 375                 380

Asp Arg Lys Ala Tyr Thr Val Leu Leu Tyr Gly Asn Gly Pro Gly Tyr
385                 390                 395                 400

Val Leu Lys Asp Gly Ala Arg Pro Asp Val Thr Glu Ser Glu Ser Gly
                405                 410                 415

Ser Pro Glu Tyr Arg Gln Gln Ser Ala Val Pro Leu Asp Glu Glu Thr
            420                 425                 430

His Ala Gly Glu Asp Val Ala Val Phe Ala Arg Gly Pro Gln Ala His
        435                 440                 445

Leu Val His Gly Val Gln Glu Gln Thr Phe Ile Ala His Val Met Ala
    450                 455                 460

Phe Ala Ala Cys Leu Glu Pro Tyr Thr Ala Cys Asp Leu Ala Pro Pro
465                 470                 475                 480

Ala Gly Thr Thr Asp Ala Ala His Pro Gly
                485                 490

<210> SEQ ID NO 58
<211> LENGTH: 236
<212> TYPE: PRT
<213> ORGANISM: Artificial Sequence
```

<220> FEATURE:
<223> OTHER INFORMATION: mCherry

<400> SEQUENCE: 58

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys
225                 230                 235

<210> SEQ ID NO 59
<211> LENGTH: 239
<212> TYPE: PRT
<213> ORGANISM: Artificial Sequence
<220> FEATURE:
<223> OTHER INFORMATION: EGFP (Enhanced Green Fluorescent Protein)

<400> SEQUENCE: 59

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu

```
              100                 105                 110
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 60
<211> LENGTH: 174
<212> TYPE: PRT
<213> ORGANISM: Artificial Sequence
<220> FEATURE:
<223> OTHER INFORMATION: MYR-GGS-GLuc (M60L/M127L variant)

<400> SEQUENCE: 60

```
Met Gly Ser Ser Lys Ser Lys Pro Lys Asp Pro Ser Gln Arg Arg Arg
1               5                   10                  15

Gly Gly Ser Gly Asp Pro Lys Pro Thr Glu Asn Asn Glu Asp Ala Asp
            20                  25                  30

Arg Gly Lys Leu Pro Gly Lys Lys Leu Pro Leu Glu Val Leu Lys Glu
        35                  40                  45

Leu Glu Ala Asn Ala Arg Lys Ala Gly Cys Thr Arg Gly Cys Leu Ile
    50                  55                  60

Cys Leu Ser His Ile Lys Cys Thr Pro Lys Met Lys Lys Phe Ile Pro
65                  70                  75                  80

Gly Arg Cys His Thr Tyr Glu Gly Asp Lys Glu Ser Ala Gln Gly Gly
                85                  90                  95

Ile Gly Glu Ala Ile Val Asp Ile Pro Glu Ile Pro Gly Phe Lys Asp
            100                 105                 110

Leu Glu Pro Leu Glu Gln Phe Ile Ala Gln Val Asp Leu Cys Val Asp
        115                 120                 125

Cys Thr Thr Gly Cys Leu Lys Gly Leu Ala Asn Val Gln Cys Ser Asp
    130                 135                 140

Leu Leu Lys Lys Trp Leu Pro Gln Arg Cys Ala Thr Phe Ala Ser Lys
145                 150                 155                 160

Ile Gln Gly Gln Val Asp Lys Ile Lys Gly Ala Gly Gly Asp
                165                 170
```

<210> SEQ ID NO 61
<211> LENGTH: 25
<212> TYPE: DNA
<213> ORGANISM: Artificial Sequence
<220> FEATURE:
<223> OTHER INFORMATION: FLAG-TAG

<400> SEQUENCE: 61

```
gattataaag atgatgacga taaag                                           25
```

<210> SEQ ID NO 62
<211> LENGTH: 90
<212> TYPE: DNA
<213> ORGANISM: Artificial Sequence
<220> FEATURE:
<223> OTHER INFORMATION: 3xFLAG
<400> SEQUENCE: 62

```
gactacaagg acgacgatga caaggattat aaagatgatg acgataaagt cgagaccgat    60
ttctacgact acaaggacga cgatgacaag                                     90
```

<210> SEQ ID NO 63
<211> LENGTH: 27
<212> TYPE: DNA
<213> ORGANISM: Artificial Sequence
<220> FEATURE:
<223> OTHER INFORMATION: HA-TAG
<400> SEQUENCE: 63

```
taccccctacg atgtgcccga ttacgct                                        27
```

<210> SEQ ID NO 64
<211> LENGTH: 27
<212> TYPE: DNA
<213> ORGANISM: Artificial Sequence
<220> FEATURE:
<223> OTHER INFORMATION: AcV5-TAG
<400> SEQUENCE: 64

```
agttggaagg atgcctctgg atggtct                                         27
```

<210> SEQ ID NO 65
<211> LENGTH: 30
<212> TYPE: DNA
<213> ORGANISM: Artificial Sequence
<220> FEATURE:
<223> OTHER INFORMATION: MYC-TAG
<400> SEQUENCE: 65

```
gagcagaaac tgatctcgga agaggatctg                                      30
```

<210> SEQ ID NO 66
<211> LENGTH: 54
<212> TYPE: DNA
<213> ORGANISM: Artificial Sequence
<220> FEATURE:
<223> OTHER INFORMATION: T2A
<400> SEQUENCE: 66

```
gagggcagag gaagtctact aacctgcgga gatgtggaag aaaatcctgg ccca           54
```

<210> SEQ ID NO 67
<211> LENGTH: 57
<212> TYPE: DNA
<213> ORGANISM: Artificial Sequence
<220> FEATURE:
<223> OTHER INFORMATION: P2A
<400> SEQUENCE: 67

```
gcaacaaact tctcactact caaacaagca ggtgacgtgg aggagaatcc cgggcct        57
```

<210> SEQ ID NO 68
<211> LENGTH: 57

<212> TYPE: DNA
<213> ORGANISM: Artificial Sequence
<220> FEATURE:
<223> OTHER INFORMATION: P2A-variant

<400> SEQUENCE: 68
gcaacaaact tctcactact caaacaagca ggtgacgtgg agcagaatcc cgggcct       57

<210> SEQ ID NO 69
<211> LENGTH: 60
<212> TYPE: DNA
<213> ORGANISM: Artificial Sequence
<220> FEATURE:
<223> OTHER INFORMATION: E2A

<400> SEQUENCE: 69
caatgcacta attacgcatt gctcaagctg gccggtgacg ttgagagtaa tcctggcccc    60

<210> SEQ ID NO 70
<211> LENGTH: 8
<212> TYPE: PRT
<213> ORGANISM: Artificial Sequence
<220> FEATURE:
<223> OTHER INFORMATION: FLAG-TAG

<400> SEQUENCE: 70

Asp Tyr Lys Asp Asp Asp Asp Lys
1               5

<210> SEQ ID NO 71
<211> LENGTH: 30
<212> TYPE: PRT
<213> ORGANISM: Artificial Sequence
<220> FEATURE:
<223> OTHER INFORMATION: 3xFLAG

<400> SEQUENCE: 71

Asp Tyr Lys Asp Asp Asp Asp Lys Asp Tyr Lys Asp Asp Asp Asp Lys
1               5                   10                  15

Val Glu Thr Asp Phe Tyr Asp Tyr Lys Asp Asp Asp Asp Lys
            20                  25                  30

<210> SEQ ID NO 72
<211> LENGTH: 9
<212> TYPE: PRT
<213> ORGANISM: Artificial Sequence
<220> FEATURE:
<223> OTHER INFORMATION: HA-TAG

<400> SEQUENCE: 72

Tyr Pro Tyr Asp Val Pro Asp Tyr Ala
1               5

<210> SEQ ID NO 73
<211> LENGTH: 9
<212> TYPE: PRT
<213> ORGANISM: Artificial Sequence
<220> FEATURE:
<223> OTHER INFORMATION: AcV5-TAG

<400> SEQUENCE: 73

Ser Trp Lys Asp Ala Ser Gly Trp Ser
1               5

<210> SEQ ID NO 74
<211> LENGTH: 10

```
<212> TYPE: PRT
<213> ORGANISM: Artificial Sequence
<220> FEATURE:
<223> OTHER INFORMATION: MYC-TAG

<400> SEQUENCE: 74

Glu Gln Lys Leu Ile Ser Glu Glu Asp Leu
1               5                   10

<210> SEQ ID NO 75
<211> LENGTH: 18
<212> TYPE: PRT
<213> ORGANISM: Artificial Sequence
<220> FEATURE:
<223> OTHER INFORMATION: T2A

<400> SEQUENCE: 75

Glu Gly Arg Gly Ser Leu Leu Thr Cys Gly Asp Val Glu Glu Asn Pro
1               5                   10                  15

Gly Pro

<210> SEQ ID NO 76
<211> LENGTH: 19
<212> TYPE: PRT
<213> ORGANISM: Artificial Sequence
<220> FEATURE:
<223> OTHER INFORMATION: P2A

<400> SEQUENCE: 76

Ala Thr Asn Phe Ser Leu Leu Lys Gln Ala Gly Asp Val Glu Glu Asn
1               5                   10                  15

Pro Gly Pro

<210> SEQ ID NO 77
<211> LENGTH: 19
<212> TYPE: PRT
<213> ORGANISM: Artificial Sequence
<220> FEATURE:
<223> OTHER INFORMATION: P2A-variant

<400> SEQUENCE: 77

Ala Thr Asn Phe Ser Leu Leu Lys Gln Ala Gly Asp Val Glu Gln Asn
1               5                   10                  15

Pro Gly Pro

<210> SEQ ID NO 78
<211> LENGTH: 20
<212> TYPE: PRT
<213> ORGANISM: Artificial Sequence
<220> FEATURE:
<223> OTHER INFORMATION: E2A

<400> SEQUENCE: 78

Gln Cys Thr Asn Tyr Ala Leu Leu Lys Leu Ala Gly Asp Val Glu Ser
1               5                   10                  15

Asn Pro Gly Pro
            20

<210> SEQ ID NO 79
<211> LENGTH: 2292
<212> TYPE: DNA
<213> ORGANISM: Artificial Sequence
<220> FEATURE:
<223> OTHER INFORMATION: FMC63-MYC-BBZ-T2A-EGFP CAR
```

<400> SEQUENCE: 79

```
atggccttac cagtgaccgc cttgctcctg ccgctggcct tgctgctcca cgccgccagg     60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa cagggtaata cgcttccgta cacgttcgga    360
ggggggacca agctggagat cacaggtggc ggtggctcgg cggtggtgg gtcgggtggc    420
ggcggatctg aggtgaaact gcaggagtca ggacctggcc tggtggcgcc ctcacagagc    480
ctgtccgtca catgcactgt ctcagggtc tcattacccg actatggtgt aagctggatt    540
cgccagcctc cacgaaaggg tctggagtgg ctggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gtcaaggaac ctcagtcacc    780
gtctcctcac gcgtagagca gaaactgatc tcggaagagg atctggcgaa gcccaccacg    840
acgccagcgc cgcgaccacc aacaccggcg cccaccatcg cgtcgcagcc cctgtccctg    900
cgcccagagg cgtgccggcc agcggcgggg ggcgcagtgc acacgagggg gctggacttc    960
gcctgtgaca tctacatctg ggcgcccttg gccgggactt gtggggtcct tctcctgtca   1020
ctggttatca ccctttactg caaacggggc agaaagaaac tcctgtatat attcaaacaa   1080
ccatttatga gaccagtaca aactactcaa gaggaagatg gctgtagctg ccgatttcca   1140
gaagaagaag aaggaggatg tgaactgaga gtgaagttca gcaggagcgc agacgccccc   1200
gcgtaccagc agggccagaa ccagctctat aacgagctga atctaggacg aagagaggag   1260
tacgatgttt tggacaagag acgtggccgg gaccctgaga tggggggaaa gccgagaagg   1320
aagaaccctc aggaaggcct gtacaatgaa ctgcagaaag ataagatggc ggaggcctac   1380
agtgagattg ggatgaaagg cgagcgccgg aggggcaagg ggcacgatgg cctttaccag   1440
ggtctcagta cagccaccaa ggacacctac gacgcccttc acatgcaggc cctgccccct   1500
cgctctagtg gctccggcga gggcagagga agtctactaa cctgcggaga tgtggaagaa   1560
aatcctggcc caatggtgag caagggcgag gagctgttca ccggggtggt gcccatcctg   1620
gtcgagctgg acggcgacgt aaacggccac aagttcagcg tgtccggcga gggcgagggc   1680
gatgccacct acggcaagct gaccctgaag ttcatctgca ccaccggcaa gctgcccgtg   1740
ccctggccca cccttgtgac cacccctgacc tacggcgtgc agtgcttcag ccgctacccc   1800
gaccacatga agcagcacga cttcttcaag tccgccatgc ccgaaggcta cgtccaggag   1860
cgcaccatct tcttcaagga cgacggcaac tacaagaccc gcgccgaggt gaagttcgag   1920
ggcgacaccc tggtgaaccg catcgagctg aagggcatcg acttcaagga ggacggcaac   1980
atcctggggc acaagctgga gtacaactac aacagccaca acgtctatat catggccgac   2040
aagcagaaga acggcatcaa ggtgaacttc aagatccgcc acaacatcga ggacggcagc   2100
gtgcagctcg ccgaccacta ccagcagaac ccccatcg gcgacggccc cgtgctgctg   2160
cccgacaacc actacctgag cacccagtcc gccctgagca agacccccaa cgagaagcgc   2220
gatcacatgg tcctgctgga gttcgtgacc gccgccggga tcactctcgg catggacgag   2280
ctgtacaagt aa                                                       2292
```

<210> SEQ ID NO 80
<211> LENGTH: 2175
<212> TYPE: DNA
<213> ORGANISM: Artificial Sequence
<220> FEATURE:
<223> OTHER INFORMATION: FMC63-Myc-BBz-T2A-PAC CAR

<400> SEQUENCE: 80

| | | | | |
|---|---|---|---|---|
| atggccttac cagtgaccgc cttgctcctg ccgctggcct tgctgctcca cgccgccagg | 60 |
| ccggacatcc agatgacaca gactacatcc tccctgtctg cctctctggg agacagagtc | 120 |
| accatcagtt gcagggcaag tcaggacatt agtaaatatt taaattggta tcagcagaaa | 180 |
| ccagatggaa ctgttaaact cctgatctac catacatcaa gattacactc aggagtccca | 240 |
| tcaaggttca gtggcagtgg gtctggaaca gattattctc tcaccattag caacctggag | 300 |
| caagaagata ttgccactta cttttgccaa cagggtaata cgcttccgta cacgttcgga | 360 |
| ggggggacca agctggagat cacaggtggc ggtggctcgg gcggtggtgg gtcgggtggc | 420 |
| ggcggatctg aggtgaaact gcaggagtca ggacctggcc tggtggcgcc ctcacagagc | 480 |
| ctgtccgtca catgcactgt ctcagggttc tcattacccg actatggtgt aagctggatt | 540 |
| cgccagcctc cacgaaaggg tctggagtgg ctgggagtaa tatggggtag tgaaaccaca | 600 |
| tactataatt cagctctcaa atccagactg accatcatca aggacaactc caagagccaa | 660 |
| gttttcttaa aaatgaacag tctgcaaact gatgacacag ccatttacta ctgtgccaaa | 720 |
| cattattact acggtggtag ctatgctatg gactactggg gtcaaggaac ctcagtcacc | 780 |
| gtctcctcac gcgtagagca gaaactgatc tcggaagagg atctggcgaa gcccaccacg | 840 |
| acgccagcgc cgcgaccacc aacaccggcg cccaccatcg cgtcgcagcc cctgtccctg | 900 |
| cgcccagagg cgtgccggcc agcggcgggg ggcgcagtgc acacgagggg gctggacttc | 960 |
| gcctgtgaca tctacatctg ggcgcccttg gccgggactt gtggggtcct tctcctgtca | 1020 |
| ctggttatca ccctttactg caaacggggc agaaagaaac tcctgtatat attcaaacaa | 1080 |
| ccatttatga gaccagtaca aactactcaa gaggaagatg gctgtagctg ccgatttcca | 1140 |
| gaagaagaag aaggaggatg tgaactgaga gtgaagttca gcaggagcgc agacgccccc | 1200 |
| gcgtaccagc agggccagaa ccagctctat aacgagctga atctaggacg aagagaggag | 1260 |
| tacgatgttt tggacaagag acgtggccgg gaccctgaga tggggggaaa gccgagaagg | 1320 |
| aagaaccctc aggaaggcct gtacaatgaa ctgcagaaag ataagatggc ggaggcctac | 1380 |
| agtgagattg ggatgaaagg cgagcgccgg aggggcaagg ggcacgatgg cctttaccag | 1440 |
| ggtctcagta cagccaccaa ggacacctac gacgcccttc acatgcaggc cctgccccct | 1500 |
| cgctctagtg gctccggcga gggcagagga agtctactaa cctgcggaga tgtggaagaa | 1560 |
| aatcctggcc cacatatgac cgagtacaag cccacggtgc gcctcgccac ccgcgacgac | 1620 |
| gtccccaggg ccgtacgcac cctcgccgcc gcgttcgccg actacccgc cacgcgccac | 1680 |
| accgtcgatc cggaccgcca catcgagcgg gtcaccgagc tgcaagaact cttcctcacg | 1740 |
| cgcgtcgggc tcgacatcgg caaggtgtgg gtcgcggacg acggcgccgc ggtggcggtc | 1800 |
| tggaccacgc cggagagcgt cgaagcgggg gcggtgttcg ccgagatcgg cccgcgcatg | 1860 |
| gccgagttga gcggttcccg gctggccgcg cagcaacaga tggaaggcct cctggcgccg | 1920 |
| caccggccca aggagcccgc gtggttcctg gccaccgtcg gcgtctcgcc cgaccaccag | 1980 |
| ggcaagggtc tgggcagcgc cgtcgtgctc cccggagtgg aggcggccga gcgcgccggg | 2040 |

| | |
|---|---|
| gtgcccgcct tcctggagac ctccgcgccc cgcaacctcc ccttctacga gcggctcggc | 2100 |
| ttcaccgtca ccgccgacgt cgaggtgccc gaaggaccgc gcacctggtg catgacccgc | 2160 |
| aagcccggtg cctga | 2175 |

<210> SEQ ID NO 81
<211> LENGTH: 2157
<212> TYPE: DNA
<213> ORGANISM: Artificial Sequence
<220> FEATURE:
<223> OTHER INFORMATION: FMC63-Myc-28z-T2A-PAC CAR

<400> SEQUENCE: 81

| | |
|---|---|
| atggccttac cagtgaccgc cttgctcctg ccgctggcct tgctgctcca cgccgccagg | 60 |
| ccggacatcc agatgacaca gactacatcc tccctgtctg cctctctggg agacagagtc | 120 |
| accatcagtt gcagggcaag tcaggacatt agtaaatatt taaattggta tcagcagaaa | 180 |
| ccagatggaa ctgttaaact cctgatctac catacatcaa gattacactc aggagtccca | 240 |
| tcaaggttca gtggcagtgg gtctggaaca gattattctc tcaccattag caacctggag | 300 |
| caagaagata ttgccactta cttttgccaa cagggtaata cgcttccgta cacgttcgga | 360 |
| ggggggacca agctggagat cacaggtggc ggtggctcgg gcggtggtgg gtcgggtggc | 420 |
| ggcggatctg aggtgaaact gcaggagtca ggacctggcc tggtggcgcc ctcacagagc | 480 |
| ctgtccgtca catgcactgt ctcaggggtc tcattacccg actatggtgt aagctggatt | 540 |
| cgccagcctc cacgaaaggg tctggagtgg ctgggagtaa tatggggtag tgaaaccaca | 600 |
| tactataatt cagctctcaa atccagactg accatcatca aggacaactc caagagccaa | 660 |
| gttttcttaa aaatgaacag tctgcaaact gatgacacag ccatttacta ctgtgccaaa | 720 |
| cattattact acggtggtag ctatgctatg gactactggg gtcaaggaac ctcagtcacc | 780 |
| gtctcctcac gcgtagagca gaaactgatc tcggaagagg atctgaaaat tgaagttatg | 840 |
| tatcctcctc cttacctaga caatgagaag agcaatggaa ccattatcca tgtgaaaggg | 900 |
| aaacacctt gtccaagtcc cctatttccc ggaccttcta agcccttttg ggtgctggtg | 960 |
| gtggttgggg gagtcctggc ttgctatagc ttgctagtaa cagtggcctt tattattttc | 1020 |
| tgggtgagga gtaagaggag caggctcctg cacagtgact acatgaacat gactccacgc | 1080 |
| cgccccggac ccaccgcaa gcattaccag ccctatgccc caccgcga cttcgcagcc | 1140 |
| tatcgctcca gagtgaagtt cagcaggagc gcagacgccc ccgcgtacca gcagggccag | 1200 |
| aaccagctct ataacgagct caatctagga cgaagagagg agtacgatgt tttggacaag | 1260 |
| agacgtggcc gggaccctga tggggggga aagccgagaa ggaagaaccc tcaggaaggc | 1320 |
| ctgtacaatg aactgcagaa agataagatg gcggaggcct acagtgagat tgggatgaaa | 1380 |
| ggcgagcgcc ggaggggcaa ggggcacgat ggcctttacc agggtctcag tacagccacc | 1440 |
| aaggacacct acgacgccct tcacatgcag gccctgcccc ctcgctctag tggctccggc | 1500 |
| gagggcagag gaagtctact aacctgcgga gatgtgaag aaaatcctgg cccacatatg | 1560 |
| accgagtaca agcccacggt gcgcctcgcc accgcgacg acgtccccag ggccgtacgc | 1620 |
| accctcgccg ccgcgttcgc cgactacccc gccacgcgcc acaccgtcga tccggaccgc | 1680 |
| cacatcgagc gggtcaccga gctgcaagaa ctcttcctca cgcgcgtcgg gctcgacatc | 1740 |
| ggcaaggtgt gggtcgcgga cgacggcgcc gcggtggcgg tctggaccac gccggagagc | 1800 |
| gtcgaagcgg ggcggtgtt cgccgagatc ggcccgcgca tggccgagtt gagcggttcc | 1860 |
| cggctggccg cgcagcaaca gatggaaggc ctcctggcgc gcaccggcc caaggagccc | 1920 |

-continued

```
gcgtggttcc tggccaccgt cggcgtctcg cccgaccacc agggcaaggg tctgggcagc    1980
gccgtcgtgc tccccggagt ggaggcggcc gagcgcgccg gggtgccccgc cttcctggag   2040
acctccgcgc cccgcaacct ccccttctac gagcggctcg gcttcaccgt caccgccgac   2100
gtcgaggtgc ccgaaggacc gcgcacctgg tgcatgaccc gcaagcccgg tgcctga      2157
```

<210> SEQ ID NO 82
<211> LENGTH: 2199
<212> TYPE: DNA
<213> ORGANISM: Artificial Sequence
<220> FEATURE:
<223> OTHER INFORMATION: CD8SP-2-CD19MM-(vL-vH)-Myc-BBz-T2A-PAC CAR

<400> SEQUENCE: 82

```
atggccctgc ctgtgacagc tctgctgctg cctctggcac tgctgctgca cgccgccaga     60
cctgacatcc agctgacaca gagccctgcc agcctggccg tgtctctggg acagagagcc    120
accatcagct gcaaggccag ccagagcgtg gactacgacg cgacagcta cctgaactgg    180
tatcagcaga tccccggcca gccccccaag ctgctgatct acgatgccag caacctggtg    240
tccggcatcc cccctagatt ttccggcagc ggctccggca ccgacttcac cctgaatatc    300
cacccccgtgg aaaaggtgga cgccgccacc taccactgcc agcagagcac cgaagatccc    360
tggaccttg gcggaggcac caagctggaa atcaagggag cggaggaag tggcggcgga    420
ggatctgggg gaggcggaag ccaggtacag ctccaacagt caggggccga gctggtacgc    480
ccagggtcca gcgtcaaaat atcatgtaag gcatctggct acgccttcag ctcttactgg    540
atgaattggg tgaaacaacg gccaggccag ggactggagt ggattggtca aatttggcca    600
ggagacgggg acacaaatta caacggaaaa ttcaagggaa aggccacact taccgccgat    660
gaaagtagtt caaccgctta tatgcagctg tcctccctcg cttctgagga ctctgctgtg    720
tactttttgcg cacgccgaga aaccaccact gtgggaagat actactacgc tatggattat    780
tggggacagg gcacaaccgt gaccgttagc agtacgcgtg agcagaaact gatctcggaa    840
gaggatctgg cgaagcccac cacgacgcca gcgccgcgac caccaacacc ggcgcccacc    900
atcgcgtcgc agcccctgtc cctgcgccca gaggcgtgcc ggccagcggc ggggggcgca    960
gtgcacacga gggggctgga cttcgcctgt gacatctaca tctgggcgcc cttggccggg   1020
acttgtgggg tccttctcct gtcactggtt atcaccctt actgcaaacg gggcagaaag   1080
aaactcctgt atatattcaa acaaccattt atgagaccag tacaaactac tcaagaggaa   1140
gatggctgta gctgccgatt tccagaagaa gaagaaggag gatgtgaact gagagtgaag   1200
ttcagcagga gcgcagacgc ccccgcgtac cagcagggcc agaaccagct ctataacgag   1260
ctgaatctag gacgaagaga ggagtacgat gttttggaca gagacgtgg ccgggaccct   1320
gagatggggg gaaagccgag aaggaagaac cctcaggaag gcctgtacaa tgaactgcag   1380
aaagataaga tggcgaggc ctacagtgag attgggatga aggcgagcg ccggaggggc   1440
aagggcacg atggcttta ccagggtctc agtacagcca ccaaggacac ctacgacgcc   1500
cttcacatgc aggcctgcc cctcgctct agtggctccg gcgagggcag aggaagtcta   1560
ctaacctgcg gagatgtgga agaaaatcct ggccccacata tgaccgagta caagccacg   1620
gtgcgcctcg ccacccgcga cgacgtcccc agggccgtac gcaccctcgc cgccgcgttc   1680
gccgactacc ccgccacgcg ccacaccgtc gatccggacc gccacatcga gcgggtcacc   1740
gagctgcaag aactcttcct cacgcgcgtc gggctcgaca tcggcaaggt gtgggtcgcg   1800
```

```
gacgacggcg ccgcggtggc ggtctggacc acgccggaga gcgtcgaagc gggggcggtg   1860
ttcgccgaga tcggcccgcg catggccgag ttgagcggtt cccggctggc cgcgcagcaa   1920
cagatggaag gcctcctggc gccgcaccgg cccaaggagc ccgcgtggtt cctggccacc   1980
gtcggcgtct cgcccgacca ccagggcaag ggtctgggca gcgccgtcgt gctccccgga   2040
gtggaggcgg ccgagcgcgc cggggtgccc gccttcctgg agacctccgc gccccgcaac   2100
ctccccttct acgagcggct cggcttcacc gtcaccgccg acgtcgaggt gcccgaagga   2160
ccgcgcacct ggtgcatgac ccgcaagccc ggtgcctga                         2199
```

<210> SEQ ID NO 83
<211> LENGTH: 2199
<212> TYPE: DNA
<213> ORGANISM: Artificial Sequence
<220> FEATURE:
<223> OTHER INFORMATION: 4C3-Myc-BBz-T2A-PAC CAR

<400> SEQUENCE: 83

```
atggccttac cagtgaccgc cttgctcctg ccgctggcct tgctgctcca cgccgccagg     60
ccggacatcg tgatgaccca gagccccagc agcctgacca tgagcgtggg ccagaaagtg    120
accatgtcct gcaagagcag ccacagcctg ctgaacagcc ggaaccagaa gaactacctg    180
gcctggttcc agcagaagcc cggccagtcc cccaagctgc tggtgtactt cgcaagcacc    240
cgcgagagcg gcgtgcccga cagattcatc ggcagcggct ccggcaccga cttcaccctg    300
accatcagca acgtgcaggc cgaggacctg gccgactact tctgccagca gcactacacc    360
accctgccca ccttcggcgg aggcaccaag ctggaaatca agggcggagg cggaagtgga    420
ggcggaggat ctggcggcgg aggctctcag atccagctgg tgcagagcgg ccctgacctg    480
aagaaacccg gcgagacagt gaagatcagt tgcaaggcct ccggctacac cttcaccaac    540
acaggcatga actgggtcaa gcaggccccct ggcaagggcc tgaagtggat gggctggatc    600
aacacctaca ccgcgagcc cacctacgcc gacgacttca agggccggtt caccttcagc    660
ctggaaacca gcgccagcac cgcctacctg cagatcaaca acctgaagaa cgaggacacc    720
gccacctatt tctgcaccag atgggggcta cggcagcagc tgtactacgc catggactac    780
tggggccagg gcaccagcgt gaccgtgtcc tctacgcgtg agcagaaact gatctcggaa    840
gaggatctgg cgaagcccac cacgacgcca gcgccgcgac caccaacacc ggcgcccacc    900
atcgcgtcgc agcccctgtc cctgcgccca gaggcgtgcc ggccagcggc ggggggcgca    960
gtgcacacga gggggctgga cttcgcctgt gacatctaca tctgggcgcc cttggccggg   1020
acttgtgggg tccttctcct gtcactggtt atcacccttt actgcaaacg gggcagaaag   1080
aaactcctgt atatattcaa acaaccattt atgagaccag tacaaactac tcaagaggaa   1140
gatggctgta gctgccgatt ccagaagaa gaagaaggag gatgtgaact gagagtgaag   1200
ttcagcagga gcgcagacgc ccccgcgtac cagcagggcc agaaccagct ctataacgag   1260
ctgaatctag gacgaagaga ggagtacgat gttttggaca gagacgtgg ccgggaccct   1320 gagatggggg gaaagccgag aaggaagaac cctcaggaag gcctgtacaa tgaactgcag   1380
aaagataaga tggcggaggc ctacagtgag attgggatga aggcgagcg ccggaggggc   1440 aaggggcacg atggccttta ccagggtctc agtacagcca ccaaggacac ctacgacgcc   1500
cttcacatgc aggccctgcc ccctcgctct agtggctccg gcgagggcag aggaagtcta   1560
ctaacctgcg gagatgtgga agaaaatcct ggccccacata tgaccgagta caagcccacg   1620
gtgcgcctcg ccaccgcga cgacgtcccc agggccgtac gcaccctcgc cgccgcgttc   1680
```

```
gccgactacc ccgccacgcg ccacaccgtc gatccggacc gccacatcga gcgggtcacc    1740
gagctgcaag aactcttcct cacgcgcgtc gggctcgaca tcggcaaggt gtgggtcgcg    1800
gacgacggcg ccgcggtggc ggtctggacc acgccgaga gcgtcgaagc ggggggcggtg    1860 ttcgccgaga tcgcccgcg catggccgag ttgagcggtt cccggctggc cgcgcagcaa    1920
cagatggaag gcctcctggc cgcgcaccgg cccaaggagc cgcgtggtt cctggccacc    1980 gtcggcgtct cgcccgacca ccagggcaag ggtctgggca gcgccgtcgt gctccccgga    2040
gtggaggcgg ccgagcgcgc cggggtgccc gccttcctgg agacctccgc gccccgcaac    2100
ctccccttct acgagcggct cggcttcacc gtcaccgccg acgtcgaggt gcccgaagga    2160
ccgcgcacct ggtgcatgac ccgcaagccc ggtgcctga                          2199
```

<210> SEQ ID NO 84
<211> LENGTH: 2754
<212> TYPE: DNA
<213> ORGANISM: Artificial Sequence
<220> FEATURE:
<223> OTHER INFORMATION: CD8SP-TROP2-h7E6-SVG-(vL-vH)-Myc-z-P2A-K13-
      Flag-T2A-PAC CAR

<400> SEQUENCE: 84

```
atggccttac cagtgaccgc cttgctcctg ccgctggcct tgctgctcca cgccgccagg     60
ccggacatcg tgatgaccca gagccccgat agcctggccg tgtctctggg agagagagcc    120
accatcaact gccgggccag caagagcgtg tccaccagcg gctacagcta catgcactgg    180
tatcagcaga agcccggcca gcccccaag ctgctgatct acctggcctc caacctggaa    240
agcggcgtgc ccgatagatt cagcggcagc ggctctggca ccgacttcac cctgaccatc    300
agttctcttc aggccgagga cgtggccgtg tactactgcc agcacagcag agagctgccc    360
tacaccttcg gccagggcac caagctggaa atcaagggcg gaggcggaag tggaggcgga    420
ggatctggcg gcgaggctc tcaggtgcaa ctccaggaat ctggccctgg ccttgtgaag    480
cccagcgaga cactgagcct gacctgtacc gtgtccggcg gcagcatcag ctcttacggc    540
gtgcactgga ttcggcagcc tccaggcaag ggcctggaat ggatcggcgt gatctggacc    600
tccggcgtga ccgactacaa cagcgccctg atgggcagag tgaccatctc cgtggacacc    660
agcaagaacc agttcagcct gaagctgagc agcgtgacag ccgccgatac cgccgtgtat    720
tattgcgcca gagatggcga ctacgaccgc tacacaatgg actactgggg ccagggaacc    780
cttgtgaccg tgtcctctac gcgtgagcag aaactgatct cggaagagga tctggcgaag    840
cccaccacga cgccagcgcc gcgaccacca acaccggcgc ccaccatcgc gtcgcagccc    900
ctgtccctgc gcccagaggc gtgccggcca cggcgggggg gcgcagtgca cacgagggggg    960 ctggacttcg cctgtgacat ctacatctgg gcgcccttgg ccgggacttg tgggtccttt   1020
ctcctgtcac tggttatcac cctttactgc gggcgcgcca gagtgaagtt cagcaggagc   1080
gcagacgccc ccgcgtacca gcagggccag aaccagctct ataacgagct gaatctagga   1140
cgaagagagg agtacgatgt tttggacaag agacgtggcc gggaccctga tgggggga   1200 aagccgagaa ggaagaaccc tcaggaaggc ctgtacaatg aactgcagaa agataagatg   1260
gcggaggcct acagtgagat tgggatgaaa ggcgagcgcc ggaggggcaa ggggcacgat   1320
ggcctttacc agggtctcag tacagccacc aaggacacct acgacgccct tcacatgcag   1380
gccctgcccc ctcgctctag aggatctgga gcaacaaact tctcactact caaacaagca   1440
ggtgacgtgg aggagaatcc cggccctggg atccacatgg ccacttacga ggttctctgt   1500
```

```
gaggtggcgc ggaaactggg cacggatgac agggaagtgg tattgttcct cctaaacgtg    1560
ttcatacctc aacccacact ggcccaatta attggagctc ttagagcttt aaaggaggag    1620
ggcaggttaa cgtttcccct gttagcggaa tgtctgtttc gtgcaggtcg cagagacctc    1680
ttgcgcgacc tgcttcactt agacccgcgt tttttagagc gccacctagc gggcacaatg    1740
agttatttca gcccttatca gctcactgtt ctccacgtag acggggagct gtgtgcgagg    1800
gatattaggt ctttgatatt tttaagcaag gacactatag ggtctcgcag cacaccacag    1860
acattcttac actgggtgta ctgtatggaa aacttagacc tactgggtcc cactgacgtg    1920
gatgccctaa tgtcaatgct tagatctttg tcaagagtag acctacagcg ccaagtgcaa    1980
accctaatgg gccttcacct ttccggccca tcacactccc aacactatcg ccatacacca    2040
ctcgagaccg atttctacga ctacaaggac gacgatgaca agactagtgg ctccggcgag    2100
ggcagaggaa gtctactaac ctgcggagat gtggaagaaa atcctggccc acatatgacc    2160
gagtacaagc ccacggtgcg cctcgccacc cgcgacgacg tccccagggc cgtacgcacc    2220
ctcgccgccg cgttcgccga ctaccccgcc acgcgccaca ccgtcgatcc ggaccgccac    2280
atcgagcggt tcaccgagct gcaagaactc ttcctcacgc gcgtcgggct cgacatcggc    2340
aaggtgtggg tcgcggacga cggcgccgcg gtggcggtct ggaccacgcc ggagagcgtc    2400
gaagcggggg cggtgttcgc cgagatcggc ccgcgcatgg ccgagttgag cggttcccgg    2460
ctggccgcgc agcaacagat ggaaggcctc ctggcgccgc accggcccaa ggagcccgcg    2520
tggttcctgg ccaccgtcgg cgtctcgccc gaccaccagg gcaagggtct gggcagcgcc    2580
gtcgtgctcc ccggagtgga ggcggccgag cgcgccgggg tgcccgcctt cctggagacc    2640
tccgcgcccc gcaacctccc cttctacgag cggctcggct tcaccgtcac cgccgacgtc    2700
gaggtgcccg aaggaccgcg cacctggtgc atgacccgca agcccggtgc ctga          2754
```

<210> SEQ ID NO 85
<211> LENGTH: 763
<212> TYPE: PRT
<213> ORGANISM: Artificial Sequence
<220> FEATURE:
<223> OTHER INFORMATION: FMC63-MYC-BBZ-T2A-EGFP CAR

<400> SEQUENCE: 85

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140
```

```
Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
            165                 170                 175

Val Ser Trp Ile Arg Gln Pro Pro Arg Lys Gly Leu Glu Trp Leu Gly
        180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
        210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Arg Val Glu Gln Lys Leu Ile Ser Glu
            260                 265                 270

Glu Asp Leu Ala Lys Pro Thr Thr Thr Pro Ala Pro Arg Pro Pro Thr
        275                 280                 285

Pro Ala Pro Thr Ile Ala Ser Gln Pro Leu Ser Leu Arg Pro Glu Ala
    290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Lys Arg Gly Arg Lys
            340                 345                 350

Lys Leu Leu Tyr Ile Phe Lys Gln Pro Phe Met Arg Pro Val Gln Thr
        355                 360                 365

Thr Gln Glu Glu Asp Gly Cys Ser Cys Arg Phe Pro Glu Glu Glu Glu
        370                 375                 380

Gly Gly Cys Glu Leu Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
        435                 440                 445

Asn Glu Leu Gln Lys Asp Lys Met Ala Glu Ala Tyr Ser Glu Ile Gly
    450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg Ser Ser Gly Ser Gly Glu Gly Arg Gly Ser Leu
            500                 505                 510

Leu Thr Cys Gly Asp Val Glu Glu Asn Pro Gly Pro Met Val Ser Lys
        515                 520                 525

Gly Glu Glu Leu Phe Thr Gly Val Val Pro Ile Leu Val Glu Leu Asp
    530                 535                 540

Gly Asp Val Asn Gly His Lys Phe Ser Val Ser Gly Glu Gly Glu Gly
545                 550                 555                 560
```

```
Asp Ala Thr Tyr Gly Lys Leu Thr Leu Lys Phe Ile Cys Thr Thr Gly
                565                 570                 575

Lys Leu Pro Val Pro Trp Pro Thr Leu Val Thr Thr Leu Thr Tyr Gly
            580                 585                 590

Val Gln Cys Phe Ser Arg Tyr Pro Asp His Met Lys Gln His Asp Phe
        595                 600                 605

Phe Lys Ser Ala Met Pro Glu Gly Tyr Val Gln Glu Arg Thr Ile Phe
    610                 615                 620

Phe Lys Asp Asp Gly Asn Tyr Lys Thr Arg Ala Glu Val Lys Phe Glu
625                 630                 635                 640

Gly Asp Thr Leu Val Asn Arg Ile Glu Leu Lys Gly Ile Asp Phe Lys
                645                 650                 655

Glu Asp Gly Asn Ile Leu Gly His Lys Leu Glu Tyr Asn Tyr Asn Ser
            660                 665                 670

His Asn Val Tyr Ile Met Ala Asp Lys Gln Lys Asn Gly Ile Lys Val
        675                 680                 685

Asn Phe Lys Ile Arg His Asn Ile Glu Asp Gly Ser Val Gln Leu Ala
    690                 695                 700

Asp His Tyr Gln Gln Asn Thr Pro Ile Gly Asp Gly Pro Val Leu Leu
705                 710                 715                 720

Pro Asp Asn His Tyr Leu Ser Thr Gln Ser Ala Leu Ser Lys Asp Pro
                725                 730                 735

Asn Glu Lys Arg Asp His Met Val Leu Leu Glu Phe Val Thr Ala Ala
            740                 745                 750

Gly Ile Thr Leu Gly Met Asp Glu Leu Tyr Lys
        755                 760

<210> SEQ ID NO 86
<211> LENGTH: 724
<212> TYPE: PRT
<213> ORGANISM: Artificial Sequence
<220> FEATURE:
<223> OTHER INFORMATION: FMC63-Myc-BBz-T2A-PAC CAR

<400> SEQUENCE: 86

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160
```

```
Leu Ser Val Thr Cys Thr Val Ser Gly Val Ser Leu Pro Asp Tyr Gly
            165                 170                 175
Val Ser Trp Ile Arg Gln Pro Pro Arg Lys Gly Leu Glu Trp Leu Gly
            180                 185                 190
Val Ile Trp Gly Ser Glu Thr Thr Tyr Tyr Asn Ser Ala Leu Lys Ser
            195                 200                 205
Arg Leu Thr Ile Ile Lys Asp Asn Ser Lys Ser Gln Val Phe Leu Lys
            210                 215                 220
Met Asn Ser Leu Gln Thr Asp Asp Thr Ala Ile Tyr Tyr Cys Ala Lys
225                 230                 235                 240
His Tyr Tyr Tyr Gly Gly Ser Tyr Ala Met Asp Tyr Trp Gly Gln Gly
            245                 250                 255
Thr Ser Val Thr Val Ser Ser Arg Val Glu Gln Lys Leu Ile Ser Glu
            260                 265                 270
Glu Asp Leu Ala Lys Pro Thr Thr Thr Pro Ala Pro Arg Pro Pro Thr
            275                 280                 285
Pro Ala Pro Thr Ile Ala Ser Gln Pro Leu Ser Leu Arg Pro Glu Ala
            290                 295                 300
Cys Arg Pro Ala Ala Gly Gly Ala Val His Thr Arg Gly Leu Asp Phe
305                 310                 315                 320
Ala Cys Asp Ile Tyr Ile Trp Ala Pro Leu Ala Gly Thr Cys Gly Val
            325                 330                 335
Leu Leu Leu Ser Leu Val Ile Thr Leu Tyr Cys Lys Arg Gly Arg Lys
            340                 345                 350
Lys Leu Leu Tyr Ile Phe Lys Gln Pro Phe Met Arg Pro Val Gln Thr
            355                 360                 365
Thr Gln Glu Glu Asp Gly Cys Ser Cys Arg Phe Pro Glu Glu Glu Glu
            370                 375                 380
Gly Gly Cys Glu Leu Arg Val Lys Phe Ser Arg Ser Ala Asp Ala Pro
385                 390                 395                 400
Ala Tyr Gln Gln Gly Gln Asn Gln Leu Tyr Asn Glu Leu Asn Leu Gly
            405                 410                 415
Arg Arg Glu Glu Tyr Asp Val Leu Asp Lys Arg Arg Gly Arg Asp Pro
            420                 425                 430
Glu Met Gly Gly Lys Pro Arg Arg Lys Asn Pro Gln Glu Gly Leu Tyr
            435                 440                 445
Asn Glu Leu Gln Lys Asp Lys Met Ala Glu Ala Tyr Ser Glu Ile Gly
450                 455                 460
Met Lys Gly Glu Arg Arg Arg Gly Lys Gly His Asp Gly Leu Tyr Gln
465                 470                 475                 480
Gly Leu Ser Thr Ala Thr Lys Asp Thr Tyr Asp Ala Leu His Met Gln
            485                 490                 495
Ala Leu Pro Pro Arg Ser Ser Gly Ser Gly Glu Gly Arg Gly Ser Leu
            500                 505                 510
Leu Thr Cys Gly Asp Val Glu Glu Asn Pro Gly Pro His Met Thr Glu
            515                 520                 525
Tyr Lys Pro Thr Val Arg Leu Ala Thr Arg Asp Asp Val Pro Arg Ala
            530                 535                 540
Val Arg Thr Leu Ala Ala Ala Phe Ala Asp Tyr Pro Ala Thr Arg His
545                 550                 555                 560
Thr Val Asp Pro Asp Arg His Ile Glu Arg Val Thr Glu Leu Gln Glu
            565                 570                 575
Leu Phe Leu Thr Arg Val Gly Leu Asp Ile Gly Lys Val Trp Val Ala
```

```
                580             585              590
Asp Asp Gly Ala Ala Val Ala Val Trp Thr Thr Pro Glu Ser Val Glu
            595                 600                605

Ala Gly Ala Val Phe Ala Glu Ile Gly Pro Arg Met Ala Glu Leu Ser
            610                 615                620

Gly Ser Arg Leu Ala Ala Gln Gln Gln Met Glu Gly Leu Leu Ala Pro
625                 630                 635                640

His Arg Pro Lys Glu Pro Ala Trp Phe Leu Ala Thr Val Gly Val Ser
            645                 650                655

Pro Asp His Gln Gly Lys Gly Leu Gly Ser Ala Val Val Leu Pro Gly
            660                 665                670

Val Glu Ala Ala Glu Arg Ala Gly Val Pro Ala Phe Leu Glu Thr Ser
            675                 680                685

Ala Pro Arg Asn Leu Pro Phe Tyr Glu Arg Leu Gly Phe Thr Val Thr
            690                 695                700

Ala Asp Val Glu Val Pro Glu Gly Pro Arg Thr Trp Cys Met Thr Arg
705                 710                 715                720

Lys Pro Gly Ala

<210> SEQ ID NO 87
<211> LENGTH: 718
<212> TYPE: PRT
<213> ORGANISM: Artificial Sequence
<220> FEATURE:
<223> OTHER INFORMATION: FMC63-Myc-28z-T2A-PAC CAR

<400> SEQUENCE: 87

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220
```

```
Met Asn Ser Leu Gln Thr Asp Asp Thr Ala Ile Tyr Tyr Cys Ala Lys
225                 230                 235                 240

His Tyr Tyr Tyr Gly Ser Tyr Ala Met Asp Tyr Trp Gly Gln Gly
            245                 250                 255

Thr Ser Val Thr Val Ser Ser Arg Val Glu Gln Lys Leu Ile Ser Glu
            260                 265                 270

Glu Asp Leu Lys Ile Glu Val Met Tyr Pro Pro Tyr Leu Asp Asn
    275                 280                 285

Glu Lys Ser Asn Gly Thr Ile Ile His Val Lys Gly Lys His Leu Cys
    290                 295                 300

Pro Ser Pro Leu Phe Pro Gly Pro Ser Lys Pro Phe Trp Val Leu Val
305                 310                 315                 320

Val Val Gly Gly Val Leu Ala Cys Tyr Ser Leu Leu Val Thr Val Ala
                325                 330                 335

Phe Ile Ile Phe Trp Val Arg Ser Lys Arg Ser Arg Leu Leu His Ser
                340                 345                 350

Asp Tyr Met Asn Met Thr Pro Arg Arg Pro Gly Pro Thr Arg Lys His
            355                 360                 365

Tyr Gln Pro Tyr Ala Pro Pro Arg Asp Phe Ala Ala Tyr Arg Ser
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg Ser
                485                 490                 495

Ser Gly Ser Gly Glu Gly Arg Gly Ser Leu Leu Thr Cys Gly Asp Val
            500                 505                 510

Glu Glu Asn Pro Gly Pro His Met Thr Glu Tyr Lys Pro Thr Val Arg
            515                 520                 525

Leu Ala Thr Arg Asp Asp Val Pro Arg Ala Val Arg Thr Leu Ala Ala
            530                 535                 540

Ala Phe Ala Asp Tyr Pro Ala Thr Arg His Thr Val Asp Pro Asp Arg
545                 550                 555                 560

His Ile Glu Arg Val Thr Glu Leu Gln Glu Leu Phe Leu Thr Arg Val
                565                 570                 575

Gly Leu Asp Ile Gly Lys Val Trp Val Ala Asp Gly Ala Ala Val
                580                 585                 590

Ala Val Trp Thr Thr Pro Glu Ser Val Glu Ala Gly Ala Val Phe Ala
            595                 600                 605

Glu Ile Gly Pro Arg Met Ala Glu Leu Ser Gly Ser Arg Leu Ala Ala
            610                 615                 620

Gln Gln Gln Met Glu Gly Leu Leu Ala Pro His Arg Pro Lys Glu Pro
625                 630                 635                 640
```

Ala Trp Phe Leu Ala Thr Val Gly Val Ser Pro Asp His Gln Gly Lys
            645             650             655

Gly Leu Gly Ser Ala Val Val Leu Pro Gly Val Glu Ala Ala Glu Arg
        660             665             670

Ala Gly Val Pro Ala Phe Leu Glu Thr Ser Ala Pro Arg Asn Leu Pro
        675             680             685

Phe Tyr Glu Arg Leu Gly Phe Thr Val Thr Ala Asp Val Glu Val Pro
    690             695             700

Glu Gly Pro Arg Thr Trp Cys Met Thr Arg Lys Pro Gly Ala
705             710             715

<210> SEQ ID NO 88
<211> LENGTH: 732
<212> TYPE: PRT
<213> ORGANISM: Artificial Sequence
<220> FEATURE:
<223> OTHER INFORMATION: CD8SP-2-CD19MM-(vL-vH)-Myc-BBz-T2A-PAC CAR

<400> SEQUENCE: 88

Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ala Ser Leu
            20                  25                  30

Ala Val Ser Leu Gly Gln Arg Ala Thr Ile Ser Cys Lys Ala Ser Gln
        35                  40                  45

Ser Val Asp Tyr Asp Gly Asp Ser Tyr Leu Asn Trp Tyr Gln Gln Ile
    50                  55                  60

Pro Gly Gln Pro Pro Lys Leu Leu Ile Tyr Asp Ala Ser Asn Leu Val
65                  70                  75                  80

Ser Gly Ile Pro Pro Arg Phe Ser Gly Ser Gly Ser Gly Thr Asp Phe
                85                  90                  95

Thr Leu Asn Ile His Pro Val Glu Lys Val Asp Ala Ala Thr Tyr His
            100                 105                 110

Cys Gln Gln Ser Thr Glu Asp Pro Trp Thr Phe Gly Gly Gly Thr Lys
        115                 120                 125

Leu Glu Ile Lys Gly Gly Gly Gly Ser Gly Gly Gly Gly Ser Gly Gly
    130                 135                 140

Gly Gly Ser Gln Val Gln Leu Gln Gln Ser Gly Ala Glu Leu Val Arg
145                 150                 155                 160

Pro Gly Ser Ser Val Lys Ile Ser Cys Lys Ala Ser Gly Tyr Ala Phe
                165                 170                 175

Ser Ser Tyr Trp Met Asn Trp Val Lys Gln Arg Pro Gly Gln Gly Leu
            180                 185                 190

Glu Trp Ile Gly Gln Ile Trp Pro Gly Asp Gly Asp Thr Asn Tyr Asn
        195                 200                 205

Gly Lys Phe Lys Gly Lys Ala Thr Leu Thr Ala Asp Glu Ser Ser Ser
    210                 215                 220

Thr Ala Tyr Met Gln Leu Ser Ser Leu Ala Ser Glu Asp Ser Ala Val
225                 230                 235                 240

Tyr Phe Cys Ala Arg Arg Glu Thr Thr Thr Val Gly Arg Tyr Tyr Tyr
                245                 250                 255

Ala Met Asp Tyr Trp Gly Gln Gly Thr Thr Val Thr Val Ser Ser Thr
            260                 265                 270

Arg Glu Gln Lys Leu Ile Ser Glu Glu Asp Leu Ala Lys Pro Thr Thr
        275                 280                 285

```
Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Lys Arg Gly Arg Lys Leu Leu Tyr Ile Phe Lys Gln
        355                 360                 365

Pro Phe Met Arg Pro Val Gln Thr Thr Gln Glu Glu Asp Gly Cys Ser
370                 375                 380

Cys Arg Phe Pro Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg Ser Ser Gly
            500                 505                 510

Ser Gly Glu Gly Arg Gly Ser Leu Leu Thr Cys Gly Asp Val Glu Glu
        515                 520                 525

Asn Pro Gly Pro His Met Thr Glu Tyr Lys Pro Thr Val Arg Leu Ala
530                 535                 540

Thr Arg Asp Asp Val Pro Arg Ala Val Arg Thr Leu Ala Ala Ala Phe
545                 550                 555                 560

Ala Asp Tyr Pro Ala Thr Arg His Thr Val Asp Pro Asp Arg His Ile
                565                 570                 575

Glu Arg Val Thr Glu Leu Gln Glu Leu Phe Leu Thr Arg Val Gly Leu
            580                 585                 590

Asp Ile Gly Lys Val Trp Val Ala Asp Gly Ala Ala Val Ala Val
        595                 600                 605

Trp Thr Thr Pro Glu Ser Val Glu Ala Gly Ala Val Phe Ala Glu Ile
610                 615                 620

Gly Pro Arg Met Ala Glu Leu Ser Gly Ser Arg Leu Ala Ala Gln Gln
625                 630                 635                 640

Gln Met Glu Gly Leu Leu Ala Pro His Arg Pro Lys Glu Pro Ala Trp
                645                 650                 655

Phe Leu Ala Thr Val Gly Val Ser Pro Asp His Gln Gly Lys Gly Leu
            660                 665                 670

Gly Ser Ala Val Val Leu Pro Gly Val Glu Ala Ala Glu Arg Ala Gly
        675                 680                 685

Val Pro Ala Phe Leu Glu Thr Ser Ala Pro Arg Asn Leu Pro Phe Tyr
690                 695                 700

Glu Arg Leu Gly Phe Thr Val Thr Ala Asp Val Glu Val Pro Glu Gly
```

```
                705                 710                 715                 720
Pro Arg Thr Trp Cys Met Thr Arg Lys Pro Gly Ala
                    725                 730

<210> SEQ ID NO 89
<211> LENGTH: 732
<212> TYPE: PRT
<213> ORGANISM: Artificial Sequence
<220> FEATURE:
<223> OTHER INFORMATION: 4C3-Myc-BBz-T2A-PAC CAR

<400> SEQUENCE: 89

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Ser Ser Leu
                20                  25                  30

Thr Met Ser Val Gly Gln Lys Val Thr Met Ser Cys Lys Ser Ser His
            35                  40                  45

Ser Leu Leu Asn Ser Arg Asn Gln Lys Asn Tyr Leu Ala Trp Phe Gln
    50                  55                  60

Gln Lys Pro Gly Gln Ser Pro Lys Leu Leu Val Tyr Phe Ala Ser Thr
65                  70                  75                  80

Arg Glu Ser Gly Val Pro Asp Arg Phe Ile Gly Ser Gly Ser Gly Thr
                85                  90                  95

Asp Phe Thr Leu Thr Ile Ser Asn Val Gln Ala Glu Asp Leu Ala Asp
                100                 105                 110

Tyr Phe Cys Gln Gln His Tyr Thr Thr Leu Pro Thr Phe Gly Gly Gly
            115                 120                 125

Thr Lys Leu Glu Ile Lys Gly Gly Gly Ser Gly Gly Gly Gly Ser
130                 135                 140

Gly Gly Gly Gly Ser Gln Ile Gln Leu Val Gln Ser Gly Pro Asp Leu
145                 150                 155                 160

Lys Lys Pro Gly Glu Thr Val Lys Ile Ser Cys Lys Ala Ser Gly Tyr
                165                 170                 175

Thr Phe Thr Asn Thr Gly Met Asn Trp Val Lys Gln Ala Pro Gly Lys
            180                 185                 190

Gly Leu Lys Trp Met Gly Trp Ile Asn Thr Tyr Thr Gly Glu Pro Thr
        195                 200                 205

Tyr Ala Asp Asp Phe Lys Gly Arg Phe Thr Phe Ser Leu Glu Thr Ser
    210                 215                 220

Ala Ser Thr Ala Tyr Leu Gln Ile Asn Asn Leu Lys Asn Glu Asp Thr
225                 230                 235                 240

Ala Thr Tyr Phe Cys Thr Arg Trp Gly Tyr Gly Ser Ser Leu Tyr Tyr
                245                 250                 255

Ala Met Asp Tyr Trp Gly Gln Gly Thr Ser Val Thr Val Ser Ser Thr
            260                 265                 270

Arg Glu Gln Lys Leu Ile Ser Glu Glu Asp Leu Ala Lys Pro Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
```

```
                340                 345                 350
Leu Tyr Cys Lys Arg Gly Arg Lys Leu Leu Tyr Ile Phe Lys Gln
            355                 360                 365
Pro Phe Met Arg Pro Val Gln Thr Thr Gln Glu Glu Asp Gly Cys Ser
        370                 375                 380
Cys Arg Phe Pro Glu Glu Glu Gly Gly Cys Glu Leu Arg Val Lys
385                 390                 395                 400
Phe Ser Arg Ser Ala Asp Ala Pro Ala Tyr Gln Gln Gly Gln Asn Gln
            405                 410                 415
Leu Tyr Asn Glu Leu Asn Leu Gly Arg Arg Glu Glu Tyr Asp Val Leu
        420                 425                 430
Asp Lys Arg Arg Gly Arg Asp Pro Glu Met Gly Gly Lys Pro Arg Arg
            435                 440                 445
Lys Asn Pro Gln Glu Gly Leu Tyr Asn Glu Leu Gln Lys Asp Lys Met
        450                 455                 460
Ala Glu Ala Tyr Ser Glu Ile Gly Met Lys Gly Glu Arg Arg Arg Gly
465                 470                 475                 480
Lys Gly His Asp Gly Leu Tyr Gln Gly Leu Ser Thr Ala Thr Lys Asp
            485                 490                 495
Thr Tyr Asp Ala Leu His Met Gln Ala Leu Pro Pro Arg Ser Ser Gly
        500                 505                 510
Ser Gly Glu Gly Arg Gly Ser Leu Leu Thr Cys Gly Asp Val Glu Glu
            515                 520                 525
Asn Pro Gly Pro His Met Thr Glu Tyr Lys Pro Thr Val Arg Leu Ala
        530                 535                 540
Thr Arg Asp Asp Val Pro Arg Ala Val Arg Thr Leu Ala Ala Ala Phe
545                 550                 555                 560
Ala Asp Tyr Pro Ala Thr Arg His Thr Val Asp Pro Asp Arg His Ile
            565                 570                 575
Glu Arg Val Thr Glu Leu Gln Glu Leu Phe Leu Thr Arg Val Gly Leu
        580                 585                 590
Asp Ile Gly Lys Val Trp Val Ala Asp Asp Gly Ala Ala Val Ala Val
            595                 600                 605
Trp Thr Thr Pro Glu Ser Val Glu Ala Gly Ala Val Phe Ala Glu Ile
        610                 615                 620
Gly Pro Arg Met Ala Glu Leu Ser Gly Ser Arg Leu Ala Ala Gln Gln
625                 630                 635                 640
Gln Met Glu Gly Leu Leu Ala Pro His Arg Pro Lys Glu Pro Ala Trp
            645                 650                 655
Phe Leu Ala Thr Val Gly Val Ser Pro Asp His Gln Gly Lys Gly Leu
        660                 665                 670
Gly Ser Ala Val Val Leu Pro Gly Val Glu Ala Ala Glu Arg Ala Gly
            675                 680                 685
Val Pro Ala Phe Leu Glu Thr Ser Ala Pro Arg Asn Leu Pro Phe Tyr
        690                 695                 700
Glu Arg Leu Gly Phe Thr Val Thr Ala Asp Val Glu Val Pro Glu Gly
705                 710                 715                 720
Pro Arg Thr Trp Cys Met Thr Arg Lys Pro Gly Ala
            725                 730

<210> SEQ ID NO 90
<211> LENGTH: 917
<212> TYPE: PRT
<213> ORGANISM: Artificial Sequence
```

-continued

<220> FEATURE:
<223> OTHER INFORMATION: CD8SP-TROP2-h7E6-SVG-(vL-vH)-Myc-z-P2A-K13-
Flag-T2A-PAC CAR

<400> SEQUENCE: 90

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Asp Ser Leu
            20                  25                  30

Ala Val Ser Leu Gly Glu Arg Ala Thr Ile Asn Cys Arg Ala Ser Lys
        35                  40                  45

Ser Val Ser Thr Ser Gly Tyr Ser Tyr Met His Trp Tyr Gln Gln Lys
    50                  55                  60

Pro Gly Gln Pro Pro Lys Leu Leu Ile Tyr Leu Ala Ser Asn Leu Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
            100                 105                 110

Cys Gln His Ser Arg Glu Leu Pro Tyr Thr Phe Gly Gln Gly Thr Lys
        115                 120                 125

Leu Glu Ile Lys Gly Gly Gly Gly Ser Gly Gly Gly Gly Ser Gly Gly
    130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Gly Ser Ile
                165                 170                 175

Ser Ser Tyr Gly Val His Trp Ile Arg Gln Pro Pro Gly Lys Gly Leu
            180                 185                 190

Glu Trp Ile Gly Val Ile Trp Thr Ser Gly Val Thr Asp Tyr Asn Ser
        195                 200                 205

Ala Leu Met Gly Arg Val Thr Ile Ser Val Asp Thr Ser Lys Asn Gln
    210                 215                 220

Phe Ser Leu Lys Leu Ser Ser Val Thr Ala Ala Asp Thr Ala Val Tyr
225                 230                 235                 240

Tyr Cys Ala Arg Asp Gly Asp Tyr Asp Arg Tyr Thr Met Asp Tyr Trp
                245                 250                 255

Gly Gln Gly Thr Leu Val Thr Val Ser Ser Thr Arg Glu Gln Lys Leu
            260                 265                 270

Ile Ser Glu Glu Asp Leu Ala Lys Pro Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Gly Arg
            340                 345                 350

Ala Arg Val Lys Phe Ser Arg Ser Ala Asp Ala Pro Ala Tyr Gln Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
```

-continued

```
            385                 390                 395                 400
        Lys Pro Arg Arg Lys Asn Pro Gln Glu Gly Leu Tyr Asn Glu Leu Gln
                            405                 410                 415

Lys Asp Lys Met Ala Glu Ala Tyr Ser Glu Ile Gly Met Lys Gly Glu
                            420                 425                 430

Arg Arg Arg Gly Lys Gly His Asp Gly Leu Tyr Gln Gly Leu Ser Thr
                    435                 440                 445

Ala Thr Lys Asp Thr Tyr Asp Ala Leu His Met Gln Ala Leu Pro Pro
                450                 455                 460

Arg Ser Arg Gly Ser Gly Ala Thr Asn Phe Ser Leu Leu Lys Gln Ala
        465                 470                 475                 480

Gly Asp Val Glu Glu Asn Pro Gly Pro Gly Ile His Met Ala Thr Tyr
                            485                 490                 495

Glu Val Leu Cys Glu Val Ala Arg Lys Leu Gly Thr Asp Asp Arg Glu
                            500                 505                 510

Val Val Leu Phe Leu Leu Asn Val Phe Ile Pro Gln Pro Thr Leu Ala
                            515                 520                 525

Gln Leu Ile Gly Ala Leu Arg Ala Leu Lys Glu Glu Gly Arg Leu Thr
                    530                 535                 540

Phe Pro Leu Leu Ala Glu Cys Leu Phe Arg Ala Gly Arg Arg Asp Leu
        545                 550                 555                 560

Leu Arg Asp Leu Leu His Leu Asp Pro Arg Phe Leu Glu Arg His Leu
                            565                 570                 575

Ala Gly Thr Met Ser Tyr Phe Ser Pro Tyr Gln Leu Thr Val Leu His
                            580                 585                 590

Val Asp Gly Glu Leu Cys Ala Arg Asp Ile Arg Ser Leu Ile Phe Leu
                    595                 600                 605

Ser Lys Asp Thr Ile Gly Ser Arg Ser Thr Pro Gln Thr Phe Leu His
                610                 615                 620

Trp Val Tyr Cys Met Glu Asn Leu Asp Leu Leu Gly Pro Thr Asp Val
        625                 630                 635                 640

Asp Ala Leu Met Ser Met Leu Arg Ser Leu Ser Arg Val Asp Leu Gln
                            645                 650                 655

Arg Gln Val Gln Thr Leu Met Gly Leu His Leu Ser Gly Pro Ser His
                            660                 665                 670

Ser Gln His Tyr Arg His Thr Pro Leu Glu Thr Asp Phe Tyr Asp Tyr
                    675                 680                 685

Lys Asp Asp Asp Asp Lys Thr Ser Gly Ser Gly Glu Gly Arg Gly Ser
                690                 695                 700

Leu Leu Thr Cys Gly Asp Val Glu Glu Asn Pro Gly Pro His Met Thr
        705                 710                 715                 720

Glu Tyr Lys Pro Thr Val Arg Leu Ala Thr Arg Asp Asp Val Pro Arg
                            725                 730                 735

Ala Val Arg Thr Leu Ala Ala Ala Phe Ala Asp Tyr Pro Ala Thr Arg
                            740                 745                 750

His Thr Val Asp Pro Asp Arg His Ile Glu Arg Val Thr Glu Leu Gln
                    755                 760                 765

Glu Leu Phe Leu Thr Arg Val Gly Leu Asp Ile Gly Lys Val Trp Val
                770                 775                 780

Ala Asp Asp Gly Ala Ala Val Ala Val Trp Thr Thr Pro Glu Ser Val
        785                 790                 795                 800

Glu Ala Gly Ala Val Phe Ala Glu Ile Gly Pro Arg Met Ala Glu Leu
                            805                 810                 815
```

```
Ser Gly Ser Arg Leu Ala Ala Gln Gln Gln Met Glu Gly Leu Leu Ala
            820                 825                 830

Pro His Arg Pro Lys Glu Pro Ala Trp Phe Leu Ala Thr Val Gly Val
        835                 840                 845

Ser Pro Asp His Gln Gly Lys Gly Leu Gly Ser Ala Val Val Leu Pro
850                 855                 860

Gly Val Glu Ala Ala Glu Arg Ala Gly Val Pro Ala Phe Leu Glu Thr
865                 870                 875                 880

Ser Ala Pro Arg Asn Leu Pro Phe Tyr Glu Arg Leu Gly Phe Thr Val
                885                 890                 895

Thr Ala Asp Val Glu Val Pro Glu Gly Pro Arg Thr Trp Cys Met Thr
            900                 905                 910

Arg Lys Pro Gly Ala
        915

<210> SEQ ID NO 91
<211> LENGTH: 7488
<212> TYPE: DNA
<213> ORGANISM: Artificial Sequence
<220> FEATURE:
<223> OTHER INFORMATION: pLenti-EF1a
<220> FEATURE:
<221> NAME/KEY: misc_feature
<222> LOCATION: (3291)..(3294)
<223> OTHER INFORMATION: n is a, c, g, or t

<400> SEQUENCE: 91
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggagaa     600
attagatcgc gatgggaaaa aattcggtta aggccagggg gaagaaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg aataggagc    1080 tttgttcctt gggttcttgg agcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
```

```
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaagaatga    1500 acaagaatta ttggaattag ataaatgggc aagtttgtgg aattggttta acataacaaa    1560
ttggctgtgg tatataaaat tattcataat gatagtagga ggcttggtag gtttaagaat    1620
agtttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcggtt    1800
aacttttaaa agaaaagggg ggattggggg gtacagtgca ggggaaagaa tagtagacat    1860
aatagcaaca gacatacaaa ctaaagaatt acaaaaacaa attacaaaat tcaaaatttt    1920
atcgataagc tttgcaaaga tggataaagt tttaaacaga gaggaatctt tgcagctaat    1980
ggaccttcta ggtcttgaaa ggagtgcctc gtgaggctcc ggtgcccgtc agtgggcaga    2040
gcgcacatcg cccacagtcc ccgagaagtt gggggagggg tcggcaatt gaaccggtgc    2100 ctagagaagt tggcgcgggg taaactggga aagtgatgtc gtgtactggc tccgcctttt    2160
tcccgagggt gggggagaac cgtatataag tgcagtagtc gccgtgaacg ttcttttcg    2220 caacgggttt gccgccagaa cacaggtaag tgccgtgtgt ggttcccgcg ggcctggcct    2280
ctttacgggt tatggcccctt gcgtgccttg aattacttcc acctggctgc agtacgtgat    2340
tcttgatccc gagcttcggg ttggaagtgg gtgggagagt tcgaggcctt gcgcttaagg    2400
agccccttcg cctcgtgctt gagttgaggc ctggcctggg cgctggggcc gccgcgtgcg    2460
aatctggtgg caccttcgcg cctgtctcgc tgctttcgat aagtctctag ccatttaaaa    2520
tttttgatga cctgctgcga cgcttttttt ctggcaagat agtcttgtaa atgcgggcca    2580
agatctgcac actggtattt cggttttttgg ggccgcgggc ggcgacgggg cccgtgcgtc    2640
ccagcgcaca tgttcggcga ggcggggcct gcgagcgcgg ccaccgagaa tcggacgggg    2700
gtagtctcaa gctggccggc ctgctctggt gcctggcctc gcgccgccgt gtatcgcccc    2760
gccctgggcg gcaaggctgg cccggtcggc accagttgcg tgagcggaaa gatggccgct    2820
tcccggccct gctgcaggga gctcaaaatg gaggacgcgg cgctcgggag agcgggcggg    2880
tgagtcaccc acacaaagga aaagggcctt tccgtcctca gccgtcgctt catgtgactc    2940
cacggagtac cgggcgccgt ccaggcacct cgattagttc tcgaccttt ggagtacgtc    3000 gtctttaggt tgggggggagg ggttttatgc gatggagttt ccccacactg agtgggtgga    3060
gactgaagtt aggccagctt ggcacttgat gtaattctcc ttggaatttg ccctttttga    3120
gtttggatct tggttcattc tcaagcctca gacagtggtt caaagttttt tcttccatt    3180 tcaggtgtcg tgaggaatta gcttggtact aatacgactc actatagggga acccaagct    3240 ggctaggtaa gcttgatatc gaattcctgc agcccggggg atctgctagc nnnngtcgac    3300
tccggatgat cagggccctg tacagatatc gacaatcaac ctctggatta caaaatttgt    3360
gaaagattga ctggtattct taactatgtt gctccttta cgctatgtgg atacgctgct    3420
ttaatgcctt tgtatcatgc tattgcttcc cgtatggctt tcattttctc ctccttgtat    3480
aaatcctggt tgctgtctct ttatgaggag ttgtggcccg ttgtcaggca acgtggcgtg    3540
gtgtgcactg tgtttgctga cgcaaccccc actggttggg gcattgccac cacctgtcag    3600
ctcctttccg ggactttcgc tttccccctc cctattgcca cggcggaact catcgccgcc    3660
```

```
tgccttgccc gctgctggac aggggctcgg ctgttgggca ctgacaattc cgtggtgttg    3720
tcggggaagc tgacgtcctt tccatggctg ctcgcctgtg ttgccacctg gattctgcgc    3780
gggacgtcct tctgctacgt cccttcggcc ctcaatccag cggaccttcc ttcccgcggc    3840
ctgctgccgg ctctgcggcc tcttccgcgt cttcgccttc gccctcagac gagtcggatc    3900
tccctttggg ccgcctcccc gctggaatt cgagctcggt acctttaaga ccaatgactt    3960
acaaggcagc tgtagatctt agccactttt taaagaaaaa gggggactg gaagggctaa    4020 ttcactccca acgaagacaa gatctgcttt tgcttgtac tgggtctctc tggttagacc    4080
agatctgagc ctgggagctc tctggctaac tagggaaccc actgcttaag cctcaataaa    4140
gcttgccttg agtgcttcaa gtagtgtgtg cccgtctgtt gtgtgactct ggtaactaga    4200
gatccctcag accccttttag tcagtgtgga aaatctctag cagtagtagt tcatgtcatc    4260
ttattattca gtatttataa cttgcaaaga aatgaatatc agagagtgag aggaacttgt    4320
ttattgcagc ttataatggt tacaaataaa gcaatagcat cacaaatttc acaaataaag    4380 cattttttc actgcattct agttgtggtt tgtccaaact catcaatgta tcttatcatg    4440
tctggctcta gctatcccgc ccctaactcc gcccatcccg ccctaactc gcccagttc    4500 cgcccattct ccgccccatg gctgactaat ttttttttatt tatgcagagg ccgaggccgc    4560
ctcggcctct gagctattcc agaagtagtg aggaggcttt tttggaggcc tagggacgta    4620
cccaattcgc cctatagtga gtcgtattac gcgcgctcac tggccgtcgt tttacaacgt    4680
cgtgactggg aaaaccctgg cgttacccaa cttaatcgcc ttgcagcaca tccccctttc    4740
gccagctggc gtaatagcga agaggcccgc accgatcgcc cttcccaaca gttgcgcagc    4800
ctgaatggcg aatgggacgc gccctgtagc ggcgcattaa gcgcggcggg tgtggtggtt    4860
acgcgcagcg tgaccgctac acttgccagc gccctagcgc ccgctccttt cgctttcttc    4920
ccttcctttc tcgccacgtt cgccggcttt ccccgtcaag ctctaaatcg ggggctccct    4980
ttagggttcc gatttagtgc tttacggcac ctcgaccccca aaaaacttga ttagggtgat    5040
ggttcacgta gtgggccatc gccctgatag acggttttc gcccttgac gttggagtcc    5100 acgttcttta atagtggact cttgttccaa actggaacaa cactcaaccc tatctcggtc    5160
tattcttttg atttataagg gattttgccg atttcggcct attggttaaa aaatgagctg    5220
atttaacaaa aatttaacgc gaattttaac aaaatattaa cgcttacaat ttaggtggca    5280
cttttcgggg aaatgtgcgc ggaaccccta tttgtttatt tttctaaata cattcaaata    5340
tgtatccgct catgagacaa taaccctgat aaatgcttca ataatattga aaaggaaga    5400 gtatgagtat tcaacatttc cgtgtcgccc ttattccctt ttttgcggca ttttgccttc    5460
ctgtttttgc tcacccagaa acgctggtga agtaaaaga tgctgaagat cagttgggtg    5520
cacgagtggg ttacatcgaa ctggatctca acagcggtaa gatccttgag agttttcgcc    5580
ccgaagaacg ttttccaatg atgagcactt taaagttct gctatgtggc gcggtattat    5640
cccgtattga cgccgggcaa gagcaactcg gtcgccgcat acactattct cagaatgact    5700
tggttgagta ctcaccagtc acagaaaagc atcttacgga tggcatgaca gtaagagaat    5760
tatgcagtgc tgccataacc atgagtgata acactgcggc caacttactt ctgacaacga    5820
tcggaggacc gaaggagcta accgcttttt tgcacaacat ggggatcat gtaactcgcc    5880 ttgatcgttg ggaaccggag ctgaatgaag ccataccaaa cgacgagcgt gacaccacga    5940
tgcctgtagc aatggcaaca acgttgcgca actattaac tggcgaacta cttactctag    6000
cttcccggca acaattaata gactggatgg aggcggataa agttgcagga ccacttctgc    6060
```

```
gctcggccct tccggctggc tggtttattg ctgataaatc tggagccggt gagcgtgggt    6120
ctcgcggtat cattgcagca ctggggccag atggtaagcc ctcccgtatc gtagttatct    6180
acacgacggg gagtcaggca actatggatg aacgaaatag acagatcgct gagataggtg    6240
cctcactgat taagcattgg taactgtcag accaagttta ctcatatata ctttagattg    6300
atttaaaact tcattttaa tttaaaagga tctaggtgaa gatcctttt gataatctca    6360 tgaccaaaat cccttaacgt gagttttcgt tccactgagc gtcagacccc gtagaaaaga    6420
tcaaaggatc ttcttgagat cctttttttc tgcgcgtaat ctgctgcttg caaacaaaaa    6480
aaccaccgct accagcggtg gtttgtttgc cggatcaaga gctaccaact cttttccga    6540 aggtaactgg cttcagcaga gcgcagatac caaatactgt tcttctagtg tagccgtagt    6600
taggccacca cttcaagaac tctgtagcac cgcctacata cctcgctctg ctaatcctgt    6660
taccagtggc tgctgccagt ggcgataagt cgtgtcttac cgggttggac tcaagacgat    6720
agttaccgga taaggcgcag cggtcgggct gaacggggg ttcgtgcaca cagcccagct    6780
tggagcgaac gacctacacc gaactgagat acctacagcg tgagctatga gaaagcgcca    6840
cgcttcccga aggagaaag gcggacaggt atccggtaag cggcagggtc ggaacaggag    6900
agcgcacgag ggagcttcca gggggaaacg cctggtatct ttatagtcct gtcgggtttc    6960
gccacctctg acttgagcgt cgatttttgt gatgctcgtc aggggggcgg agcctatgga    7020
aaaacgccag caacgcggcc ttttacggtt cctggccttt tgctggcct tttgctcaca    7080 tgttctttcc tgcgttatcc cctgattctg tggataaccg tattaccgcc tttgagtgag    7140
ctgataccgc tcgccgcagc cgaacgaccg agcgcagcga gtcagtgagc gaggaagcgg    7200
aagagcgccc aatacgcaaa ccgcctctcc ccgcgcgttg gccgattcat taatgcagct    7260
ggcacgacag gtttcccgac tggaaagcgg gcagtgagcg caacgcaatt aatgtgagtt    7320
agctcactca ttaggcaccc caggctttac actttatgct tccggctcgt atgttgtgtg    7380
gaattgtgag cggataacaa tttcacacag gaaacagcta tgaccatgat tacgccaagc    7440
gcgcaattaa ccctcactaa agggaacaaa agctggagct gcaagctt                 7488
```

<210> SEQ ID NO 92
<211> LENGTH: 7512
<212> TYPE: DNA
<213> ORGANISM: Artificial Sequence
<220> FEATURE:
<223> OTHER INFORMATION: pLENTI-NLuc-AcV5-Blasticidin-Pa08

<400> SEQUENCE: 92

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca ggagagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggggaga     600
```

-continued

```
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgata   1800
agcttggagt tccgcgtta cataacttac ggtaaatggc ccgcctggct gaccgcccaa   1860
cgacccccgc ccattgacgt caataatgac gtatgttccc atagtaacgc caatagggac   1920
tttccattga cgtcaatggg tggagtattt acggtaaact gcccacttgg cagtacatca   1980
agtgtatcat atgccaagta cgccccctat tgacgtcaat gacggtaaat ggcccgcctg   2040
gcattatgcc cagtacatga ccttatggga ctttcctact tggcagtaca tctacgtatt   2100
agtcatcgct attaccatgg tgatgcggtt ttggcagtac atcaatgggc gtggatagcg   2160
gtttgactca cggggatttc caagtctcca ccccattgac gtcaatggga gtttgttttg   2220
gcaccaaaat caacgggact ttccaaaatg tcgtaacaac tccgccccat tgacgcaaat   2280
gggcggtagg cgtgtacggt gggaggtcta tataagcaga gctcgtttag tgaaccgtca   2340
gatcgcctgg agacgccatc cacgctgttt tgacctccat agaagacacc gactctagag   2400
gatccccacc atggtcttca cactcgaaga tttcgttggg gactggcgac agacagccgg   2460
ctacaacctg gaccaagtcc ttgaacaggg aggtgtgtcc agtttgtttc agaatctcgg   2520
ggtgtccgta actccgatcc aaaggattgt cctgagcggt gaaatgggc tgaagatcga   2580 catccatgtc atcatcccgt atgaaggtct gagcggcgac caaatgggcc agatcgaaaa   2640
aatttttaag gtggtgtacc ctgtggatga tcatcacttt aaggtgatcc tgcactatgg   2700
cacactggta atcgacgggg ttacgccgaa catgatcgac tatttcggac ggccctatga   2760
aggcatcgcc gtgttcgacg gcaaaaagat cactgtaaca gggaccctgt ggaacggcaa   2820
caaaattatc gacgagcgcc tgatcaaccc cgacggctcc ctgctgttcc gagtaaccat   2880
caacggagtg accggctggc ggctgtgcga acgcattctg gcgagttgga aggatgcctc   2940
tggatggtct taagtcgaga ccgatttcta ccccctacgat gtgcccgatt acgcttagtc   3000
```

-continued

```
tagagggccc gcggttcgaa ggtaagccta tccctaaccc tctcctcggt ctcgattcta    3060
cgcgtaccgg ttagtaatga gtttggaatt aattctgtgg aatgtgtgtc agttagggtg    3120
tggaaagtcc ccaggctccc caggcaggca gaagtatgca aagcatgcat ctcaattagt    3180
cagcaaccag gtgtggaaag tccccaggct ccccagcagg cagaagtatg caaagcatgc    3240
atctcaatta gtcagcaacc atagtcccgc ccctaactcc gcccatcccg cccctaactc    3300
cgcccagttc cgcccattct ccgcccatg gctgactaat ttttttatt tatgcagagg    3360 ccgaggccgc ctctgcctct gagctattcc agaagtagtg aggaggcttt tttggaggcc    3420
taggcttttg caaaaagctc ccgggagctt gtatatccat tttcggatct gatcagcacg    3480
tgttgacaat taatcatcgg catagtatat cggcatagta taatacgaca aggtgaggaa    3540
ctaaaccatg gccaagcctt tgtctcaaga agaatccacc ctcattgaaa gagcaacggc    3600
tacaatcaac agcatcccca tctctgaaga ctacagcgtc gccagcgcag ctctctctag    3660
cgacggccgc atcttcactg gtgtcaatgt atatcatttt actgggggac cttgtgcaga    3720
actcgtggtg ctgggcactg ctgctgctgc ggcagctggc aacctgactt gtatcgtcgc    3780
gatcggaaat gagaacaggg gcatcttgag cccctgcgga cggtgccgac aggtgcttct    3840
cgatctgcat cctgggatca aagccatagt gaaggacagt gatggacagc cgacggcagt    3900
tgggattcgt gaattgctgc cctctggtta tgtgtgggag ggctaagcac aattcgagct    3960
cggtaccttt aagaccaatg acttacaagg cagctgtaga tcttagccac ttttttaaaag    4020 aaaagggggg actggaaggg ctaattcact cccaacgaag acaagatctg cttttttgctt    4080 gtactgggtc tctctggtta ccagatctg agcctggga gctctctggc taactaggga    4140
acccactgct taagcctcaa taaagcttgc cttgagtgct tcaagtagtg tgtgcccgtc    4200
tgttgtgtga ctctggtaac tagagatccc tcagacccctt ttagtcagtg tggaaaatct    4260
ctagcagtag tagttcatgt catcttatta ttcagtattt ataacttgca aagaaatgaa    4320
tatcagagag tgagaggaac ttgttattg cagcttataa tggttacaaa taaagcaata    4380
gcatcacaaa tttcacaaat aaagcatttt tttcactgca ttctagttgt ggtttgtcca    4440
aactcatcaa tgtatcttat catgtctggc tctagctatc ccgcccctaa ctccgcccat    4500
cccgccccta actccgccca gttccgccca ttctccgccc catggctgac taatttttttt    4560 tatttatgca gaggccgagg ccgcctcggc ctctgagcta ttccagaagt agtgaggagg    4620
cttttttgga ggcctaggga cgtacccaat cgccctata gtgagtcgta ttacgcgcgc    4680
tcactggccg tcgttttaca acgtcgtgac tgggaaaacc ctggcgttac ccaacttaat    4740
cgccttgcag cacatccccc tttcgccagc tggcgtaata gcgaagaggc ccgcaccgat    4800
cgcccttccc aacagttgcg cagcctgaat ggcgaatggg acgcgccctg tagcggcgca    4860
ttaagcgcgg cgggtgtggt ggttacgcgc agcgtgaccg ctacacttgc cagcgcccta    4920
gcgcccgctc ctttcgcttt cttcccttcc tttctcgcca cgttcgccgg ctttccccgt    4980
caagctctaa atcgggggct ccctttaggg ttccgattta gtgctttacg gcacctcgac    5040
cccaaaaaac ttgattaggg tgatggttca cgtagtgggc catcgccctg atagacggtt    5100
tttcgccctt tgacgttgga gtccacgttc tttaatagtg gactcttgtt ccaaactgga    5160
acaacactca accctatctc ggtctattct tttgatttat aagggatttt gccgatttcg    5220
gcctattggt taaaaatga gctgatttaa caaaaattta acgcgaattt taacaaaata    5280
ttaacgctta caatttaggt ggcactttc ggggaaatgt gcgcggaacc cctatttgtt    5340
```

```
tatttttcta aatacattca aatatgtatc cgctcatgag acaataaccc tgataaatgc    5400
ttcaataata ttgaaaaagg aagagtatga gtattcaaca tttccgtgtc gcccttattc    5460
ccttttttgc ggcattttgc cttcctgttt ttgctcaccc agaaacgctg gtgaaagtaa    5520
aagatgctga agatcagttg ggtgcacgag tgggttacat cgaactggat ctcaacagcg    5580
gtaagatcct tgagagtttt cgccccgaag aacgttttcc aatgatgagc acttttaaag    5640
ttctgctatg tggcgcggta ttatcccgta ttgacgccgg gcaagagcaa ctcggtcgcc    5700
gcatacacta ttctcagaat gacttggttg agtactcacc agtcacagaa aagcatctta    5760
cggatggcat gacagtaaga gaattatgca gtgctgccat aaccatgagt gataacactg    5820
cggccaactt acttctgaca acgatcggag gaccgaagga gctaaccgct tttttgcaca    5880
acatggggga tcatgtaact cgccttgatc gttgggaacc ggagctgaat gaagccatac    5940
caaacgacga gcgtgacacc acgatgcctg tagcaatggc aacaacgttg cgcaaactat    6000
taactggcga actacttact ctagcttccc ggcaacaatt aatagactgg atggaggcgg    6060
ataaagttgc aggaccactt ctgcgctcgg cccttccggc tggctggttt attgctgata    6120
aatctggagc cggtgagcgt gggtctcgcg gtatcattgc agcactgggg ccagatggta    6180
agccctcccg tatcgtagtt atctacacga cggggagtca ggcaactatg gatgaacgaa    6240
atagacagat cgctgagata ggtgcctcac tgattaagca ttggtaactg tcagaccaag    6300
tttactcata tatactttag attgatttaa aacttcattt ttaatttaaa aggatctagg    6360
tgaagatcct ttttgataat ctcatgacca aaatccctta acgtgagttt cgttccact     6420 gagcgtcaga ccccgtagaa aagatcaaag gatcttcttg agatcctttt tttctgcgcg    6480
taatctgctg cttgcaaaca aaaaaaccac cgctaccagc ggtggtttgt ttgccggatc    6540
aagagctacc aactctttt ccgaaggtaa ctggcttcag cagagcgcag ataccaaata    6600
ctgttcttct agtgtagccg tagttaggcc accacttcaa gaactctgta gcaccgccta    6660
catacctcgc tctgctaatc ctgttaccag tggctgctgc cagtggcgat aagtcgtgtc    6720
ttaccgggtt ggactcaaga cgatagttac cggataaggc gcagcggtcg gctgaacgg    6780 ggggttcgtg cacacagccc agcttggagc gaacgaccta caccgaactg agatacctac    6840
agcgtgagct atgagaaagc gccacgcttc ccgaagggag aaaggcggac aggtatccgg    6900
taagcggcag ggtcggaaca ggagagcgca cgagggagct tccaggggga aacgcctggt    6960
atctttatag tcctgtcggg tttcgccacc tctgacttga gcgtcgattt ttgtgatgct    7020
cgtcaggggg gcggagccta tggaaaaacg ccagcaacgc ggccttttta cggttcctgg    7080
ccttttgctg gccttttgct cacatgttct ttcctgcgtt atcccctgat tctgtggata    7140
accgtattac cgcctttgag tgagctgata ccgctcgccg cagccgaacg accgagcgca    7200
gcgagtcagt gagcgaggaa gcggaagagc gcccaatacg caaaccgcct ctccccgcgc    7260
gttggccgat tcattaatgc agctggcacg acaggtttcc cgactggaaa gcgggcagtg    7320
agcgcaacgc aattaatgtg agttagctca ctcattaggc accccaggct ttacacttta    7380
tgcttccggc tcgtatgttg tgtggaattg tgagcggata acaatttcac acaggaaaca    7440
gctatgacca tgattacgcc aagcgcgcaa ttaaccctca ctaaagggaa caaaagctgg    7500
agctgcaagc tt                                                        7512
```

<210> SEQ ID NO 93
<211> LENGTH: 7476
<212> TYPE: DNA
<213> ORGANISM: Artificial Sequence
<220> FEATURE:
<223> OTHER INFORMATION: pLENTI-TurboLuc-16-X3Flag-Blast-C04

<400> SEQUENCE: 93

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggagaa     600
attagatcgc gatgggaaaa aattcggtta aggccagggg gaaagaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
agtttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgata    1800
agcttgggag ttccgcgtta cataacttac ggtaaatggc ccgcctggct gaccgcccaa    1860
cgacccccgc ccattgacgt caataatgac gtatgttccc atagtaacgc caatagggac    1920
tttccattga cgtcaatggg tggagtattt acggtaaact gcccacttgg cagtacatca    1980
agtgtatcat atgccaagta cgccccctat tgacgtcaat gacggtaaat ggcccgcctg    2040
gcattatgcc cagtacatga ccttatggga ctttcctact tggcagtaca tctacgtatt    2100
agtcatcgct attaccatgg tgatgcggtt ttggcagtac atcaatgggc gtggatagcg    2160
gtttgactca cggggatttc caagtctcca ccccattgac gtcaatggga gtttgttttg    2220
```

-continued

```
gcaccaaaat caacgggact ttccaaaatg tcgtaacaac tccgccccat tgacgcaaat      2280
gggcggtagg cgtgtacggt gggaggtcta tataagcaga gctcgtttag tgaaccgtca      2340
gatcgcctgg agacgccatc cacgctgttt tgacctccat agaagacacc gactctagag      2400
gatccccatg gaagccgagg ccgagagagg caagctgccc ggcaaaaagc tgcccctgga      2460
agtgctgatc gagctggaag ccaacgccag aaaggccggc tgcaccagag gctgcctgat      2520
ctgcctgagc aagatcaagt gcaccgccaa gatgaagaag tacatccccg gcagatgcgc      2580
cgactacggc ggcgataaga aaacaggcca ggccggcatc gtgggagcca tcgtggatat      2640
ccctgagatc agcggcttca agaaatgga acccatggaa cagtttatcg cccaggtgga      2700
ccgctgcgcc gattgcacaa caggctgtct gaagggcctg gctaacgtga agtgcagcga      2760
cctgctgaag aagtggctgc ctggcagatg tgccaccttc gccgacaaga tccagagcga      2820
ggtggacaac atcaagggac tggccggcga cctcgagacc gatttctacg actacaagga      2880
cgacgatgac aaggattata agatgatga cgataaagtc gagaccgatt tctacgacta      2940
caaggacgac gatgacaagt agtctagagg gcccgcggtt cgaaggtaag cctatcccta      3000
accctctcct cggtctcgat tctacgcgta ccggttagta atgagtttgg aattaattct      3060
gtggaatgtg tgtcagttag ggtgtggaaa gtccccaggc tccccaggca ggcagaagta      3120
tgcaaagcat gcatctcaat tagtcagcaa ccaggtgtgg aaagtcccca ggctccccag      3180
caggcagaag tatgcaaagc atgcatctca attagtcagc aaccatagtc ccgcccctaa      3240
ctccgcccat cccgccccta actccgccca gttccgccca ttctccgccc catggctgac      3300
taattttttt tatttatgca gaggccgagg ccgcctctgc ctctgagcta ttccagaagt      3360
agtgaggagg cttttttgga ggcctaggct tttgcaaaaa gctcccggga gcttgtatat      3420
ccattttcgg atctgatcag cacgtgttga caattaatca tcggcatagt atatcggcat      3480
agtataatac gacaaggtga ggaactaaac catggccaag cctttgtctc aagaagaatc      3540
caccctcatt gaaagagcaa cggctacaat caacagcatc cccatctctg aagactacag      3600
cgtcgccagc gcagctctct ctagcgacgg ccgcatcttc actggtgtca atgtatatca      3660
ttttactggg ggaccttgtg cagaactcgt ggtgctgggc actgctgctg ctgcggcagc      3720
tggcaacctg acttgtatcg tcgcgatcgg aaatgagaac agggggcatct tgagcccctg      3780 cggacggtgc cgacaggtgc ttctcgatct gcatcctggg atcaaagcca tagtgaagga      3840
cagtgatgga cagccgacgg cagttgggat tcgtgaattg ctgccctctg gttatgtgtg      3900
ggagggctaa gcacaattcg agctcggtac ctttaagacc aatgacttac aaggcagctg      3960
tagatcttag ccactttta aaagaaaagg ggggactgga agggctaatt cactcccaac      4020
gaagacaaga tctgcttttt gcttgtactg ggtctctctg gttagaccag atctgagcct      4080
gggagctctc tggctaacta gggaacccac tgcttaagcc tcaataaagc ttgccttgag      4140
tgcttcaagt agtgtgtgcc cgtctgttgt gtgactctgg taactagaga tccctcagac      4200
ccttttagtc agtgtggaaa atctctagca gtagtagttc atgtcatctt attattcagt      4260
atttataact tgcaaagaaa tgaatatcag agagtgagag gaacttgttt attgcagctt      4320
ataatggtta caaataaagc aatagcatca caaatttcac aaataaagca tttttttcac      4380
tgcattctag ttgtggtttg tccaaactca tcaatgtatc ttatcatgtc tggctctagc      4440
tatcccgccc ctaactccgc ccatcccgcc cctaactccg cccagttccg cccattctcc      4500
gccccatggc tgactaattt ttttatttta tgcagaggcc gaggccgcct cggcctctga      4560
gctattccag aagtagtgag gaggcttttt tggaggccta gggacgtacc caattcgccc      4620
```

```
tatagtgagt cgtattacgc gcgctcactg gccgtcgttt tacaacgtcg tgactgggaa    4680
aaccctggcg ttacccaact taatcgcctt gcagcacatc cccctttcgc cagctggcgt    4740
aatagcgaag aggcccgcac cgatcgccct tcccaacagt tgcgcagcct gaatggcgaa    4800
tgggacgcgc cctgtagcgg cgcattaagc gcggcgggtg tggtggttac gcgcagcgtg    4860
accgctacac ttgccagcgc cctagcgccc gctcctttcg ctttcttccc ttcctttctc    4920
gccacgttcg ccggctttcc ccgtcaagct ctaaatcggg gctcccttt agggttccga    4980 tttagtgctt tacggcacct cgaccccaaa aaacttgatt agggtgatgg ttcacgtagt    5040
gggccatcgc cctgatagac ggttttcgc cctttgacgt tggagtccac gttctttaat    5100
agtggactct tgttccaaac tggaacaaca ctcaaccta tctcggtcta ttcttttgat    5160
ttataaggga ttttgccgat ttcggcctat tggttaaaaa atgagctgat ttaacaaaaa    5220
tttaacgcga attttaacaa atattaacg cttacaattt aggtggcact tttcggggaa    5280
atgtgcgcgg aacccctatt tgtttatttt tctaaataca ttcaaatatg tatccgctca    5340
tgagacaata accctgataa atgcttcaat aatattgaaa aaggaagagt atgagtattc    5400
aacatttccg tgtcgccctt attcccttt ttgcggcatt ttgccttcct gtttttgctc    5460
acccagaaac gctggtgaaa gtaaaagatg ctgaagatca gttgggtgca cgagtgggtt    5520
acatcgaact ggatctcaac agcggtaaga tccttgagag ttttcgcccc gaagaacgtt    5580
ttccaatgat gagcactttt aaagttctgc tatgtggcgc ggtattatcc cgtattgacg    5640
ccgggcaaga gcaactcggt cgccgcatac actattctca gaatgacttg gttgagtact    5700
caccagtcac agaaaagcat cttacggatg gcatgacagt aagagaatta tgcagtgctg    5760
ccataaccat gagtgataac actgcggcca acttacttct gacaacgatc ggaggaccga    5820
aggagctaac cgcttttttg cacaacatgg ggatcatgt aactcgcctt gatcgttggg    5880
aaccggagct gaatgaagcc ataccaaacg acgagcgtga caccacgatg cctgtagcaa    5940
tggcaacaac gttgcgcaaa ctattaactg gcgaactact tactctagct tcccggcaac    6000
aattaataga ctggatggag gcggataaag ttgcaggacc acttctgcgc tcggcccttc    6060
cggctggctg gtttattgct gataaatctg gagccggtga gcgtgggtct cgcggtatca    6120
ttgcagcact ggggccagat ggtaagccct cccgtatcgt agttatctac acgacgggga    6180
gtcaggcaac tatggatgaa cgaaatagac agatcgctga gataggtgcc tcactgatta    6240
agcattggta actgtcagac caagtttact catatatact ttagattgat ttaaaacttc    6300
atttttaatt taaaaggatc taggtgaaga tcctttttga taatctcatg accaaaatcc    6360
cttaacgtga gttttcgttc cactgagcgt cagaccccgt agaaaagatc aaaggatctt    6420
cttgagatcc ttttttttctg cgcgtaatct gctgcttgca acaaaaaaa ccaccgctac    6480 cagcggtggt ttgtttgccg gatcaagagc taccaactct ttttccgaag gtaactggct    6540
tcagcagagc gcagatacca atactgttc ttctagtgta gccgtagtta ggccaccact    6600
tcaagaactc tgtagcaccg cctacatacc tcgctctgct aatcctgtta ccagtggctg    6660
ctgccagtgg cgataagtcg tgtcttaccg ggttggactc aagacgatag ttaccggata    6720
aggcgcagcg gtcgggctga acggggggtt cgtgcacaca gcccagcttg gagcgaacga    6780
cctacaccga actgagatac ctacagcgtg agctatgaga aagcgccacg cttcccgaag    6840
ggagaaaggc ggacaggtat ccggtaagcg gcagggtcgg aacaggagag cgcacgaggg    6900
agcttccagg gggaaacgcc tggtatcttt atagtcctgt cgggtttcgc cacctctgac    6960
```

```
ttgagcgtcg attttgtgta tgctcgtcag ggggcggag cctatggaaa aacgccagca    7020
acgcggcctt tttacggttc ctggccttt gctggccttt tgctcacatg ttctttcctg    7080
cgttatcccc tgattctgtg gataaccgta ttaccgcctt tgagtgagct gataccgctc   7140
gccgcagccg aacgaccgag cgcagcgagt cagtgagcga ggaagcggaa gagcgcccaa   7200
tacgcaaacc gcctctcccc gcgcgttggc cgattcatta atgcagctgg cacgacaggt   7260
ttcccgactg gaaagcgggc agtgagcgca acgcaattaa tgtgagttag ctcactcatt   7320
aggcacccca ggctttacac tttatgcttc cggctcgtat gttgtgtgga attgtgagcg   7380
gataacaatt tcacacagga aacagctatg accatgatta cgccaagcgc gcaattaacc   7440
ctcactaaag ggaacaaaag ctggagctgc aagctt                             7476
```

<210> SEQ ID NO 94
<211> LENGTH: 8663
<212> TYPE: DNA
<213> ORGANISM: Artificial Sequence
<220> FEATURE:
<223> OTHER INFORMATION: pLenti-EF1a-Pac-T2A-Gluc-B07

<400> SEQUENCE: 94

```
aatgtagtct tatgcaatac tcttgtagtc ttgcaacatg gtaacgatga gttagcaaca     60
tgccttacaa ggagagaaaa agcaccgtgc atgccgattg gtggaagtaa ggtggtacga    120
tcgtgcctta ttaggaaggc aacagacggg tctgacatgg attggacgaa ccactgaatt   180
gccgcattgc agagatattg tatttaagtg cctagctcga tacataaacg ggtctctctg    240
gttagaccag atctgagcct gggagctctc tggctaacta gggaacccac tgcttaagcc   300
tcaataaagc ttgccttgag tgcttcaagt agtgtgtgcc cgtctgttgt gtgactctgg   360
taactagaga tccctcagac ccttttagtc agtgtggaaa atctctagca gtggcgcccg    420
aacagggact tgaaagcgaa agggaaacca ggagctctct cgacgcag actcggctt    480
gctgaagcgc gcacggcaag aggcgagggg cggcgactgg tgagtacgcc aaaaattttg   540
actagcggag gctagaagga gagagatggg tgcgagagcg tcagtattaa gcggggaga    600
attagatcgc gatgggaaaa aattcggtta aggccagggg gaagaaaaa atataaatta    660
aaacatatag tatgggcaag cagggagcta gaacgattcg cagttaatcc tggcctgtta   720
gaaacatcag aaggctgtag acaaatactg ggacagctac aaccatccct tcagacagga   780
tcagaagaac ttagatcatt atataataca gtagcaaccc tctattgtgt gcatcaaagg   840
atagagataa aagacaccaa ggaagcttta gacaagatag aggaagagca aaacaaaagt   900
aagaccaccg cacagcaagc ggccgctgat cttcagacct ggaggaggag atatgaggga   960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagataccc taaaggatca gcagctcctgg ggatttgggg   1320
ttgctctgga aaactcattt gcaccactgc tgtgccttgg aatgctagtt ggagtaataa   1380
atctctggaa cagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
```

```
ttggctgtgg tatataaaat tattcataat gatagtagga ggcttggtag gtttaagaat    1620
agtttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcggtt    1800
aacttttaaa agaaaagggg ggattggggg gtacagtgca ggggaaagaa tagtagacat    1860
aatagcaaca gacatacaaa ctaaagaatt acaaaaacaa attacaaaat tcaaaatttt    1920
atcgataagc tttgcaaaga tggataaagt tttaaacaga gaggaatctt tgcagctaat    1980
ggaccttcta ggtcttgaaa ggagtgcctc gtgaggctcc ggtgcccgtc agtgggcaga    2040
gcgcacatcg cccacagtcc ccgagaagtt ggggggaggg gtcggcaatt gaaccggtgc    2100
ctagagaagg tggcgcgggg taaactggga aagtgatgtc gtgtactggc tccgcctttt    2160
tcccgagggt gggggagaac cgtatataag tgcagtagtc gccgtgaacg ttcttttttcg   2220
caacgggttt gccgccagaa cacaggtaag tgccgtgtgt ggttcccgcg ggcctggcct    2280
ctttacgggt tatggccctt gcgtgccttg aattacttcc acctggctgc agtacgtgat    2340
tcttgatccc gagcttcggg ttggaagtgg gtgggagagt tcgaggcctt gcgcttaagg    2400
agccccttcg cctcgtgctt gagttgaggc ctggcctggg cgctggggcc gccgcgtgcg    2460
aatctggtgg caccttcgcg cctgtctcgc tgctttcgat aagtctctag ccatttaaaa    2520
ttttttgatga cctgctgcga cgctttttttt ctggcaagat agtcttgtaa atgcgggcca   2580
agatctgcac actggtattt cggttttttgg ggccgcgggc ggcgacgggg cccgtgcgtc    2640
ccagcgcaca tgttcggcga ggcggggcct gcgagcgcgg ccaccgagaa tcggacgggg    2700
gtagtctcaa gctggccggc ctgctctggt gcctggcctc gcgccgccgt gtatcgcccc    2760
gccctgggcg gcaaggctgg cccggtcggc accagttgcg tgagcggaaa gatggccgct    2820
tcccggccct gctgcaggga gctcaaaatg gaggacgcgg cgctcgggag agcgggcggg    2880
tgagtcaccc acacaaagga aaagggcctt tccgtcctca gccgtcgctt catgtgactc    2940
cacggagtac cgggcgccgt ccaggcacct cgattagttc tcgacctttt ggagtacgtc    3000
gtctttaggt tgggggggagg ggttttatgc gatggagttt ccccacactg agtgggtgga   3060
gactgaagtt aggccagctt ggcacttgat gtaattctcc ttggaatttg ccctttttga    3120
gtttggatct tggttcattc tcaagcctca gacagtggtt caaagttttt ttcttccatt    3180
tcaggtgtcg tgaggaatta gcttggtact aatacgactc actatagggga gacccaagct   3240
ggctagttaa gcttgatatc gaattcctgc agcccggggg atctgctagc atgaccgagt    3300
acaagcccac ggtgcgcctc gccacccgcg acgacgtccc cagggccgta cgcaccctcg    3360
ccgccgcgtt cgccgactac cccgccacgc gccacaccgt cgatccggac cgccacatcg    3420
agcgggtcac cgagctgcaa gaactcttcc tcacgcgcgt cgggctcgac atcggcaagg    3480
tgtgggtcgc ggacgacggc gccgcggtgg cggtctggac cacgccggag agcgtcgaag    3540
cgggggcggt gttcgccgag atcggcccgc gcatggccga gttgagcggt tcccggctgg    3600
ccgcgcagca acagatggaa ggcctcctgg cgccgcaccg gcccaaggag cccgcgtggt    3660
tcctggccac cgtcggcgtc tcgcccgacc accaggcaa gggtctgggc agcgccgtcg    3720
tgctccccgg agtggaggcg gccgagcgcg ccggggtgcc cgccttcctg gagacctccg    3780
cgccccgcaa cctccccttc tacgagcggc tcggcttcac cgtcaccgcc gacgtcgagg    3840
tgcccgaagg accgcgcacc tggtgcatga cccgcaagcc cggtgccact agtggctccg    3900
```

-continued

```
gcgagggcag aggaagtcta ctaacctgcg gagatgtgga agaaaatcct ggcccacata      3960
tgaagcccac cgagaacaac gaagacttca acatcgtggc cgtggccagc aacttcgcga      4020
ccacggatct cgatgctgac cgcgggaagt tgcccggcaa gaagctgccg ctggaggtgc      4080
tcaaagagat ggaagccaat gcccggaaag ctggctgcac caggggctgt ctgatctgcc      4140
tgtcccacat caagtgcacg cccaagatga agaagttcat cccaggacgc tgccacacct      4200
acgaaggcga caaagagtcc gcacagggcg gcataggcga ggcgatcgtc gacattcctg      4260
agattcctgg gttcaaggac ttggagccca tggagcagtt catcgcacag gtcgatctgt      4320
gtgtggactg cacaactggc tgcctcaaag ggcttgccaa cgtgcagtgt tctgacctgc      4380
tcaagaagtg gctgccgcaa cgctgtgcga ccttttgccag caagatccag ggccaggtgg      4440
acaagatcaa gggggccggt ggtgactaac tcgactccgg atgatcaggg ccctgtacag      4500
atatcgacaa tcaacctctg gattacaaaa tttgtgaaag attgactggt attcttaact      4560
atgttgctcc ttttacgcta tgtggatacg ctgctttaat gcctttgtat catgctattg      4620
cttcccgtat ggctttcatt ttctcctcct tgtataaatc ctggttgctg tctctttatg      4680
aggagttgtg gcccgttgtc aggcaacgtg gcgtggtgtg cactgtgttt gctgacgcaa      4740
cccccactgg ttggggcatt gccaccacct gtcagctcct ttccgggact ttcgctttcc      4800
ccctccctat tgccacggcg gaactcatcg ccgcctgcct tgcccgctgc tggacagggg      4860
ctcggctgtt gggcactgac aattccgtgg tgttgtcggg gaagctgacg tcctttccat      4920
ggctgctcgc ctgtgttgcc acctggattc tgcgcgggac gtccttctgc tacgtccctt      4980 cggcccctcaa tccagcggac cttccttccc gcggcctgct gccggctctg cggcctcttc      5040
cgcgtcttcg ccttcgccct cagacgagtc ggatctccct ttgggccgcc tccccgcctg      5100
gaattcgagc tcggtacctt taagaccaat gacttacaag gcagctgtag atcttagcca      5160
ctttttaaaa gaaaaggggg gactggaagg gctaattcac tcccaacgaa gacaagatct      5220 gcttttttgct tgtactgggt ctctctggtt agaccagatc tgagcctggg agctctctgg      5280
ctaactaggg aacccactgc ttaagcctca ataaagcttg ccttgagtgc ttcaagtagt      5340
gtgtgcccgt ctgttgtgtg actctggtaa ctagagatcc ctcagaccct tttagtcagt      5400
gtggaaaatc tctagcagta gtagttcatg tcatcttatt attcagtatt tataacttgc      5460
aaagaaatga atatcagaga gtgagaggaa cttgtttatt gcagcttata atggttacaa      5520
ataaagcaat agcatcacaa atttcacaaa taaagcattt ttttcactgc attctagttg      5580
tggtttgtcc aaactcatca atgtatctta tcatgtctgg ctctagctat cccgccccta      5640
actccgccca tcccgcccct aactccgccc agttccgccc attctccgcc ccatggctga      5700
ctaatttttt ttatttatgc agaggccgag gccgcctcgg cctctgagct attccagaag      5760
tagtgaggag gcttttttgg aggcctaggg acgtacccaa ttcgccctat agtgagtcgt      5820
attacgcgcg ctcactggcc gtcgttttac aacgtcgtga ctgggaaaac cctggcgtta      5880
cccaacttaa tcgccttgca gcacatcccc ctttcgccag ctggcgtaat agcgaagagg      5940
cccgcaccga tcgcccttcc caacagttgc gcagcctgaa tggcgaatgg gacgcgccct      6000
gtagcggcgc attaagcgcg gcgggtgtgg tggttacgcg cagcgtgacc gctacacttg      6060
ccagcgccct agcgcccgct cctttcgctt tcttcccttc ctttctcgcc acgttcgccg      6120
gctttccccg tcaagctcta aatcgggggc tccctttagg gttccgattt agtgctttac      6180
ggcacctcga ccccaaaaaa cttgattagg gtgatggttc acgtagtggg ccatcgccct      6240
gatagacggt ttttcgccct ttgacgttgg agtccacgtt ctttaatagt ggactcttgt      6300
```

```
tccaaactgg aacaacactc aaccctatct cggtctattc ttttgattta taagggattt    6360
tgccgatttc ggcctattgg ttaaaaaatg agctgattta acaaaaattt aacgcgaatt    6420
ttaacaaaat attaacgctt acaatttagg tggcacttttt cggggaaatg tgcgcggaac   6480
ccctatttgt ttattttttct aaatacattc aaatatgtat ccgctcatga acaataacc   6540 ctgataaatg cttcaataat attgaaaaag gaagagtatg agtattcaac atttccgtgt    6600
cgcccttatt ccctttttttg cggcatttttg ccttcctgtt tttgctcacc cagaaacgct  6660
ggtgaaagta aaagatgctg aagatcagtt gggtgcacga gtgggttaca tcgaactgga    6720
tctcaacagc ggtaagatcc ttgagagttt tcgccccgaa gaacgttttc caatgatgag    6780
cacttttaaa gttctgctat gtggcgcggt attatcccgt attgacgccg ggcaagagca    6840
actcggtcgc cgcatacact attctcagaa tgacttggtt gagtactcac cagtcacaga    6900
aaagcatctt acggatggca tgacagtaag agaattatgc agtgctgcca taaccatgag    6960
tgataacact gcggccaact tacttctgac aacgatcgga ggaccgaagg agctaaccgc    7020
ttttttgcac aacatggggg atcatgtaac tcgccttgat cgttgggaac cggagctgaa    7080
tgaagccata ccaaacgacg agcgtgacac cacgatgcct gtagcaatgg caacaacgtt    7140
gcgcaaacta ttaactggcg aactacttac tctagcttcc cggcaacaat aatagactg    7200 gatggaggcg gataaagttg caggaccact tctgcgctcg gcccttccgg ctggctggtt    7260
tattgctgat aaatctggag ccggtgagcg tgggtctcgc ggtatcattg cagcactggg    7320
gccagatggt aagccctccc gtatcgtagt tatctacacg acggggagtc aggcaactat    7380
ggatgaacga aatagacaga tcgctgagat aggtgcctca ctgattaagc attggtaact    7440
gtcagaccaa gtttactcat atatacttta gattgattta aaacttcatt tttaatttaa    7500
aaggatctag gtgaagatcc tttttgataa tctcatgacc aaaatccctt aacgtgagtt    7560
ttcgttccac tgagcgtcag accccgtaga aaagatcaaa ggatcttctt gagatccttt    7620
ttttctgcgc gtaatctgct gcttgcaaac aaaaaaacca ccgctaccag cggtggtttg    7680
tttgccggat caagagctac caactctttt tccgaaggta actggcttca gcagagcgca    7740
gataccaaat actgttcttc tagtgtagcc gtagttaggc caccacttca agaactctgt    7800
agcaccgcct acatacctcg ctctgctaat cctgttacca gtggctgctg ccagtggcga    7860
taagtcgtgt cttaccgggt tggactcaag acgatagtta ccggataagg cgcagcggtc    7920
gggctgaacg ggggggttcgt gcacacagcc cagcttggag cgaacgacct acaccgaact    7980
gagataccta cagcgtgagc tatgagaaag cgccacgctt cccgaaggga aaaggcgga    8040 caggtatccg gtaagcggca gggtcggaac aggagagcgc acgagggagc ttccaggggg    8100
aaacgcctgg tatctttata gtcctgtcgg gtttcgccac ctctgacttg agcgtcgatt    8160
tttgtgatgc tcgtcagggg ggcggagcct atggaaaaac gccagcaacg cggccttttt    8220
acggttcctg gccttttgct ggccttttgc tcacatgttc tttcctgcgt tatccctga    8280 ttctgtggat aaccgtatta ccgcctttga gtgagctgat accgctcgcc gcagccgaac    8340
gaccgagcgc agcgagtcag tgagcgagga agcggaagag cgcccaatac gcaaaccgcc    8400
tctccccgcg cgttggccga ttcattaatg cagctggcac gacaggtttc ccgactggaa    8460
agcgggcagt gagcgcaacg caattaatgt gagttagctc actcattagg caccccaggc    8520
tttacacttt atgcttccgg ctcgtatgtt gtgtggaatt gtgagcggat aacaatttca    8580
cacaggaaac agctatgacc atgattacgc caagcgcgca attaaccctc actaaaggga    8640
```

```
acaaaagctg gagctgcaag ctt                                          8663

<210> SEQ ID NO 95
<211> LENGTH: 7566
<212> TYPE: DNA
<213> ORGANISM: Artificial Sequence
<220> FEATURE:
<223> OTHER INFORMATION: MSCVhygro-GLuc-HA-G02

<400> SEQUENCE: 95
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaatgaccc tgtgccttat ttgaactaac caatcagttc    300
gcttctcgct tctgttcgcg cgcttctgct ccccgagctc aataaaagag cccacaaccc    360
ctcactcggc gcgccagtcc tccgatagac tgcgtcgccc gggtacccgt attcccaata    420
aagcctcttg ctgtttgcat ccgaatcgtg gactcgctga tccttgggag ggtctcctca    480
gattgattga ctgcccacct cggggggtctt tcatttggag gttccaccga gatttggaga    540
cccctgccca gggaccaccg accccccgc cgggaggtaa gctggccagc ggtcgtttcg    600
tgtctgtctc tgtctttgtg cgtgtttgtg ccggcatcta atgtttgcgc ctgcgtctgt    660
actagttagc taactagctc tgtatctggc ggacccgtgg tggaactgac gagttctgaa    720
cacccggccg caaccctggg agacgtccca gggactttgg gggccgtttt tgtggcccga    780
cctgaggaag ggagtcgatg tggaatccga ccccgtcagg atatgtggtt ctggtaggag    840
acgagaacct aaaacagttc ccgcctccgt ctgaattttt gctttcggtt tggaaccgaa    900
gccgcgcgtc ttgtctgctg cagcgctgca gcatcgttct gtgttgtctc tgtctgactg    960
tgtttctgta tttgtctgaa aattagggcc agactgttac cactcccta agtttgacct   1020 taggtcactg gaaagatgtc gagcggatcg ctcacaacca gtcggtagat gtcaagaaga   1080
gacgttgggt taccttctgc tctgcagaat ggccaacctt taacgtcgga tggccgcgag   1140
acggcacctt taaccgagac ctcatcaccc aggttaagat caaggtcttt tcacctggcc   1200
cgcatggaca cccagaccag gtcccctaca tcgtgacctg ggaagccttg cttttgacc   1260 ccctccctg ggtcaagccc tttgtacacc ctaagcctcc gcctcctctt cctccatccg   1320
ccccgtctct cccccttgaa cctcctcgtt cgacccccgcc tcgatcctcc ctttatccag   1380
ccctcactcc ttctctaggc gccggaatta gatccccacc atgaagccca ccgagaacaa   1440
cgaagacttc aacatcgtgg ccgtggccag caacttcgcg accacggatc tcgatgctga   1500
ccgcgggaag ttgcccggca agaagctgcc gctggaggtg ctcaaagaga tggaagccaa   1560
tgcccggaaa gctggctgca ccaggggctg tctgatctgc ctgtcccaca tcaagtgcac   1620
gcccaagatg aagaagttca tcccaggacg ctgccacacc tacgaaggcg acaaagagtc   1680
cgcacagggc ggcataggcg aggcgatcgt cgacattcct gagattcctg gttcaagga   1740 cttggagccc atggagcagt tcatcgcaca ggtcgatctg tgtgtggact gcacaactgg   1800
ctgcctcaaa gggcttgcca acgtgcagtg ttctgacctg ctcaagaagt ggctgccgca   1860
acgctgtgcg acctttgcca gcaagatcca gggccaggtg gacaagatca ggggggccgg   1920
tggtgacctc gagaccgatt tctaccccta cgatgtgccc gattacgctt agtctagagg   1980
gccctattct atagtgtcac ctaagtcgag gttaacgaat tctaccgggt aggggaggcg   2040
```

```
cttttcccaa ggcagtctgg agcatgcgct ttagcagccc cgctgggcac ttggcgctac   2100
acaagtggcc tctggcctcg cacacattcc acatccaccg gtaggcgcca accggctccg   2160
ttctttggtg gccccttcgc gccaccttct actcctcccc tagtcaggaa gttcccccc    2220 gccccgcagc tcgcgtcgtg caggacgtga caaatgaaag tagcacgtct cactagtctc   2280
gtgcagatgg acagcaccgc tgagcaatgg aagcgggtag gcctttgggg cagcggccaa   2340
tagcagcttt gctccttcgc tttctgggct cagaggctgg gaagggtgg gtccgggggc    2400 gggctcaggg gcgggctcag gggcggggcg ggcgcccgaa ggtcctccgg aggcccggca   2460
ttctgcacgc ttcaaaagcg cacgtctgcc gcgctgttct cctcttcctc atctccgggc   2520
ctttcgacct gcatcccgcc accatgaaaa agcctgaact caccgcgacg tctgtcgaga   2580
agtttctgat cgaaaagttc gacagcgtct ccgacctgat gcagctctcg gagggcgaag   2640
aatctcgtgc tttcagcttc gatgtaggag ggcgtggata tgtcctgcgg gtaaatagct   2700
gcgccgatgg tttctacaaa gatcgttatg tttatcggca ctttgcatcg gccgcgctcc   2760
cgattccgga agtgcttgac attggggaat tcagcgagag cctgacctat tgcatctccc   2820
gccgtgcaca gggtgtcacg ttgcaagacc tgcctgaaac cgaactgccc gctgttctgc   2880
agccggtcgc ggaggccatg gatgcgatcg ctgcggccga tcttagccag acgagcgggt   2940
tcggcccatt cggaccgcaa ggaatcggtc aatacactac atggcgtgat ttcatatgcg   3000
cgattgctga tccccatgtg tatcactggc aaactgtgat ggacgacacc gtcagtgcgt   3060
ccgtcgcgca ggctctcgat gagctgatgc tttgggccga ggactgcccc gaagtccggc   3120
acctcgtgca cgcggatttc ggctccaaca atgtcctgac ggacaatggc cgcataacag   3180
cggtcattga ctggagcgag gcgatgttcg gggattccca atacgaggtc gccaacatct   3240
tcttctggag gccgtggttg gcttgtatgg agcagcagac gcgctacttc gagcggaggc   3300
atccggagct gcaggatcg ccgcggctcc ggggcgtata tgctccgcat tggtcttgac    3360
caactctatc agagcttggt tgacggcaat ttcgatgatg cagcttgggc gcagggtcga   3420
tgcgacgcaa tcgtccgatc cggagccggg actgtcgggc gtacacaaat cgcccgcaga   3480
agcgcggccg tctggaccga tggctgtgta gaagtactcg ccgatagtgg aaaccgacgc   3540
cccagcactc gtccgagggc aaaggaatag agtagatgcc gaccgaacaa gagctgattt   3600
cgagaacgcc tcagccagca actcgcgcga gcctagcaag gcaaatgcga gagaacggcc   3660
ttacgcttgg tggcacagtt ctcgtccaca gttcgctaag ctcgctcggc tgggtcgcgg   3720
gagggccggt cgcagtgatt caggcccttc tggattgtgt tggtcccag gcacgattg     3780 tcatgcccac gcactcgggt gatctgactg atcccgcaga ttggagatcg ccgccgtgc    3840 ctgccgattg ggtgcagatc cgtcgacctg cagccaagct tatcgataaa ataaaagatt   3900
ttatttagtc tccagaaaaa ggggggaatg aaagacccca cctgtaggtt tggcaagcta   3960
gcttaagtaa cgccatttg caaggcatgg aaaatacata actgagaata gagaagttca    4020
gatcaaggtt aggaacagag agacagcaga atatgggcca acaggatat ctgtggtaag    4080 cagttcctgc cccggctcag ggccaagaac agatggtccc cagatgcggt cccgccctca   4140
gcagtttcta gagaaccatc agatgtttcc agggtgcccc aaggacctga atgaccctg    4200 tgccttattt gaactaacca atcagttcgc ttctcgcttc tgttcgcgcg cttctgctcc   4260
ccgagctcaa taaagagcc cacaacccct cactcggcgc gccagtcctc cgatagactg    4320
cgtcgcccgg gtaccgtgt atccaataaa ccctcttgca gttgcatccg acttgtggtc    4380
```

```
tcgctgttcc ttgggagggt ctcctctgag tgattgacta cccgtcagcg ggggtctttc    4440
atgggtaaca gtttcttgaa gttggagaac aacattctga gggtaggagt cgaatattaa    4500
gtaatcctga ctcaattagc cactgttttg aatccacata ctccaatact cctgaaatag    4560
ttcattatgg acagcgcaga agagctgggg agaattaatt cgtaatcatg gtcatagctg    4620
tttcctgtgt gaaattgtta tccgctcaca attccacaca acatacgagc cggaagcata    4680
aagtgtaaag cctggggtgc ctaatgagtg agctaactca cattaattgc gttgcgctca    4740
ctgcccgctt tccagtcggg aaacctgtcg tgccagctgc attaatgaat cggccaacgc    4800
gcggggagag gcggtttgcg tattgggcgc tcttccgctt cctcgctcac tgactcgctg    4860
cgctcggtcg ttcggctgcg gcgagcggta tcagctcact caaaggcggt aatacggtta    4920
tccacagaat cagggga taa cgcaggaaag aacatgtgag caaaaggcca gcaaaaggcc    4980
aggaaccgta aaaaggccgc gttgctggcg ttttt ccata ggctccgccc cctgacgag    5040 catcacaaaa atcgacgctc aagtcagagg tggcgaaacc cgacaggact ataaagatac    5100
caggcgtttc ccc ctggaag ctccctcgtg cgctctcctg ttccgaccct gccgcttacc    5160
ggatacctgt ccgcctttct cccttcggga agcgtggcgc tttctcatag ctcacgctgt    5220
aggtatctca gttcggtgta ggtcgttcgc tccaagctgg gctgtgtgca cgaaccccc    5280 gttcagcccg accgctgcgc cttatccggt aactatcgtc ttgagtccaa cccggtaaga    5340
cacgacttat cgccactggc agcagccact ggtaacagga ttagcagagc gaggtatgta    5400
ggcggtgcta cagagttctt gaagtggtgg cctaactacg gctacactag aaggacagta    5460
tttggtatct gcgctctgct gaagccagtt accttcggaa aaagagttgg tagctcttga    5520
tccggcaaac aaaccaccgc tggtagcggt ggtttttttg tttgcaagca gcagattacg    5580
cgcagaaaaa aaggatctca agaagatcct ttgatctttt ctacggggtc tgacgctcag    5640
tggaacgaaa actcacgtta agggattttg gtcatgagat tatcaaaaag gatcttcacc    5700
tagatccttt taaattaaaa atgaagtttt aaatcaatct aaagtatata tgagtaaact    5760
tggtctgaca gttaccaatg cttaatcagt gaggcaccta tctcagcgat ctgtctattt    5820
cgttcatcca tagttgcctg actccccgtc gtgtagataa ctacgatacg ggagggctta    5880
ccatctggcc ccagtgctgc aatgataccg cgagacccac gctcaccggc tccagattta    5940
tcagcaataa accagccagc cggaagggcc gagcgcagaa gtggtcctgc aactttatcc    6000
gcctccatcc agtctattaa ttgttgccgg gaagctagag taagtagttc gccagttaat    6060
agtttgcgca acgttgttgc cattgctaca ggcatcgtgg tgtcacgctc gtcgtttggt    6120
atggcttcat tcagctccgg ttcccaacga tcaaggcgag ttacatgatc ccccatgttg    6180
tgcaaaaaag cggttagctc cttcggtcct ccgatcgttg tcagaagtaa gttggccgca    6240
gtgttatcac tcatggttat ggcagcactg cataattctc ttactgtcat gccatccgta    6300
agatgctttt ctgtgactgg tgagtactca accaagtcat tctgagaata gtgtatgcgg    6360
cgaccgagtt gctcttgccc ggcgtcaata cgggataata ccgcgccaca tagcagaact    6420
ttaaaagtgc tcatcattgg aaaacgttct tcggggcgaa aactctcaag gatcttaccg    6480
ctgttgagat ccagttcgat gtaacccact cgtgcaccca actgatcttc agcatctttt    6540
actttcacca gcgtttctgg gtgagcaaaa acaggaaggc aaaatgccgc aaaaaaggga    6600
ataagggcga cacggaaatg ttgaatactc atactcttcc tttttcaata ttattgaagc    6660
atttatcagg gttattgtct catgagcgga tacatatttg aatgtattta gaaaaataaa    6720
caaatagggg ttccgcgcac atttccccga aaagtgccac ctgacgtcta agaaaccatt    6780
```

```
attatcatga cattaaccta taaaaatagg cgtatcacga ggccctttcg tctcgcgcgt    6840
ttcggtgatg acggtgaaaa cctctgacac atgcagctcc cggagacggt cacagcttgt    6900
ctgtaagcgg atgccgggag cagacaagcc cgtcagggcg cgtcagcggg tgttggcggg    6960
tgtcggggct ggcttaacta tgcggcatca gagcagattg tactgagagt gcaccatatg    7020
cggtgtgaaa taccgcacag atgcgtaagg agaaaatacc gcatcaggcg ccattcgcca    7080
ttcaggctgc gcaactgttg ggaagggcga tcggtgcggg cctcttcgct attacgccag    7140
ctggcgaaag ggggatgtgc tgcaaggcga ttaagttggg taacgccagg gttttcccag    7200
tcacgacgtt gtaaaacgac ggcgcaagga atggtgcatg caaggagatg cgcccaaca    7260
gtcccccggc cacggggcct gccaccatac ccacgccgaa acaagcgctc atgagcccga    7320
agtggcgagc ccgatcttcc ccatcggtga tgtcggcgat ataggcgcca gcaaccgcac    7380
ctgtggcgcc ggtgatgccg gccacgatgc gtccggcgta gaggcgatta gtccaatttg    7440
ttaaagacag gatatcagtg gtccaggctc tagttttgac tcaacaatat caccagctga    7500
agcctataga gtacgagcca tagataaaat aaaagatttt atttagtctc cagaaaaagg    7560
ggggaa                                                              7566
```

<210> SEQ ID NO 96
<211> LENGTH: 6884
<212> TYPE: DNA
<213> ORGANISM: Artificial Sequence
<220> FEATURE:
<223> OTHER INFORMATION: MSCVpac-GLUC-HA-R03

<400> SEQUENCE: 96

```
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaatgaccc tgtgccttat ttgaactaac caatcagttc     300
gcttctcgct tctgttcgcg cgcttctgct ccccgagctc aataaaagag cccacaaccc     360
ctcactcggc gcgccagtcc tccgatagac tgcgtcgccc gggtacccgt attcccaata     420
aagcctcttg ctgtttgcat ccgaatcgtg gactcgctga tccttgggag ggtctcctca     480
gattgattga ctgcccacct cggggtctt tcatttggag gttccaccga gatttggaga     540
cccctgccca gggaccaccg acccccccgc cgggaggtaa gctggccagc ggtcgtttcg     600
tgtctgtctc tgtctttgtg cgtgtttgtg ccggcatcta atgtttgcgc ctgcgtctgt     660
actagttagc taactagctc tgtatctggc ggacccgtgg tggaactgac gagttctgaa     720
cacccggccg caaccctggg agacgtccca gggactttgg gggccgtttt tgtggcccga     780
cctgaggaag ggagtcgatg tggaatccga ccccgtcagg atatgtggtt ctggtaggag     840
acgagaacct aaaacagttc ccgcctccgt ctgaatttt gctttcggtt tggaaccgaa     900
gccgcgcgtc ttgtctgctg cagcgctgca gcatcgttct gtgttgtctc tgtctgactg     960
tgtttctgta tttgtctgaa aattagggcc agactgttac cactccctta agtttgacct    1020
taggtcactg gaaagatgtc gagcggatcg ctcacaacca gtcggtagat gtcaagaaga    1080
gacgttggga taccttctgc tctgcagaat ggccaacctt aacgtcgga tggccgcgag    1140
acggcacctt taaccgagac ctcatcaccc aggttaagat caaggtcttt tcacctggcc    1200
```

```
cgcatggaca cccagaccag gtcccctaca tcgtgacctg ggaagccttg gcttttgacc    1260
cccctccctg ggtcaagccc tttgtacacc ctaagcctcc gcctcctctt cctccatccg    1320
ccccgtctct cccccttgaa cctcctcgtt cgaccccgcc tcgatcctcc ctttatccag    1380
ccctcactcc ttctctaggc gccggaatta gatcccacc atgaagccca ccgagaacaa     1440
cgaagacttc aacatcgtgg ccgtggccag caacttcgcg accacggatc tcgatgctga    1500
ccgcgggaag ttgcccggca agaagctgcc gctggaggtg ctcaaagaga tggaagccaa    1560
tgcccggaaa gctggctgca ccaggggctg tctgatctgc ctgtcccaca tcaagtgcac    1620
gcccaagatg aagaagttca tcccaggacg ctgccacacc tacgaaggcg acaaagagtc    1680
cgcacagggc ggcataggcg aggcgatcgt cgacattcct gagattcctg ggttcaagga    1740
cttggagccc atggagcagt tcatcgcaca ggtcgatctg tgtgtggact gcacaactgg    1800
ctgcctcaaa gggcttgcca acgtgcagtg ttctgacctg ctcaagaagt ggctgccgca    1860
acgctgtgcg acctttgcca gcaagatcca gggccaggtg acaagatca aggggggccgg    1920
tggtgacctc gagaccgatt tctacccta cgatgtgccc gattacgctt agtctagagg     1980
gcctattct atagtgtcac ctaagtcgag gttaacgaat tctaccgggt aggggaggcg     2040
cttttcccaa ggcagtctgg agcatgcgct ttagcagccc cgctgggcac ttggcgctac    2100
acaagtggcc tctggcctcg cacacattcc acatccaccg gtaggcgcca accggctccg    2160
ttctttggtg gccccttcgc gccaccttct actcctcccc tagtcaggaa gttcccccc     2220
gccccgcagc tcgcgtcgtg caggacgtga caaatggaag tagcacgtct cactagtctc    2280
gtgcagatgg acagcaccgc tgagcaatgg aagcgggtag gccttttgggg cagcggccaa    2340
tagcagcttt gctccttcgc tttctgggct cagaggctgg aaggggtgg gtccggggc     2400
gggctcaggg gcgggctcag gggcggggcg gcgcccgaa ggtcctccgg aggcccggca     2460
ttctgcacgc ttcaaaagcg cacgtctgcc gcgctgttct cctcttcctc atctccgggc    2520
cttttcgacct gcagcccaag cttaccatga ccgagtacaa gcccacggtg cgcctcgcca    2580
cccgcgacga cgtccccagg gccgtacgca ccctcgccgc cgcgttcgcc gactacccg     2640
ccacgcgcca caccgtcgat ccggaccgcc acatcgagcg ggtcaccgag ctgcaagaac    2700
tcttcctcac gcgcgtcggg ctcgacatcg gcaaggtgtg ggtcgcggac gacggcgccg    2760
cggtggcggt ctggaccacg ccggagagcg tcgaagcggg ggcggtgttc gccgagatcg    2820
gcccgcgcat ggccgagttg agcggttccc ggctggccgc gcagcaacag atggaaggcc    2880
tcctggcgcc gcaccggccc aaggagcccg cgtggttcct ggccaccgtc ggcgtctcgc    2940
ccgaccacca gggcaagggt ctgggcagcg ccgtcgtgct ccccggagtg gaggcggccg    3000
agcgcgccgg ggtgcccgcc ttcctggaga cctccgcgcc ccgcaacctc cccttctacg    3060
agcggctcgg cttcaccgtc accgccgacg tcgaggtgcc cgaaggaccg cgcacctggt    3120
gcatgacccg caagcccggt gcctgacgcc cgcccacga cccgcagcgc ccgaccgaaa    3180
ggagcgcacg acccatgca tcgataaat aaaagatttt atttagtctc cagaaaaagg     3240
ggggaatgaa agaccccacc tgtaggtttg gcaagctagc ttaagtaacg ccattttgca    3300
aggcatggaa aatacataac tgagaataga gaagttcaga tcaaggttag aacagagag    3360
acagcagaat atgggccaaa caggatatct gtggtaagca gttcctgccc cggctcaggg    3420
ccaagaacag atggtcccca gatgcggtcc cgccctcagc agtttctaga gaaccatcag    3480
atgtttccag ggtgccccaa ggacctgaaa tgacctgtg ccttatttga actaaccaat     3540
cagttcgctt ctcgcttctg ttcgcgcgct tctgctcccc gagctcaata aaagagccca    3600
```

```
caacccctca ctcggcgcgc cagtcctccg atagactgcg tcgcccgggt acccgtgtat    3660
ccaataaacc ctcttgcagt tgcatccgac ttgtggtctc gctgttcctt gggagggtct    3720
cctctgagtg attgactacc cgtcagcggg ggtctttcat gggtaacagt ttcttgaagt    3780
tggagaacaa cattctgagg gtaggagtcg aatattaagt aatcctgact caattagcca    3840
ctgttttgaa tccacatact ccaatactcc tgaaatagtt cattatggac agcgcagaag    3900
agctggggag aattaattcg taatcatggt catagctgtt tcctgtgtga aattgttatc    3960
cgctcacaat tccacacaac atacgagccg aagcataaa  gtgtaaagcc tggggtgcct    4020
aatgagtgag ctaactcaca ttaattgcgt tgcgctcact gcccgctttc cagtcgggaa    4080
acctgtcgtg ccagctgcat taatgaatcg gccaacgcgc ggggagaggc ggtttgcgta    4140
ttgggcgctc ttccgcttcc tcgctcactg actcgctgcg ctcggtcgtt cggctgcggc    4200
gagcggtatc agctcactca aaggcggtaa tacggttatc cacagaatca ggggataacg    4260
caggaaagaa catgtgagca aaaggccagc aaaaggccag gaaccgtaaa aaggccgcgt    4320
tgctggcgtt tttccatagg ctccgccccc ctgacgagca tcacaaaaat cgacgctcaa    4380
gtcagaggtg gcgaaacccg acaggactat aaagatacca ggcgtttccc cctggaagct    4440
ccctcgtgcg ctctcctgtt ccgaccctgc cgcttaccgg atacctgtcc gcctttctcc    4500
cttcgggaag cgtggcgctt tctcatagct cacgctgtag gtatctcagt tcggtgtagg    4560
tcgttcgctc caagctgggc tgtgtgcacg aaccccccgt tcagcccgac cgctgcgcct    4620
tatccggtaa ctatcgtctt gagtccaacc cggtaagaca cgacttatcg ccactggcag    4680
cagccactgg taacaggatt agcagagcga ggtatgtagg cggtgctaca gagttcttga    4740
agtggtggcc taactacggc tacactagaa ggacagtatt tggtatctgc gctctgctga    4800
agccagttac cttcggaaaa agagttggta gctcttgatc cggcaaacaa accaccgctg    4860
gtagcggtgg tttttttgtt tgcaagcagc agattacgcg cagaaaaaaa ggatctcaag    4920
aagatccttt gatcttttct acggggtctg acgctcagtg gaacgaaaac tcacgttaag    4980 ggatttggt  catgagatta tcaaaaagga tcttcaccta gatcctttta aattaaaaat    5040
gaagttttaa atcaatctaa agtatatatg agtaaacttg gtctgacagt taccaatgct    5100
taatcagtga ggcacctatc tcagcgatct gtctatttcg ttcatccata gttgcctgac    5160
tccccgtcgt gtagataact acgatacggg agggcttacc atctggcccc agtgctgcaa    5220
tgataccgcg agacccacgc tcaccggctc cagatttatc agcaataaac cagccagccg    5280
gaagggccga gcgcagaagt ggtcctgcaa ctttatccgc ctccatccag tctattaatt    5340
gttgccggga agctagagta agtagttcgc cagttaatag tttgcgcaac gttgttgcca    5400
ttgctacagg catcgtggtg tcacgctcgt cgtttggtat ggcttcattc agctccggtt    5460
cccaacgatc aaggcgagtt acatgatccc ccatgttgtg caaaaaagcg gttagctcct    5520
tcggtcctcc gatcgttgtc agaagtaagt tggccgcagt gttatcactc atggttatgg    5580
cagcactgca taattctctt actgtcatgc catccgtaag atgcttttct gtgactggtg    5640
agtactcaac caagtcattc tgagaatagt gtatgcggcg accgagttgc tcttgcccgg    5700
cgtcaatacg ggataatacc gcgccacata gcagaacttt aaaagtgctc atcattggaa    5760
aacgttcttc ggggcgaaaa ctctcaagga tcttaccgct gttgagatcc agttcgatgt    5820
aacccactcg tgcacccaac tgatcttcag catcttttac tttcaccagc gtttctgggt    5880
gagcaaaaac aggaaggcaa aatgccgcaa aaaagggaat aagggcgaca cggaaatgtt    5940
```

```
gaatactcat actcttcctt tttcaatatt attgaagcat ttatcagggt tattgtctca    6000
tgagcggata catatttgaa tgtatttaga aaaataaaca aatagggggtt ccgcgcacat    6060 ttccccgaaa agtgccacct gacgtctaag aaaccattat tatcatgaca ttaacctata    6120
aaaataggcg tatcacgagg cccttttcgtc tcgcgcgttt cggtgatgac ggtgaaaacc    6180
tctgacacat gcagctcccg gagacggtca cagcttgtct gtaagcggat gccgggagca    6240
gacaagcccg tcagggcgcg tcagcgggtg ttggcgggtg tcggggctgg cttaactatg    6300
cggcatcaga gcagattgta ctgagagtgc accatatgcg gtgtgaaata ccgcacagat    6360
gcgtaaggag aaaataccgc atcaggcgcc attcgccatt caggctgcgc aactgttggg    6420
aagggcgatc ggtgcgggcc tcttcgctat tacgccagct ggcgaaaggg ggatgtgctg    6480
caaggcgatt aagttgggta acgccagggt tttcccagtc acgacgttgt aaaacgacgg    6540
cgcaaggaat ggtgcatgca aggagatggc gcccaacagt cccccggcca cggggcctgc    6600
caccataccc acgccgaaac aagcgctcat gagcccgaag tggcgagccc gatcttcccc    6660
atcggtgatg tcgcgatat aggcgccagc aaccgcacct gtggcgccgg tgatgccggc    6720
cacgatgcgt ccggcgtaga ggcgattagt ccaatttgtt aaagacagga tatcagtggt    6780
ccaggctcta gttttgactc aacaatatca ccagctgaag cctatagagt acgagccata    6840
gataaaataa aagatttat ttagtctcca gaaaagggg ggaa    6884
```

<210> SEQ ID NO 97
<211> LENGTH: 7188
<212> TYPE: DNA
<213> ORGANISM: Artificial Sequence
<220> FEATURE:
<223> OTHER INFORMATION: MSCVneo-Lucia-Luc-x3-Flag-B08

<400> SEQUENCE: 97

```
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaatgaccc tgtgccttat ttgaactaac caatcagttc     300
gcttctcgct tctgttcgcg cgcttctgct ccccgagctc aataaaagag cccacaaccc     360
ctcactcggc gcgccagtcc tccgatagac tgcgtcgccc gggtacccgt attcccaata     420
aagcctcttg ctgtttgcat ccgaatcgtg gactcgctga tccttgggag ggtctcctca     480
gattgattga ctgcccacct cgggggtctt tcatttggag gttccaccga gatttggaga     540
cccctgccca gggaccaccg accccccgc cgggaggtaa gctggccagc ggtcgtttcg     600
tgtctgtctc tgtctttgtg cgtgtttgtg ccggcatcta atgtttgcgc ctgcgtctgt     660
actagttagc taactagctc tgtatctggc ggacccgtgg tggaactgac gagttctgaa     720
cacccggccg caaccctggg agacgtccca gggactttgg gggccgtttt tgtggcccga     780
cctgaggaag ggagtcgatg tggaatccga ccccgtcagg atatgtggtt ctggtaggag     840
acgagaacct aaaacagttc ccgcctccgt ctgaattttt gctttcggtt tggaaccgaa     900
gccgcgcgtc ttgtctgctg cagcgctgca gcatcgttct gtgttgtctc tgtctgactg     960
tgtttctgta tttgtctgaa aattagggcc agactgttac cactcccttta agtttgacct    1020 taggtcactg gaaagatgtc gagcggatcg ctcacaacca gtcggtagat gtcaagaaga    1080
gacgttgggt taccttctgc tctgcagaat ggccaacctt taacgtcgga tggccgcgag    1140
```

```
acggcacctt taaccgagac ctcatcaccc aggttaagat caaggtcttt tcacctggcc    1200
cgcatggaca cccagaccag gtcccctaca tcgtgacctg ggaagccttg gcttttgacc    1260
cccctccctg ggtcaagccc tttgtacacc ctaagcctcc gcctcctctt cctccatccg    1320
ccccgtctct cccccttgaa cctcctcgtt cgacccgcc tcgatcctcc ctttatccag    1380
ccctcactcc ttctctaggc gccggaatta gatccccacc atgaaaccca ctgaaatcaa    1440
tgaagacctc aatatagctg ctgtggcctc caactttgcc accacagatc ttgagactga    1500
cctgttcacc aactgggaga ccatgaatgt gattagcact gacacagagc aggtgaacac    1560
agatgctgac aggggcaagc tgcctggcaa aaaactcccc ccagatgtcc tgagggagct    1620
ggaggccaat gccagaaggg ctggttgcac aagaggctgc ctcatttgcc tctcccacat    1680
taagtgcacc cctaagatga agaaatttat ccctggcagg tgccacactt atgaaggtga    1740
aaaggagtct gctcagggag ggattggaga ggcaattgtt gatatcccag agattcctgg    1800
cttcaaggat aaggagccac tggaccagtt tattgctcaa gtggacctct gtgctgattg    1860
caccactggc tgtctgaagg gccttgccaa tgtccagtgc tctgacctcc tgaagaagtg    1920
gcttccccag aggtgtacca cttttgccag caagattcag ggtagggtgg acaaaatcaa    1980
gggtctggct ggggacagac tcgagaccga tttctacgac tacaaggacg acgatgacaa    2040
ggattataaa gatgatgacg ataaagtcga gaccgatttc tacgactaca aggacgacga    2100
tgacaagtag tctagagggc cctattctat agtgtcacct aagtcgacga attctaccgg    2160
gtaggggagg cgcttttccc aaggcagtct ggagcatgcg ctttagcagc cccgctgggc    2220
acttggcgct acacaagtgg cctctggcct cgcacacatt ccacatccac cggtaggcgc    2280
caaccggctc cgttctttgg tggcccttc gcgccacctt ctactcctcc cctagtcagg    2340
aagttccccc ccgcccgca gctcgcgtcg tgcaggacgt gacaaatgga agtagcacgt    2400
ctcactagtc tcgtgcagat ggacagcacc gctgagcaat ggaagcgggt aggccttggg    2460
ggcagcggcc aatagcagct ttgctccttc gctttctggg ctcagaggct gggaaggggt    2520
gggtccgggg gcgggctcag gggcgggctc aggggcgggg cggcgcccg aaggtcctcc    2580 ggaggcccgg cattctgcac gcttcaaaag cgcacgtctg ccgcgctgtt ctcctcttcc    2640
tcatctccgg gcctttcgac ctgcagccaa tatgggatcg gccattgaac aagatggatt    2700
gcacgcaggt tctccggccg cttgggtgga gaggctattc ggctatgact gggcacaaca    2760
gacaatcggc tgctctgatg ccgccgtgtt ccggctgtca gcgcaggggc gcccggttct    2820
ttttgtcaag accgacctgt ccggtgccct gaatgaactg caggacgagg cagcgcggct    2880
atcgtggctg gccacgacgg gcgttccttg cgcagctgtg ctcgacgttg tcactgaagc    2940
gggaagggac tggctgctat tgggcgaagt gccggggcag gatctcctgt catctcacct    3000
tgctcctgcc gagaaagtat ccatcatggc tgatgcaatg cggcggctgc atacgcttga    3060
tccggctacc tgcccattcg accaccaagc gaaacatcgc atcgagcgag cacgtactcg    3120
gatggaagcc ggtcttgtcg atcaggatga tctggacgaa gagcatcagg ggctcgcgcc    3180
agccgaactg ttcgccaggc tcaaggcgcg catgcccgac ggcgaggatc tcgtcgtgac    3240
ccatggcgat gcctgcttgc cgaatatcat ggtggaaaat ggccgctttt ctggattcat    3300
cgactgtggc cggctgggtg tggcggaccg ctatcaggac atagcgttgg ctacccgtga    3360
tattgctgaa gagcttggcg gcgaatgggc tgaccgcttc ctcgtgcttt acggtatcgc    3420
cgctcccgat tcgcagcgca tcgccttcta tcgccttctt gacgagttct tctgagggga    3480
```

```
tccgtcgacc tgcagccaag cttatcgata aaataaaaga tttttatttag tctccagaaa    3540 aagggggaa tgaaagaccc cacctgtagg tttggcaagc tagcttaagt aacgccattt      3600
tgcaaggcat ggaaaataca taactgagaa tagagaagtt cagatcaagg ttaggaacag    3660
agagacagca gaatatgggc caaacaggat atctgtggta agcagttcct gccccggctc    3720
agggccaaga acagatggtc cccagatgcg gtcccgccct cagcagtttc tagagaacca   3780
tcagatgttt ccagggtgcc ccaaggacct gaaatgaccc tgtgccttat ttgaactaac    3840
caatcagttc gcttctcgct tctgttcgcg cgcttctgct ccccgagctc aataaaagag    3900
cccacaaccc ctcactcggc gcgccagtcc tccgatagac tgcgtcgccc gggtacccgt    3960
gtatccaata aaccctcttg cagttgcatc cgacttgtgg tctcgctgtt ccttgggagg    4020
gtctcctctg agtgattgac tacccgtcag cggggtcttt catgggtaa cagtttcttg    4080 aagttggaga acaacattct gagggtagga gtcgaatatt aagtaatcct gactcaatta   4140
gccactgttt tgaatccaca tactccaata ctcctgaaat agttcattat ggacagcgca  4200
gaagagctgg ggagaattaa ttcgtaatca tggtcatagc tgtttcctgt gtgaaattgt    4260
tatccgctca caattccaca caacatacga gccggaagca taaagtgtaa agcctggggt   4320
gcctaatgag tgagctaact cacattaatt gcgttgcgct cactgcccgc tttccagtcg    4380
ggaaacctgt cgtgccagct gcattaatga atcggccaac gcgcggggag aggcggtttg   4440
cgtattgggc gctcttccgc ttcctcgctc actgactcgc tgcgctcggt cgttcggctg    4500
cggcgagcgg tatcagctca ctcaaaggcg gtaatacggt tatccacaga atcaggggat   4560
aacgcaggaa agaacatgtg agcaaaaggc cagcaaaagg ccaggaaccg taaaaaggcc   4620
gcgttgctgg cgttttttcca taggctccgc cccctgacg agcatcacaa aaatcgacgc   4680
tcaagtcaga ggtggcgaaa cccgacagga ctataaagat accaggcgtt ccccctggaa   4740
agctccctcg tgcgctctcc tgttccgacc ctgccgctta ccggatacct gtccgccttt    4800
ctcccttcgg gaagcgtggc gctttctcat agctcacgct gtaggtatct cagttcggtg    4860
taggtcgttc gctccaagct gggctgtgtg cacgaacccc ccgttcagcc cgaccgctgc    4920
gccttatccg gtaactatcg tcttgagtcc aacccggtaa gacacgactt atcgccactg    4980
gcagcagcca ctggtaacag gattagcaga gcgaggtatg taggcggtgc tacagagttc    5040
ttgaagtggt ggcctaacta cggctacact agaaggacag tatttggtat ctgcgctctg   5100
ctgaagccag ttaccttcgg aaaaagagtt ggtagctctt gatccggcaa acaaaccacc   5160
gctggtagcg gtggttttttt tgtttgcaag cagcagatta cgcgcagaaa aaaggatct    5220 caagaagatc ctttgatctt ttctacgggg tctgacgctc agtggaacga aaactcacgt    5280
taagggattt tggtcatgag attatcaaaa aggatcttca cctagatcct tttaaattaa   5340
aaatgaagtt ttaaatcaat ctaaagtata tatgagtaaa cttggtctga cagttaccaa   5400
tgcttaatca gtgaggcacc tatctcagcg atctgtctat ttcgttcatc catagttgcc    5460
tgactccccg tcgtgtagat aactacgata cgggagggct taccatctgg ccccagtgct   5520
gcaatgatac cgcgagaccc acgctcaccg gctccagatt tatcagcaat aaaccagcca   5580
gccgaagggg ccgagcgcag aagtggtcct gcaactttat ccgcctccat ccagtctatt   5640
aattgttgcc gggaagctag agtaagtagt tcgccagtta atagtttgcg caacgttgtt   5700
gccattgcta caggcatcgt ggtgtcacgc tcgtcgtttg gtatggcttc attcagctcc   5760
ggttcccaac gatcaaggcg agttacatga tcccccatgt tgtgcaaaaa agcggttagc   5820
tccttcggtc ctccgatcgt tgtcagaagt aagttggccg cagtgttatc actcatggtt   5880
```

```
atggcagcac tgcataattc tcttactgtc atgccatccg taagatgctt ttctgtgact    5940
ggtgagtact caaccaagtc attctgagaa tagtgtatgc ggcgaccgag ttgctcttgc    6000
ccggcgtcaa tacggataa taccgcgcca catagcagaa ctttaaaagt gctcatcatt    6060
ggaaaacgtt cttcggggcg aaaactctca aggatcttac cgctgttgag atccagttcg    6120
atgtaaccca ctcgtgcacc caactgatct tcagcatctt ttactttcac cagcgtttct    6180
gggtgagcaa aaacaggaag gcaaaatgcc gcaaaaaagg gaataagggc gacacggaaa    6240
tgttgaatac tcatactctt cctttttcaa tattattgaa gcatttatca gggttattgt    6300
ctcatgagcg gatacatatt tgaatgtatt tagaaaaata aacaaatagg ggttccgcgc    6360
acatttcccc gaaaagtgcc acctgacgtc taagaaacca ttattatcat gacattaacc    6420
tataaaaata ggcgtatcac gaggcccttt cgtctcgcgc gtttcggtga tgacggtgaa    6480
aacctctgac acatgcagct cccggagacg gtcacagctt gtctgtaagc ggatgccggg    6540
agcagacaag cccgtcaggg cgcgtcagcg ggtgttggcg ggtgtcgggg ctggcttaac    6600
tatgcggcat cagagcagat tgtactgaga gtgcaccata tgcggtgtga ataccgcac     6660
agatgcgtaa ggagaaaata ccgcatcagg cgccattcgc cattcaggct gcgcaactgt    6720
tgggaagggc gatcggtgcg ggcctcttcg ctattacgcc agctggcgaa agggggatgt    6780
gctgcaaggc gattaagttg ggtaacgcca gggttttccc agtcacgacg ttgtaaaacg    6840
acggccaag gaatggtgca tgcaaggaga tggcgcccaa cagtccccg gccacggggc      6900
ctgccaccat acccacgccg aaacaagcgc tcatgagccc gaagtggcga gcccgatctt    6960
ccccatcggt gatgtcggcg atataggcgc cagcaaccgc acctgtggcg ccggtgatgc    7020
cggccacgat gcgtccggcg tagaggcgat tagtccaatt tgttaaagac aggatatcag    7080
tggtccaggc tctagttttg actcaacaat atcaccagct gaagcctata gagtacgagc    7140
catagataaa ataaaagatt ttatttagtc tccagaaaaa ggggggaa              7188
```

<210> SEQ ID NO 98
<211> LENGTH: 7476
<212> TYPE: DNA
<213> ORGANISM: Artificial Sequence
<220> FEATURE:
<223> OTHER INFORMATION: pLENTI-Gluc-Flag-blast-B07

<400> SEQUENCE: 98

```
aatgtagtct tatgcaatac tcttgtagtc ttgcaacatg gtaacgatga gttagcaaca     60
tgccttacaa ggagagaaaa agcaccgtgc atgccgattg gtggaagtaa ggtggtacga    120
tcgtgcctta ttaggaaggc aacagacggg tctgacatgg attggacgaa ccactgaatt    180
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac ccttttagtc agtgtggaaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcggggggaga    600
attagatcgc gatgggaaaa aattcggtta aggccagggg gaagaaaaaa atataaatta    660
aaacatatag tatgggcaag cagggagcta gaacgattcg cagttaatcc tggcctgtta    720
```

```
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620 agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgata   1800
agcttgggag ttccgcgtta cataacttac ggtaaatggc ccgcctggct gaccgcccaa   1860
cgacccccgc ccattgacgt caataatgac gtatgttccc atagtaacgc caatagggac   1920
tttccattga cgtcaatggg tggagtattt acggtaaact gcccacttgg cagtacatca   1980
agtgtatcat atgccaagta cgccccctat tgacgtcaat gacggtaaat ggcccgcctg   2040
gcattatgcc cagtacatga ccttatggga ctttcctact tggcagtaca tctacgtatt   2100
agtcatcgct attaccatgg tgatgcggtt ttggcagtac atcaatgggc gtggatagcg   2160
gtttgactca cggggatttc caagtctcca ccccattgac gtcaatggga gtttgttttg   2220
gcaccaaaat caacgggact ttccaaaatg tcgtaacaac tccgccccat tgacgcaaat   2280
gggcggtagg cgtgtacggt gggaggtcta tataagcaga gctcgtttag tgaaccgtca   2340
gatcgcctgg agacgccatc cacgctgttt tgacctccat agaagacacc gactctagag   2400 gatcccacc atgaagccca ccgagaacaa cgaagacttc aacatcgtgg ccgtggccag   2460
caacttcgcg accacggatc tcgatgctga ccgcgggaag ttgcccggca agaagctgcc   2520
gctggaggtg ctcaaagaga tggaagccaa tgcccggaaa gctggctgca ccaggggctg   2580
tctgatctgc ctgtcccaca tcaagtgcac gcccaagatg aagaagttca tcccaggacg   2640
ctgccacacc tacgaaggcg acaaagagtc cgcacagggc ggcataggcg aggcgatcgt   2700
cgacattcct gagattcctg ggttcaagga cttggagccc atggagcagt tcatcgcaca   2760
ggtcgatctg tgtgtggact gcacaactgg ctgcctcaaa gggcttgcca acgtgcagtg   2820
ttctgacctc ctcaagaagt ggctgccgca acgctgtgcg acctttgcca gcaagatcca   2880
gggccaggtg gacaagatca aggggccgg tggtgacctc gagaccgatt tctacgacta   2940
caaggacgac gatgacaagt agtctagagg gcccgcggtt cgaaggtaag cctatcccta   3000 acccctctcct cggtctcgat tctacgcgta ccggttagta atgagtttgg aattaattct   3060
gtggaatgtg tgtcagttag ggtgtggaaa gtccccaggc tccccaggca ggcagaagta   3120
```

```
tgcaaagcat gcatctcaat tagtcagcaa ccaggtgtgg aaagtcccca ggctccccag   3180
caggcagaag tatgcaaagc atgcatctca attagtcagc aaccatagtc ccgcccctaa   3240
ctccgcccat cccgccccta actccgccca gttccgccca ttctccgccc catggctgac   3300 taatttttt tatttatgca gaggccgagg ccgcctctgc ctctgagcta ttccagaagt   3360
agtgaggagg cttttttgga ggcctaggct tttgcaaaaa gctcccggga gcttgtatat   3420 ccatttcgg atctgatcag cacgtgttga caattaatca tcggcatagt atatcggcat   3480
agtataatac gacaaggtga ggaactaaac catggccaag cctttgtctc aagaagaatc   3540
caccctcatt gaaagagcaa cggctacaat caacagcatc cccatctctg aagactacag   3600
cgtcgccagc gcagctctct ctagcgacgg ccgcatcttc actggtgtca atgtatatca   3660
ttttactggg ggaccttgtg cagaactcgt ggtgctgggc actgctgctg ctgcggcagc   3720
tggcaacctg acttgtatcg tcgcgatcgg aaatgagaac aggggcatct tgagcccctg   3780
cggacggtgc cgacaggtgc ttctcgatct gcatcctggg atcaaagcca tagtgaagga   3840
cagtgatgga cagccgacgg cagttgggat tcgtgaattg ctgccctctg ttatgtgtg   3900 ggagggctaa gcacaattcg agctcggtac ctttaagacc aatgacttac aaggcagctg   3960
tagatcttag ccacttttta aagaaaagg ggggactgga agggctaatt cactcccaac   4020
gaagacaaga tctgcttttt gcttgtactg ggtctctctg gttagaccag atctgagcct   4080
gggagctctc tggctaacta gggaacccac tgcttaagcc tcaataaagc ttgccttgag   4140
tgcttcaagt agtgtgtgcc cgtctgttgt gtgactctgg taactagaga tccctcagac   4200
ccttttagtc agtgtggaaa atctctagca gtagtagttc atgtcatctt attattcagt   4260
atttataact tgcaaagaaa tgaatatcag agagtgagag gaacttgttt attgcagctt   4320
ataatggtta caaataaagc aatagcatca caaatttcac aaataaagca tttttttcac   4380
tgcattctag ttgtggtttg tccaaactca tcaatgtatc ttatcatgtc tggctctagc   4440
tatcccgccc ctaactccgc ccatcccgcc cctaactccg cccagttccg cccattctcc   4500
gccccatggc tgactaattt ttttatttta tgcagaggcc gaggccgcct cggcctctga   4560
gctattccag aagtagtgag gaggcttttt tggaggccta gggacgtacc caattcgccc   4620
tatagtgagt cgtattacgc gcgctcactg gccgtcgttt tacaacgtcg tgactgggaa   4680
aaccctggcg ttacccaact taatcgcctt gcagcacatc cccctttcgc cagctggcgt   4740
aatagcgaag aggcccgcac cgatcgccct tcccaacagt tgcgcagcct gaatggcgaa   4800
tgggacgcgc cctgtagcgg cgcattaagc gcggcgggtg tggtggttac gcgcagcgtg   4860
accgctacac ttgccagcgc cctagcgccc gctcctttcg ctttcttccc ttcctttctc   4920
gccacgttcg ccggctttcc ccgtcaagct ctaaatcggg gctccctt agggttccga   4980 tttagtgctt tacggcacct cgaccccaaa aaacttgatt agggtgatgg ttcacgtagt   5040
gggccatcgc cctgatagac ggtttttcgc cctttgacgt tggagtccac gttctttaat   5100
agtggactct tgttccaaac tggaacaaca ctcaacccta tctcggtcta ttcttttgat   5160
ttataaggga ttttgccgat ttcggcctat tggttaaaaa atgagctgat ttaacaaaaa   5220
tttaacgcga attttaacaa aatattaacg cttacaattt aggtggcact tttcggggaa   5280
atgtgcgcgg aacccctatt tgtttatttt tctaaataca ttcaaatatg tatccgctca   5340
tgagacaata accctgataa atgcttcaat aatattgaaa aaggaagagt atgagtattc   5400
aacatttccg tgtcgccctt attccctttt ttgcggcatt ttgccttcct gttttgctc   5460
```

| | | | | |
|---|---|---|---|---|
| acccagaaac | gctggtgaaa | gtaaaagatg | ctgaagatca | gttgggtgca cgagtgggtt | 5520 |
| acatcgaact | ggatctcaac | agcggtaaga | tccttgagag | ttttcgcccc gaagaacgtt | 5580 |
| ttccaatgat | gagcactttt | aaagttctgc | tatgtggcgc | ggtattatcc cgtattgacg | 5640 |
| ccgggcaaga | gcaactcggt | cgccgcatac | actattctca | gaatgacttg gttgagtact | 5700 |
| caccagtcac | agaaaagcat | cttacggatg | gcatgacagt | aagagaatta tgcagtgctg | 5760 |
| ccataaccat | gagtgataac | actgcggcca | acttacttct | gacaacgatc ggaggaccga | 5820 |
| aggagctaac | cgcttttttg | cacaacatgg | gggatcatgt | aactcgcctt gatcgttggg | 5880 |
| aaccggagct | gaatgaagcc | ataccaaacg | acgagcgtga | caccacgatg cctgtagcaa | 5940 |
| tggcaacaac | gttgcgcaaa | ctattaactg | gcgaactact | tactctagct tcccggcaac | 6000 |
| aattaataga | ctggatggag | gcggataaag | ttgcaggacc | acttctgcgc tcggcccttc | 6060 |
| cggctggctg | gtttattgct | gataaatctg | gagccggtga | gcgtgggtct cgcggtatca | 6120 |
| ttgcagcact | ggggccagat | ggtaagccct | cccgtatcgt | agttatctac acgacgggga | 6180 |
| gtcaggcaac | tatggatgaa | cgaaatagac | agatcgctga | gataggtgcc tcactgatta | 6240 |
| agcattggta | actgtcagac | caagtttact | catatatact | ttagattgat ttaaaacttc | 6300 |
| attttttaatt | taaaaggatc | taggtgaaga | tcctttttga | taatctcatg accaaaatcc | 6360 |
| cttaacgtga | gttttcgttc | cactgagcgt | cagaccccgt | agaaaagatc aaaggatctt | 6420 |
| cttgagatcc | ttttttttctg | cgcgtaatct | gctgcttgca | acaaaaaaaa ccaccgctac | 6480 |
| cagcggtggt | ttgtttgccg | gatcaagagc | taccaactct | ttttccgaag gtaactggct | 6540 |
| tcagcagagc | gcagatacca | aatactgttc | ttctagtgta | gccgtagtta ggccaccact | 6600 |
| tcaagaactc | tgtagcaccg | cctacatacc | tcgctctgct | aatcctgtta ccagtggctg | 6660 |
| ctgccagtgg | cgataagtcg | tgtcttaccg | ggttggactc | aagacgatag ttaccggata | 6720 |
| aggcgcagcg | gtcgggctga | acggggggtt | cgtgcacaca | gcccagcttg gagcgaacga | 6780 |
| cctacaccga | actgagatac | ctacagcgtg | agctatgaga | aagcgccacg cttcccgaag | 6840 |
| ggagaaaggc | ggacaggtat | ccggtaagcg | gcagggtcgg | aacaggagag cgcacgaggg | 6900 |
| agcttccagg | gggaaacgcc | tggtatcttt | atagtcctgt | cgggtttcgc cacctctgac | 6960 |
| ttgagcgtcg | atttttgtga | tgctcgtcag | ggggcggag | cctatggaaa aacgccagca | 7020 |
| acgcggcctt | tttacggttc | ctggcctttt | gctggccttt | tgctcacatg ttctttcctg | 7080 |
| cgttatcccc | tgattctgtg | gataaccgta | ttaccgcctt | tgagtgagct gataccgctc | 7140 |
| gccgcagccg | aacgaccgag | cgcagcgagt | cagtgagcga | ggaagcggaa gagcgcccaa | 7200 |
| tacgcaaacc | gcctctcccc | gcgcgttggc | cgattcatta | atgcagctgg cacgacaggt | 7260 |
| ttcccgactg | gaaagcgggc | agtgagcgca | acgcaattaa | tgtgagttag ctcactcatt | 7320 |
| aggcacccca | ggctttacac | tttatgcttc | cggctcgtat | gttgtgtgga attgtgagcg | 7380 |
| gataacaatt | tcacacagga | aacagctatg | accatgatta | cgccaagcgc gcaattaacc | 7440 |
| ctcactaaag | ggaacaaaag | ctggagctgc | aagctt | | 7476 |

<210> SEQ ID NO 99
<211> LENGTH: 9294
<212> TYPE: DNA
<213> ORGANISM: Artificial Sequence
<220> FEATURE:
<223> OTHER INFORMATION: pLENTI-EF1a-fFLuc-Blasticidin-A07

<400> SEQUENCE: 99

| | | |
|---|---|---|
| aatgtagtct tatgcaatac tcttgtagtc ttgcaacatg gtaacgatga gttagcaaca | | 60 |

```
tgccttacaa ggagagaaaa agcaccgtgc atgccgattg gtggaagtaa ggtggtacga    120
tcgtgcctta ttaggaaggc aacagacggg tctgacatgg attggacgaa ccactgaatt    180
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac ccttttagtc agtgtggaaa atctctagca gtggcgcccg    420
aacagggact tgaaagcgaa agggaaacca ggagagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcggggggaga   600 attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt ataatacaa gtagcaaccc tctattgtgt gcatcaaagg     840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620 agttttgct gtactttcta tagtgaatag agttaggcag ggatattcac cattatcgtt    1680
tcagacccac ctcccaaccc cgaggggacc cgacaggccc gaaggaatag aagaagaagg   1740
tggagagaga gacagagaca gatccattcg attagtgaac ggatctcgac ggtatcgata   1800
agctttgcaa agatggataa agttttaaac agagaggaat ctttgcagct aatggacctt   1860
ctaggtcttg aaaggagtgc ctcgtgaggc tccggtgccc gtcagtgggc agagcgcaca   1920
tcgcccacag tccccgagaa gttgggggga ggggtcggca attgaaccgg tgcctagaga   1980
aggtggcgcg gggtaaactg ggaaagtgat gtcgtgtact ggctccgcct ttttcccgag   2040
ggtgggggag aaccgtatat aagtgcagta gtcgccgtga cgttcttttt cgcaacggg    2100 tttgccgcca gaacacaggt aagtgccgtg tgtggttccc gcgggcctgg cctctttacg   2160
ggttatggcc cttgcgtgcc ttgaattact tccacctggc tgcagtacgt gattcttgat   2220
cccgagcttc gggttggaag tgggtgggag agttcgaggc cttgcgctta aggagcccct   2280
tcgcctcgtg cttgagttga ggcctggcct gggcgctggg gccgccgcgt gcgaatctgg   2340
tggcaccttc gcgcctgtct cgctgctttc gataagtctc tagccattta aaattttga   2400
```

-continued

```
tgacctgctg cgacgctttt tttctggcaa gatagtcttg taaatgcggg ccaagatctg   2460
cacactggta tttcggtttt tggggccgcg ggcggcgacg gggcccgtgc gtcccagcgc   2520
acatgttcgg cgaggcgggg cctgcgagcg cggccaccga gaatcggacg ggggtagtct   2580
caagctggcc ggcctgctct ggtgcctggc ctcgcgccgc cgtgtatcgc cccgccctgg   2640
gcggcaaggc tggcccggtc ggcaccagtt gcgtgagcgg aaagatggcc gcttcccggc   2700
cctgctgcag ggagctcaaa atggaggacg cggcgctcgg gagagcgggc gggtgagtca   2760
cccacacaaa ggaaaagggc ctttccgtcc tcagccgtcg cttcatgtga ctccacggag   2820
taccgggcgc cgtccaggca cctcgattag ttctcgacct tttggagtac gtcgtcttta   2880
ggttgggggg aggggtttta tgcgatggag tttccccaca ctgagtgggt ggagactgaa   2940
gttaggccag cttggcactt gatgtaattc tccttggaat ttgccctttt tgagtttgga   3000
tcttggttca ttctcaagcc tcagacagtg gttcaaagtt ttttcttcc atttcaggtg    3060 tcgtgaggaa ttagcttggt actaatacga ctcactatag ggagacccaa gctggctagt   3120
taagcttgat atcgaattcc tgcagcccgg ggatctgct agtccagtgt ggtggaattc     3180
gaagctcgag ccaccatgga agacgccaaa aacataaaga aaggcccggc gccattctat   3240
ccgctggaag atggaaccgc tggagagcaa ctgcataagg ctatgaagag atacgccctg   3300
gttcctggaa caattgcttt tacagatgca catatcgagg tggacatcac ttacgctgag   3360
tacttcgaaa tgtccgttcg gttggcagaa gctatgaaac gatatgggct gaatacaaat   3420
cacagaatcg tcgtatgcag tgaaaactct cttcaattct ttatgccggt gttgggcgcg   3480
ttatttatcg gagttgcagt tgcgcccgcg aacgacattt ataatgaacg tgaattgctc   3540
aacagtatgg gcatttcgca gcctaccgtg gtgttcgttt ccaaaaaggg gttgcaaaaa   3600
attttgaacg tgcaaaaaaa gctcccaatc atccaaaaaa ttattatcat ggattctaaa   3660
acggattacc agggatttca gtcgatgtac acgttcgtca catctcatct acctcccggt   3720
tttaatgaat acgattttgt gccagagtcc ttcgataggg acaagacaat tgcactgatc   3780
atgaactcct ctggatctac tggtctgcct aaaggtgtcg ctctgcctca tagaactgcc   3840
tgcgtgagat tctcgcatgc cagagatcct atttttggca atcaaatcat tccggatact   3900
gcgattttaa gtgttgttcc attccatcac ggttttggaa tgtttactac actcggatat   3960
ttgatatgtg gatttcgagt cgtcttaatg tatagatttg aagaagagct gtttctgagg   4020
agccttcagg attacaagat tcaaagtgcg ctgctggtgc caacccctatt ctccttcttc   4080 gccaaaagca ctctgattga caaatacgat ttatctaatt tacacgaaat tgcttctggt   4140
ggcgctcccc tctctaagga agtcggggaa gcggttgcca agaggttcca tctgccaggt   4200
atcaggcaag gatatgggct cactgagact acatcagcta ttctgattac acccgagggg   4260
gatgataaac cgggcgcggt cggtaaagtt gttccatttt ttgaagcgaa ggttgtggat   4320
ctggataccg ggaaaacgct gggcgttaat caaagaggcg aactgtgtgt gagaggtcct   4380
atgattatgt ccggttatgt aaacaatccg gaagcgacca acgccttgat tgacaaggat   4440
ggatggctac attctggaga catagcttac tgggacgaag acgaacactt cttcatcgtt   4500
gaccgcctga agtctctgat taagtacaaa ggctatcagg tggctcccgc tgaattggaa   4560
tccatcttgc tccaacaccc caacatcttc gacgcaggtg tcgcaggtct tcccgacgat   4620
gacgccggtg aacttcccgc cgccgttgtt gttttggagc acggaaagac gatgacggaa   4680
aaagagatcg tggattacgt cgccagtcaa gtaacaaccg cgaaaaagtt gcgcggagga   4740
gttgtgtttg tggacgaagt accgaaaggt cttaccggaa aactcgacgc aagaaaaatc   4800
```

```
agagagatcc tcataaaggc caagaagggc ggaaagatcg ccgtgtaacc ggttagtaat    4860
gagtttggaa ttaattctgt ggaatgtgtg tcagttaggg tgtggaaagt ccccaggctc    4920
cccaggcagg cagaagtatg caaagcatgc atctcaatta gtcagcaacc aggtgtggaa    4980
agtccccagg ctccccagca ggcagaagta tgcaaagcat gcatctcaat tagtcagcaa    5040
ccatagtccc gccctaact ccgcccatcc cgccctaac tccgcccagt tccgcccatt    5100
ctccgcccca tggctgacta atttttttta tttatgcaga ggccgaggcc gcctctgcct    5160
ctgagctatt ccagaagtag tgaggaggct ttttggagg cctaggcttt tgcaaaaagc    5220
tcccgggagc ttgtatatcc attttcggat ctgatcagca cgtgttgaca attaatcatc    5280
ggcatagtat atcggcatag tataatacga caaggtgagg aactaaacca tggccaagcc    5340
tttgtctcaa gaagaatcca ccctcattga aagagcaacg gctacaatca acagcatccc    5400
catctctgaa gactacagcg tcgccagcgc agctctctct agcgacggcc gcatcttcac    5460
tggtgtcaat gtatatcatt ttactggggg accttgtgca gaactcgtgg tgctgggcac    5520
tgctgctgct gcggcagctg gcaacctgac ttgtatcgtc gcgatcggaa atgagaacag    5580
gggcatcttg agcccctgcg gacggtgccg acaggtgctt ctcgatctgc atcctgggat    5640
caaagccata gtgaaggaca gtgatggaca gccgacggca gttgggattc gtgaattgct    5700
gccctctggt tatgtgtggg agggctaagc acaattcgag ctcggtacct ttaagaccaa    5760
tgacttacaa ggcagctgta gatcttagcc acttttaaa agaaaagggg ggactggaag    5820
ggctaattca ctcccaacga agacaagatc tgcttttgc ttgtactggg tctctctggt    5880
tagaccagat ctgagcctgg gagctctctg gctaactagg gaacccactg cttaagcctc    5940
aataaagctt gccttgagtg cttcaagtag tgtgtgcccg tctgttgtgt gactctggta    6000
actagagatc cctcagaccc ttttagtcag tgtggaaaat ctctagcagt agtagttcat    6060
gtcatcttat tattcagtat ttataacttg caaagaaatg aatatcagag agtgagagga    6120
acttgtttat tgcagcttat aatggttaca aataaagcaa tagcatcaca aatttcacaa    6180
ataaagcatt ttttcactg cattctagtt gtggtttgtc caaactcatc aatgtatctt    6240
atcatgtctg gctctagcta tcccgcccct aactccgccc atcccgcccc taactccgcc    6300
cagttccgcc cattctccgc cccatggctg actaatttt tttatttatg cagaggccga    6360
ggccgcctcg gcctctgagc tattccagaa gtagtgagga ggcttttttg gaggcctagg    6420
gacgtaccca attcgcccta gtgagtcg tattacgcgc gctcactggc cgtcgtttta    6480
caacgtcgtg actgggaaaa ccctggcgtt acccaactta atcgccttgc agcacatccc    6540
cctttcgcca gctggcgtaa tagcgaagag gcccgcaccg atcgcccttc ccaacagttg    6600
cgcagcctga atggcgaatg gacgcgccc tgtagcggcg cattaagcgc ggcgggtgtg    6660
gtggttacgc gcagcgtgac cgctacactt gccagcgccc tagcgcccgc tcctttcgct    6720
ttcttccctt cctttctcgc cacgttcgcc ggctttcccc gtcaagctct aaatcggggg    6780
ctccctttag ggttccgatt tagtgcttta cggcacctcg accccaaaaa acttgattag    6840
ggtgatggtt cacgtagtgg gccatcgccc tgatagacgg ttttcgccc tttgacgttg    6900 gagtccacgt tctttaatag tggactcttg ttccaaactg gaacaacact caaccctatc    6960
tcggtctatt cttttgattt ataagggatt ttgccgattt cggcctattg gttaaaaaat    7020
gagctgattt aacaaaaatt taacgcgaat tttaacaaaa tattaacgct tacaatttag    7080
gtggcacttt tcggggaaat gtgcgcggaa cccctatttg tttattttc taaatacatt    7140
```

```
caaatatgta tccgctcatg agacaataac cctgataaat gcttcaataa tattgaaaaa    7200
ggaagagtat gagtattcaa catttccgtg tcgcccttat tcccttttt gcggcatttt     7260
gccttcctgt ttttgctcac ccagaaacgc tggtgaaagt aaaagatgct gaagatcagt    7320
tgggtgcacg agtgggttac atcgaactgg atctcaacag cggtaagatc cttgagagtt    7380
ttcgccccga agaacgtttt ccaatgatga gcacttttaa agttctgcta tgtggcgcgg    7440
tattatcccg tattgacgcc gggcaagagc aactcggtcg ccgcatacac tattctcaga    7500
atgacttggt tgagtactca ccagtcacag aaaagcatct tacggatggc atgacagtaa    7560
gagaattatg cagtgctgcc ataaccatga gtgataacac tgcggccaac ttacttctga    7620
caacgatcgg aggaccgaag gagctaaccg cttttttgca acatggggg atcatgtaa      7680
ctcgccttga tcgttgggaa ccggagctga atgaagccat accaaacgac gagcgtgaca    7740
ccacgatgcc tgtagcaatg gcaacaacgt tgcgcaaact attaactggc gaactactta    7800
ctctagcttc ccgcaacaa ttaatagact ggatggaggc ggataaagtt gcaggaccac      7860
ttctgcgctc ggcccttccg ctggctggt ttattgctga taaatctgga gccggtgagc      7920
gtgggtctcg cggtatcatt gcagcactgg ggccagatgg taagccctcc cgtatcgtag    7980
ttatctacac gacggggagt caggcaacta tggatgaacg aaatagacag atcgctgaga    8040
taggtgcctc actgattaag cattggtaac tgtcagacca agtttactca tatatacttt    8100
agattgattt aaaacttcat ttttaattta aaaggatcta ggtgaagatc cttttgata    8160
atctcatgac caaaatccct taacgtgagt tttcgttcca ctgagcgtca gaccccgtag    8220
aaaagatcaa aggatcttct tgagatcctt ttttttctgcg cgtaatctgc tgcttgcaaa   8280
caaaaaaacc accgctacca gcggtggttt gtttgccgga tcaagagcta ccaactcttt    8340
ttccgaaggt aactggcttc agcagagcgc agataccaaa tactgttctt ctagtgtagc    8400
cgtagttagg ccaccacttc aagaactctg tagcaccgcc tacatacctc gctctgctaa    8460
tcctgttacc agtggctgct gccagtgcg ataagtcgtg tcttaccggg ttggactcaa      8520
gacgatagtt accggataag gcgcagcggt cgggctgaac ggggggttcg tgcacacagc    8580
ccagcttgga gcgaacgacc tacaccgaac tgagatacct acagcgtgag ctatgagaaa    8640
gcgccacgct tcccgaaggg agaaaggcgg acaggtatcc ggtaagcggc agggtcggaa    8700
caggagagcg cacgagggag cttccagggg gaaacgcctg gtatctttat agtcctgtcg    8760
ggtttcgcca cctctgactt gagcgtcgat ttttgtgatg ctcgtcaggg ggcggagcc     8820
tatgaaaaaa cgccagcaac gcggcctttt tacggttcct ggccttttgc tggccttttg    8880
ctcacatgtt ctttcctgcg ttatcccctg attctgtgga taaccgtatt accgcctttg    8940
agtgagctga taccgctcgc cgcagccgaa cgaccgagcg cagcgagtca gtgagcgagg    9000
aagcggaaga gcgcccaata cgcaaaccgc ctctccccgc gcgttggccg attcattaat    9060
gcagctggca cgacaggttt cccgactgga aagcgggcag tgagcgcaac gcaattaatg    9120
tgagttagct cactcattag gcaccccagg ctttacactt tatgcttccg gctcgtatgt    9180
tgtgtggaat tgtgagcgga taacaatttc acacaggaaa cagctatgac catgattacg    9240
ccaagcgcgc aattaaccct cactaaaggg aacaaaagct ggagctgcaa gctt          9294
```

<210> SEQ ID NO 100
<211> LENGTH: 9839
<212> TYPE: DNA
<213> ORGANISM: Artificial Sequence
<220> FEATURE:
<223> OTHER INFORMATION: pLenti-EF1-LucPPe-146-1H2-Flag-Pac-R01

<400> SEQUENCE: 100

```
aatgtagtct tatgcaatac tcttgtagtc ttgcaacatg gtaacgatga gttagcaaca    60
tgccttacaa ggagagaaaa agcaccgtgc atgccgattg gtggaagtaa ggtggtacga   120
tcgtgcctta ttaggaaggc aacagacggg tctgacatgg attggacgaa ccactgaatt   180
gccgcattgc agagatattg tatttaagtg cctagctcga tacataaacg ggtctctctg   240
gttagaccag atctgagcct gggagctctc tggctaacta gggaacccac tgcttaagcc   300
tcaataaagc ttgccttgag tgcttcaagt agtgtgtgcc cgtctgttgt gtgactctgg   360
taactagaga tccctcagac cctttttagtc agtgtggaaa atctctagca gtggcgcccg   420
aacagggact tgaaagcgaa agggaaacca gaggagctct ctcgacgcag gactcggctt   480
gctgaagcgc gcacggcaag aggcgagggg cggcgactgg tgagtacgcc aaaaattttg   540
actagcggag gctagaagga gagagatggg tgcgagagcg tcagtattaa gcggggggaga   600
attagatcgc gatgggaaaa aattcggtta aggccagggg gaaagaaaaa atataaatta   660
aaacatatag tatgggcaag cagggagcta gaacgattcg cagttaatcc tggcctgtta   720
gaaacatcag aaggctgtag acaaatactg ggacagctac aaccatccct tcagacagga   780
tcagaagaac ttagatcatt ataataca gtagcaaccc tctattgtgt gcatcaaagg   840
atagagataa aagacaccaa ggaagcttta gacaagatag aggaagagca aaacaaaagt   900
aagaccaccg cacagcaagc ggccgctgat cttcagacct ggaggaggag atatgaggga   960
caattggaga agtgaattat ataaatataa agtagtaaaa attgaaccat taggagtagc  1020
acccaccaag gcaaagagaa gagtggtgca gagagaaaaa agagcagtgg gaataggagc  1080
tttgttcctt gggttcttgg gagcagcagg aagcactatg ggcgcagcgt caatgacgct  1140
gacggtacag gccagacaat tattgtctgg tatagtgcag cagcagaaca atttgctgag  1200
ggctattgag gcgcaacagc atctgttgca actcacagtc tggggcatca agcagctcca  1260
ggcaagaatc ctggctgtgg aaagatacct aaaggatcaa cagctcctgg ggatttgggg  1320
ttgctctgga aaactcattt gcaccactgc tgtgccttgg aatgctagtt ggagtaataa  1380
atctctggaa cagatttgga atcacacgac ctggatggag tgggacagag aaattaacaa  1440
ttacacaagc ttaatacact ccttaattga agaatcgcaa aaccagcaag aaaagaatga  1500
acaagaatta ttggaattag ataaatgggc aagtttgtgg aattggttta cataacaaa  1560
ttggctgtgg tatataaaat tattcataat gatagtagga ggcttggtag gtttaagaat  1620
agttttttgct gtactttcta tagtgaatag agttaggcag ggatattcac cattatcgtt  1680
tcagacccac ctcccaaccc cgaggggacc cgacaggccc gaaggaatag aagaagaagg  1740
tggagagaga gacagagaca gatccattcg attagtgaac ggatctcgac ggtatcggtt  1800
aacttttaaa agaaaagggg ggattggggg gtacagtgca ggggaaagaa tagtagacat  1860
aatagcaaca gacatacaaa ctaaagaatt acaaaacaa attacaaaat tcaaaatttt  1920
atcgataagc tttgcaaaga tggataaagt tttaaacaga gaggaatctt tgcagctaat  1980
ggaccttcta ggtcttgaaa ggagtgcctc gtgaggctcc ggtgcccgtc agtgggcaga  2040
gcgcacatcg cccacagtcc ccgagaagtt gggggggaggg gtcggcaatt gaaccggtgc  2100
ctagagaagg tggcgcgggg taaactggga aagtgatgtc gtgtactggc tccgcctttt  2160
tcccgagggt gggggagaac cgtatataag tgcagtagtc gccgtgaacg ttcttttttcg  2220
caacgggttt gccgccagaa cacaggtaag tgccgtgtgt ggttcccgcg ggcctggcct  2280
```

```
ctttacgggt tatggccctt gcgtgccttg aattacttcc acctggctgc agtacgtgat    2340
tcttgatccc gagcttcggg ttggaagtgg gtgggagagt tcgaggcctt gcgcttaagg    2400
agccccttcg cctcgtgctt gagttgaggc ctggcctggg cgctggggcc gccgcgtgcg    2460
aatctggtgg caccttcgcg cctgtctcgc tgctttcgat aagtctctag ccatttaaaa    2520 ttttgatga cctgctgcga cgcttttttt ctggcaagat agtcttgtaa atgcgggcca    2580
agatctgcac actggtattt cggttttggg gccgcgggc ggcgacgggg cccgtgcgtc     2640
ccagcgcaca tgttcggcga ggcggggcct gcgagcgcgg ccaccgagaa tcggacgggg    2700
gtagtctcaa gctggccggc ctgctctggt gcctggcctc gcgccgccgt gtatcgcccc    2760
gccctgggcg gcaaggctgg cccggtcggc accagttgcg tgagcggaaa gatggccgct    2820
tcccggccct gctgcaggga gctcaaaatg gaggacgcgg cgctcgggag agcgggcggg    2880
tgagtcaccc acacaaagga aaagggcctt tccgtcctca gccgtcgctt catgtgactc    2940
cacggagtac cgggcgccgt ccaggcacct cgattagttc tcgaccttt ggagtacgtc     3000 gtctttaggt tggggggagg ggttttatgc gatggagttt ccccacactg agtgggtgga    3060
gactgaagtt aggccagctt ggcacttgat gtaattctcc ttggaatttg cccttttga    3120 gtttggatct tggttcattc tcaagcctca gacagtggtt caaagtttt tcttccatt     3180 tcaggtgtcg tgaggaatta gcttggtact aatacgactc actatagga gacccaagct     3240 ggctaggtaa gcttgatatc gaattcctgc agcccggggg atctgctagc ggatccacca    3300
tggccgacaa gaacatcctg tacggccccg agcctttcta ccctctggaa gatggaacag    3360
ccggcgagca gatgttcgac gccctgagca gatatgccgc cattcctgga tgtatcgccc    3420
tgacaaacgc ccacaccaaa gaaaacgtgc tgtacgaaga gttcctgaag ctgagctgtc    3480
ggctggccga gagcttcaag aagtacgcc tgaagcagaa cgacacaatc gccgtgtgca     3540
gcgagaacag cctccagttc ttcctgcctg tgatcgccag cctgtacctg gcattattg     3600 tggcccctgt gaacgacaag tacatcgaga gagcctgat ccacagcctg gcatcgtga     3660 agccccggat cgtgttctgc tccaagaaca ccttccagaa ggtgctgaac gtcaagagca    3720
agctgaagtc catcgagaca atcatcatcc tggaccttga cgaggacctc ggcggctacc    3780
agtgcctgaa caacttcatc agccagaaca gcgacagcaa cctggacgtg aagaagttca    3840
agccctacag cttcaaccgg gacgaccagg tggcctccat catgtttagc agcggcacca    3900
ccggactgcc caaaggcgtt atgctgaccc acaagaatat cgtggcccgg ttctctatcg    3960
ctaaggaccc caccttcggc aacgccatca atcctacaag cgctatcctg acagtgatcc    4020
ccttccacca cggcttcggc atgatgacca cactgggcta cttcacctgt ggcttcagag    4080
tggtgctgat gcacaccttc gaggaaaagc tgtttctcca gagcctccag gactacaagg    4140
tggaaagcac cctgctggtg cctactctga tggccttcct ggctaagtct gccctggtcg    4200
agaagtacga tctgagccac ctgaaagaga tcgcctctgg cggagccct ctgagcaaag    4260 aaatcggcga gatggtcaag aagcggttca agctgaactt cgtgcggcaa ggctatggcc    4320
tgaccgagac aacaagcgcc gtgctgatta cccctaaggg cgacgccaag cctggcagca    4380
caggcaaaat tgtgcctctg cacgccgtga aggtggtgga ccctaccaca ggcaagatcc    4440
tgggacctaa tgagcccggc gagctgtact tcaagggacc catgattatg aagggctact    4500
acaacaacga ggaagccacc aaggccatta tcgacaacga cggctggctg cggagcggcg    4560
atattgccta ctacgacaat gacggccact tctatatcgt ggacagactg aagtccctca    4620
tcaagtacaa gggctatcag gtggcccccag ccgagatcga gggtatcctg ctgcaacacc    4680
```

```
cctatatcgt ggatgccggc gtgacaggca tccctgatga agctgctggc gaacttccag    4740
cagctggcgt ggtggttcag accggcaagt acctgaatga gcagatcgtg caggactacg    4800
tggcctctca ggtgtccaca gccaaatggc tgagaggcgg cgtgaagttc ctggacgaga    4860
tcccaaaggg ctctaccggc aagatcgaca gaaaggtgct gcggcagatg ctggaaaagc    4920
acaccaatgg cctcgagacc gatttctacg actacaagga cgacgatgac aagactagtg    4980
gctccggcga gggcagagga agtctactaa cctgcggaga tgtggaagaa aatcctggcc    5040
cacatatgac cgagtacaag cccacggtgc gcctcgccac ccgcgacgac gtccccaggg    5100
ccgtacgcac cctcgccgcc gcgttcgccg actaccccgc cacgcgccac accgtcgatc    5160
cggaccgcca catcgagcgg gtcaccgagc tgcaagaact cttcctcacg cgcgtcgggc    5220
tcgacatcgg caaggtgtgg gtcgcggacg acggcgccgc ggtggcggtc tggaccacgc    5280
cggagagcgt cgaagcgggg gcggtgttcg ccagatcgg cccgcgcatg gccgagttga    5340
gcggttcccg gctggccgcg cagcaacaga tggaaggcct cctggcgccg caccggccca    5400
aggagcccgc gtggttcctg gccaccgtcg gcgtctcgcc cgaccaccag ggcaagggtc    5460
tgggcagcgc cgtcgtgctc cccggagtgg aggcggccga gcgcgccggg gtgcccgcct    5520
tcctggagac ctccgcgccc cgcaacctcc ccttctacga gcggctcggc ttcaccgtca    5580
ccgccgacgt cgaggtgccc gaaggaccgc gcacctggtg catgacccgc aagcccggtg    5640
cctgagtcga ctccggatga tcagggccct gtacagatat cgacaatcaa cctctggatt    5700
acaaaatttg tgaaagattg actggtattc ttaactatgt tgctccttt acgctatgtg    5760 gatacgctgc tttaatgcct ttgtatcatg ctattgcttc ccgtatggct ttcattttct    5820
cctccttgta taaatcctgg ttgctgtctc tttatgagga gttgtggccc gttgtcaggc    5880
aacgtggcgt ggtgtgcact gtgtttgctg acgcaacccc cactggttgg ggcattgcca    5940
ccacctgtca gctcctttcc gggactttcg ctttcccct ccctattgcc acggcggaac    6000
tcatcgccgc ctgccttgcc cgctgctgga caggggctcg gctgttgggc actgacaatt    6060
ccgtggtgtt gtcggggaag ctgacgtcct ttccatggct gctcgcctgt gttgccacct    6120
ggattctgcg cgggacgtcc ttctgctacg tcccttcggc cctcaatcca gcggaccttc    6180
cttcccgcgg cctgctgccg gctctgcggc ctcttccgcg tcttcgcctt cgccctcaga    6240
cgagtcggat ctccctttgg gccgcctccc cgcctggaat tcgagctcgg tacctttaag    6300
accaatgact acaaggcag ctgtagatct tagccacttt ttaaaagaaa aggggggact    6360
ggaagggcta attcactccc aacgaagaca agatctgctt tttgcttgta ctgggtctct    6420
ctggttagac cagatctgag cctgggagct ctctggctaa ctagggaacc cactgcttaa    6480
gcctcaataa agcttgcctt gagtgcttca agtagtgtgt gcccgtctgt tgtgtgactc    6540
tggtaactag agatccctca gacccttta gtcagtgtgg aaaatctcta gcagtagtag    6600
ttcatgtcat cttattattc agtatttata acttgcaaag aaatgaatat cagagagtga    6660
gaggaacttg tttattgcag cttataatgg ttacaaataa agcaatagca tcacaaattt    6720
cacaaataaa gcatttttt cactgcattc tagttgtggt ttgtccaaac tcatcaatgt    6780
atcttatcat gtctggctct agctatcccg cccctaactc cgcccatccc gcccctaact    6840
ccgcccagtt ccgcccattc tccgccccat ggctgactaa ttttttttat ttatgcagag    6900
gccgaggccg cctcggcctc tgagctattc cagaagtagt gaggaggctt ttttggaggc    6960
ctagggacgt acccaattcg ccctatagtg agtcgtatta cgcgcgctca ctggccgtcg    7020
```

```
ttttacaacg tcgtgactgg gaaaaccctg gcgttaccca acttaatcgc cttgcagcac    7080
atcccccttt cgccagctgg cgtaatagcg aagaggcccg caccgatcgc ccttcccaac    7140
agttgcgcag cctgaatggc gaatgggacg cgccctgtag cggcgcatta agcgcggcgg    7200
gtgtggtggt tacgcgcagc gtgaccgcta cacttgccag cgccctagcg cccgctcctt    7260
tcgctttctt cccttccttt ctcgccacgt tcgccggctt tccccgtcaa gctctaaatc    7320
gggggctccc tttagggttc cgatttagtg ctttacggca cctcgacccc aaaaaacttg    7380
attagggtga tggttcacgt agtgggccat cgccctgata cggttttt cgcccttga     7440
cgttggagtc cacgttcttt aatagtggac tcttgttcca aactggaaca cactcaacc    7500
ctatctcggt ctattctttt gatttataag ggattttgcc gatttcggcc tattggttaa    7560
aaaatgagct gatttaacaa aaatttaacg cgaattttaa caaaatatta acgcttacaa    7620
tttaggtggc acttttcggg gaaatgtgcg cggaacccct atttgtttat ttttctaaat    7680
acattcaaat atgtatccgc tcatgagaca ataaccctga taaatgcttc aataatattg    7740
aaaaggaag agtatgagta ttcaacattt ccgtgtcgcc cttattccct ttttgcggc     7800
attttgcctt cctgttttg ctcacccaga aacgctggtg aaagtaaaag atgctgaaga    7860
tcagttgggt gcacgagtgg gttacatcga actggatctc aacagcggta agatccttga    7920
gagttttcgc cccgaagaac gttttccaat gatgagcact tttaaagttc tgctatgtgg    7980
cgcggtatta tcccgtattg acgccgggca agagcaactc ggtcgccgca tacactattc    8040
tcagaatgac ttggttgagt actcaccagt cacagaaaag catcttacgg atggcatgac    8100
agtaagagaa ttatgcagtg ctgccataac catgagtgat aacactgcgg ccaacttact    8160
tctgacaacg atcggaggac cgaaggagct aaccgctttt ttgcacaaca tgggggatca    8220
tgtaactcgc cttgatcgtt gggaaccgga gctgaatgaa gccataccaa acgacgagcg    8280
tgacaccacg atgcctgtag caatggcaac aacgttgcgc aaactattaa ctggcgaact    8340
acttactcta gcttcccggc aacaattaat agactggatg gaggcggata agttgcagg    8400
accacttctg cgctcggccc ttccggctgg ctggtttatt gctgataaat ctggagccgg    8460
tgagcgtggg tctcgcggta tcattgcagc actggggcca gatggtaagc cctcccgtat    8520
cgtagttatc tacacgacgg ggagtcaggc aactatggat gaacgaaata gacagatcgc    8580
tgagataggt gcctcactga ttaagcattg gtaactgtca gaccaagttt actcatatat    8640
actttagatt gatttaaaac ttcattttta atttaaaagg atctaggtga agatcctttt    8700
tgataatctc atgaccaaaa tcccttaacg tgagttttcg ttccactgag cgtcagaccc    8760
cgtagaaaag atcaaaggat cttcttgaga tcctttttt ctgcgcgtaa tctgctgctt    8820
gcaaacaaaa aaaccaccgc taccagcggt ggtttgtttg ccggatcaag agctaccaac    8880
tcttttccg aaggtaactg gcttcagcag agcgcagata ccaaatactg ttcttctagt    8940
gtagccgtag ttaggccacc acttcaagaa ctctgtagca ccgcctacat acctcgctct    9000
gctaatcctg ttaccagtgg ctgctgccag tggcgataag tcgtgtctta ccgggttgga    9060
ctcaagacga tagttaccgg ataaggcgca gcggtcgggc tgaacggggg gttcgtgcac    9120
acagcccagc ttggagcgaa cgacctacac cgaactgaga tacctacagc gtgagctatg    9180
agaaagcgcc acgcttcccg aagggagaaa ggcggacagg tatccggtaa gcggcagggt    9240
cggaacagga gagcgcacga gggagcttcc agggggaaac gcctggtatc tttatagtcc    9300
tgtcgggttt cgccacctct gacttgagcg tcgatttttg tgatgctcgt cagggggcg    9360
gagcctatgg aaaaacgcca gcaacgcggc cttttacgg ttcctggcct tttgctggcc    9420
```

```
tttttgctcac atgttctttc ctgcgttatc ccctgattct gtggataacc gtattaccgc    9480
ctttgagtga gctgataccg ctcgccgcag ccgaacgacc gagcgcagcg agtcagtgag    9540
cgaggaagcg gaagagcgcc caatacgcaa accgcctctc cccgcgcgtt ggccgattca    9600
ttaatgcagc tggcacgaca ggtttcccga ctggaaagcg ggcagtgagc gcaacgcaat    9660
taatgtgagt tagctcactc attaggcacc ccaggcttta cactttatgc ttccggctcg    9720
tatgttgtgt ggaattgtga gcggataaca atttcacaca ggaaacagct atgaccatga    9780
ttacgccaag cgcgcaatta accctcacta aagggaacaa aagctggagc tgcaagctt    9839
```

<210> SEQ ID NO 101
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(4)
<223> OTHER INFORMATION: Xaa can be any amino acid
<220> FEATURE:
<221> NAME/KEY: MISC_FEATURE
<222> LOCATION: (7)..(8)
<223> OTHER INFORMATION: Xaa can be any amino acid
<220> FEATURE:
<221> NAME/KEY: MISC_FEATURE
<222> LOCATION: (10)..(13)
<223> OTHER INFORMATION: Xaa can be any amino acid
<220> FEATURE:
<221> NAME/KEY: MISC_FEATURE
<222> LOCATION: (15)..(22)
<223> OTHER INFORMATION: Xaa can be any amino acid
<220> FEATURE:
<221> NAME/KEY: MISC_FEATURE
<222> LOCATION: (24)..(24)
<223> OTHER INFORMATION: Xaa can be any amino acid

<400> SEQUENCE: 101

Cys Xaa Xaa Xaa Cys Leu Xaa Xaa Leu Xaa Xaa Xaa Xaa Cys Xaa Xaa
1               5                   10                  15

Xaa Xaa Xaa Xaa Xaa Xaa Pro Xaa Arg Cys
            20                  25

<210> SEQ ID NO 102
<211> LENGTH: 56
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(8)
<223> OTHER INFORMATION: X can be any amino acid
<220> FEATURE:
<221> NAME/KEY: MISC_FEATURE
<222> LOCATION: (15)..(17)
<223> OTHER INFORMATION: X can be any amino acid
<220> FEATURE:
<221> NAME/KEY: MISC_FEATURE
<222> LOCATION: (20)..(20)
<223> OTHER INFORMATION: X can be any amino acid
<220> FEATURE:
<221> NAME/KEY: MISC_FEATURE
<222> LOCATION: (22)..(22)
<223> OTHER INFORMATION: X can be any amino acid
<220> FEATURE:
<221> NAME/KEY: MISC_FEATURE
<222> LOCATION: (26)..(26)
<223> OTHER INFORMATION: X can be any amino acid
<220> FEATURE:

<221> NAME/KEY: MISC_FEATURE
<222> LOCATION: (29)..(29)
<223> OTHER INFORMATION: X can be any amino acid
<220> FEATURE:
<221> NAME/KEY: MISC_FEATURE
<222> LOCATION: (34)..(34)
<223> OTHER INFORMATION: X can be any amino acid
<220> FEATURE:
<221> NAME/KEY: MISC_FEATURE
<222> LOCATION: (37)..(40)
<223> OTHER INFORMATION: X can be any amino acid
<220> FEATURE:
<221> NAME/KEY: MISC_FEATURE
<222> LOCATION: (46)..(46)
<223> OTHER INFORMATION: X can be any amino acid
<220> FEATURE:
<221> NAME/KEY: MISC_FEATURE
<222> LOCATION: (48)..(55)
<223> OTHER INFORMATION: X can be any amino acid

<400> SEQUENCE: 102

Lys Xaa Xaa Xaa Xaa Xaa Xaa Glu Met Glu Ala Asn Ala Xaa Xaa
1               5                   10                  15

Xaa Gly Cys Xaa Arg Xaa Cys Leu Ile Xaa Leu Ser Xaa Ile Lys Cys
            20                  25                  30

Thr Xaa Lys Met Xaa Xaa Xaa Xaa Pro Gly Arg Cys His Xaa Tyr Xaa
        35                  40                  45

Xaa Xaa Xaa Xaa Xaa Xaa Xaa Gly
    50                  55

<210> SEQ ID NO 103
<211> LENGTH: 64
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(9)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid
<220> FEATURE:
<221> NAME/KEY: MISC_FEATURE
<222> LOCATION: (14)..(15)
<223> OTHER INFORMATION: Xaa can be any amino acid
<220> FEATURE:
<221> NAME/KEY: MISC_FEATURE
<222> LOCATION: (18)..(19)
<223> OTHER INFORMATION: Xaa can be any amino acid
<220> FEATURE:
<221> NAME/KEY: MISC_FEATURE
<222> LOCATION: (21)..(22)
<223> OTHER INFORMATION: Xaa can be any amino acid
<220> FEATURE:
<221> NAME/KEY: MISC_FEATURE
<222> LOCATION: (24)..(26)
<223> OTHER INFORMATION: Xaa can be any amino acid
<220> FEATURE:
<221> NAME/KEY: MISC_FEATURE
<222> LOCATION: (34)..(35)
<223> OTHER INFORMATION: Xaa can be any amino acid
<220> FEATURE:
<221> NAME/KEY: MISC_FEATURE
<222> LOCATION: (38)..(39)
<223> OTHER INFORMATION: Xaa can be any amino acid
<220> FEATURE:
<221> NAME/KEY: MISC_FEATURE

```
<222> LOCATION: (41)..(43)
<223> OTHER INFORMATION: Xaa can be any amino acid
<220> FEATURE:
<221> NAME/KEY: MISC_FEATURE
<222> LOCATION: (46)..(46)
<223> OTHER INFORMATION: Xaa can be any amino acid
<220> FEATURE:
<221> NAME/KEY: MISC_FEATURE
<222> LOCATION: (49)..(50)
<223> OTHER INFORMATION: Xaa can be any amino acid
<220> FEATURE:
<221> NAME/KEY: MISC_FEATURE
<222> LOCATION: (52)..(54)
<223> OTHER INFORMATION: Xaa can be any amino acid
<220> FEATURE:
<221> NAME/KEY: MISC_FEATURE
<222> LOCATION: (56)..(63)
<223> OTHER INFORMATION: Xaa can be any amino acid

<400> SEQUENCE: 103

Ile Xaa Gly Xaa Xaa Xaa Xaa Xaa Met Xaa Gln Phe Xaa Xaa Gln
1               5                   10                  15

Val Xaa Xaa Cys Xaa Xaa Cys Xaa Xaa Xaa Cys Leu Lys Gly Leu Ala
            20                  25                  30

Asn Xaa Xaa Cys Ser Xaa Xaa Leu Xaa Xaa Xaa Leu Pro Xaa Arg Cys
            35                  40                  45

Xaa Xaa Phe Xaa Xaa Xaa Ile Xaa Xaa Xaa Xaa Xaa Xaa Xaa Gly
50                  55                  60
```

NON-RADIOACTIVE CYTOTOXICITY ASSAYS

CROSS-REFERENCE TO RELATED APPLICATION

This application is a continuation of U.S. application Ser. No. 16/333,980, filed Mar. 15, 2019, which application claims priority as a U.S. National Stage Application filed under 35 U.S.C. § 371 to International Application No. PCT/US2017/052344, filed Sep. 19, 2017, which application claims the benefit of priority under 35 U.S.C. § 119(e) of U.S. Provisional Patent Application No. 62/396,650, filed on Sep. 19, 2016, the contents of which are incorporated herein by reference in their entirety.

STATEMENT REGARDING FEDERALLY SPONSORED RESEARCH OR DEVELOPMENT

This invention was made with government support under Grant No. DE019811 and DE025804 awarded by National Institutes of Health. The government has certain rights in the invention.

INCORPORATION BY REFERENCE OF SEQUENCE LISTING

Accompanying this filing is a Sequence Listing entitled "Sequence_ST25.txt", with a creation date of Apr. 18, 2022 and having 285,480 bytes of data, machine formatted on IBM-PC, MS-Windows operating system. The sequence listing is hereby incorporated herein by reference in its entirety for all purposes.

FIELD OF THE INVENTION

Provided herein are non-radioactive assays to assess cytotoxicity of a compound or a therapeutic agent.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Current rational for development of targeted therapeutic approaches largely relies on development of agents that selectively induce cytotoxicity and eliminate diseased cells associated with pathological conditions including cancer. These agents range from small molecules or biologics such as peptides, antibodies or shRNAs or T cells genetically engineered to selectively recognize tumor antigens. Successful selection and optimization of these agents for downstream application in immune-oncology, adoptive cellular therapy, CAR and antibody therapy depends on the accuracy and sensitivity of assays employed to measure cytotoxicity. In addition to drug discovery, methods to determine cell viability or cytotoxicity in response to exposure to a given test agent are also key to environmental testing and pesticide and herbicide testing. In short, to determine whether a given agent presents a real or potential risk when exposed to a given cell type requires a method that reliably, precisely, and accurately measures cell toxicity and/or viability after exposure to the test agent.

Several assays have been developed to measure cytotoxicity. Of these, radioactive chromium ($Cr^{51}$) release assay developed in 1968 is most commonly used worldwide. In this assay, target cells labeled with $Cr^{51}$ are incubated with effector cells and $Cr^{51}$ released upon their lysis serves as a measure of the effector cell cytotoxicity. However, several limitations including the hazards associated with harmful effects of radioactivity, additional costs of disposal of radioactive waste and requirement of additional equipment like gamma counters, have prompted researchers to seek safer alternative approaches. For example, cell membranes of target cells can be labeled with fluorescent dyes and cytotoxic response can be evaluated using multicolor flow cytometric analysis. However, the successful application of this approach demands careful calibration and labor intensive data analysis to efficiently distinguish the target and effector cell populations.

Non-viable cells that have lost membrane integrity leak cytoplasmic components into the surrounding medium. Cell death can be measured by monitoring the concentration of these leaked cellular components in the surrounding medium. Some cytotoxicity assays are based on quantification of the release of enzymes such as lactose dehydrogenase (LDH), glyceraldehyde 3-phosphate dehydrogenase (G3PDH) or adenylate kinase (AK) from dead cells. All these assays measure enzyme activity either directly by providing substrates that would be converted to fluorescent or luminescent products or include a second step wherein products of the primary reaction indirectly generate substrate for a luciferase reaction. Most of these enzymatic methods require a two-step procedure to remove culture medium to a separate container and thus are non-homogeneous. Additionally, these methods, in general, have poor sensitivity and, importantly, are unable to distinguish between death of target and effector cells, since both types of cells release cellular enzymes upon lysis.

Bioluminescence is inherited endogenously across a variety of species including bacteria, insects, fungi, and marine organisms. It happens when an enzyme, called a luciferase, oxidizes a light-emitting substrate (e.g. luciferin or coelenterazine). Because of their ability to provide highly sensitive quantitation with broad linearity, luciferases have been used extensively as reporters (Thorne, Inglese et al. 2010). Beetle luciferases form a distinct class with unique structure, evolutionary history and chemical mechanism. Firefly luciferases form a distinct subgroup of Beetle luciferases. Historically, the term "firefly luciferase" or FLuc or FfLuc referred to the enzyme LucPpy from a single species of *Photinus pyralis*. A luciferase release-based cytotoxicity assay was first described by Schafer et al in 1997 using Fluc (Schafer, Schafer et al. 1997). However, the shorter half-life of Fluc (<30 minutes) in tissue culture medium hindered its wider use (Thompson, Hayes et al. 1991, Schafer, Schafer et al. 1997). Fu et al also tried to develop a T cell cytotoxicity assay based on measurement of Fluc that has been released in the medium of Fluc-expressing target cells upon incubation with cytotoxic T cells (Fu, Tao et al. 2010). Surprisingly, incubation of cytotoxic T cells with the tumor cell targets did not result in significant release of luciferase in the culture medium (Fu, Tao et al. 2010). Therefore, these investigators abandoned the idea of measuring release of luciferase in the supernatant as an assay for cytotoxicity (Schafer, Schafer et al. 1997, Fu, Tao et al. 2010).

A number of novel luciferases have been discovered from deep sea marine organisms. These marine luciferases are smaller in size, ATP-independent and have much brighter luminescence as compared to Fluc (Takenaka, Yamaguchi et al. 2012). All of them have an N-terminal 17-22 amino acid consensus sequence that signals secretion (Takenaka, Yamaguchi et al. 2012). In addition to marine luciferase and their engineered-derivatives, thermostable variants of luciferases from *Photuris pennsylvanica* and *Pyrophorus plagiothalamus* have been described (PCT/US99/30925). Finally, thermostable variants of alkaline phosphatase are known in the art.

In view of the number of therapeutic antibody and cellular products that are now on the market or in development, there is a need for in vitro assays to allow the cytotoxic activity of antibodies and cellular products to be determined. In particular, there is a need for a high-throughput, label-free cytotoxicity assay that is sensitive, inexpensive, quick, homogenous (i.e. can be performed in one step) and also distinguishes between the death of target and effector cells.

SUMMARY OF THE INVENTION

The following embodiments and aspects thereof are described and illustrated in conjunction with systems, compositions and methods which are meant to be exemplary and illustrative, not limiting in scope.

The invention is directed to a class of assays, termed Matador assays, for determining the cytotoxic effect of a given test compound (including but not limited to chemotherapy agents, antibodies, biologicals, cytotoxic cell (e.g. T cell, NK cell), or a given set of test conditions. The method includes expression of a reporter in target cells in a manner so that it is preferentially retained within the healthy cells but is either released from dead and dying cells or whose activity can be preferentially measured in dead and dying cells. In one embodiment, the inventive method measures the activity of the reporter that has been released from the dead and dying cells. In some embodiments, the reporters are any one or more of: 1) non-secreted forms of luciferases from the copepods, such as *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri, Pleuromamma scutullata* or their homologs; 2) engineered luciferase reporters from deep sea shrimp, such as NanoLuc; 3) Renilla luciferase; 4) beetle luciferases, including firefly luciferases and engineered variants such as LucPPe-146-1H2. Other reporters, such as Green Fluorescent Protein, mCherry, and heat-stable alkaline phosphatase may also be used with the assays described herein. However, any molecule (e.g. DNA, RNA or protein) that is not expressed naturally in the target cells, is retained inside the healthy cells but is released from dead and dying cells, can be used. The preferred reporter is stable in the cell culture medium and is not degraded during the conditions of the cytotoxicity assay. As most cytotoxicity assays are carried out at 37° C., the preferred reporter for the assay is also thermostable. Vectors for expressing the reporter genes in stable and transient fashion, engineered cell lines stably expressing the reporter genes, and kits for practicing the invention are also disclosed. In some embodiments, the methods described herein measure the activity of the reporter inside dead and dying cells by addition of a substrate or a cofactor that is required for the activity of the reporter and which is excluded from the healthy cells but preferentially enters dead and dying cells.

Provided herein are methods for assessing cytotoxicity of an agent. The methods include providing a target cell that has been engineered to express intracellularly a reporter; exposing the target cell to an agent capable of modulating cytotoxicity; and assaying the activity of the reporter. In one embodiment, the reporter is not expressed endogenously by the target cell. In another embodiment, the reporter is expressed endogenously by the target cell at a level lower than what is achieved by engineered expression. In one embodiment, a change in reporter activity relative to a reference value is indicative of the agent being able to modulate cytotoxicity of the target cell. In one embodiment, a change in reporter activity is an increase in reporter activity relative to a reference value. In some embodiments, the reporter is expressed endogenously by the target cell at a level that is at least 10-25%, 25-50%, 50-75% or 75-100% lower than what is achieved by engineered expression.

In on embodiment, the reporter activity is assayed in the cell media containing the target cells. In another embodiment, the reporter activity is assayed in the cell supernatant that is free of the target cells.

In various embodiments, the cytotoxicity of an agent is measured by obtaining (assaying) the reporter activity in cell pellet and cell free supernatant and normalizing the reporter activity measured in the cell free supernatant. In various embodiments, normalizing comprises dividing the activity in the cell free supernatant by the reporter activity measured in the cell pellet In various embodiments, the reporter is a non-secretory form of an enzyme that is stable under the assay conditions at 37° C. for more than 15 min, for more than 30 min, for more than 1 hour, for more than 2 hours, for more than 3 hours, for more than 4 hours, for more than 12 hours, 24 hours, for more than 36 hours, for more than 48 hours or for at least 96 hours.

In various embodiments, the reporter is a non-secretory form of a luciferase. In some embodiments, the non-secretory form of luciferase is obtained from copepods, deep sea shrimp, beetle, firefly, or homologs or orthologs thereof or mutants or variants or derivatives thereof.

In exemplary embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri*, and *Pleuromamma scutullata*.

In various embodiments, the luciferase is any one or more of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), Lucia Luc, Renilla Luc, Firefly luciferase (FfLuc or Fluc), LucPPe-146-1H2, LucPPe-133-1B2, LucPPe-78-OB10, LucPPe49-7C6A, LucPpL-81-6G1 or CBGRluc or homologs or orthologs or mutants or variants or derivatives thereof.

In various embodiments, the reporter is a non-secretory form of a luciferase obtained from copepods, deep sea shrimp, beetle, firefly or homologs or orthologs thereof or mutant or derivatives thereof and the reporter activity is assayed by exposing the target cells to a luciferase specific substrate.

In various embodiments, the luciferase-specific substrate is coelenterazine or an imidazopyrazinone substrate (furimazine) or a derivative thereof.

In one embodiment, the luciferase-specific substrate is D-luciferin or a derivative thereof.

In one embodiment, the reporter is a thermostable luciferase. In one embodiment, the reporter is a thermostable beetle luciferase. In an embodiment, the thermostable beetle luciferase is obtained from *Photuris pennsylvanica* and *Pyrophorus plagiothalamus*

In some embodiments, the reporter is a non-secretory form of an alkaline phosphatase. In one embodiment, the alkaline phosphatase is a heat-stable alkaline phosphatase.

In some embodiments, the reporter is a non-secretory form of a fluorescent protein. In one embodiment, the non-secretory form of a fluorescent protein is green fluorescent protein.

In some embodiments, the non-secretory form of a fluorescent protein is mCherry protein.

In one embodiment, the reporter is a DNA sequence that is not present in the target cells endogenously. In one embodiment, the reporter is an RNA sequence that is not present in the target cells endogenously.

In one embodiment, the target cells express a single type of reporter. In another embodiment, the target cells express more than one type of reporter. In various embodiments, the activity of the two reporters can be measured independent of each other either simultaneously or sequentially.

In some embodiments, the substrate for one of the reporters is coelenterazine or an imidazopyrazinone substrate (e.g., furimazine) or a derivative thereof and the substrate for the other reporter is D-luciferin or a derivative thereof.

In some embodiments, the substrate for one of the reporters is coelenterazine or an imidazopyrazinone substrate (e.g., furimazine) or a derivative thereof and the substrate for the other reporter is pNNP or a derivative thereof.

In some embodiments, the target cells expressing two or more reporters are mixed together prior to the assay.

In some embodiments, the target cells express the non-secretory form of reporter as a fusion protein with one or more of chitin binding protein (CBP), glutathione-S-transferase (GST), polyhistidine (His) tag, FLAG tag, HA tag, Myc tag, V5 tag, AcV5 tag, Myristoylation (Myr) tag or a combination thereof.

In some embodiments, the reference value is the reporter activity in any one or more of (i) target cells that do not express reporter, (ii) target cells that express reporter but are not treated with the test agent(s); (iii) the target cells that are left untreated; (iv) target cells that are not treated with the substrate for the reporter, or (iii) a combination thereof.

In some embodiments, the agent capable of modulating cytotoxicity is any one or more of an antibody, small molecule, chemical compound, radiation agent, cytotoxic cells, biologics or combinations thereof.

In some embodiments, the cytotoxic cells are any one or more of T cells, NK cells, PBMCs or combinations thereof. In some embodiments, the cytotoxic cells are modified to express a chimeric or synthetic receptor or a T cell receptor.

In some embodiments, the antibodies are any one or more of chimeric antibodies, human antibodies, humanized antibodies, bispecific antibodies, bispecific T cell engager, DART, antibody drug conjugates or combination thereof.

In exemplary embodiments, the agent capable of modulating cytotoxicity targets one or more of the antigens selected from a group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRviii); ganglioside G2 (GD2); ganglioside GD3 (aNeu5Ac(2-8)aNeu5Ac(2-3)bD-Galp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); FmsLike Tyrosine Kinase 3 (FLT3); Tumor-associated glycoprotein 72 (TAG72); CD38; CD44v6; a glycosylated CD43 epitope expressed on acute leukemia or lymphoma but not on hematopoietic progenitors, a glycosylated CD43 epitope expressed on non-hematopoietic cancers, Carcinoembryonic antigen (CEA); Epithelial cell adhesion molecule (EPCAM); B7H3 (CD276); KIT (CD 117); Interleukin-13 receptor subunit alpha-2 (IL-13Ra2 or CD213A2); Mesothelin; Interleukin 11 receptor alpha (IL-llRa); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gpl00); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDClalp(1-4)bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ES0-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGEl); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCT A-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B 1 (CYP1B 1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1), MPL, Biotin, c-MYC epitope Tag, CD34, LAMP1 TROP2, GFRalpha4, CDH17, CDH6, NYBR1, CDH19, CD200R, Slea (CA19.9; Sialyl Lewis Antigen) Fucosyl-GM1, PTK7, gpNMB, CDH1-CD324, DLL3, CD276/B7H3, ILi11Ra, IL13Ra2, CD179b-IGL11, ALK TCRgamma-delta, NKG2D, CD32 (FCGR2A), Tn ag, CSPG4-HMW-MAA, Tim1−/HVCR1, CSF2RA (GM-CSFR-alpha), TGFbetaR2, VEGFR2/KDR, Lews Ag, TCR-beta1 chain, TCR-beta2 chain, TCR-gamma chain, TCR-delta chain, FITC, Leutenizing hormone receptor (LHR), Follicle stimulating hormone receptor (FSHR), Chorionic Gonadotropin Hormone receptor (CGHR), CCR4, GD3, SLAMF6, SLAMF4, HIV1 envelope glycoprotein, HTLV1-Tax, CMV pp65, EBV-EBNA3c, influenza A hemagglutinin (HA), GAD, PDL1, Guanylyl cyclase C (GCC), KSHV-K8.1 protein, KSHV-gHprotein, HLA, HLA-A, HLA-A2, HLA-B, HLA-C, HLA-DP, HLA-DM, HLA-DOA, HLA-DOB, HLA-DQ, HLA-DR or HLA-G.

In some embodiments, the reporter is expressed in cells by any one or more of plasmid vector, adenoviral vector, adenoassociated viral vector, sleeping beauty transposon, piggyback transposon, pCMV (cytomegalovirus) vectors, vaccinia virus vectors, retroviral vectors, lentiviral vectors, SV40 virus vectors, transfection of naked DNA or transfection of in vitro transcribed RNA. In some embodiments, the reporter is expressed using a non-vector method. In some embodiments, the reporter is expressed from a foreign promoter. In some embodiments, the reporter is expressed from a natural promoter.

In some embodiments, the target cells are exposed to the test agent in vitro. In some embodiments, the target cells are exposed to the test agent in vivo.

In some embodiments, the assay is performed in vitro. In some embodiments, the assay is performed in a high throughput fashion. In some embodiments, the assay is performed in vivo. In some embodiments, the target cells are present in a transgenic animal. In some embodiments, the assay is performed to identify agents that increase, decrease or have no effect on the cytotoxicity of an agent on a target cell. In some embodiments, the assay is performed with one or more agents used alone or in combination.

In some embodiments, the non-secretory form of the reporter is expressed using vectors encoding the non-secretory forms of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), Lucia Luc, Renilla Luc, Firefly luciferase (FfLuc or Fluc), LucPPe-146-1H2, LucPPe-133-1B2, LucPPe-78-OB10, LucPPe49-7C6A, LucPpL-81-6G1 or CBGRluc or homologs or orthologs or mutants or derivatives thereof.

In some embodiments, the target cell is a cell line expressing the non-secretory forms of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), Renilla Luc, Firefly luciferase (FfLuc or Fluc), LucPPe-146-1H2, LucPPe-133-1B2, LucPPe-78-OB10, LucPPe49-7C6A, LucPpL-81-6G1, CBGRluc, thermostable alkaline phosphatase or homologs or orthologs or mutants or derivatives or variant thereof.

In some embodiments, the target cell is a primary cell expressing the non-secretory forms of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), Renilla Luc, Firefly luciferase (FfLuc or Fluc), LucPPe-146-1H2, LucPPe-133-1B2, LucPPe-78-OB10, LucPPe49-7C6A, LucPpL-81-6G1 or CBGRluc or homologs or orthologs or mutants or derivatives thereof.

In some embodiments, the target cell of expresses one or more of the antigens selected from a group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRviii); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); FmsLike Tyrosine Kinase 3 (FLT3); Tumor-associated glycoprotein 72 (TAG72); CD38; CD44v6; a glycosylated CD43 epitope ex-persed-expressed on acute leukemia or lymphoma but not on hematopoietic progenitors, a glycosylated CD43 epitope expressed on non-hematopoietic cancers, Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-llRa); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gpl00); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDClalp(1-4)bDGlcp(1-1)Cer); transglutaminase 5 (TGS5); high molecular weight melanoma associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97;

CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ES0-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B 1 (CYP1B 1); CCCTC-Binding Factor (Zinc Finger Protein)-Like (BORIS or Brother of the Regulator of lmprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1), MPL, Biotin, c-MYC epitope Tag, CD34, LAMP1 TROP2, GFRalpha4, CDH17, CDH6, NYBR1, CDH19, CD200R, Slea (CA19.9; Sialyl Lewis Antigen) Fucosyl-GM1, PTK7, gpNMB, CDH1-CD324, DLL3, CD276/B7H3, IL11Ra, IL13Ra2, CD179b-IGL11, ALK TCRgamma-delta, NKG2D, CD32 (FCGR2A), Tn ag, CSPG4-HMW-MAA, Tim1–/HVCR1, CSF2RA (GM-CSFR-alpha), TGFbetaR2, VEGFR2/KDR, Lews Ag, TCR-betal chain, TCR-beta2 chain, TCR-gamma chain, TCR-delta chain, FITC, Leutenizing hormone receptor (LHR), Follicle stimulating hormone receptor (FSHR), Chorionic Gonadotropin Hormone receptor (CGHR), CCR4, GD3, SLAMF6, SLAMF4, HIV1 envelope glycoprotein, HTLV1-Tax, CMV pp65, EBV-EBNA3c, influenza A hemagglutinin (HA), GAD, PDL1, Guanylyl cyclase C (GCC), KSHV-K8.1 protein, KSHV-gHprotein, HLA, HLA-A, HLA-A2, HLA-B, HLA-C, HLA-DP, HLA-DM, HLA-DOA, HLA-DOB, HLA-DQ, HLA-DR or HLA-G.

In some embodiments, the target cell has been modified and/or selected to lack the expression of one or more antigens. In exemplary embodiments, the target cell has been modified and/or selected to lack the expression of one or more antigens selected from a group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRviii); ganglioside G2 (GD2); ganglioside GD3 (aNeu5Ac(2-8) aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); FmsLike Tyrosine Kinase 3 (FLT3); Tumor-associated glycoprotein 72 (TAG72); CD38; CD44v6; a glycosylated CD43 epitope ex-persed-expressed on acute leukemia or lymphoma but not on hematopoietic progenitors, a glycosylated CD43 epitope expressed on non-hematopoietic cancers, Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-llRa); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gpl00); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDClalp(1-4) bDGlcp(1-1)Cer); transglutaminase 5 (TGS5); high molecular weight melanoma associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ES0-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53$^3$); p53 mutant; prostein; surviving; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin Bi; v-myc avian myelocytomatosis viral oncogene neuroblastoma derived homolog (MYCN); Ras Homolog Family Member C (RhoC); Tyrosinase-related protein 2 (TRP-2); Cytochrome P450 1B 1 (CYP1B 1); CCCTC-Binding Factor (Zinc Finger Protein)-Like (BORIS or Brother of the Regulator of lmprinted Sites), Squamous Cell Carcinoma Antigen Recognized By T Cells 3 (SART3); Paired box protein Pax-5 (PAX5); proacrosin binding protein sp32 (OY-TESl); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RUl); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRl); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLLl), MPL, Biotin, c-MYC epitope Tag, CD34, LAMP1 TROP2, GFRalpha4, CDH17, CDH6, NYBR1, CDH19, CD200R, Slea (CA19.9; Sialyl Lewis Antigen) Fucosyl-GM1, PTK7, gpNMB, CDH1-CD324, DLL3, CD276/B7H3, IL11Ra, IL13Ra2, CD179b-IGL11, ALK TCRgamma-delta, NKG2D, CD32 (FCGR2A), Tn ag, CSPG4-HMW-MAA, Tim1−/HVCR1, CSF2RA (GM-CSFR-alpha), TGFbetaR2, VEGFR2/KDR, Lews Ag, TCR-betal chain, TCR-beta2 chain, TCR-gamma chain, TCR-delta chain, FITC, Leutenizing hormone receptor (LHR), Follicle stimulating hormone receptor (FSHR), Chorionic Gonadotropin Hormone receptor (CGHR), CCR4, GD3, SLAMF6, SLAMF4, HIV1 envelope glycoprotein, HTLV1-Tax, CMV pp65, EBV-EBNA3c, influenza A hemagglutinin (HA), GAD, PDL1, Guanylyl cyclase C (GCC), KSHV-K8.1 protein, KSHV-gHprotein, HLA, HLA-A, HLA-A2, HLA-B, HLA-C, HLA-DP, HLA-DM, HLA-DOA, HLA-DOB, HLA-DQ, HLA-DR and HLA-G.

In some embodiments, the target cells is derived from a disease selected from the group consisting of a proliferative disease, a precancerous condition, a cancer, an infectious disease, an immune disease, an allergic disease or a degenerative disease.

In some embodiments, the target cell is derived from a cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, primary effusion lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia, colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, Merkel cell cancer, epidermoid cancer, squamous cell cancer, T-cell lymphoma, environmentally induced cancers, combinations of said cancers, and metastatic lesions of said cancers.

In some embodiments, the target cell is associated with infection by a virus including but not limited to HIV1, HIV2, HTLV1, Epstein Barr virus (EBV), cytomegalovirus (CMV), adenovirus, adeno-associated virus, BK virus, Human Herpesvirus 6, Human Herpesvirus 8 influenza virus, parainfluenza virus, avian flu virus, MERS and SARS coronaviruses, Crimean Congo Hemorrhagic fever virus, rhino virus, enterovirus, Dengue virus, West Nile virus, Ebola virus, Marburg virus, Lassa fever virus, zika virus, RSV, measles virus, mumps virus, rhino virus, varicella virus, herpes simplex virus 1 and 2, varicella zoster virus, HIV-1, HTLV1, Hepatitis virus, enterovirus, hepatitis B virus, Hepatitis C virus, Nipah and Rift valley fever viruses, Japanese encephalitis virus, Merkel cell polyomavirus, or is associated with infection with a bacteria, *Mycobacterium tuberculosis*, atypical mycobacteria species, *Pneumocystis jirovecii*, toxoplasmosis, *rickettsia, nocardia, aspergillus, mucor,* or *candida*.

In some embodiments, the target cell is exposed to an agent capable of modulating cytotoxicity for less than 1 second or for more than 1 second, 30 seconds, 1 minute, 30 minutes, 1 hour, 4 hours, 12 hours, 24 hours, 48 hours, 72 hours, 96 hours, 7 days, or 12 days.

Further provided herein are vectors and/or compositions comprising vectors wherein the vectors encode non-secretory forms of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), Lucia Luc, Renilla Luc, Firefly luciferase (FfLuc or Fluc), LucPPe-146-1H2, LucPPe-133-1B2, LucPPe-78-0B10, LucPPe49-7C6A, LucPpL-81-6G1 or CBGRluc or homologs or orthologs or mutants or derivatives thereof.

Also provided herein are cell lines and/or compositions comprising cell lines wherein the cell lines express the non-secretory forms of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, Turbo-Luc16 (TLuc), Renilla Luc, Firefly luciferase (FfLuc or Fluc), LucPPe-146-1H2, LucPPe-133-1B2, LucPPe-78-0B10, LucPPe49-7C6A, LucPpL-81-6G1, CBGRluc, thermostable alkaline phosphatase or homologs or orthologs or mutants or derivatives thereof for the purpose of use as a target cell line for measuring cytotoxicity. In various embodiments, the cell lines are modified and/or selected to lack the expression of one or more antigens.

Also provided herein are primary cells and/or compositions comprising primary cells wherein the primary cells express the non-secretory forms of GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), Renilla Luc, Firefly luciferase (FfLuc or Fluc), LucPPe-146-1H2, LucPPe-133-1B2, LucPPe-78-0B10, LucPPe49-7C6A, LucPpL-81-6G1 or CBGRluc or homologs or orthologs or mutants or derivatives thereof. In various embodiments, the primary cell lines are modified and/or selected to lack the expression of one or more antigens.

Further provided herein are target cells and/or compositions comprising target cells wherein the target cells express one or more of the antigens selected from a group consisting of. CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRviii); ganglioside G2 (GD2); ganglioside GD3 (aNeu5Ac(2-8)aNeu5Ac(2-3)bDGalp(1-4)bDGlcp(1-1) Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); FmsLike Tyrosine Kinase 3 (FLT3); Tumor-associated glycoprotein 72 (TAG72); CD38; CD44v6; a glycosylated CD43 epitope expressed on acute leukemia or lymphoma but not on hematopoietic progenitors, a glycosylated CD43 epitope expressed on non-hematopoietic cancers, Carcinoembryonic antigen (CEA); Epithelial cell adhesion molecule (EP-CAM); B7H3 (CD276); KIT (CD117); Interleukin-13 receptor subunit alpha-2 (IL-13Ra2 or CD213A2); Mesothelin; Interleukin 11 receptor alpha (IL-llRa); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gpl00); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDClalp(1-4)bDGlcp(1-1)Cer); transglutaminase 5 (TGS5); high molecular weight melanoma associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGEl); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCT A-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B 1 (CYP1B 1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRl); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLLl), MPL, Biotin, c-MYC epitope Tag, CD34, LAMP1 TROP2, GFRalpha4, CDH17, CDH6, NYBR1, CDH19, CD200R, Slea (CA19.9; Sialyl Lewis Antigen) Fucosyl-GM1, PTK7, gpNMB, CDH1-CD324, DLL3, CD276/B7H3, IL11Ra, IL13Ra2, CD179b-IGL11, ALK TCR-gamma-delta, NKG2D, CD32 (FCGR2A), Tn ag, CSPG4-HMW-MAA, Tim1–/HVCR1, CSF2RA (GM-CSFR-alpha), TGFbetaR2, VEGFR2/KDR, Lews Ag, TCR-betal chain, TCR-beta2 chain, TCR-gamma chain, TCR-delta chain, FITC, Leutenizing hormone receptor (LHR), Follicle stimulating hormone receptor (FSHR), Chorionic Gonadotropin Hormone receptor (CGHR), CCR4, GD3, SLAMF6, SLAMF4, HIV1 envelope glycoprotein, HTLV1-Tax, CMV pp65, EBV-EBNA3c, influenza A hemagglutinin (HA), GAD, PDL1, Guanylyl cyclase C (GCC), KSHV-K8.1 protein, KSHV-gHprotein, HLA, HLA-A, HLA-A2, HLA-B, HLA-C, HLA-DP, HLA-DM, HLA-DOA, HLA-DOB, HLA-DQ, HLA-DR or HLA-G.

In various embodiments, the cell lines, primary cells and/or target cells are modified and/or selected to lack the expression of one or more antigens selected from a group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRviii); ganglioside G2 (GD2); ganglioside GD3 (aNeu5Ac(2-8)aNeu5Ac(2-3)bDGalp(1-4)bDGlcp(1-1) Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); FmsLike Tyrosine Kinase 3 (FLT3); Tumor-associated glycoprotein 72 (TAG72); CD38; CD44v6; a glycosylated CD43 epitope expressed on acute leukemia or lymphoma but not on hematopoietic progenitors, a glycosylated CD43 epitope expressed on non-hematopoietic cancers, Carcinoembryonic antigen (CEA); Epithelial cell adhesion molecule (EP-CAM); B7H3 (CD276); KIT (CD117); Interleukin-13 receptor subunit alpha-2 (IL-13Ra2 or CD213A2); Mesothelin; Interleukin 11 receptor alpha (IL-llRa); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDClalp(1-4)bDGlcp(1-1)Cer); transglutaminase 5 (TGS5); high molecular weight melanoma associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGEl); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 ($p53^3$); p53 mutant; prostein; surviving; telomerase; prostate carcinoma tumor antigen-1 (PCT A-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B 1 (CYP1B 1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TESl); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RUl); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRl); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLLl), MPL, Biotin, c-MYC epitope Tag, CD34, LAMP1 TROP2, GFRalpha4, CDH17, CDH6, NYBR1, CDH19, CD200R, Slea (CA19.9; Sialyl Lewis Antigen) Fucosyl-GM1, PTK7, gpNMB, CDH1-CD324, DLL3, CD276/B7H3, IL11Ra, IL13Ra2, CD179b-IGL11, ALK TCR-gamma-delta, NKG2D, CD32 (FCGR2A), Tn ag, CSPG4-HMW-MAA, Tim1–/HVCR1, CSF2RA (GM-CSFR-alpha), TGFbetaR2, VEGFR2/KDR, Lews Ag, TCR-betal chain, TCR-beta2 chain, TCR-gamma chain, TCR-delta chain, FITC, Leutenizing hormone receptor (LHR), Follicle stimulating hormone receptor (FSHR), Chorionic Gonadotropin Hormone receptor (CGHR), CCR4, GD3, SLAMF6, SLAMF4, HIV1 envelope glycoprotein, HTLV1-Tax, CMV pp65, EBV-EBNA3c, influenza A hemagglutinin (HA), GAD, PDL1, Guanylyl cyclase C (GCC), KSHV-K8.1 protein, KSHV-gHprotein, HLA, HLA-A, HLA-A2, HLA-B, HLA-C, HLA-DP, HLA-DM, HLA-DOA, HLA-DOB, HLA-DQ, HLA-DR and HLA.

Further provided herein are kits comprising components for assessing cytotoxicity of an agent. In various embodiments, the kits include target cells (for example, cells engineered to express intracellularly one or more reporters and/or cell lines expressing one or more reporters and/or primary cells expressing one or more reporters), and substrates for activating the reporter. The target cells, reporters and substrates are as described herein. In various embodiments, the kits further comprise instructions for use of the kit.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 5A-FIG. 5B depicts in accordance with various embodiments of the invention, that Digitonin-treatment of K562 and RAJI cells stably expressing TurboLuc16 (TLuc) resulted in increase in TLuc activity.

FIG. 6 depicts in accordance with various embodiments of the invention, increase in Renilla Luc activity upon induction of death of K562 cells expressing Renilla-Luc by NK92MI cells or by treatment with Digitonin.

FIG. 9A-9C depicts in accordance with various embodiments of the invention, FIG. 9A: induction of K562-GLuc cell death by NK92MI cells results in significant and near equivalent increase in GLuc activity when measured either by directly adding 0.5×CTZ assay buffer to the wells containing cells plus supernatant or when added to supernatant that had been cleared of cells by a centrifugation step. FIG. 9B: supernatants from cell death assay containing GLuc and Renilla can be frozen and re-thawed after 2 weeks without loss of luciferase activities. FIG. 9C: GLuc assay conducted using the Renilla Luciferin substrate gave similar results as those obtained after addition of 0.5×CTZ assay buffer containing native coelenterazine.

FIG. 10C depicts in accordance with various embodiment of the invention that there is slight increase in GLuc activity even in the cell pellet fraction with increase in number of K562-GLuc target cells upon co-culture with NK92MI effector cells.

FIG. 11A-FIG. 11B depicts in accordance with various embodiments of the invention, GLuc-based Matador cytotoxicity assay can be used to monitor cytotoxicity induced by CAR expressing effector cells.

FIG. 12 depicts in accordance with various embodiments of the invention, that induction of RAJI cell death by T cells expressing CD19-specific CAR results in increase in GLuc activity, whereas no increase in GLuc activity was observed by co-culture with uninfected T cells or those expressing a negative control CAR (i.e. 4C3) whose target antigen is not expressed in RAJI cells.

FIG. 13 depicts in accordance with various embodiments of the invention, inhibition of CD19MM-(vL-vH)-Myc-BBz-T2A-PAC(062915-D03)[SEQ ID NO:82]-CAR-T cells induced cell death by 50 nM and 100 nM Dasatinib (Das), while Imatinib (IM) has no effect.

FIG. 17A: co-culture of RAJI-NLuc cells with NK92MI cells expressing a FMC63-MYC-BBZ-T2A-EGFP chimeric antigen receptor resulted in significant increase in NLuc activity as compared to co-culture with NK92MI cells expressing a control (4C3-MYC-BBZ-T2A-EGFP) chimeric antigen receptor or culture without NK92MI cells (medium alone). FIG. 17B: co-culture of RAJI-NLuc cells with T cells expressing FMC63-MYC-BBZ-T2A-PAC chimeric antigen receptor resulted in significant increase in NLuc activity as compared to co-culture with T cells expressing a control (4C3-MYC-BBZ-T2A-PAC) chimeric antigen receptor or culture without T cells (medium alone)

FIG. 20A: co-culture of RAJI cells that had been stably transduced with MSCVhygro-GLuc vector with T cells in the presence of Blincyto (Blinatumomab) results in increase in luciferase activity as compared to untreated cells or cells treated with T cells or Binatumomab alone, demonstrating that the Matador assay can be used to monitor Binatumomab-induced cell death. FIG. 20B: increase in % specific lysis of RAJI-GLuc cells upon co-culture with T cells in the presence of Binatumomab. FIG. 20C: co-culture of RAJI-GLuc cells that had been stably transduced with pLenti-GLuc vector with T cells in the presence of Blincyto (Blinatumomab) results in increase in luciferase activity as compared to untreated cells or cells treated with T cells or Binatumomab alone, demonstrating that the GLuc-based Matador assay can be used to monitor Binatumomab-induced cell death. FIG. 20D: co-culture of RAJI cells stably expressing MLuc7 with T cells in the presence of Blincyto (Blinatumomab) results in increase in luciferase activity as compared to untreated cells or cells treated with T cells or Binatumomab alone, demonstrating that increase in MLuc7 activity can be used to monitor Binatumomab-induced cell death in Matador assay.

FIG. 28A: Digitonin-induced cell death of GFP transfected 293FT cells resulted in increase in GFP release in the supernatant fraction as measured by Western blotting with an antibody against GFP. FIG. 28B: Digitonin-induced cell death of mCherry-HA transfected 293FT cells resulted in increase in mCherry release in the supernatant fraction as measured by Western blotting with an antibody against the HA tag. FIG. 28C: significant increase in fluorescence in cell supernatant collected from cells that had been transfected with vectors encoding GFP and mCherry-HA, respectively, and then treated with Digitonin as compared to untreated cells.

FIG. 29 depicts in accordance with various embodiments of the invention, increase in % specific lysis of RAJI-NLuc cells when co-cultured with CD19-directed FMC63-Myc-BBZ and FMC63-Myc-CD28z CAR constructs.

FIG. 30A-C, depict in accordance with various embodiments of the invention, the effect of different assay conditions and sample types on production of glow-type luminescence by NLuc when used in Matador cytotoxicity assay.

FIG. 36A-B depicts in accordance with various embodiments of the invention, FIG. 36A: increase in luciferase activity upon induction of cell death by co-culture of K562 cells stably expressing LucPPe-146-1H2 with NK92MI cells or by treatment with Digitonin. FIG. 36B: treatment with Digitonin results in increase in luciferase activity in case of 293FT cells transiently transfected with the LucPPe-146-1H2 expression construct.

FIG. 37 depicts in accordance with various embodiments of the invention, stability of the LucPPe-146-1H2 luciferase in the cell culture supernatant at 37° C. under the conditions of Matador cytotoxicity assay.

DETAILED DESCRIPTION OF INVENTION

Figure 1A:
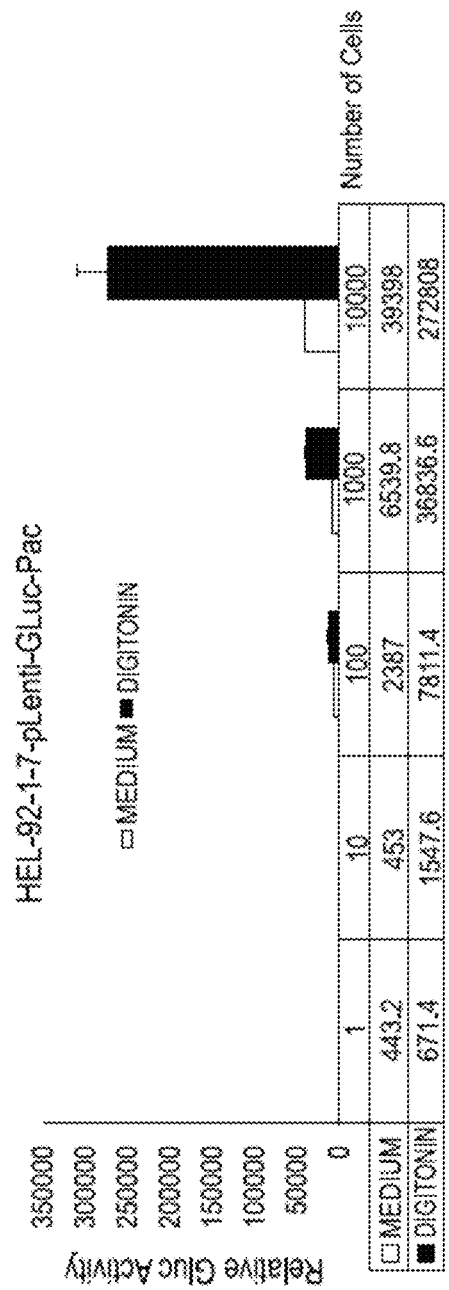
FIG. 1A-FIG. 1B depicts in accordance with various embodiments of the invention, that induction of cell death by treatment of HEL-92-1-17 and RAJI cells stably expressing GLuc (SEQ ID NO: 1) with Digitonin resulted in an increase in GLuc luciferase activity which was detectable even at 1 cell/well level and there was a progressive increase in luciferase activity with increase in cell number.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed, Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, NY 2006); Smith, *March's Advanced Organic Chemistry Reactions*, Mechanisms and Structure 7$^{th}$ ed., J. Wiley & Sons (New York, NY 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor NY, 2013); Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Definitions

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the term "about" refers to a measurable value such as an amount, a time duration, and the like, and encompasses variations of ±20%, ±10%, ±5%, ±1%, ±0.5% or ±0.1% from the specified value.

As used herein, "matador assay" or "matador cytotoxicity assay" refers to an assay of cellular cytotoxicity which involves the measurement of activity of a reporter that is not expressed endogenously by the target cell or is expressed endogenously by the target cell at a level much lower than what is achieved by engineered expression. The assay takes advantage of the fact that non-viable cells lose cell membrane integrity and either leak the reporter into the surrounding media or allow enhanced entry of the substrate of the reporter into the cell or both, resulting in an enhanced interaction between the reporter and its substrate, which in turn, results in an increase in the reporter activity. The preferred reporter for use in the matador assay is non-secretory form of a thermostable luciferase, such as GLuc, NLuc, PaLuc1, TLuc, MLuc7, Lucia Luc and LucPPe-146-1H2. The activity of the reporter in the Matador assay can be assayed in a homogenous format (i.e. single step) by adding the assay reagent containing the reporter substrate to the cell culture media containing the target cells. In an alternate embodiment, the activity of the reporter in the Matador assay can be assayed by adding the assay reagent containing the reporter substrate to the cell culture media that has been separated from the target cells (i.e. supernatant).

As used herein "non-vector method" refers to a method of introducing and/or expressing a reporter in a cell that does not involve the use of a vector. Several non-vector methods of gene transfer and expression are known in the art, such as transfection of naked DNA or electroporation of in vitro transcribed RNA.

As used herein, "foreign promoter" refers to a promoter that is not naturally present in the target cell expressing the reporter of the invention. Examples of foreign promoters include CMV immediate early promoter and SV40 promoter. The expression of TurboLuc-16 reporter is driven by CMV promoter in the exemplary vector pLENTI-TurboLuc-16-X3Flag-Blast-C04 (SEQ ID NO: 93).

As used herein, "natural promoter" refers to promoter that is naturally present in the target cell expressing the reporter of the invention. Examples of natural promoters include Elongation Factor 1α (EF1α) promoter and beta actin promoter. The natural promoter may be introduced into the target cells as part of the vector encoding the reporter of the invention. For example, the expression of LucPPe-146-1H2 reporter is driven by EF1α promoter in the vector pLenti-EF1-LucPPe-146-1H2-Flag-Pac-R01 (SEQ ID NO: 100). Alternatively, the DNA fragment encoding the reporter of the invention could be inserted downstream of an endogenously occurring natural promoter by homologous recombination. For example, GLuc cDNA could be inserted downstream of one of the genomic copies of the endogenous EF1α promoter using techniques of homologous recombination known in the art.

As used herein, "cell line" refers to cells that demonstrate the potential for indefinite subculture in vitro. A cell line is generally derived from one cell or set of cells of the same type. Examples of cell lines include K562, RAJI, Jurkat and HeLa.

As used herein, "primary cells" refers to cells derived directly from the parent tissue. Primary cells generally have the same karyotype and chromosome number as those in the original tissue. Examples of primary cells include primary T cells, primary B cells and primary vascular endothelial cells.

"Chimeric antigen receptor" or "CAR" or "CARs" as used herein refers to engineered receptors, which graft an antigen specificity onto cells (for example T cells such as naïve T cells, central memory T cells, effector memory T cells or combination thereof). CARs are also known as artificial T-cell receptors, chimeric T-cell receptors, or chimeric immunoreceptors. As used herein, the term "CAR" or "CARs" also encompasses newer approaches to conferring antigen specificity onto cells, such as Antibody-TCR chimeric molecules or AbTCR (WO 2017/070608 A1), TCR receptor fusion proteins or TFP (WO 2016/187349 A1) and Synthetic Immune Receptors or SIR (U.S. 62/429,597).

"Linker" (L) or "linker domain" or "linker region" as used herein refer to an oligo- or polypeptide region from about 1 to 100 amino acids in length, which links together two or more domains of the invention. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers, for example T2A (SEQ ID NO: 66), P2A (SEQ ID NO: 67) and E2A (SEQ ID NO: 69), 2A-like linkers or functional equivalents thereof and combinations thereof. Other linkers will be apparent to those of skill in the art and may be used in connection with alternate embodiments of the invention.

"Co-express" as used herein refers to simultaneous expression of two or more genes. Genes may be nucleic acids encoding, for example, a single protein or a chimeric protein as a single polypeptide chain.

"Single chain variable fragment", "single-chain antibody variable fragments" or "scFv" antibodies as used herein refer to forms of antibodies comprising the variable regions of only the heavy ($V_H$) and light ($V_L$) chains, connected by a linker peptide. The scFvs are capable of being expressed as a single chain polypeptide. The scFvs retain the specificity of the intact antibody from which it is derived. The light and heavy chains may be in any order, for example, $V_H$-linker-$V_L$ or $V_L$-linker-$V_H$, so long as the specificity of the scFv to the target antigen is retained.

"Cancer" and "cancerous" refer to or describe the physiological condition in mammals that is typically characterized by unregulated cell growth. The term "cancer" is meant to include all types of cancerous growths or oncogenic processes, metastatic tissues or malignantly transformed cells, tissues, or organs, irrespective of histopathologic type or stage of invasiveness.

It is to be inferred without explicit recitation and unless otherwise intended, that when the present disclosure relates to a polypeptide, protein, polynucleotide, antibody or fragment thereof, an equivalent or a biologically equivalent of such is intended within the scope of this disclosure. As used herein, the term "biological equivalent thereof" is intended to be synonymous with "equivalent thereof" when referring to a reference protein, antibody or fragment thereof, polypeptide or nucleic acid, intends those having minimal homology while still maintaining desired structure or functionality. Unless specifically recited herein, it is contemplated that any of the above also includes equivalents thereof. For example, an equivalent intends at least about 70% homology or identity, or at least 80% homology or identity and alternatively, or at least about 85%, or alternatively at least about 90%, or alternatively at least about 95%, or alternatively at least 98% percent homology or identity and exhibits substantially equivalent biological activity to the reference protein, polypeptide, antibody or fragment thereof or nucleic acid. Alternatively, when referring to polynucleotides, an equivalent thereof is a polynucleotide that hybridizes under stringent conditions to the reference polynucleotide or its complement. Alternatively, when referring to polypeptides or proteins, an equivalent thereof is a expressed polypeptide or protein from a polynucleotide that hybridizes under stringent conditions to the polynucleotide or its complement that encodes the reference polypeptide or protein.

Cloning and expression methods will be apparent to a person of skill in the art and may be as described in WO 2015/142675; Sambrook et al., 2012, MOLECULAR CLONING: A LABORATORY MANUAL, volumes 1-4, Cold Spring Harbor Press, NY; June et al. 2009 Nature Reviews Immunology 9.10: 704-716; WO 01/96584; WO 01/29058; U.S. Pat. No. 6,326,193, the contents of each of which are herein incorporated by reference in their entirety as though set forth herein.

Physical methods for introducing polynucleotides of into host cells such as calcium phosphate transfection and the like are well known in the art and will be apparent to a person of skill in the art. In exemplary embodiments, such methods are set forth in Sambrook et al., 2012, MOLECULAR CLONING: A LABORATORY MANUAL, volumes 1-4, Cold Spring Harbor Press, NY); U.S. Pat. Nos. 5,350, 674 and 5,585,362, the contents of each of which are herein incorporated by reference in their entirety as though set forth herein.

As used herein, "amino acid" is meant to include both natural and synthetic amino acids, and both D and L amino acids. "Standard amino acid" means any of the twenty L-amino acids commonly found in naturally occurring peptides. "Nonstandard amino acid" means any amino acid, other than the standard amino acids, regardless of whether it is prepared synthetically or derived from a natural source.

Herein, "peptide" and "protein" are used interchangeably, and refer to a compound comprised of at least two amino acid residues covalently linked by peptide bonds or modified peptide bonds (e.g., peptide isosteres). No limitation is placed on the maximum number of amino acids which may comprise a protein or peptide. The amino acids comprising the peptides or proteins described herein and in the appended claims are understood to be either D or L amino acids with L amino acids being preferred. The amino acid comprising the peptides or proteins described herein may also be modified either by natural processes, such as post-translational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide. Also, a given peptide may contain many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W.H. Freeman and Company, New York, 1993 and Wold F, Posttranslational Protein Modifications: Perspectives and Prospects, pgs. 1-12 in Posttranslational Covalent Modification of Proteins, B. C. Johnson, Ed., Academic Press, New York, 1983; Seifter et al., "Analysis for protein modifications and nonprotein cofactors," Meth. Enzymol. (1990) 182: 626-646 and Rattan et al. (1992), "Protein Synthesis: Posttranslational Modifications and Aging," Ann NY Acad Sci 663: 48-62.

"Polynucleotide" as used herein includes but is not limited to DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA.

As used herein, the term "polypeptide" encompasses amino acid chains of any length, including full length proteins (i.e., antigens), wherein the amino acid residues are linked by covalent peptide bonds.

A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% homology to the identified polypeptides. For polypeptides with immunoreactive properties, variants can, alternatively, be identified by modifying the amino acid sequence of one of the above polypeptides, and evaluating the immunoreactivity of the modified polypeptide. Such modified sequences can be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, fly asp, gln, asn, set, thr; (2) cys, ser, fyr, thr; (3) val, ile, leu, met, ala, phe; (4) lys, arg, his; and (5) phe, tyr, trp, his.

Variants can also, or alternatively, contain other modifications, including the deletion or addition of amino acids that have minimal influence on the antigenic properties, secondary structure and hydropathic nature of the polypeptide. For example, a polypeptide can be conjugated to a signal (or leader) sequence at the N-terminal end of the protein which co-translationally or post-translationally directs transfer of the protein. The polypeptide can also be conjugated to a linker or other sequence for ease of synthesis, purification or identification of the polypeptide (e.g., poly-His), or to enhance binding of the polypeptide to a solid support. For example, a polypeptide can be conjugated to an immunoglobulin Fc region.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

RNA Transfection

The nucleic acids encoding the reporters of the invention can be introduced into target cells using RNA transfection. Methods for producing an in vitro transcribed RNA reporters are disclosed herein. A method for generating mRNA for use in transfection can involve in vitro transcription (IVT) of a template with specially designed primers, followed by poly A addition, to produce a construct containing 3' and 5' untranslated sequence ("UTR"), a 5' cap and/or Internal Ribosome Entry Site (IRES), the nucleic acid to be expressed, and a poly A tail, typically 50-2000 bases in length. RNA so generated can efficiently transfect different kinds of cells. In one aspect, the template includes sequences for the reporter.

In one aspect, a reporter (e.g., GLuc or NLuc) of the present invention is encoded by an mRNA or an in vitro transcribed RNA (IVTR). In one aspect, the IVTR encoding a reporter described herein is introduced into a target cell, e.g., a primary cell or a cell line, for production of a reporter-expressing cell for use in the Matador assays as described herein.

In one embodiment, the in vitro transcribed RNA reporter can be introduced to a cell using transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, plasmid DNA, phage DNA, cDNA, synthetic DNA sequence or any other appropriate source of DNA. The desired template for in vitro transcription is a reporter, such as GLuc or NLuc coding sequence lacking the signal peptide, described herein.

PCR is used to generate a template for in vitro transcription of mRNA which is used for transfection. Methods for performing PCR are well known in the art. Any DNA polymerase useful for PCR can be used in the methods disclosed herein. The reagents and polymerases are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter. Other useful promoters include, but are not limited to, T3 and SP6 RNA polymerase promoters. Consensus nucleotide sequences for T7 and SP6 promoters are known in the art.

In an embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines. Poly(A) tails of RNAs can be further extended following in vitro transcription with the use of a poly(A) polymerase, such as *E. coli* poly A polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. [00138] 5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

An internal ribosome entry site (IRES) sequence can be present in the RNAs produced by the methods disclosed herein. The IRES sequence may be any viral, chromosomal or artificially designed sequence which initiates cap-independent ribosome binding to mRNA and promotes the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendorf, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001) or by causing transient perturbations in cell membranes using a microfluidic device (see, for example, patent applications WO 2013/059343 A1 and PCT/US2012/060646).

Vectors

Vectors which may be used to express the reporters of the invention include but are not limited to lentivirus vectors, gamma retrovirus vectors, foamy virus vectors, AAV vectors, adeno virus vectors, engineered hybrid viruses, (including but not limited to transposon mediated vectors, such as Sleeping Beauty, Piggybak, and Integrases such as Phi31.

The term "recombinant DNA molecule", as used herein, refers to a DNA molecule which is comprised of segments of DNA joined together by means of molecular biological techniques known to one of skill in the art, including but not limited to genetic recombination (i.e., molecular cloning).

The term "recombinant protein" or "recombinant polypeptide", as used herein, refers to a protein molecule which is expressed from a recombinant DNA molecule.

"Recombinant virus" refers to a virus that has been genetically altered (e.g., by the addition or insertion of a heterologous nucleic acid construct into the particle).

A reporter transgene may also include regulatory sequences and intron regions. Promoters that would regulate reporter expression may include constitutive, inducible and tissue-specific promoters. The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence. The promoter region may comprise of or be linked to additional regulatory sequences, such as enhancers, that modulate the expression of the reporter transgene. The preferred promoter for expressing the reporters of the invention is a strong constitutive promoter, e.g., Elongation Factor a promoter or a CMV immediate early promoter.

A "gene" or "coding sequence" or a sequence which "encodes" a particular protein is a nucleic acid molecule that is transcribed (in the case of DNA) and translated (in the case of mRNA) into a polypeptide in vitro or in vivo when placed under the control of appropriate regulatory sequences.

The term "transfection" is used herein to refer to the uptake of foreign DNA or RNA by a cell. A cell has been "transfected" when exogenous DNA or RNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA or RNA molecule to a recipient cell either in vivo or in vitro, via any method of gene delivery, including viral vector delivery.

The term "transformation" as used herein refers to a change in a cell's genetic characteristics, and a cell has been transformed when it has been modified to contain a new DNA. For example, a cell is transformed where it is genetically modified from its native state. Following transfection, the transforming nucleic acid can recombine with that of the cell by physically integrating into a chromosome of the cell, can be maintained transiently as an episomal element without being replicated, or can replicate independently as a plasmid. A cell is considered to have been stably transformed when the transforming nucleic acid is replicated with the division of the cell.

Various methods produce stable transfectants which express the reporters of the invention. In one embodiment, a method of stably transfecting and re-directing cells is by electroporation using naked DNA. By using naked DNA, the time required to produce redirected cells may be significantly reduced. Additional methods to genetically engineer cells include but are not limited to chemical transformation methods (e.g., using calcium phosphate, dendrimers, liposomes and/or cationic polymers), non-chemical transformation methods (e.g., electroporation, optical transformation, gene electrotransfer, transient perturbation in cell membranes and/or hydrodynamic delivery) and/or particle-based methods (e.g., impalefection, using a gene gun and/or magnetofection). Viral transduction methods may also be used to generate redirected cells which express the reporters of the invention.

As used herein an "expression vector" refers to a DNA molecule, or a clone of such a molecule, which has been modified through human intervention to contain segments of DNA combined and juxtaposed in a manner that would not otherwise exist in nature. DNA constructs can be engineered to include a first DNA segment encoding an acetylation-resistant engineered PDCL3 polypeptide described herein operably linked to additional DNA segments encoding a desired recombinant protein of interest. In addition, an expression vector can comprise additional DNA segments, such as promoters, transcription terminators, enhancers, and other elements. One or more selectable markers can also be included. DNA constructs useful for expressing cloned DNA segments in a variety of prokaryotic and eukaryotic host cells can be prepared from readily available components or purchased from commercial suppliers.

After transfection, the host cell can be maintained either transiently transformed or stably transformed with said nucleic acid or expression vector. Introduction of multiple nucleic acids or expression vectors, and selection of cells containing the multiple nucleic acids or expression vectors can be done either simultaneously or, more preferably, sequentially. The technique of establishing a cell line stably transformed with a genetic material or expression vector is well known in the art (Current Protocols in Molecular Biology). In general, after transfection, the growth medium will select for cells containing the nucleic acid construct by, for example, drug selection or deficiency in an essential nutrient, which is complemented by a selectable marker on the nucleic acid construct or co-transfected with the nucleic acid construct. Cultured mammalian cells are generally cultured in commercially available serum-containing or serum-free medium. Selection of a medium appropriate for the particular host cell used is within the level of ordinary skill in the art.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells can be cultured in suspension or while attached to a solid substrate. Fluidized bed bioreactors, hollow fiber bioreactors, roller bottles, shake flasks, or stirred tank bioreactors, with or without microcarriers, can be used.

As used herein, "cell culture medium" is a media suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. "Serum-free" applies to a cell culture medium that does not contain animal sera, such as fetal bovine serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Serum-free versions of such culture media are also available.

Suitable selectable markers for drug selection used with the compositions and methods described herein include, but are not limited to, neomycin (G418), hygromycin, puromycin, zeocin, colchine, methotrexate, and methionine sulfoximine.

Once a drug resistant cell population is established, individual clones may be selected and screened for high expressing clones. Methods of establishing cloned cell line are well known in the art, including, but not limited to, using a cloning cylinder, or by limiting dilution. Expression of the recombinant protein of interest from each clone can be measured by methods such as, but not limited to, immunoassay, enzymatic assay, or chromogenic assay. A cell line stably transformed with a first nucleic acid construct may be then used as host cell for transfection with a second or more nucleic acid constructs, and subjected to different drug selections.

The terms "T-cell" and "T-lymphocyte" are interchangeable and used synonymously herein. Examples include but are not limited to naïve T cells, central memory T cells, effector memory T cells or combinations thereof.

The term "thermostable" generally refers to the resilience of a substance to relatively high temperature treatment. A thermostable enzyme is an enzyme that retains its definitive enzymatic activity despite exposure to relatively high temperature. A thermostable reporter is a reporter that retains its definitive reporter activity despite exposure to relatively high temperature. As most cytotoxic assays are carried out at temperature of 37° C., a thermostable reporter suitable for cytotoxic assay of the invention has a half-life (the length of time it takes for a reporter to lose one half of its initial activity) of greater than 10 min; of greater than 30 min; of greater than 60 min; of greater than 2 hours; of greater than 4 hours; of preferably greater than 8 hour; of more preferably greater than 24 hours; of even more preferably greater than 96 hours at a temperature of 37° C. under tissue culture conditions used in the cytotoxicity assay.

The term "functional" when used in conjunction with "derivative" or "variant" or "fragment" refers to a polypeptide which possess a biological activity that is substantially similar to a biological activity of the entity or molecule of which it is a derivative or variant or fragment thereof.

"Luciferase" or "Luciferases" as used herein refer class of oxidative enzymes that produce bioluminescence. The non-secretory form of luciferases for use in the compositions and methods described herein lack the N-terminal secretory sequence but produce bioluminescence. In the preferred embodiment, the non-secretory form of luciferase is stable under the cell culture conditions of the Matador assay. In the preferred embodiment, the non-secretory form of luciferase is thermostable under the cell culture conditions of the Matador assay. Methods of generating thermostable luciferases are known in the art (e.g, PCT/US99/30925). In exemplary embodiments, the luciferase is obtained from copepods, deep sea shrimp, beetle or homologs or orthologs thereof or mutants or derivatives thereof. In some embodiments, the copepods are any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri*, and *Pleuromamma scutullata*. In some embodiments, the beetles are any one or more of *Photuris pennsylvania* and *Pyrophorus plagiothalamus*. In exemplary embodiments, the luciferases are any one or more of GLuc, NanoLuc (NLuc), MLuc7, HtLuc, LoLuc, PaLuc1, PaLuc2, MpLuc1, McLuc1, MaLuc1, MoLuc1, MoLuc2, MLuc39, PsLuc1, LocLuc1-3, HtLuc2 Renilla, TurboLuc16 (TLuc), Lucia-Luc, Flue or FfLuc (Firefly Luc), LucPpe1, LucPpe2, LucPPe-146-1H2, LucPPe-133-1B2, LucPPe-78-0B10, LucPPe49-7C6A, LucPpL-81-6G1, CBGRluc or any of the thermostable luciferases described in PCT/US99/30925 or homologs or orthologs thereof or mutants or functional derivatives or variants thereof. In various embodiments, mutants or functional derivatives of the luciferases retain at least 100%, 90%, 80%, 70%, 60%, 50%, 40%, 30%, 20%, 10%, 5% of the bioluminescence activity of the parent luciferase from which the mutant or function derivative is derived. As described in Takenaka et al (Evolution of bioluminescence in marine planktonic copepods. 2012 *Mol Biol Evol* 29(6): 1669-1681), the copepod luciferases comprise two domains and each domain includes conserved sequences across the various luciferases. In some embodiments, any luciferase comprising the consensus sequence C-x(3)-C-L-x(2)-L-x(4)-C-x(8)-P-x-R-C(SEQ ID NO: 101) in each of domains 1 and 2 as described by Takenaka et al., may be used in the compositions and methods described herein. In some embodiments, any luciferase comprising the consensus sequence K-x(7)-E-M-E-A-N-A-x(3)-G-C-x-R-x-C-L-I-x-L-S-x-I-K-C-T-x-K-M-x(4)-P-G-R-C-H-X-Y-x(8)-G (SEQ ID NO: 102) in domain 1 as described by Takenaka et al. and consensus sequences I-x-G-x(6)-M-x-Q-F-x(2)-Q-V-x(2)-C-x(2)-C-x(3)-C-L-K-G-L-A-N-x(2)-C-S-x(2)-L-x(3)-L-P-x-R-C-x(2)-F-x(3)-I-X(8)-G (SEQ ID NO: 103) in domain 2 as described by Takenaka et al., may be used in the compositions and methods described herein. In various embodiments, the functional fragments or mutants of luciferases for use with the compositions or methods described herein comprise the consensus sequence C-x(3)-C-L-x(2)-L-x(4)-C-x(8)-P-x-R-C (SEQ ID NO: 101) in domain 1 as described by Takenaka et al. In various embodiments, the functional fragments or mutants of luciferases for use with the compositions or methods described herein comprise the consensus sequence C-x(3)-C-L-x(2)-L-x(4)-C-x(8)-P-x-R-C (SEQ ID NO: 101) in domain 2 as described by Takenaka et al. In various embodiments, the functional fragments or mutants of luciferases for use with the compositions or methods described herein comprise the consensus sequence C-x(3)-C-L-x(2)-L-x(4)-C-x(8)-P-x-R-C (SEQ ID NO: 101) in domain 1 and in domain 2, as described by Takenaka et al.

The term "reporter" means a gene or a protein whose product is easily and quantifiably assayed when expressed in a cell. The introduction and expression of reporters into cells is described in U.S. Pat. No. 5,298,429, incorporated herein by reference. Representative reporters include β-galactosidase (lacZ), chloramphenicol acetyltransferase (cat), β-glucuronidase (GUS), and the like, and luciferase. A preferred reporter of the invention is a thermostable luciferase.

As the term is used herein, a "cytotoxicity assay" refers to an assay for the quantitative or qualitative detection of the death of a cell. Examples of cytotoxicity assays include LDH release assay and $Cr^{51}$ release assay. A cytotoxicity assay generally involves exposure of target cell(s) to an agent or agents capable to modulating cell death for a period of time ranging for a few seconds to several days followed by quantitative or qualitative detection of the death of the exposed cell(s).

As the term is used herein, a "bioluminescence assay" or "luciferase assay" refers to an assay for the quantitative or qualitative detection of the luciferase protein by its enzymatic activity.

As used herein, bioluminescence substrate refers to the compound that is oxidized in the presence of a luciferase, and any necessary activators, and generates light. These substrates are referred to as luciferins herein, are substrates that undergo oxidation in a bioluminescence reaction. These bioluminescence substrates include any luciferin or analog thereof or any synthetic compound with which a luciferase interacts to generate light. Preferred substrates are those that are oxidized in the presence of a luciferase or protein in a light-generating reaction. Bioluminescence substrates, thus, include those compounds that those of skill in the art recognize as luciferins. Luciferins, for example, include firefly luciferin, coelenterazine, bacterial luciferin, as well as synthetic analogs of these substrates or other compounds that are oxidized in the presence of a luciferase in a reaction that produces bioluminescence. As described in Hall M P et al, ACS Chemical Biology, bioluminescence is found across a diversity of life that includes bacteria, insects, fungi, and an abundance of marine organisms. It occurs when a photon-emitting substrate (luciferin) is oxidized by a generic class of enzymes called luciferases. These enzymes have been popular as reporters of cellular physiology because of their ability to provide highly sensitive quantitation with broad linearity. Firefly (FLuc, or FfLuc, 61 kDa) and Renilla (RLuc, 36 kDa) luciferases have accounted for the majority of such applications, particularly for elucidating molecular processes coupled to gene expression. More recently, bioluminescence has been applied to other aspects of cellular analysis. The widely recognized utility of bioluminescence has spurred investigation of alternative luciferases, predominantly from marine organisms. Luciferase genes have been derived from the copepods *Gaussia princeps* (20 kDa) and *Metridia longa* (24 kDa), the ostracod *Cypridina noctiluca* (61 kDa), the dinoflagellate *Pyrocystis lunula* (40 kDa), and the deep sea shrimp, *Oplophorus gracilirostris* (106 kDa). Takenaka Y et al. has provided a description of the structure and evolutionary history of copepod luciferase genes (Takenaka, Yamaguchi et al. 2012). They classified Copepod luciferases into two groups of Metridinidae and Heterorhabdidae/Lucicutiidae families based on phylogenetic analyses, with confirmation of the interrelationships within the Calanoida using 18S ribosomal DNA sequences. The specific activity of luciferases isolated from copepods in the family Metridinidae (MpLuc1, MpLuc2, MoLuc1, MoLuc2, PaLuc1, and PaLuc2) was notably higher than that of luciferases from the Heterorhabdidae family (HtLuc1, HtLuc2, HmLuc1, and HmLuc2). LoLuc, isolated from *L. ovaliformis*, which belongs to the Lucicutiidae family, showed intermediate levels of activity. Two catalytic domains had been identified in *Gaussia* luciferase (Inouye and Sahara 2008), and Takenake Y et al confirmed the presence of two short repeat sequences in the primary structures of the novel copepod luciferases isolate by them (Takenaka, Yamaguchi et al. 2012). Alignment of two repeat sequences consisting of 62-64 amino acid residues (referred as domains 1 and 2, respectively) from 12 luciferases revealed consensus sequence of C-x(3)-C-L-x(2)-L-x(4)-Cx(8)-P-x-R-C(X, amino acid residue) in both domains (Takenaka, Yamaguchi et al. 2012). Thus, highly conserved amino acid residues, C-x(3)-C-L-x(2)-L-x(4)-C-x(8)-P-x-R-C, which are present in both domains, were considered one of the criteria for the copepod luciferase (Takenaka, Yamaguchi et al. 2012). Because the similarity in the structure of the two domains was found in all of the copepod luciferases isolated in this study, the authors assumed this similarity in the structure of the two domains to be very characteristic of the luciferases isolated from *Augaptiloidea* species (Takenaka, Yamaguchi et al. 2012). Substitution of all cysteine residues with alanine in domains 1 and 2 of MpLuc1 resulted in complete loss of activity when it was expressed in *Escherichia coli*, suggesting an essential role of cysteine residues in luciferase activity (Takenaka, Yamaguchi et al. 2012). Thus, the presence of two domains with sequence similarity along with the highly conserved amino acid residues, C-x(3)-C-L-x(2)-L-x(4)-C-x(8)-P-x-R-C, which are present in both domains, can be used to identify any new luciferases isolated from *Augaptiloidea* species.

*Gaussia* luciferase in particular has been used as a secreted reporter in mammalian cells, reportedly providing increased assay sensitivity owing to its bright luminescence and accumulation in the cell culture medium. However, the light intensity decays rapidly under most conditions, thus requiring luminometers equipped with injectors to measure the transient peak luminescence. Mutants of GLuc have been described that provide Glow type luminescence, which may be suitable for HTS applications (Degeling, Bovenberg et al. 2013). Additionally, presence of 0.1% Triton X-100 in the assay buffer has been shown to stabilize *Gaussia princeps* luminescence resulting in sustained signal. Other methods of stabilizing the luminescent signal form GLuc and related luciferases are known in the art and have been described in the U.S. Pat. No. 7,939,286 B2.

Furthermore, the coelenterazine substrate is prone to chemical instability and high auto-luminescence background, properties that make sample handling difficult and decrease assay sensitivity. Although bright luminescence is generally desirable, a sustained signal with low background is necessary to enable efficient assay methods with high sensitivity. Preferably the luciferase should be small, monomeric, and structurally stable to environmental conditions. Recently, Promega engineered both an enzyme and substrate in combination to create a novel bioluminescence system capable of more efficient light emission with superior biochemical and physical characteristics (U.S. Pat. No. 8,557,970-B2) (Hall, Unch et al. 2012). Using a small luciferase subunit (19 kDa) from the deep sea shrimp *Oplophorus gracilirostris*, they improved luminescence expression in mammalian cells ~2.5 million-fold by merging optimization of protein structure with development of a novel imidazopyrazinone substrate (furimazine). The new luciferase, Nano-Luc (NLuc), produces glow-type luminescence (signal half-life >2 h) with a specific activity ~150-fold greater than that of either firefly (*Photinus pyralis*) or Renilla luciferases similarly configured for glow-type assays. In mammalian cells, NanoLuc (NLuc) shows no evidence of posttranslational modifications or subcellular partitioning. The enzyme exhibits high physical stability, retaining activity with incubation up to 55° C. or in culture medium for >15 h at 37° C.

Reporter quantitation is achievable even at very low expression levels to facilitate more reliable coupling with endogenous cellular processes.

As stated above, a major limitation of LDH release assay is its inability to distinguish between the death of target and effector cells. To overcome this limitation, the inventor engineered the target cells so that they express a reporter that is not expressed by the effector cells. In order to develop a sensitive assay of cell death, without being bound to a particular theory the inventor hypothesized that the reporter should ideally have the following properties: 1) it should be preferentially retained inside the cells and not secreted outside; 2) it should be relatively non-toxic to the host cells; 3) it should be relatively small in size so that it can readily leak outside when the integrity of the cell membrane is compromised; 4) it should be monomeric and not make aggregates inside the cells which could potentially prevent its leakage; 5) it should preferably not bound to any cellular proteins, which would prevent its leakage upon cell damage; 6) it should be relatively stable with relatively long half-life and not prone to degradation when released in the extracellular compartment; 7) it should be preferably resistant to proteases that are present in the serum and that are released during the process of cell death; 8) it should be preferably heat stable at 37° C.; 8) its activity should be readily measured by an assay which is quick, inexpensive, sensitive, homogenous (i.e. single step), with a broad linear range, and amenable to high-throughput screening applications; 9) if the reporter requires a substrate for the detection of its activity, then the substrate should not readily enter a live cell but should readily enter a dead or dying cell that has lost its cell membrane integrity. It is to be noted, however, that a reporter for the invention need not possess all the above properties.

In various embodiments, the reporter is a non-secretory form of a luciferase. In various embodiments, the non-secretory form of luciferase is obtained from copepods, deep sea shrimp, a beetle luciferase or homologs or orthologs thereof or mutants or functional variants or derivatives thereof. In various embodiments, the reporter is a non-secretory form of a thermostable alkaline phosphatase.

In exemplary embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri*, and *Pleuromamma scutullata*.

In exemplary embodiments, the reporter luciferase is a non-secretory form of any one or more of GLuc, NanoLuc (NLuc), MLuc7, HtLuc, LoLuc, PaLuc1, PaLuc2, MpLuc1, McLuc1, MaLuc1, MoLuc1, MoLuc2, MLuc39, PsLuc1, LocLuc1-3, HtLuc2, TurboLuc16 (TLuc), Lucia-Luc, LucPPe-146-1H2, LucPPe-133-1B2, LucPPe-78-OB10, LucPPe49-7C6A, LucPpL-81-6G1, CBGRluc, Renilla (RLuc), Firefly Luc (Fluc or FfLuc of fFLuc) or homologs or orthologs thereof or mutants or functional variants or derivatives thereof. All the reporters of the invention are designed to be expressed intracellularly and, therefore, lack a secretory signal. The DNA and Protein (PRT) SEQ IDs of several exemplary reporters of the invention, including luciferases, are provided in Table 1.

TABLE 1

Exemplary Reporters for use with in the compositions and methods described herein.

| SEQ ID (DNA) | SEQ ID (Prt) | REPORTER NAME |
| --- | --- | --- |
| 1 | 31 | GLuc (Gaussia princeps Luc) |
| 2 | 32 | NLuc (NanoLuc) |
| 3 | 33 | TLuc (TurboLuc16) |
| 4 | 34 | MLuc7 (Metrida longa Luc7) M43L/M110L variant |
| 5 | 35 | LoLuc (Lucicutia ovaliformis Luc) |
| 6 | 36 | HtLuc (Heterorhabdus tanneri Luc) |
| 7 | 37 | PaLuc1 (Pleuromamma abdominalis Luc1) |
| 8 | 38 | PaLuc2 (Pleuromamma abdominalis Luc2) |
| 9 | 39 | MpLuc1 [Metridia pacifica Luc1] |
| 10 | 40 | McLuc1 [Metridia curticauda Luc1] |
| 11 | 41 | MaLuc1 [Metridia asymmetrica Luc1] |
| 12 | 42 | MoLuc1 [Metridia okhotensis Luc1] |
| 13 | 43 | MoLuc2 [Metridia okhotensis Luc2] |
| 14 | 44 | MLuc39 [Metridia longa Luc39] |
| 15 | 45 | PsLuc1 [Pleuromamma scutullata Luc1] |
| 16 | 46 | LoLuc1-3 [Lucicutia ovaliformis Luc1-3] |
| 17 | 47 | HtLuc2 tanneri Luc 2 |
| 18 | 48 | Lucia-Luc |
| 19 | 49 | RLuc (Renilla Luc) |
| 20 | 50 | Fluc or FfLuc (Firefly Luc) |
| 21 | 51 | LucPPe-146-1H2 |
| 22 | 52 | LucPPe-133-1B2 |
| 23 | 53 | LucPPe-78-OB10 |
| 24 | 54 | LucPPe49-7C6A |
| 25 | 55 | LucPpL-81-6G1 |
| 26 | 56 | CBGRluc |
| 27 | 57 | Embryonic Alkaline Phosphatase (EAP) |
| 28 | 58 | mCherry |
| 29 | 59 | EGFP (Enhanced Green Fluorescent Protein) |
| 30 | 60 | MYR-GGS-GLuc (M60L/M127L variant) |

In one embodiment, the reporter luciferase is GLuc (*Gaussia princeps* Luc) and comprises, consists of or consists essentially of the sequence set forth in SEQ ID NO: 1 or SEQ ID NO: 31 or a sequence with 70-99% homology to the sequence set forth in SEQ ID NO: 1 or SEQ ID NO: 31.

In another embodiment, the reporter luciferase is NLuc (NanoLuc) and comprises, consists of or consists essentially of the sequence set forth in SEQ ID NO: 2 or SEQ ID NO:

32 or a sequence with 70-99% homology to sequence set forth in SEQ ID NO: 2 or SEQ ID NO: 32.

In a further embodiment, the reporter luciferase is TLuc (TurboLuc16) and comprises, consists of or consists essentially of the sequence set forth in SEQ ID NO: 3 or SEQ ID NO: 33 or a sequence with 70-99% homology to the sequence set forth in SEQ ID NO: 3 or SEQ ID NO: 33.

In a further embodiment, the reporter luciferase is MLuc7-(*Metrida longa* Luc) M43L/M110L variant and comprises, consists of or consists essentially of the sequence set forth in SEQ ID NO: 4 or SEQ ID NO: 34 or a sequence with 70-99% homology to the sequence set forth in SEQ ID NO: 4 or SEQ ID NO: 34.

In another embodiment, the reporter luciferase is LoLuc (*Lucicutia ovaliformis* Luc) and comprises, consists of or consists essentially of the sequence set forth in SEQ ID NO: 5 or SEQ ID NO: 35 or a sequence with 70-99% homology to the sequence set forth in SEQ ID NO: 5 or SEQ ID NO: 35.

In another embodiment, the reporter luciferase is HtLuc (*Heterorhabdus tanneri* Luc) and comprises, consists of or consists essentially of the sequence set forth in SEQ ID NO: 6 or SEQ ID NO: 36 or a sequence with 70-99% homology to sequence set forth in SEQ ID NO: 6 or SEQ ID NO: 36.

In another embodiment, the reporter luciferase is PaLuc1 (*Pleuromamma abdominalis* Luc) and comprises, consists of or consists essentially of the sequence set forth in SEQ ID NO: 7 or SEQ ID NO: 37 or a sequence with 70-99% homology to the sequence set forth in SEQ ID NO: 7 or SEQ ID NO: 37.

In another embodiment, the reporter luciferase is PaLuc2 (*Pleuromamma abdominalis* Luc2) and comprises, consists of or consists essentially of the sequence set forth in SEQ ID NO: 8 or SEQ ID NO: 38 or a sequence with 70-99% homology to the sequence set forth in SEQ ID NO: 8 or SEQ ID NO: 38.

In another embodiment, the reporter luciferase is MpLuc1 (*Metridia pacifica* Luc1) and comprises, consists of or consists essentially of the sequence set forth in SEQ ID NO: 9 or SEQ ID NO: 39 or a sequence with 70-99% homology to sequence set forth in SEQ ID NO: 9 or SEQ ID NO: 39.

In another embodiment, the reporter luciferase is McLuc1 (*Metridia curticauda* Luc1) and comprises, consists of or consists essentially of the sequence set forth in SEQ ID NO: 10, or SEQ ID NO: 40 or a sequence with 70-99% homology to the sequence set forth in SEQ ID NO: 10 or SEQ ID NO: 40.

In another embodiment, the reporter luciferase is MaLuc1 (*Metridia asymmetrica* Luc1) and comprises, consists of or consists essentially of the sequence set forth in SEQ ID NO: 11 or SEQ ID NO: 41 or a sequence with 70-99% homology to sequence set forth in SEQ ID NO: 11 or SEQ ID NO: 41.

In another embodiment, the reporter luciferase is MoLuc1 (*Metridia okhotensis* Luc1) and comprises, consists of or consists essentially of the sequence set forth in SEQ ID NO: 12 or SEQ ID NO: 42 or a sequence with 70-99% homology to sequence set forth in SEQ ID NO: 12 or SEQ ID NO: 42.

In another embodiment, the reporter luciferase is MoLuc2 (*Metridia okhotensis* Luc2) and comprises, consists of or consists essentially of the sequence set forth in SEQ ID NO: 13 or SEQ ID NO: 43 or a sequence with 70-99% homology to sequence set forth in SEQ ID NO: 13 or SEQ ID NO: 43.

In another embodiment, the reporter luciferase is MLuc39 (*Metridia longa* Luc39) and comprises, consists of or consists essentially of the sequence set forth in SEQ ID NO: 14 or 44 or a sequence with 70-99% homology to sequence set forth in SEQ ID NO: 14 or SEQ ID NO: 44.

In another embodiment, the reporter luciferase is PsLuc1 (*Pleuromamma scutullata* Luc1) and comprises, consists of or consists essentially of the sequence set forth in SEQ ID NO:15 or SEQ ID NO: 45 or a sequence with 70-99% homology to sequence set forth in SEQ ID NO:15 or SEQ ID NO: 45.

In another embodiment, the reporter luciferase is LoLuc1-3 (*Lucicutia ovaliformis* Luc1-3) and comprises, consists of or consists essentially of the sequence set forth in SEQ ID NO: 16 or SEQ ID NO: 46 or a sequence with 70-99% homology to sequence set forth in SEQ ID NO:16 or SEQ ID NO: 46.

In another embodiment, the reporter luciferase is HtLuc2 (*Heterorhabdus tanneri* Luc2) and comprises, consists of or consists essentially of the sequence set forth in SEQ ID NO: 17 or SEQ ID NO: 47 or a sequence with 70-99% homology to the sequence set forth in SEQ ID NO:17 or SEQ ID NO: 47.

In another embodiment, the reporter luciferase is Lucia-Luc and comprises, consists of or consists essentially of the sequence set forth in SEQ ID NO: 18 or SEQ ID NO: 48 or a sequence with 70-99% homology to sequence set forth in SEQ ID NO: 18 or SEQ ID NO: 48.

In another embodiment, the reporter luciferase is Renilla Luc (RLuc) and comprises, consists of or consists essentially of the sequence set forth in SEQ ID NO: 19 or SEQ ID NO: 49 or a sequence with 70-99% homology to the sequence set forth in SEQ ID NO: 19 or SEQ ID NO: 49.

In another embodiment, the reporter luciferase is Firefly Luc (FLuc or FfLuc or fFLuc) and comprises, consists of or consists essentially of the sequence set forth in SEQ ID NO: 20 or SEQ ID NO: 50 or a sequence with 70-99% homology to the sequence set forth in SEQ ID NO: 20 or SEQ ID NO: 50.

In another embodiment, the reporter luciferase is LucPPe-146-1H2 and comprises, consists of or consists essentially of the sequence set forth in SEQ ID NO: 21 or SEQ ID NO: 51 or a sequence with 70-99% homology to the sequence set forth in SEQ ID NO: 21 or SEQ ID NO: 51.

In another embodiment, the reporter luciferase is LucPPe-133-1B2 and comprises, consists of or consists essentially of the sequence set forth in SEQ ID NO: 22 or SEQ ID NO: 52 or a sequence with 70-99% homology to the sequence set forth in SEQ ID NO: 22 or SEQ ID NO: 52.

In another embodiment, the reporter luciferase is LucPPe-78-0B10 and comprises, consists of or consists essentially of the sequence set forth in SEQ ID NO: 23 or SEQ ID NO: 53 or a sequence with 70-99% homology to the sequence set forth in SEQ ID NO: 23 or SEQ ID NO: 53.

In another embodiment, the reporter luciferase is LucPPe49-7C6A and comprises, consists of or consists essentially of the sequence set forth in SEQ ID NO: 24 or SEQ ID NO: 54 or a sequence with 70-99% homology to the sequence set forth in SEQ ID NO: 24 or SEQ ID NO: 54.

In another embodiment, the reporter luciferase is LucPpL-81-6G1 and comprises, consists of or consists essentially of the sequence set forth in SEQ ID NO: 25 or SEQ ID NO: 55 or a sequence with 70-99% homology to the sequence set forth in SEQ ID NO: 25 or SEQ ID NO: 55.

In another embodiment, the reporter luciferase is CBGRluc and comprises, consists of or consists essentially of the sequence set forth in SEQ ID NO: 26 or SEQ ID NO: 56 or a sequence with 70-99% homology to the sequence set forth in SEQ ID NO: 26 or SEQ ID NO: 56.

In another embodiment, the reporter is a thermostable alkaline phosphatase (e.g., Embryonic Alkaline Phosphatase) and comprises, consists of or consists essentially of the sequence set forth in SEQ ID NO: 27 or SEQ ID NO: 57 or a sequence with 70-99% homology to the sequence set forth in SEQ ID NO: 27 or SEQ ID NO: 57.

In another embodiment, the reporter fluorescent protein is mCherry and comprises, consists of or consists essentially of the sequence set forth in SEQ ID NO: 28 or SEQ ID NO: 58 or a sequence with 70-99% homology to the sequence set forth in SEQ ID NO: 28 or SEQ ID NO: 58.

In another embodiment, the reporter fluorescent protein is EGFP and comprises, consists of or consists essentially of the sequence set forth in SEQ ID NO:29 or SEQ ID NO: 59 or a sequence with 70-99% homology to the sequence set forth in SEQ ID NO: 29 or SEQ ID NO: 59.

In another embodiment, the reporter luciferase is GLuc (M60L/M127L) variant and comprises, consists of or consists essentially of the luciferase sequence set forth in SEQ ID NO:30 or SEQ ID NO: 60 or a sequence with 70-99% homology to the luciferase sequence set forth in SEQ ID NO: 30 or SEQ ID NO: 60.

The present invention provides methods of assaying cytotoxicity in vitro and in vivo. The methods are non-radioactive and do not require labeling the cells prior to each assay, and thus are easier and safer to perform than assays which require labeling cells prior to each assay. The methods provided can help distinguish between the death of target and effector cells and are highly sensitive with broader linearity than standard cytotoxicity assays, allowing minor differences in the cytotoxicity kinetics of different products to be detected. Further, in some embodiments the simplicity of the methods provided herein means that they are homogenous and faster than standard cytotoxicity assays, and also have the potential to be optimized for high-throughput screening to identify compounds that have cytotoxic activity of their own or can modulate (i.e. increase or decrease) the cytotoxic activity of different agents. The methods can be used to detect the cytotoxic activity of different drugs, small molecules, biologicals (e.g. antibodies), and cells, including lymphocytes and NK cells and immune cells that have been modified to express chimeric and synthetic receptors and T cell receptors. The methods also can be performed on both adherent cells and cells in suspension. The methods can be performed on both eukaryotic and prokaryotic cells and both in vitro and in vivo. The methods can be performed on primary cells as well as cell lines. The method can be performed on normal cells or diseased cells or disease-associated cells, such as cancer cells or cells infected with infectious organisms. The method can be also adapted to detect the toxicity of different agents on vital organs in vivo. In addition, the methods can be adapted for multiplexing so that cytotoxic activity of a therapeutic agent on different cell types (i.e. normal vs. cancer; liver cancer vs. lung cancer etc.) and different organs (e.g. liver vs. kidney) can be measured in the same assay and in the same animal, respectively.

The method can be used to detect the cytotoxicity of any agent targeting any molecule or antigens expressed in a cell. In some embodiments, the methods can be used to measure cytotoxicity of one or more agents that target one or more of the antigens selected from a group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRviii); ganglioside G2 (GD2); ganglioside GD3 (aNeu5Ac(2-8) aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); FmsLike Tyrosine Kinase 3 (FLT3); Tumor-associated glycoprotein 72 (TAG72); CD38; CD44v6; a glycosylated CD43 epitope expressed on acute leukemia or lymphoma but not on hematopoietic progenitors, a glycosylated CD43 epitope expressed on non-hematopoietic cancers, Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-llRa); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gpl00); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDClalp(1-4) bDGlcp(1-1)Cer); transglutaminase 5 (TGS5); high molecular weight melanoma associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein coupled class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ES0-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGEl); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCT A-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B 1 (CYP1B 1);

CCCTC-Binding Factor (Zinc Finger Protein)-Like (BORIS or Brother of the Regulator of lmprinted Sites), Squamous Cell Carcinoma Antigen Recognized By T Cells 3 (SART3); Paired box protein Pax-5 (PAX5); proacrosin binding protein sp32 (OY-TESl); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1), MPL, Biotin, c-MYC epitope Tag, CD34, LAMP1 TROP2, GFRalpha4, CDH17, CDH6, NYBR1, CDH19, CD200R, Slea (CA19.9; Sialyl Lewis Antigen) Fucosyl-GM1, PTK7, gpNMB, CDH1-CD324, DLL3, CD276/B7H3, IL11Ra, IL13Ra2, CD179b-IGL11, ALK TCRgamma-delta, NKG2D, CD32 (FCGR2A), Tn ag, CSPG4-HMW-MAA, Tim1–/HVCR1, CSF2RA (GM-CSFR-alpha), TGFbetaR2, VEGFR2/KDR, Lews Ag, TCR-beta1 chain, TCR-beta2 chain, TCR-gamma chain, TCR-delta chain, FITC, Leutenizing hormone receptor (LHR), Follicle stimulating hormone receptor (FSHR), Chorionic Gonadotropin Hormone receptor (CGHR), CCR4, GD3, SLAMF6, SLAMF4, HIV1 envelope glycoprotein, HTLV1-Tax, CMV pp65, EBV-EBNA3c, influenza A hemagglutinin (HA), GAD, PDL1, Guanylyl cyclase C (GCC), KSHV-K8.1 protein, KSHV-gHprotein, HLA, HLA-A, HLA-A2, HLA-B, HLA-C, HLA-DP, HLA-DM, HLA-DOA, HLA-DOB, HLA-DQ, HLA-DR or HLA-G.

The method is based on the principle that cell membrane integrity is lost upon cell death. In one embodiment, provided herein are assays using any reporter that can be expressed intracellularly and the measure of whose activity is increased upon cell damage. The increase in the measured activity of the reporter upon cell damage can happen due the release or leakage of the reporter into the extracellular compartment where it can readily interact with its substrate. Alternatively, the increase in the increase in the measured activity of the reporter upon cell damage can happen due to loss of cell membrane integrity that results in the increased or faster penetration of the substrate into dead and dying cells where it can readily interact with the reporter still trapped inside the cell. Finally, both the above processes may contribute to the increase in the reporter activity upon cell damage.

In some embodiments, the assays include the steps of i) providing a target cell expressing non-secretory form of a reporter; ii) exposing the target cell to a test agent capable of inducing cytotoxicity and a control agent not capable of inducing cytotoxicity; iii) exposing the target cell from (ii) or the medium (i.e. supernatant) from target cell from (ii) or the target cell with the medium from (ii) to a reporter-specific substrate; iv) assaying the reporter-specific activity; and v) comparing the reporter-specific activity between the test agent- and the control agent-treated samples. In some embodiments, an increase in the reporter-specific activity in the test agent-treated samples as compared to the control agent-treated samples is indicative of the test agent being cytotoxic to the target cell In some embodiments, an increase in reporter activity relative to a reference value is indicative of the agent being cytotoxic to the target cell.

In some embodiments, the reference value is the reporter activity in any one or more of (i) mean or median reporter activity in target cells that do not express the reporter, (ii) mean or median reporter activity in target cells that express reporter but are not treated with the test agent(s); (iii) mean or median reported activity in target cells that are left untreated; (iv) mean or median reporter activity in target cells that are not treated with the substrate for the reporter, or (iii) a combination thereof. In some embodiments, a change in reporter activity is an increase in reporter activity relative to the reference value. In some embodiments, reporter activity is increased relative to the reference value by at least or about 10%, 20%, 30%, 40%, 50%, 60%, 70%, 80%, 90% or 100%. In some embodiments, reporter activity is increased relative to the reference value by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

In some embodiments, the reporter is non-secretory form of a reporter that is stable under the culture conditions. The preferred reporter for the cytotoxicity assay is stable under the conditions of the cytotoxicity assay. In the preferred embodiment, the reporter is stable under the culture conditions of the cytotoxicity assay for more than 20 minutes; for more than 30 minutes; for more than 1 hour; for more than 2 hours; for more than 4 hours; for more than 6 hours; for more than 12 hour; for more than 24 hours; preferably for more than 48 hours; or more preferably for more than 96 hours at 37° C. In some embodiments, the reporter is non-secretory form of luciferase, preferentially a thermostable luciferase, for example, GLuc, NLuc, MLuc7, Lucia-Luc, PaLuc1, TurboLuc16 (TLuc), Renilla, thermostable luciferases from *Photuris pennsylvanica* and *Pyrophorus plagiothalamus* (as described in PCT/US99/30925) or any of their functional variants or homologs. In the preferred embodiments, the reporter is non-secretory form of a reporter whose activity is not negatively affected by cellular processes activated before, during or after induction of cell death, such as activation of cell death proteases or change in redox potential.

In some embodiments, the target cells express one reporter. In an alternate embodiment, the target cells express more than one reporter. In some embodiment, the two reporters belong to the same class, e.g. two marine luciferases. In other embodiments, the two reporters belong to different classes, for example a marine luciferase (e.g. NLuc) and a beetle luciferase (e.g. LucPPe-146-1H2) or a marine luciferase and an embryonic alkaline phosphatase.

In various embodiments, vectors that may express the reporter include but are not limited to plasmid vectors (e.g. pCDNA3), retroviral vector (e.g. MSCVpac, MSCVneo, MSCVhygro), lentiviral vectors (e.g. pLenti-EF1α), adenoviral vectors, adenoassociated viral vector, sleeping beauty transposon, piggyback transposon. In other embodiment, the reporter can be introduced in the cells without the use of a vector, such as by transfection of DNA, RNA or protein encoding the reporter. Various methods of introducing DNA, RNA or protein inside cells have been described in the literature, including lipofection, electroporation, nucleofection and by causing transient perturbation in cell membrane (US2012/060646 and WO 2013/059343) (Sharel, Adamo et al.) In some embodiments, the target cell can be any one or more of healthy cells, cancer cells, infected cells (for example, infected by virus, bacteria, and/or parasites). In some embodiments, the agent that results in cellular cytotoxicity is an effector cell. In exemplary embodiments, effector cells may be any one or more of peripheral blood mononuclear cells (PBMCs), natural killer (NK) cells, monocytes, T cells, cytotoxic T cells, recombinant (for example, expressing CARs or TCR) T cells, neutrophils or combinations thereof.

In some embodiments, the assays described herein may be used to screen a candidate antibody for its ability to induce antibody-dependent cellular cytotoxicity (ADCC) against target cells. In some embodiments, the assays described herein may be used to identify a patient having a disease associated with target cells that is suitable for treatment with a candidate antibody. In some embodiments, the assays described herein may be used to screen for compounds for the ability to modulate ADCC. In some embodiments, the assays described herein may be used to determine the optimal concentration of an antibody to induce an ADCC response in a subject.

In some embodiments, the assays described herein may be used to test the effects of an agent, for example, T cells expressing exogenous T cell receptor, or chimeric and synthetic receptors. The assay may be also used to test the effect of bispecific antibodies, BiTEs, DART (dual affinity retargeting) monoclonal antibodies (mAbs), non-immunoglobulin binding scaffolds (e.g. affibodies, DARINS etc), radiolabelled antibodies and/or antibody drug conjugates on target cells (for example, in drug discovery).

In some embodiments, the assays described herein may be used to carry out high throughput screening for agents, such as chemical compounds including small molecule compounds, biological and cytokines, that can modulate (enhance or decrease) the function of other agents, such as CARs, TCRs, biologicals (e.g. TNF, Interferons), bispecific antibodies (including BiTE), DART (Dual affinity retargeting), monoclonal antibodies and antibody-drug conjugates (ADCs), when used alone or in combination.

In some embodiments, the assays described herein may be used in quality control as potency assays, for example, at the site of production of a cellular therapy product. For example, CARs targeting CD19 antigen for the treatment of acute and chronic lymphocytic leukemias, lymphoma and myeloma may need to be developed for each patient individually and need to be tested at the time of manufacturing to ensure consistency and reliable performance. Potency assays are mandated by US Congress before a cell therapy product, such as CAR-T, can be released for administration and are an FDA-requirement for product release. Matador cytotoxicity assays based on RAJI-GLuc, RAJI-NLuc and RAJI-MLuc7 cell lines, as described herein, may be used as potency assays to ensure the quality of the CAR product since the assays described herein are extremely sensitive (down to a single cell level), quick, non-radioactive and easy to use. In an embodiment, the assay is performed on CAR-T cell products being manufactured on different days of manufacturing to monitor the potency of the product. In a standard cytotoxicity assay, target cells are co-cultured with the effector cells for 4 hours to 96 hours. The extreme sensitivity of the Matador assay allows shortening of the co-culture period to an hour or less. This would result in significant time-saving in the CAR-T cell manufacturing and product-release process, and hence carries significant commercial value.

The inventor has shown that the Matador assays can be performed on primary patient samples. The assays described herein have the advantage of directly measuring the activity of the cell therapy product on patient's cancer cells and assessing the sensitivity of patient's sample to the therapeutic product. For example, even though the therapeutic product (for example, CAR-T cell) may be effective and functional in a cell line model, in rare cases a patient's leukemia cells may still not respond to the therapeutic product because the leukemia cells express inhibitory receptors that block the function of the therapeutic product (for example, CAR modified T cells). In some embodiments, the assays described herein may be used to test the efficacy of other cellular therapy and biological products, including but not limited to NK cells, donor lymphocytes, T cells and their subsets, microtransplantation, monoclonal antibodies, antibody drug conjugates and bispecific antibodies (including BiTE), when used alone or combinations thereof.

The CAR-T cells are living drugs as the cells once infused can multiply in the patient. They can also kill a target cell that expresses as few as 100 molecules of their target antigen. In addition, CAR cells can kill healthy cells that do not express their target via a bystander effect through production of cytokines. Therefore, toxicity of the CAR and other cellular therapy products (including antibody drug conjugates, and Bispecific T cell engagers or BiTE, DART) on normal tissues is a major concern as even low level expression of the CAR target-antigen on a vital organ can be lethal. The assay described herein is sensitive (down to a single cell level) and provides a useful platform to monitor and assure the safety of each lot of CAR-T cell product that is generated. For example, a panel of cell lines of different tissue origins expressing GLuc (or NLuc or any of the other reporter of the invention) can be used to rapidly test for killing by each lot of the CAR-T cell product, which would be helpful in predicting their toxicity on normal tissues. In some embodiments, the panel of primary cells or cell lines to be used in the Matador assay may express different levels of the target antigen. In some embodiments, the panel of primary cells or cell lines to be used in the Matador assay may be selected to have lost a particular target antigen so as to determine the off-target toxicity of the test product (e.g., a CAR-T cell).

In various embodiments, in vitro and in vivo applications of the assay are described and include: 1) Immuno-binding the reporter (e.g., GLuc) by an antibody as has been described (Bovenberg, Degeling et al. 2012) and then measuring the activity of the reporter. This may be useful in case of interfering substances in the media or blood or serum that can interfere with the assay for the reporter; 2) Epitope tagging the reporter (e.g. GLuc, NLuc, TurboLuc or MLuc7 or any of the other reporters) with tags such as Flag, HA, His, Myc, V5, AcV5 or Glu (van Rijn, Nilsson et al. 2013, van Rijn, Wurdinger et al. 2014) and then using such tagged reporter constructs to generate target cells ectopically expressing the reporter or reporters; 3) It is also possible to use the reporters in combination. For example, it is possible to use GLuc in combination with a thermostable beetle luciferase (e.g. LucPPe-146-1H2) as they have different substrates. As an example, RAJI cells (CD19$^+$) stably expressing GLuc are mixed with HL60 cells (CD19$^-$) stably expressing LucPPe-146-1H2 in a 1:1 ratio and are co-cultured for 4 hours with CD19 CAR-T cells. At the end of the co-culture period, the cell supernatant is tested for GLuc activity using coelenterazine as its substrate and for LucPPe-146-1H2 activity using D-luciferin as a substrate to determine the relative cytotoxicity of the CD19 CAR-T cells against RAJI and HL60 cells, respectively. It is also possible to use GLuc in combination with NLuc, TurboLuc16, MLuc7 or other reporters. As an example, RAJI cells (CD19+) stably expressing GLuc-Flag are mixed with HL60 cells (CD19-) stably expressing NLuc-Myc in a 1:1 ratio and are co-cultured with CD19 CAR-T cells. At the end of the co-culture period, the cell supernatant is collected and GLuc-Flag and NLuc-Myc proteins are separated by immunobinding with Flag and Myc antibody containing beads or control beads. Subsequently, the GLuc and NLuc activities are measured on the Flag and Myc antibody-bound fractions using coelenterazine as a substrate.GLucGLucGLucGLuc-GLucGLuc; 4) using mutants of GLuc and NLuc that emit light at different wavelengths; 5) having the target cells express one reporter (e.g., GLuc) and the effector cells (e.g., NK or T cells) express a different reporter (e.g. LucPPe-146-1H2NLuc-Myc) and measuring the cell death of both target and effector cells from the same experiment by measuring GLuc and LucPPe-146-1H2 activities. GLuc; 6) monitoring the susceptibility of leukemic and cancer cells to cytotoxic cells derived from different allogeneic donors. This may include infecting the leukemic or cancer cells with a viral vector expressing the appropriate reporter construct or by transient transfection with reporter plasmid or in vitro transcribed RNA and then exposing the reporter-expressing cells to cytotoxic cells (NK, T cells, peripheral blood mononuclear cells) from different donors to identify the donor most suitable for the patient; 7) performing in vivo assay by xenografting the reporter cell line expressing the reporter (e.g., GLuc or LucPPe-146-1H2) in an animal and treating the animal with appropriate agent (drug, irradiation or cytotoxic effector cell) and then measuring the released GLuc or LucPPe-146-1H2 activity in blood, urine, plasma, serum, CSF or other body fluids directly or after immunobinding using assay described above and known in the art; 8) the above method can be also adapted for use in cells of other origin such as bacterial, yeast and insect cells and then used for screening drugs/compounds that exert cytotoxicity or inhibit cytotoxicity on these cells.

Currently, there is no easy, sensitive and inexpensive way to monitor toxicity of different drugs or interventions on different organs. The Matador assay described herein can be adapted for generating animals that can be used for quickly detecting toxicity of different agents or to monitor efficacy of different interventions against diseases (e.g., Alzheimer, stroke, ischemia), which are accompanied by cellular toxicity and injury. In an exemplary embodiment, transgenic animals can be generated that express GLuc constitutively or in a tissue-specific manner by using tissue- or cell lineage-specific promoters. The animals can be exposed to a candidate agent (e.g. a new drug or a CAR-T cell product) and toxicity of agent monitored by assaying for GLuc activity in body fluids (e.g., serum, blood, plasma, urine, CSF, ascites fluid etc.) either directly or by including the step of immunobinding to purify GLuc from the body fluid.

In another embodiment, transgenic animals can be generated that express a reporter, such as GLuc, with different tags in different cellular compartments, lineages or organs using methodologies known in the art. Thus, it is possible to generate transgenic animals expressing GLuc-Flag in liver, GLuc-HA in heart, GLuc-V5 in kidneys, and GLuc-AcV5 in gastrointestinal tract. Using the techniques known in the art, it is possible to generate single, double, triple or multiple transgenic animals expressing the above constructs singly or in combination. It is also possible to generate transgenic animals expressing different reporter (e.g, GLuc or NLuc) constructs in different lineages or compartments of a single organ (e.g. proximal and distal tubules of kidney or different cellular compartments of gut or CNS or heart or liver, or lungs.). Such single or multiple transgenic animals can be exposed to a candidate test agent and its toxicity measured by checking for the reporter activity in the body fluid either directly or after immunobinding using antibodies against different epitope tags that could be linked to the reporters or using antibodies against different reporters (e.g. antibodies against GLuc or NLuc).

To increase the half-life of the reporters of the invention in the blood and other body fluids, it is possible to generate their fusion variants by adding the sequence encoding albumin or an albumin binding domain (ABD) to their coding region. The fusion proteins of the reporters with albumin (e.g. GLuc-Alb) or with ABD (e.g. GLuc-ABD) are expected to have longer half lives as they will not be filtered through the urine. In an exemplary embodiment, cell lines can be generated expressing GLuc-Alb or GLuc-ABD or GLuc-ABD-Flag and used in Matador assay in vivo. It is also possible to increase the half-life of a reporter by fusing it (with or without via a flexible Glycine-serine linker) to an antibody or antibody fragment (e.g. scFV) or a single domain antibody (e.g. nanobody) directed against albumin. An example of a nanobody against albumin is provided in patent WO 2011/144749 A1.

In another embodiment, transgenic animals expressing the reporters of the invention can be used to measure the efficacy of an agent or endeavor to reduce cell toxicity or cell death, such as in the case of Alzheimer disease, stroke, degenerative disease, or autoimmune diseases. In an exemplary embodiment, transgenic animals expressing GLuc in neurons are generated using neuron-specific Thy1 or Nestin promoter. Such animals are used to test the efficacy of a candidate anti-stroke agent in an appropriate stroke model known in the art. In case the test agent is effective, it will reduce the death of neurons and the release of GLuc from them. The GLuc activity, in turn, can be measured ex vivo in blood, urine or CSF or by in vivo bioluminescence imaging following injection of coelenterazine.

In another embodiment, the reporters of the invention are expressed in different cells of an animal using viral vectors (e.g. AAV, Adeno, lentiviral etc.) and then these animals are used for monitoring cytotoxicity.

Kits

In various embodiments, the present invention provides a kit for assessing cytotoxicity of an agent. In various embodiments, the kits comprise vectors, target cells, primary cells, agents of interest or combinations thereof and instructions for carrying out the assays.

The kit is an assemblage of materials or components, including at least one of the inventive reporters, substrates, buffers, vectors and cell lines. Thus, in some embodiments the kit contains a cell or a cell line expressing non-secretory forms of a reporter (for example, GLuc) and the substrate for the reporter. For kits of the invention the reporter(s), the reporter substrate(s), and buffers and other chemicals can each be contained in a separate container, or they can be contained in a single container. The kits can also optionally comprise a second substrate or a quenching agent for a luminescent enzyme reaction.

The exact nature of the components configured in the inventive kit depends on its intended purpose. In one embodiment, the kit is configured particularly for research and development. In another embodiment, the kit is configured particularly for quality control testing or potency testing in manufacturing of a drug, antibody, biological or cellular therapy product. In yet another embodiment, the kit is configured for testing human samples. In further embodiments, the kit is configured for veterinary applications.

Instructions for use may be included in the kit. "Instructions for use" typically include a tangible expression describing the technique to be employed in using the components of the kit to effect a desired outcome, such as to test the cytotoxicity of a CAR-T cell product. Still in accordance with the present invention, "instructions for use" may include a tangible expression describing the preparation of components for use with the assays described herein. Optionally, the kit also contains other useful components, such as, measuring tools, diluents, buffers reporter substrates or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition containing a volume of the non-secretory form of GLuc encoding vector. The packaging material generally has an external label which indicates the contents and/or purpose of the kit and/or its components

EXAMPLES

Example 1

Expression Vectors

The pcDNA3 mammalian expression vector was obtained from Invitrogen, ThermoFisher Scientific. The pLENTI-Blast vector was derived from pLenti6v5gw_lacz vector (Invitrogen; ThermoFisher Scientific) by removal of the LacZ gene. The expression of the inserted gene in this vector is driven by CMV promoter. pLenti-MP2 was a gift from Pantelis Tsoulfas (Addgene plasmid #36097) and was used to generate pLENTI-EF1αlentiviral vector (SEQ ID NO: 91) by replacement of the CMV promoter with human EF1α promoter using standard molecular biology techniques. psPAX2 was a gift from Didier Trono (Addgene plasmid #12260). The pLP/VSVG envelope plasmid and 293FT cells were obtained from Invitrogen (ThermoFisher Scientific). The retroviral transfer vector MSCVneo, MSCVhygro, and MSCVpac and the packaging vector pKAT were obtained from Dr. Robert Illaria's laboratory. phRGTK Renilla Luciferase plasmid was from Promega. To construct lentiviral constructs encoding FMC63-BBZ Chimeric antigen receptor (CAR), the gene fragment encoding FMC63 CAR was synthesized by GeneArt™ using the published sequence as template. The gene fragment was then used as a template in a PCR reaction to amplify the encoded sequence which was then cloned in a lentiviral vector driven by an EF1α promoter and in frame with T2A ribosomal skip sequence followed by EGFP nucleotide sequence using standard molecular biology techniques. The resulting construct was labeled pLenti-EF1α-FMC63-MYC-BBZ-T2A-EGFP. The DNA and protein sequences of this CAR insert are provided in SEQ ID NO: 79 and SEQ ID NO: 85, respectively. A lentiviral construct, pLenti-EF1α-FMC63-MYC-BBZ-T2A-PAC, was also constructed by replacement of EGFP gene with a Puromycin resistance gene. The DNA and protein sequences of this CAR insert are provided in SEQ ID NO: 80 and SEQ ID NO: 86, respectively. Finally, a pLenti-EF1α-FMC63-MYC-CD28Z-T2A-Pac construct was made by using a synthetic CD28Z gene fragment (synthesized by IDT) as a template for PCR amplification and standard molecular biology techniques to replace the BBZ cassette with CD28Z cassette. The DNA and protein sequences of this CAR insert are provided in SEQ ID NO: 81 and SEQ ID NO: 87, respectively. CAR constructs targeting other antigens (e.g., CD22, MPL etc.) were generated similarly by replacing the nucleotide sequence encoding the FMC63 scFV with the nucleotide sequence encoding scFVs targeting the different antigens.

All the luciferase constructs used in this invention were designed to lack a secretory signal. The nucleotide sequences encoding NLuc, MLuc7-MM-LL, TurboLuc16, PaLuc1, *Lucicutia ovaliformis* luciferase, *Heterorhabdus tanneri* luciferase, Lucia-luciferase and LucPPe-146-1H2 were codon optimized using GeneArt™ software (Thermo Fisher Scientific) and gene-fragments encoding the optimized sequences were synthesized by GeneArt™ or Integrated DNA Technologies (IDT). The gene fragments were used as template in PCR reactions using custom primers to amplify the corresponding DNAs (lacking the secretory signal), which were then cloned in different expression vectors using standard molecular biology techniques. In all cases, where the nucleotide sequence containing the secretory signal was deleted, an ATG start codon was included in the 5' custom primer that was used to amplify the DNAs. In some cases, the amplified fragments were cloned in-frame with nucleotide sequences encoding different epitope tags, such as FLAG (SEQ ID NO: 61), 3×FLAG (SEQ ID NO: 62), AcV5 (SEQ ID NO: 64), MYC (SEQ ID NO: 65) and HA (SEQ ID NO: 63). Essentially a similar strategy was used to clone codon optimized GLuc (also called hGLuc), Fire-Fly luciferase (FLUC or FfLuc) and Renilla Luciferase except the plasmids encoding the corresponding cDNAs were used as template in PCR reactions. Unless indicated otherwise, all luciferases (e.g., GLuc, NLuc, TLuc, PaLuc, Lucia-Luc etc.) described in this invention were used lacking their signal peptide or the secretory signal to target their expression to the cytosolic compartment. The sequences of several exemplary vectors encoding the different luciferases are provided in SEQ ID NO: 92 to SEQ ID NO: 100. These vectors can be used to clone any new reporter by replacing the existing reporter inserts using standard molecular biology techniques.

The sequence of inserts was confirmed by automated sequencing. The DNA and protein SEQ ID NOs of the different reporters used in this invention are shown in Tables 1. Table 2 provides the characteristics of exemplary expression constructs used in this invention.

TABLE 2

Characteristics of Exemplary Expression Constructs

| | Construct Name | Vector Backbone | Promoter | Antibiotic for Selection of mammalian cells |
|---|---|---|---|---|
| 1 | pL enti-EF1a (or pLenti-EF1α) | pLenti-EF1a | EF1a | None |
| 2 | pLENTI-NLuc-AcV5-Blasticidin-Pa08 | pLenti6v5gw_lacz | CMV | Blasticidin |
| 3 | pLENTI-TurboLuc-16-X3Flag-Blast-C04 | pLenti6v5gw_lacz | CMV | Blasticidin |
| 4 | pLenti-EF1a-Pac-T2A-GLuc-B07 | pLenti-EF1a | CMV | Puromycin |
| 5 | MSCVhygro-GLuc-HA-G02 | MSCVhygro | MSCV LTR | G418 |
| 6 | MSCVpac-GLuc-HA-R03 | MSCVpac | MSCV LTR | Puromycin |
| 7 | MSCVneo-Lucia-Luc-x3-Flag-B08 | MSCVneo | MSCV LTR | G418 |
| 8 | pLENTI-GLuc-Flag-blast-B07 | pLenti6v5gw_lacz | CMV | Blasticidin |
| 9 | MSCVneo-GLuc-X3-FLAG-Q02 | MSCVneo | MSCV LTR | G418 |
| 10 | MSCVhygro-MLuc7-MM-LL-HA-R03 | MSCVhygro | MSCV LTR | Hygromycin |
| 11 | MSCVhygro-Renilla-V03 | MSCVhygro | MSCV LTR | Hygromycin |
| 12 | MSCV-hygro-NLuc-AcV5-D07 | MSCVhygro | MSCV LTR | Hygromycin |
| 13 | pLENTI-EF1a-FfLuc-Blasticidin-A07 | pLenti6v5gw_lacz | EF1a | Blasticidin |
| 14 | Plenti-MLuc7-MM-LL-HA-C03 | pLenti6v5gw_lacz | CMV | Blasticidin |
| 15 | MSCVhygro-2xFLAG-L-ovaliformis-AcV5-D04 | MSCVhygro | MSCV LTR | Hygromycin |
| 16 | MSCV-neo-NLuc-AcV5-B04 | MSCVneo | MSCV LTR | G418 |
| 17 | MSCVpac-Nluc-AcV5-C08 | MSCVpac | MSCV LTR | Puromycin |
| 18 | pLenti-H-tanneri-Luc-x3-Flag-T05 | pLenti6v5gw_lacz | CMV | Blasticidin |
| 19 | MSCVhygro-H-tanneri-Luc-Flag-UO2 | MSCVhygro | MSCV LTR | Hygromycin |
| 20 | pLenti-2XFLAG-L-ovaliformis-AcV5-S01 | pLenti6v5gw_lacz | CMV | Blasticidin |
| 21 | pLenti-LucPPe-146-1H2-3X-FLAG-S01 | pLenti6v5gw_lacz | CMV | Blasticidin |
| 22 | pLenti-EF1-LucPPe-146-1H2-Xho-Flag-Pac-R01 | pLenti-EF1a | EF1a | Puromycin |
| 23 | MSCVhygro-PaLuc1-x3Flag-001 | MSCVhygro | MSCV LTR | Hygromycin |
| 24 | pCDNA3 | pCDNA3 | CMV | G418 |

Lentivirus and Retrovirus Viruses

Lentiviruses were generated by calcium phosphate based transfection in 293FT cells essentially as described previously (Matta, Hozayev et al. 2003). Briefly, 293FT cells were grown in DMEM with 10% FCS 4 mM L-Glutamine, 0.1 mM MEM Non-Essential Amino Acids, and 1 mM MEM Sodium Pyruvate (hereby referred to as DMEM-10). For generation of lentiviruses, 293FT cells were plated in 10 ml of DMEM-10% FCS medium without antibiotics in a 10 cm tissue culture plate so that they will be approximately 80 confluent on the day of transfection. The following day, the cells were transfected by calcium phosphate transfection method using 10 μg of lentiviral expression plasmid encoding different genes, 7.5 μg of PSPAX2 plasmid and 2 μg of PLP/VSVG plasmid. Approximately 15-16 hours post-transfection, 9 ml of media was removed and replaced with 5 ml of fresh media. Approximately, 48 hours post-transfection, 5 ml of supernatant was collected (first collection) and replaced with fresh 5 ml media. Approximately 72 hours post-transfection, all media was collected (second collection, usually around 6 ml). The collected supernatants were pooled and centrifuged at 1000 rpm for 1 minute to remove any cell debris and non-adherent cells. The cell-free supernatant was filtered through 0.45 m syringe filter. In some cases, the supernatant was further concentrated by ultracentrifugation at 18500 rpm for 2 hours at 4° C. The viral pellet was re-suspended in ⅒ of the initial volume. The virus was either used fresh to infect the target cells or stored frozen in aliquots at −80° C. In general, primary cells (e.g. T cells) were infected using spin-infection (1800 rpm for 90 minutes at 37° C. with 300 μl of concentrated virus in the presence of 8 μg/ml of Polybrene® (Sigma, Catalog no. H9268) in the morning. The media was changed in the evening and the infection was repeated for two more days for a total of 3 infections. After the 3rd infection, the cells were pelleted and resuspended in the media with respective antibiotics and place in the cell culture flask for selection, unless indicated otherwise. In cases, where cells were infected with a lentivirus expressing EGFP, they were expanded without drug-selection or flow-sorted to enrich for EGFP-expressing cells. For infection of cancer cell lines, approximately 500,000 cells were infected with 2 ml of the un-concentrated viral supernatant in a total volume of 3 ml with Polybrene® (Sigma, Catalog no. H9268). Then next morning, the cells were pelleted and resuspended in the media with respective antibiotics and place in the cell culture flask for selection.

Essentially a similar procedure as described above for lentivirus vector production was used for generation of retroviral vectors with the exception that 293FT cells were generally transfected in 10 cm tissue culture plates in 10 ml of DMEM-10% FCS medium using 10 μg of retroviral construct, 4 μg of pKAT and 2 μg of VSVG plasmid. The virus collection and infection of target cells was carried out essentially as described above for lentiviral vectors.

Cell Lines and Cells

K562, chronic myelogenous leukemia (CML), Raji (Burkitt's lymphoma), HEL 92.1.7, (erythroleukemia; also called HEL), and RS; 411 (acute lymphoblastic leukemia; also called RS411) cell lines were obtained from ATCC and maintained in RPMI1640 medium with 10% FBS. Jurkat (acute T cell leukemia) cell line was obtained from Dr Shao-Cong-Sun laboratory (Pennsylvania State University College of Medicine) and maintained in RPMI1640 medium with 10% FBS. Primary Effusion Lymphoma (PEL) derived cell lines BC-1, BC-3 and BCBL-1, which are infected with Kaposi's sarcoma associated herpes virus, were obtained from Dr. J. Jung (University of Southern California; USC) and maintained in RPMI1640 with 20% FBS. KSHV-transformed primary rat embryonic metanephric mesenchymal precursor (MM; a gift from Dr. S. J. Gao, University of Southern California) were cultured in DMEM 10% FBS.

Hodgkin lymphoma cells (L428, L540, L1236, KMH2) were obtained from Dr. Mapara and cultured in RPMI 20% FBS. SK-BR-3 (breast adenocarcinoma) was obtained from ATCC and grown in McCoy's 5a medium with 10% FBS. Other cell lines were obtained from ATCC and maintained in the medium recommended by the supplier. Buffy coat cells were obtained from the Blood Bank at Children Hospital of Los Angeles and used to isolate peripheral blood mononuclear cells (PBMC) by Ficoll-Hypaque gradient centrifugation. PBMC were subsequently used to isolate T cells using CD3 magnetic microbeads (Miltenyi Biotech) and following the manufacturer's instructions. All cells were cultured at 37° C., in a 5% CO2 humidified incubator.

Antibodies and Drugs

Blinatumomab was obtained from Amgen, Brentuximab vedotin (Adcetris) was obtained from Seattle Genetics, Rituximab was obtained from Genentech. BIIB021 was from Selleck chemicals and JQ1 was provided by Dr. James Bradner (Dana Farber Cancer Institute). Digitonin was purchased from Sigma (Cat. no D141) and a stock solution of 100 mg/ml was made in DMSO. A diluted stock of 1 mg/ml was made in PBS. Unless indicated otherwise, final concentration of Digitonin used for cell lysis was 30 μg/ml.

Assay for Copepods Luciferases

A 100×stock solution of native coelenterazine (CTZ; Nanolight, cat #303) was made by dissolving 1 mg of lyophilized CTZ powder in 1.1 ml of 100% Methanol supplemented with 30 μl of 6N HCl to avoid oxidation of CTZ with time. To make CTZ assay buffer, the 100×stock solution of CTZ was diluted to 0.5×concentration in PBS. Unless indicated otherwise, a total volume of 15 μl of the CTZ assay buffer (as prepared above) was added using an auto-injector to each well of a 384-well white plate (Greiner, 384 well white plate cat #781075) containing cells expressing the non-secretory form of a copepod luciferase in approximately 50-60 μl volume of medium and plates were read for luminescence in well-mode using BioTek synergyH4 plate reader. In the well-mode, an auto-injector or dispenser is used and assay buffer is added in one well, luminescence is read in that well, then the assay buffer is added to next well and luminescence is read in that well. Where indicated, assay was also conducted in the endpoint mode. In the endpoint mode, an autoinjector or dispenser is not used, the assay buffer is added in all wells manually using a pipette and then luminescence is read in all wells of the plate. For 96 well plates, cells were plated in 200 μl of media and approximately 50 μl of 0.5×CTZ assay buffer was added. Unless indicated otherwise, the 0.5×CTZ assay buffer was used for assaying the activity of copepod luciferase (e.g., GLuc, NLuc, MLuc7, HTLuc, PaLuc1, PaLuc2, MpLuc1, McLuc1, MaLuc1, MoLuc1, MoLuc2, MLuc39, PsLuc1, LoLuc1-3, HtLuc2, TurboLuc16 (TLuc), and Lucia Luc). The CTZ assay buffer (diluted to 0.125×concentration) was also used for measurement of NLuc activity in most experiments. Unless indicated otherwise, the volume of 0.5×CTZ assay buffer added was approximately ¼$^{th}$ of the volume of the liquid in the well containing the cells, although the assay also worked when the 0.5×CTZ assay was added to the media containing the cells in 1:1 volume.

NLuc Assay

Nano-Glo® Luciferase Assay System (Promega) was used for measurement of NLuc activity in some experiments by following the manufacturer's instructions. Briefly, Nano-Glo® Reagent was prepared by adding 5 μl of Nano-Glo® substrate in 1 ml of Nano-Glo® assay buffer (Promega). 15 μl of Nano-Glo® Reagent prepared above was added directly either manually or using auto-injector to each well of a 384-well white plate containing cells in 60 μl of media. For 96 well plates, cells were plated in 200 μl of media and approximately 50 μl of assay buffer was added. Plates were read for luminescence in endpoint mode using BioTek synergyH4 plate reader without prior cell lysis. In some experiments, NLuc activity was measured using CTZ assay buffer but here the buffer was diluted to final concentration of 0.125×. When CTZ assay buffer was used for measurement of NLuc activity, a total volume of approximately 15 μl (unless indicated otherwise) of the 0.125×CTZ assay buffer was added by auto-injector to each well of a 384-well white plate (Greiner, 384 well white plate cat #781075) containing cells in approximately 50-60 μl volume of medium and plates were read for luminescence using BioTek synergyH4 plate reader. For 96 well plates, cells were generally plated in 200 μl of media and approximately 50 μl of 0.125×CTZ assay buffer was added.

Measurement of Maximum Cell Death

For measurement of maximum cell death, cells were treated with 30 μl of Digitonin dissolved in DMSO (final concentration 30 μg/ml) for approximately 90 min prior to measurement of activities of luciferases, such as GLuc, NLuc, TurboLuc, MLuc7, ovaliformis, H. tanneri and *renilla* luciferases. Percentage Specific lysis was calculated using the luciferase activity of Digitonin-treated cells as maximum cell death and untreated cells as spontaneous cell death and using the formula % specific lysis=100×[(experimental data−spontaneous cell death)/(maximum cell death−spontaneous cell death)].

Renilla Luc Assay

Unless indicated otherwise, for measurement of Renilla Luciferase activity, the Renilla Luciferase Assay System Kit from Promega (Cat #E2820) was used. Renilla Luciferase Assay Reagent was prepared by adding 1 volume of 100× Renilla Luciferase Assay Substrate to 100 volumes of Renilla Luciferase Assay Buffer and the reagent used in the assay as per manufacturer's instructions. In some experiments, Renilla Luciferase activity was also measured using CTZ assay buffer.

Assay for Beetle Luciferase (for Fire Fly-Luc (FfLuc or Fluc), LucPPe, LucPpL and CBGR-Luc)

Unless indicated otherwise, for measurement of FFLuc, CBGRLuc and LucPPe-146-1H2 activities, a 10× Luciferin stock solution was prepared consisting of 1 mM D-luciferin synthetic crystalline (Sigma), 25 mM glycylglycine, pH 7.8. A stock solution of luciferin assay buffer was prepared containing 25 mM glycylglycine, pH 7.8, 15 mM potassium phosphate, pH 7.8, 15 mM MgSO$_4$, 4 mM EGTA, 2 mM ATP (Sigma). Working solution of Luciferase assay buffer for each 1.0 ml consisted of 885.5 μl assay buffer+1 μl DTT (IM stock)+100 μl of 10× Luciferin stock solution+13.5 μl ATP (100 mM stock). The assay buffer containing substrate was generally added to the media containing cells or cellular supernatants at 1:1 (v/v) ratio, unless indicated otherwise.

Cell Lysis

Unless indicated otherwise, cell lysates were prepared in 1× Renilla Luciferase Assay Lysis Buffer immediately before performing assays by diluting one volume of 5× Renilla Luciferase Assay Lysis Buffer (Promega, Cat #E2820) into four volumes of distilled water. Cell lysis was performed following the manufacturer's instructions.

Transient Transfection of 293FT Cells with Retro- and Lentiviral Based Luciferase Expression Vectors The 293FT cells were transfected in a 24-well plate with various expression plasmids (500 ng/well) using calcium phosphate. Approximately, 18 hours post-transfection, the cells were either left untreated or treated with 30 μg/ml Digitonin to induce cell death, followed by the detection of luminescence as described under luciferase assays.

Generation of NK92MI Cells Stably Expressing CARs

NK92MI cells stably expressing second generation CAR constructs and coexpressing EGFP were generated by infecting with concentrated lentiviruses as described for primary human T cells. The EGFP positive cells were sorted using BD FACSAria II and expanded.

Example 2

Construction and Testing of Vectors Expressing Gaussia Luciferase (GLuc) and NanoLuc (NLuc) for Use in Matador Cytotoxicity Assay We cloned the a gene fragment encoding GLuc lacking its signal peptide (amino acid residues 1-17) and encoding its amino acid residues 18 to 185 preceded by an ATG start codon in retroviral vectors MSCVneo and MSCVhygro and lentiviral vector pLenti-Blast. We also expressed the GLuc cDNA lacking the signal peptide from a lentiviral vector pLenti-EF1α in which its expression was driven by the constitutively active Elongation Factor 1-alpha promoter. This construct also expressed the puromycin resistance gene (pac) upstream and in-frame with the GLuc cDNA and separated from it by a T2A ribosomal skip sequence. The nucleotide sequences of GLuc constructs pLenti-EF1a-Pac-T2A-Gluc-B07, MSCVhygro-GLuc-HA-G02, MSCVpac-GLUC-HA-R03 and pLENTI-Gluc-Flag-blast-B07 are provided in SEQ ID NOs: 94, 95, 96 and 98, respectively. We generated polyclonal population of several cell lines stably expressing GLuc and confirmed GLuc expression by measuring the GLuc luciferase activity in the cell lysates following addition of an assay buffer containing coelenterazine. In general the level of expression of GLuc was higher in cells infected with the lentiviral vectors as compared to those infected with the retroviral (i.e. MSCV) vectors. We also cloned the NanoLuc (NLuc; Promega) cDNA lacking a signal peptide into the pLenti-Blast vector, in which NLuc expression was being driven by CMV promoter, and used this vector to generate cells stably expressing NLuc. The DNA sequence of this vector is provided in SEQ ID NO: 92.

Example 3

Figure 1B:
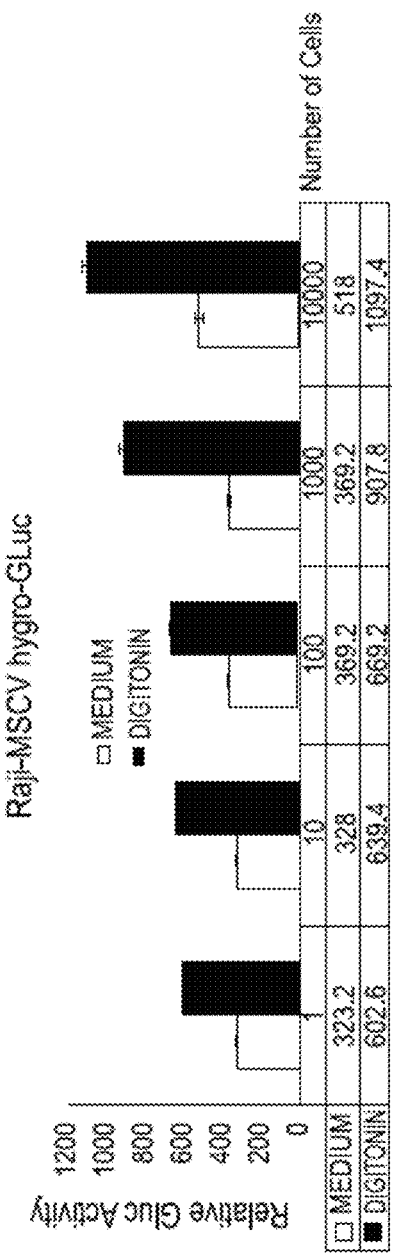

GLuc can be Used in Matador Cytotoxicity Assay to Measure Cell Death with Sensitivity Down to a Single Cell Level HEL-92-1-17 (obtained from ATCC) cells stably expressing GLuc from the pLenti-EF1α-PAC-T2A-GLuc-B07 vector (SEQ ID NO: 94) were grown in complete medium (RPMI 1640 media+10% FBS). Cells were washed with growth medium, and diluted to $3.3 \times 10^6$ cells/ml in complete medium (100K cells/30 1). Cells were then serially diluted tenfold in complete medium to a final concentration of 10,000 cells/30 μl, 1000 cells/30 μl, 100 cells/30 μl and 1 cell/30 μl. A total volume of 30 μl of cells was plated per well in 10 wells of white 384-well plates for each concentration. The cells were either treated with 30 μl of PBS (n=5 wells at each cell concentration) or treated (n=5 wells at each cell concentration) with 30 μl of Digitonin (final concentration 30 μg/ml) and incubated for 1 hour at 37° C. in a 5% $CO_2$ incubator. A total volume of 15 μl of 0.5×CTZ assay buffer was added by autoinjector directly to each well of the 384-well white plate containing cells in 60 μl of volume (30 μl of RPMI-10% FBS+30 μl of Digitonin) without prior cell lysis and plates were read for luminescence using BioTek synergy H4 plate reader in well mode. FIG. 1 shows that induction of cell death by treatment of HEL-92-1-17 cells stably expressing GLuc with Digitonin resulted in an increase in GLuc luciferase activity, which was evident even in wells containing a single cell. Essentially similar results were obtained upon Digitonin treatment of RAJI cells stably expressing GLuc from the MSCVhygro-GLuc-HA-G02 vector (SEQ ID NO: 95). Thus, GLuc is not degraded by proteases released during cell death, making it a suitable candidate for the development of an assay of cellular cytotoxicity. These results further demonstrate that the CTZ assay buffer (CTZ dissolved in PBS) is not cytotoxic to cells as otherwise the GLuc activity in the samples with and without Digitonin treatment would have been similar, making it impractical to conduct the assay in a homogenous format.

Example 4

Figure 2A:
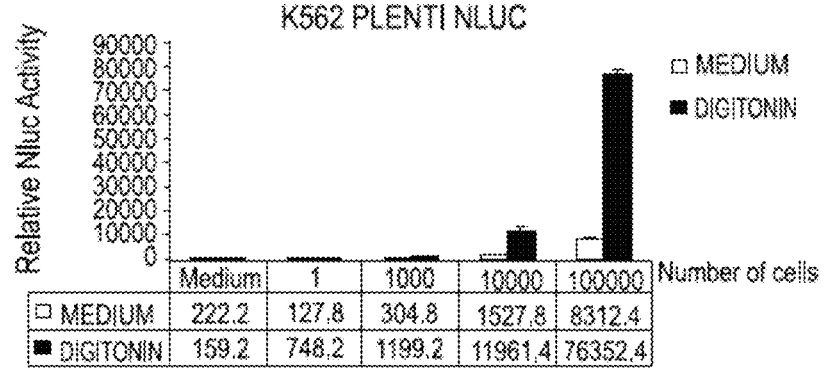
FIG. 2A-FIG. 2C depicts in accordance with various embodiments of the invention, that Digitonin treatment of NLuc expressing K562, HEL-91-1-17 and RAJI cells resulted in increase in NLuc activity which was detectable even at 1 cell/well level and there was a progressive increase in luciferase activity with increase in cell number.
Figure 2B:
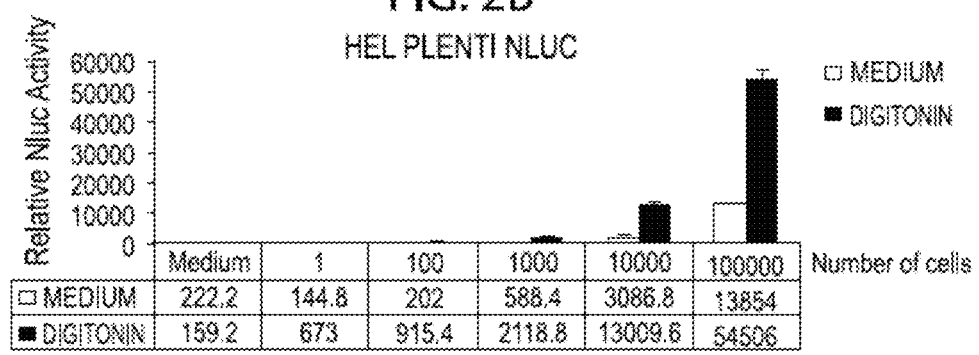
Figure 2C:
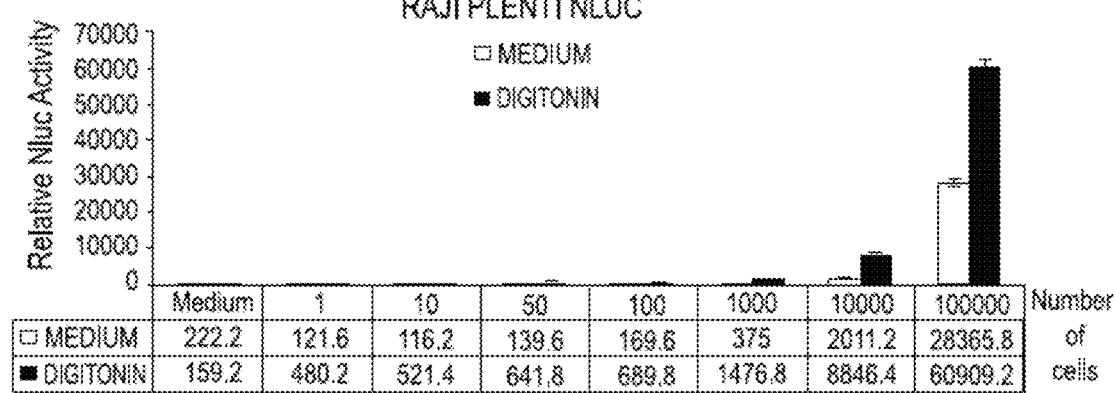

NLuc can be Used in Matador Cytotoxicity Assay to Measure Cell Death with Sensitivity Down to a Single Cell Level A similar experiment was conducted with K562, HEL-91-1-17 and RAJI cells stably expressing NLuc from pLENTI-NLuc-AcV5-Blasticidin-Pa08 vector (SEQ ID NO: 92). Cells plated in 30 μl of medium per well were either treated with 30 μl of PBS or 30 μl of PBS containing Digitonin (final concentration 30 μg/ml) for 1 hour at 37° C., in a 5% $CO_2$ incubator. For measurement of NLuc activity, 0.5×CTZ assay buffer was added by automated injector directly to each well of the 384-well white plate containing cells in 60 μl of volume (30 μl of RPMI-10% FBS+30 μl of Digitonin) without prior cell lysis and plates were read for luminescence using BioTek synergy H4 plate reader in well mode. FIG. 2 shows that Digitonin treatment of NLuc expressing K562, HEL-91-1-17 and RAJI cells resulted in increase in NLuc activity, which was evident even in wells containing a single cell. Furthermore, even though there was a progressive increase in the NLuc activity in both the untreated and Digitonin-treated samples with increase in cell number, the ratio (fold increase) of NLuc activity between Digitonin-treated and untreated (medium alone) samples was relatively stable and independent of the number of plated cells. Thus, NLuc is not degraded by proteases released during cell death, making it a suitable candidate for the development of an assay of cellular cytotoxicity.

Example 5

Use of MLuc7 in Matador Cytotoxicity Assay

Figure 3A:
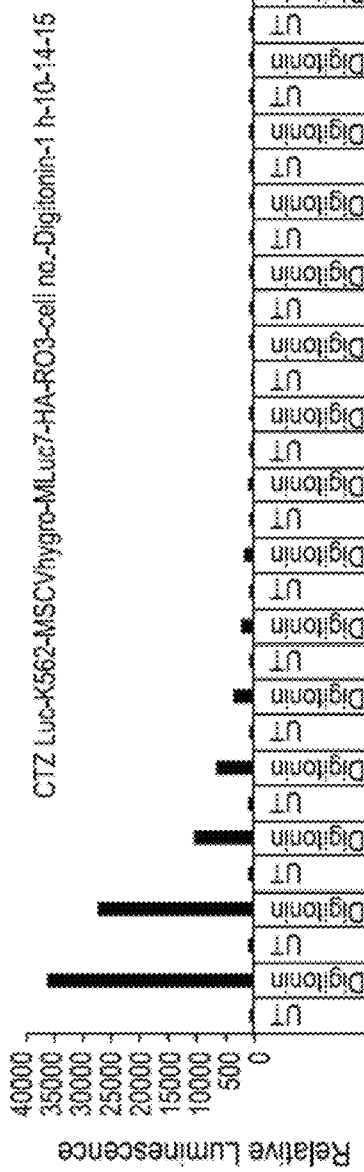
FIG. 3A-FIG. 3B depicts in accordance with various embodiments of the invention, that induction of cell death by Digitonin results in increase in MLuc7 activity that was detectable even at 1 cell/well level and there was a progressive increase in MLuc7 activity with increase in cell number up to 400K cells/well.
Figure 3B:
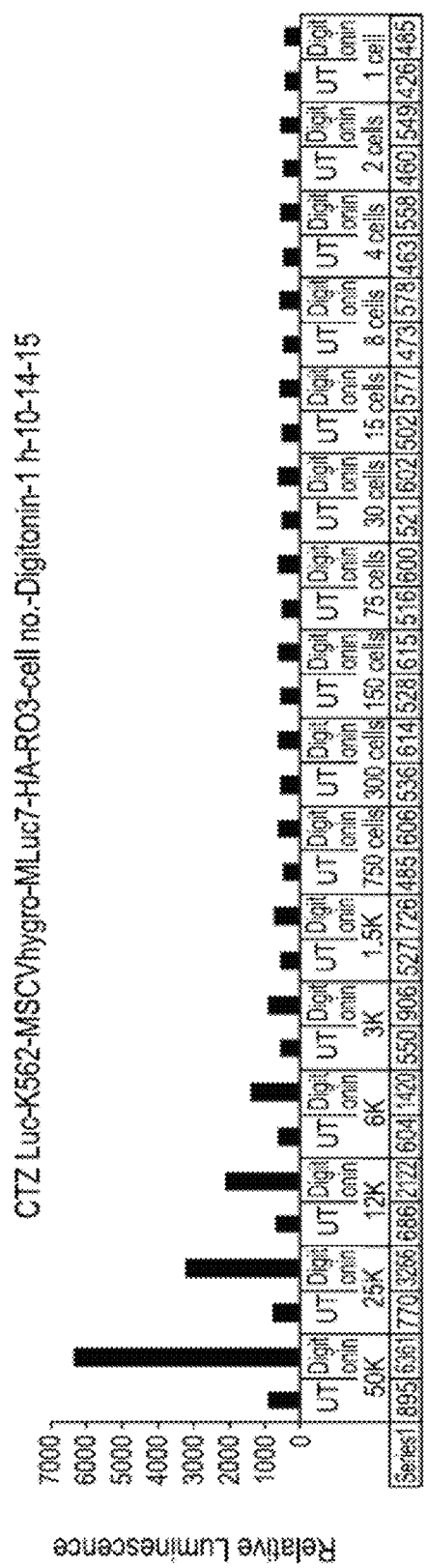

To test if other copepod luciferases may be used similarly to GLuc for development of Matador cellular cytotoxicity assay, we cloned a gene fragment coding the non-secretory (lacking the signal peptide) form of Metridia longa luciferase 7 (MLuc7) into MSCVhygro vector. The MLuc7 gene fragment (SEQ ID NO: 4) also carried M43L and M110L substitutions. The corresponding substitutions in GLuc have been previously shown to result in Glow type luminescence suitable for high throughput applications (Welsh, Patel et al. 2009). Stable population of K562 cells expressing MLuc7-M43L-M110L mutant and carrying a carboxy terminal HA epitope tag were generated by retroviral mediated gene transfer and selection with hygromycin. K562-MLuc7-expressing target cells were washed with growth medium, and diluted to $4.0 \times 10^6$ cells/ml in complete medium. Cells were then serially diluted in complete medium to a final concentration of 200K cells/30 μl, 100K cells/30 μl, 50K cells/30 1, 25K cells/30 μl, 12K cells/30 μl, 6K cells/30 μl, 3.0K cells/30 μl, 1.5K cells/30 μl, 750 cells/30 μl, 300 cells/30 μl, 150 cells/30 μl, 75 cells/30 μl, 30 cells/30 μl, 15 cells/30 μl, 8 cells/30 µl, 4 cells/30 µl, 2 cells/30 µl and 1 cells/30 µl. A total volume of 30 µl of target cells was plated per well in 3 wells for each concentration in a Greiner 384-well flat bottom white opaque plate. The cells were either treated with Digitonin for measurement of maximum cell death or left untreated and incubated for 1 hour in a 37° C., 5% CO2 incubator. The luciferase activity in K562-MLuc7-expressing cells was precisely measured by BioTek synergy plate reader that directly injected 15 µl of the 0.5×CTZ assay buffer into the 384 well plates in well mode. FIG. 3 shows that induction of cell death by Digitonin results in increase in MLuc7 activity that was detectable even at 1 cell/well level and there was a progressive increase in MLuc7 activity with increase in cell number up to 400K cells/well. The lower panel is derived from the data in the upper panel and focuses on the range from 1 cell/well to 50K cells/well. Even though the MLuc7-M43L-M110L mutant was used in the above example, we believe that the non-secretory form of wild type MLuc7 could be used in the development of the above assay as well. Thus, MLuc7 is not degraded by proteases released during cell death, making it a suitable candidate for the development of the Matador assay of cellular cytotoxicity.

MLuc7 Assay (Additional Example)

Figure 4:
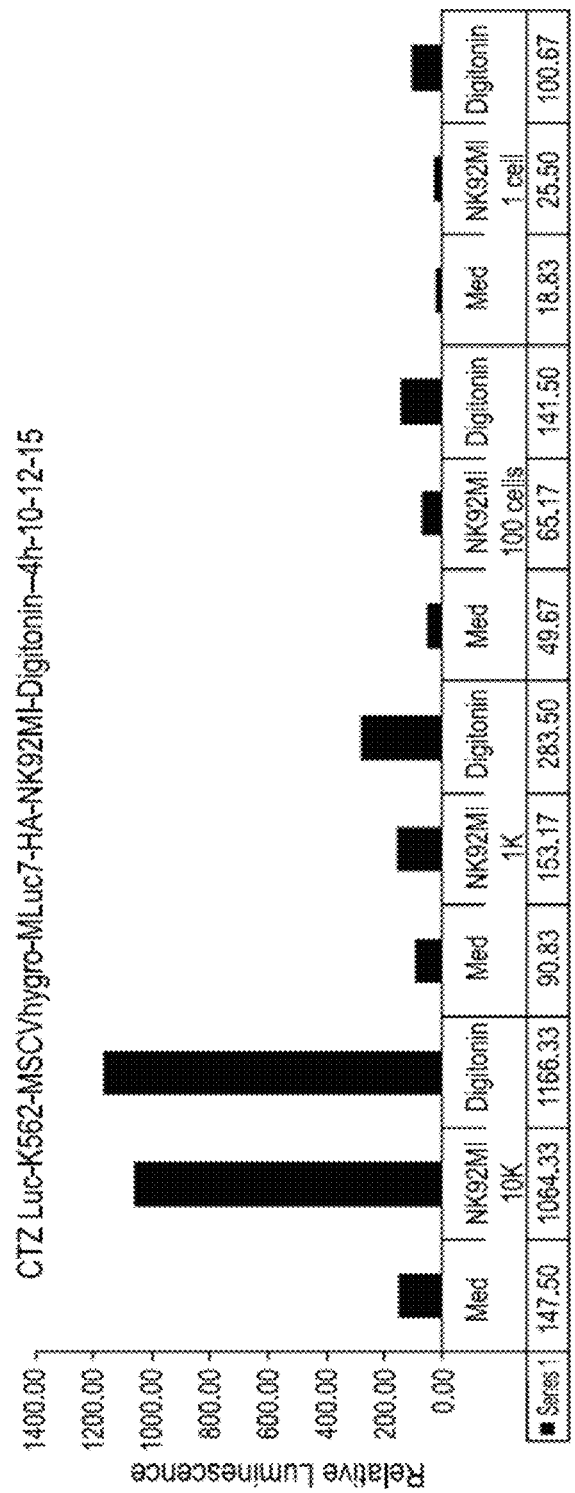
FIG. 4 depicts in accordance with various embodiments of the invention, that induction of cell death by Digitonin and NK92MI cells resulted in increase in MLuc7 activity that was detectable even at 1 cell/well level and there was a progressive increase in MLuc7 activity with increase in cell number up to 10K cells/well.

K562-M7-Luc (MSCVhygro-MLuc7-MM-LL-HA-RO3)-expressing target cells were plated at a final concentration of 10K cells/30 µl, 1K cells/30 µl, 100 cells/30 µl, and 1 cell/30 µl. A total volume of 30 µl of target cells was plated per well into 3 wells for each concentration in a Greiner 384-well flat bottom white opaque plate. The cells were either left untreated or co-cultured with NK92MI effector cells at a Effector (E) to Target (T) ratio of 0.5:1 and incubated for 4 hours in a 37° C., 5% CO2 incubator. Cells were treated with Digitonin (final concentration 30 µg/ml) for maximum cell death. Total volume in each well was 60 µl where Effector and Target cells were co-cultured and 30 µl of culture media was added in other wells to make a total volume of 60 µl in all the wells. The luciferase activity in K562-MLuc7-expressing cells was precisely measured by BioTek synergy plate reader by directly injecting 15 µl 0.5×CTZ assay buffer containing native coelenterazine (Nanaolight) into the 384 well plates in a well mode. FIG. 4 shows that induction of cell death by Digitonin and NK92MI cells results in increase in MLuc7 activity that was detectable even at 1 cell/well level and there was a progressive increase in MLuc7 activity with increase in cell number up to 10K cells/well. These results further demonstrate that MLuc7 activity is stable even under conditions when cell death is induced by NK92MI cells. Thus, cell death proteases released during NK92MI-induced cell death do not degrade MLuc7 and this luciferase can be used for the development of an assay of cellular cytotoxicity.

Example 6

Use of TurboLuc16 (TLuc) in Matador Cytotoxicity Assay

Stable population of K562 and RAJI cells expressing TurboLuc16 (TLuc) and carrying a carboxy terminal x3FLAG epitope tag were generated by lentiviral mediated gene transfer of pLENTI-TurboLuc-16-X3Flag-Blast-C04 construct (SEQ ID NO: 93) and selection with blasticidin. Cells were plated in 384 well plates (25,000 cells/well) in 25 µl media and treated with 5 of PBS or PBS containing Digitonin (5 µl) for 90 min. The TurboLuc activity was measured by BioTek synergy plate reader by directly injecting 30 µl of 0.5×CTZ assay buffer containing native-coelenterazine into the 384 well plates in well mode. FIG. 5 shows that induction of cell death by Digitonin results in increase in TLuc activity in both K562 and RAJI cells. Thus, TLuc is not degraded by proteases released during cell death and it can be used for the development of an assay of cellular cytotoxicity.

Example 7

Use of Renilla Luc in Matador Cytotoxicity Assay

K562 cells were infected with MSCVhygro-Renilla-Luc retroviral vector and selected in hygromycin to generate polyclonal population of cells stably expressing Renilla Luc in the cytosol. Approximately $2.5 \times 10^4$ cells were plated in each well of a 384 well plate in 20 µl of medium. Cells were either treated with 20 µl of medium alone, 20 µl of medium containing NK92MI cells (E:T ratio of 1:1), 20 µl of DMSO (control) or 20 µl of Digitonin dissolved in DMSO. Treatment with Digitonin was for 2 hours, while all other treatments were for approximately 4 hours. Cell death was measured by injection of 0.5×CTZ assay buffer. FIG. 6 shows increase in Renilla Luc activity upon induction of cell death by NK92MI cells or by treatment with Digitonin.

Example 8

Use of CBGRluc in Matador Cytotoxicity Assay

Figure 7:
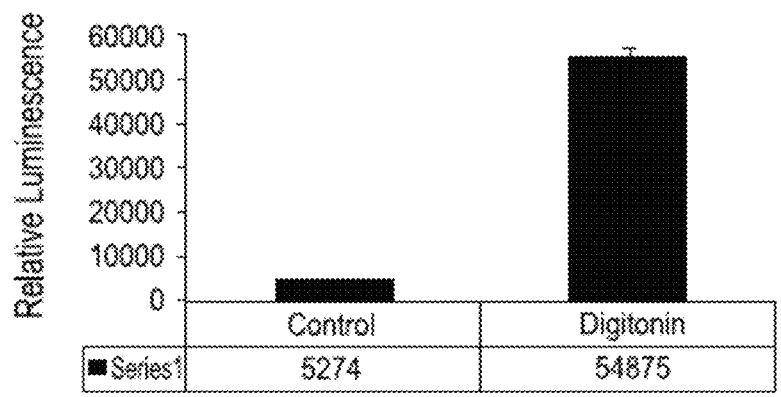
FIG. 7 depicts in accordance with various embodiments of the invention, that there is an increase in CBGR-Luc activity upon induction of death of CBGR-Luc-transfected 293FT cells following treatment with Digitonin.

293FT cells were transfected with pLenti-CBGRluc construct in a 100 mM plate. 72 hours post-transfection, cells were trypsinized and plated in 6-well plates. For induction of cell death, cells in some wells were treated with Digitonin (50 µg/mL final concentration). CBGRluc activity was determined by adding assay buffer (1 mM D-Luciferin, 25 mM glycylglycine, 15 mM potassium phosphate, 15 mM $MgSO_4$, 4 mM EGTA, 2 mM ATP, and 1 mM DTT) in a well mode. The assay buffer with substrate was added at 1:1 (v/v) ratio. FIG. 7 shows increase in CBGRluc activity upon induction of cell death with Digitonin. Thus, CBGRLuc is not degraded by proteases released during cell death and it can be used for the development of an assay of cellular cytotoxicity.

Example 9

Use of Matador Assay to Measure Cell-Induced Cytotoxicity Mediated by NK Cells

Figure 8:
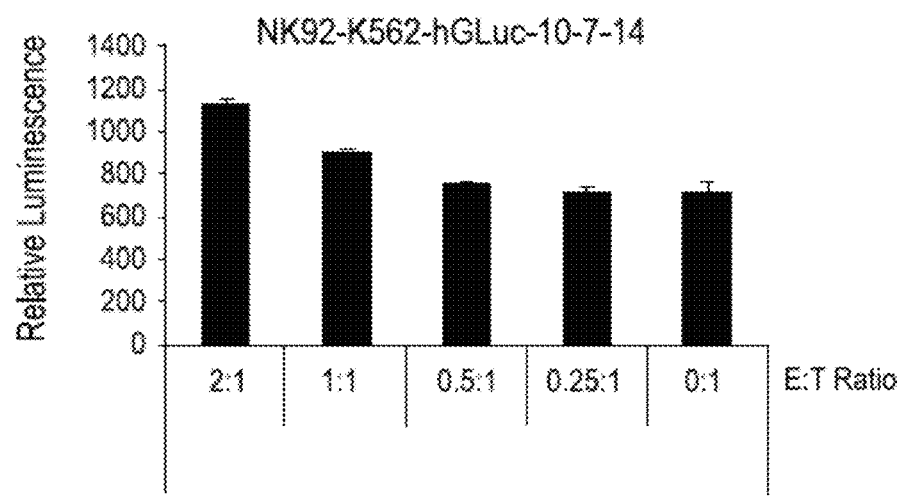
FIG. 8 depicts in accordance with various embodiments of the invention, that there is a progressive increase in GLuc activity with increase in E:T ratio upon co-culture of K562-GLuc cells with NK92MI cells.

To demonstrate that Matador assay can be used to measure cell induced cytotoxicity, K562-GLuc cells were used as a target for cytotoxicity mediated by the natural killer derived cell line NK92MI (effector cells). K562-GLuc cells were plated at a concentration of 100,000 cells/well and co-cultured for 24 h with NK92MI cells at E:T ratios of 2:1, 1:1, 0.5:1, 0.25:1 and 0:1, respectively. At the end of the culture period, GLuc activity was measured by addition of coelenterazine containing assay buffer to the wells in well mode. FIG. 8 shows that there is a progressive increase in GLuc activity with increase in E:T ratio of NK92MI cells.

Example 10

Matador Assay can be Used to Measure Cytotoxicity in a Single Step Manner (Homogenous)

The NK92-sensitive K562 cells were engineered to express either a *Gaussia princeps* (GLuc) or a Fire-fly (FFLuc), luciferase construct by transducing these cells with MSCVhygro-GLuc or pRetro-FFLuc encoding viruses.

Cells were selected with hygromycin and puromycin, respectively, to make stable populations of K562-GLuc and K562-FFLuc target cells, respectively. K562 were also co-transfected with phRGTK Renilla Luciferase (Promega) with pCMV-puro plasmid DNA and selected with puromycin to generate K562-Renilla Luc cells. K562-GLuc, K562-FFLuc and K562-Renilla Luc cells were plated either alone or in combination with NK92MI effector cells at concentration of 100K cells/well in 2 wells of a flat-bottom 24 well plate in 500 µl of phenol-red-free RPMI medium at a E:T ratio of 0.5:1. After 4 hours of co-culture, the cells were mixed well, collected in 1.5 ml microfuge tubes and divided into 3 groups of 166 µl each. From the first group, the cells with cell supernatant were directly assayed for luciferase activity by plating 50p of cells/well in a white 384 well plate in triplicate. Second group of 166 µl of cells were centrifuged and only cell supernatants were collected in a new tube and plated at 50 µl/well in a 384 well plate in triplicate. The third group samples were centrifuged, supernatant was removed, cells were re-suspended in PBS to assess luciferase activity in the cells by plating 50 µl of re-suspended cells per well in 384-well plate in triplicate. The luciferase activity was precisely measured by BioTek synergy plate reader that directly injecting 0.5×CTZ assay buffer containing native coelenterazine (Nanaolight) into the 384 well plates in a well mode. FIG. 9A shows that induction of K562-GLuc cell death by NK92MI cells results in significant and near equivalent increase in GLuc activity when measured either by directly adding 0.5×CTZ assay buffer to the wells containing cells plus supernatant or when the assay buffer is added to supernatant that had been cleared of cells by centrifugation step. These results demonstrate that the centrifugation step to collect the supernatant freed of cells may be omitted without significantly compromising the sensitivity of the Matador assay, thereby yielding a single step homogenous assay. There was also a slight increase in GLuc activity in the pellet of K562-GLuc cells that had been incubated with NK92MI cells. This could be due to the fact that loss of cell membrane integrity results in increased penetration of coelenterazine into the dead and dying cells where it interacts with any GLuc that has been trapped inside the cells and has not yet leaked out.

FIG. 9A also shows that induction of death of K562-Renilla Luc cell by NK92MI cells also resulted in a slight increase in Renilla luciferase activity when measured either by directly adding 0.5×CTZ assay buffer to the wells containing cells plus supernatant or when added to supernatant that had been cleared of cells by the centrifugation step.

FIG. 9A also shows that addition of 0.5×CTZ assay buffer to cells plus supernatant fraction, supernatant only fraction or cell pellet only fraction of K562-FFluc cells did not result in an increase in luciferase activity, which is consistent with the fact that coelenterazine is not a substrate for firefly luciferase.

To test whether the GLuc and Renilla Luc activities are stable after freezing and thawing, the supernatant fractions collected from K562-GLuc, K562-Renilla-Luc and K562-FFluc cells that had been assayed above were frozen. Two weeks later, the supernatants were thawed and then re-assayed after addition of coelenterazine. As shown in FIG. 9B, there was no major change in the Gluc and Renilla Luc activities as compared to the results obtained in FIG. 9A.

The supernatant fractions after thawing was also assayed using the Renilla Luciferin substrate (Promega). FIG. 9C shows that the assay conducted using the Renilla Luciferin substrate gave similar results as those obtained after addition of 0.5×CTZ assay buffer containing native coelenterazine.

Example 11

Matador Assay can be Used as a Single Step Homogeneous Assay

Figure 10A:
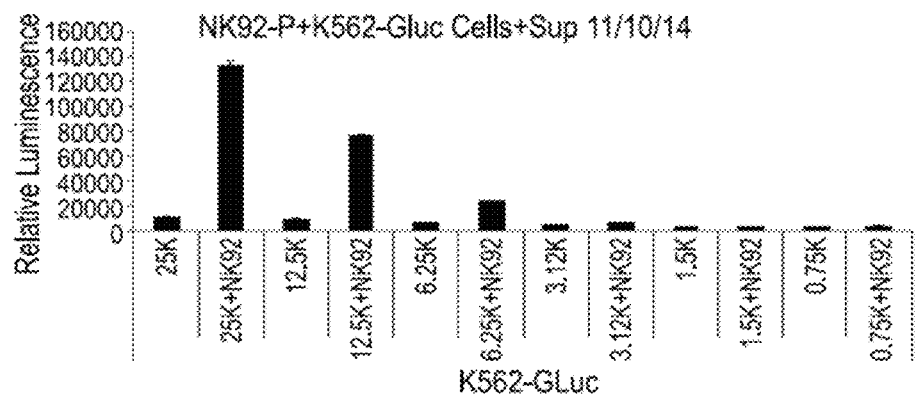
FIG. 10A-FIG. 10C depict in accordance with various embodiments of the invention, that there is a progressive and nearly equivalent increase in GLuc activity in both the supernatant fraction and the cells plus supernatant fraction with increase in number of K562-GLuc target cells upon co-culture with NK92MI effector cells (FIG. 10A and FIG. 10B).
Figure 10B:
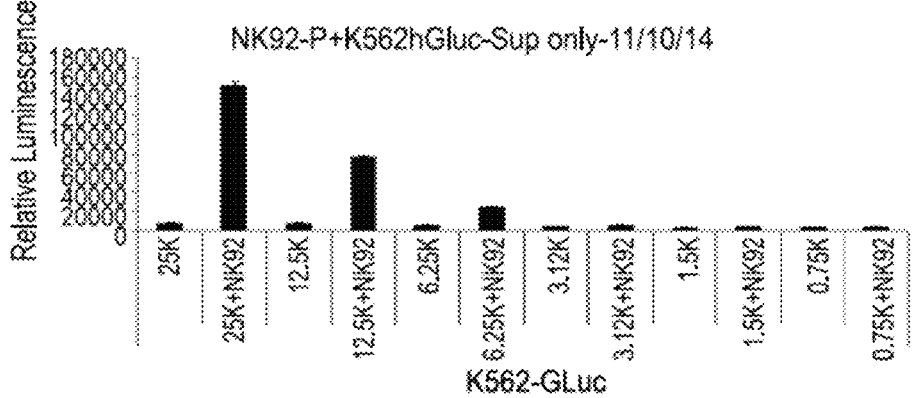
Figure 10C:
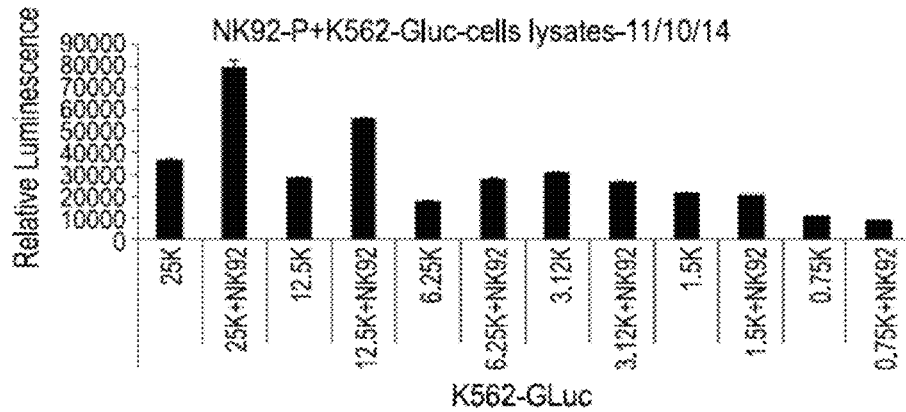

K562-GLuc cells were plated either alone or in combination with NK92MI effector cells at the indicated cell concentrations/well in 2 wells of a flat-bottom 24 well plate in 500 µl phenol-red-free RPMI medium. The effector to target cell ratio (E:T) was kept constant at 0.5:1 in each well. After 4 hours of co-culture, the cells were mixed well, collected in 1.5 ml microfuge tubes and divided into 3 groups of 166 µl each. From the first group, the cells with cell supernatant were directly assayed for luciferase activity by plating 50 µl/well in a white 384 well plate in triplicate. Second group of 166 µl cells were centrifuged and only cell supernatants were collected in new tubes and plated in a 384 well-plate at 50 µl/well in triplicate. The third group of samples were centrifuged, supernatants were removed, cells were re-suspended in PBS to assess luciferase activity by plating 50 µl of re-suspended cells per well in a 384-well plate in triplicate. For fractions derived from K562-GLuc (FIGS. 10A-10C), the GLuc activity was precisely measured by BioTek synergy plate reader by directly injecting 15 µl of 0.5×CTZ assay buffer containing native coelenterazine into the 384 well plates in well mode. FIG. 10A-10B show that there is a progressive increase in GLuc activity in both the supernatant fraction and the cells plus supernatant fraction with increase in number of target cells from 0.75K to 25K. Additionally, there was a near equivalent increase in GLuc activity when measured either by directly adding 0.5×CTZ assay buffer to the wells containing cells plus supernatant or when added to the supernatant fractions that had been cleared of cells by centrifugation step. These results confirm that the centrifugation step to collect the supernatant freed of cells can be omitted without compromising the sensitivity of the assay, thereby yielding a single step homogenous assay. Finally, there was also an increase in GLuc activity in the pellet of K562-GLuc cells that have been incubated with NK92MI cells (FIG. 10C; compare lanes showing result with 6.25K, 12.5K and 25K cells with and without NK92MI cells). This could be due to the fact that loss of cell membrane integrity results in increased penetration of coelenterazine into the dead and dying cells where it reacts with any GLuc that had been trapped inside the cells and has not yet leaked out. Thus, the cytotoxicity assay described in this invention when performed in the homogeneous format is based not only on the release of the reporter (e.g., GLuc or NLuc) into the extracellular compartment but also on the increased penetration of the substrate required for the reporter activity into cells that have lost membrane integrity.

Example 12

Use of Matador Cytotoxicity to Monitor Cytotoxicity Induced by Chimeric Antigen Receptor Modified NK Cells RS411-GLuc cells were plated at concentration of 1×10$^6$ cells/well either alone or in combination with NK92MI effector cells expressing either an empty vector (GFP) or a chimeric antigen receptor targeting CD19 (FMC63-MYC-BBZ-T2A-EGFP; SEQ ID NO: 79)) in 2 wells of a flat-bottom 24 well plate in 500 µl phenol-red-free RPMI medium. The effector to target cell ratio (E:T) was kept constant at 0.25:1 in each well. After the indicated time intervals, fractions containing cells plus supernatant, supernatant only or cells only were collected and 50l of each fraction was plated in 384 well plate as described in the preceding sections. GLuc activity was measured by injecting 15 µl of 0.5×CTZ assay buffer in a well mode. FIG. 11A shows the absolute values while the FIG. 11B shows fold increase in activity when normalized relative to the activity observed in RS411-GLuc cells that had been incubated with NK92MI cells expressing GFP. The results show that Matador cytotoxicity assay can be used to monitor cytotoxicity induced by CAR-expressing effector cells and the assay can be performed as a single step homogenous assay (i.e. cells +supernatant) format by directly adding 0.5×CTZ assay buffer to the wells or by adding 0.5×CTZ assay buffer to the supernatant fraction that has been separated from the cells.

Example 13

Use of Matador Cytotoxicity to Monitor Cytotoxicity Induced by Chimeric Antigen Receptor Modified T (CAR-T) Cells CD19-expressing Raji-MSCV-hygro-GLuc cells were cultured for 4 hours with uninfected T cells (T-UI) or T cells that had been infected with lentiviral vectors expressing chimeric antigen receptors FMC63-BBZ (directed against human CD19 antigen) and 4C3-BBZ (negative control CAR targeted against an irrelevant protein). GLuc activity was measured by addition of coelenterazine assay buffer to the wells as described above. The results (FIG. 12) show that induction of RAJI cell death by T cells expressing CD19-specific CAR-T results in increase in GLuc activity, whereas no increase in GLuc activity was observed by co-culture with uninfected T cells or those expressing a negative control CAR (i.e. 4C3) whose target antigen is not expressed in RAJI cells. Essentially similar results were obtained by T cells expressing multiple additional CARs (e.g. targeting CD20, CD22, CD123, FR1 etc) when co-cultured with their target cells expressing different marine luciferases (e.g. GLuc, NLuc etc.).

Example 14

Use of Matador Assay for Measuring Cytotoxicity by Chimeric Antigen Expressing Cells and its Inhibition by Drug Treatment Human peripheral blood T cells isolated using CD3 magnetic beads were infected with lentiviruses expressing the CAR construct CD8SP2-CD19MM-(vL-vH)-Myc-BBz-T2A-PAC [SEQ ID NO: 82] targeting CD19 and selected with puromycin. CAR-T cells were pre-incubated with the indicated concentrations of Dasatinib and Imatinib for approximately 30 min at 37° C. The drug-treated and untreated T cells were plated in a white 384-well plate. RAJI cells stably expressing GLuc were added to the wells containing the T cells at a concentration of 30K cells/well to give an E:T ratio was 5:1. Dasatinib (Das) and Imatinib (Imat) were added to the wells to maintain the final concentrations as indicated. After 4 hours of co-culture, CAR-T cells mediated induction of lysis of target cells was assayed by increase of GLuc activity by directly injecting 0.5×CTZ assay buffer containing native coelenterazine in a well mode. FIG. 13 shows inhibition of CAR CD8SP2-CD19MM-(vL-vH)-Myc-BBz-T2A-PAC-induced cell death by 50 nM and 100 nM Dasatinib, while Imatinib has no effect. These results demonstrate that Matador cytotoxicity assay can be used to study cytotoxicity by CAR-T cells and its modulation by drug treatment. Therefore, the assay can be used to screen for and identify candidate compounds that modulate the activity of cytotoxic cells, such as cytotoxic T cells, NK cells, CAR-T cells and T cells expressing engineered TCRs.

Example 15

Figure 14:
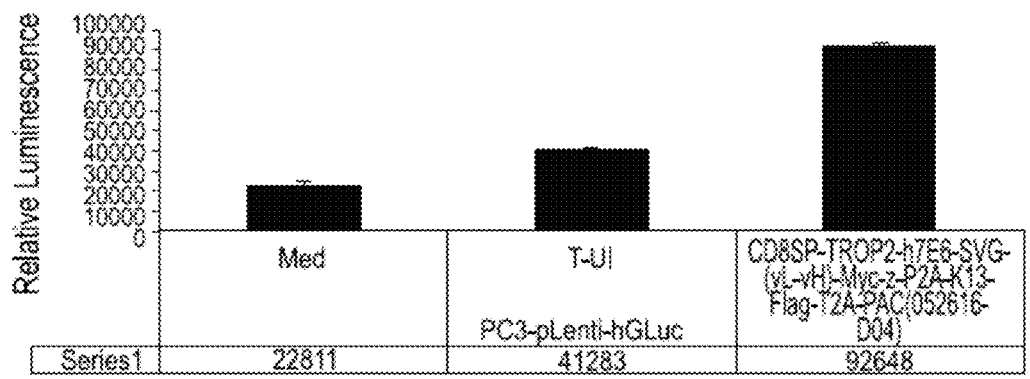
FIG. 14 depicts in accordance with various embodiments of the invention, an increase in GLuc activity upon co-culture of PC3-GLuc cells with T cells infected with a lentivirus encoding a CAR targeting TROP2 (CD8SP-TROP2-h7E6-SVG-(vL-vH)-Myc-z-P2A-K13-Flag-T2A-PAC) as compared with co-culture with uninfected T cells (UI).

Use of Matador Cytotoxicity Assay for Measuring Death of Solid Tumor Derived Cells Prostate cancer derived PC3 cells were grown as adherent culture in DMEM, 10% FCS. Human peripheral blood T cells isolated using CD3 magnetic beads were infected with lentiviruses expressing the construct CD8SP-TROP2-h7E6-SVG-(vL-vH)-Myc-z-P2A-K13-Flag-T2A-PAC [SEQ ID NO: 84] targeting TROP2 and selected with puromycin and tested for the ability to kill PC3 (prostate cancer) cells expressing GLuc using the assay described previously. PC3-Gluc cells were plated in a flat bottom 384 well plate as adherent culture and co-cultured overnight with the CAR-T cells targeting TROP2 at an E:T ratio of 10:1. CAR-T cells mediated induction of lysis of target cells was assayed by increase of GLuc activity by directly injecting 0.5×CTZ assay buffer containing native coelenterazine using automatic injector. FIG. 14 shows effective killing of PC3 cells by T cells expressing the CD8SP-TROP2-h7E6-SVG-(vL-vH)-Myc-z-P2A-K13-Flag-T2A-PAC CAR construct as measured by increase in GLuc activity, thereby demonstrating the utility of the Matador assay to monitor death of solid-tumor derived cells grown as adherent culture.

Example 16

Use of Matador Assay for Measuring Cellular Cytotoxicity Against Primary Cells

Figure 15:
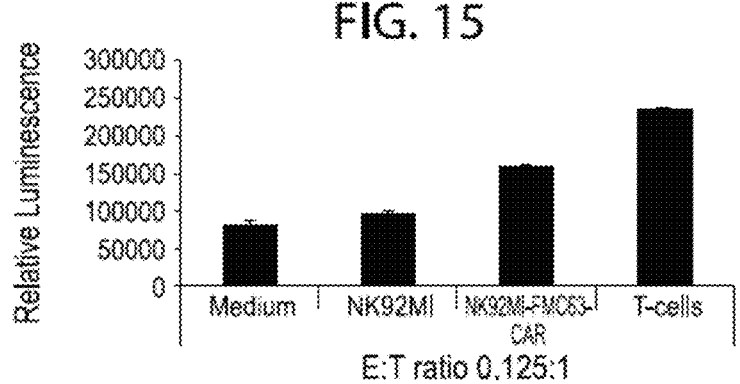
FIG. 15 depicts in accordance with various embodiments of the invention, that co-culture of primary leukemia blast cells that have been infected with a GLuc-encoding lentivirus with NK92MI cells expressing the FMC63-BBZ-CAR targeting the CD19 antigen or primary human T cells resulted in significant increase in GLuc activity.

The preceding examples showed that the Matador assay can be used to measure death of established cell lines. To examine if this assay can be also used to measure death of primary cells, leukemic blasts were isolated from a de-identified leukemia patient using Ficoll-Hypaque gradient centrifugation and then transduced with pLenti-EF1α-Pac-T2A-Gluc-B07 (SEQ ID NO: 94) lentiviral vector to generate primary leukemia blast cells (Chrt3) expressing the non-secretory form of GLuc cDNA. Briefly, 1 million primary leukemic blasts were cultured in XVIVO medium in a 6-well plate in the presence of GLuc lentiviral supernatant and polybrene (5 µg/ml) and centrifuged at 2,800 rpm at 32° C. for 2 hours followed by incubation of cells at 37° C. for 24 hours in XVIVO medium. To measure the killing of Chrt3-GLuc cells, the transduced cells were plated at a density of 20,000 cells per well in 30 µl of medium in triplicate in a white 384 well plate and co-cultured with the effector cells for 4 hours at an E: T ratio of 0.125:1. Cell death was assayed by the single-step homogenous GLuc assay by injecting 0.5×CTZ assay buffer in well mode. As shown in FIG. 15, co-culture with NK92MI effector cells expressing the FMC63-BBZ-CAR targeting the CD19 antigen resulted in significant increase in GLuc activity, indicating cytotoxicity. Similarly, co-culture with primary T cells isolated from a healthy unrelated donor resulted in a marked increase in GLuc activity. These results demonstrate that primary patient-derived cells can be effectively modified to express the non-secretory form of GLuc. These results further demonstrate that the GLuc release assay can be used to measure cell death of primary patient derived cells. Finally, primary cells in the above example were used without prior drug selection to select for lentiviral transduced GLuc-expressing cells. Thus, the GLuc release assay can be used on target cells in which only a fraction of cells express the non-secretory form of GLuc and the assay does not require generation of target cells uniformly expressing the non-secretory form of GLuc. Two additional primary leukemia samples are infected with GLuc encoding lentiviral vector and cell death is induced by treatment with Digitonin. Induction of cell death in both cases by treatment with Digitonin is shown to results in an increase in GLuc activity as compared to untreated cells.

Example 17

Figure 16:
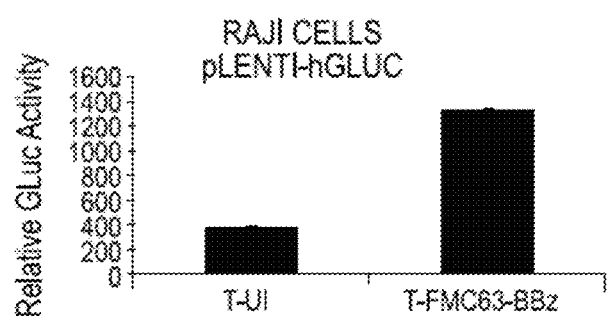
FIG. 16 depicts in accordance with various embodiments of the invention, co-culture of RAJI cells transiently transfected with the non-secretory form of GLuc cDNA with T cells expressing an FMC63-BBz chimeric antigen receptor resulted in increase in GLuc activity as compared to uninfected T cells, indicative of cell death.

Matador Assay can be Used to Measure Death of Target Cells in which Non-Secretory Forms of GLuc is Expressed in Target Cells by Transient Transfection To determine if transient transfection of a cDNA encoding GLuc can be used to develop Matador cytotoxicity assay, RAJI (CD19+ve) cells were transfected with pLenti-EF1a-Pac-T2A-Gluc-B07 (SEQ ID NO: 94) plasmid DNA using Fugene HD (Promega). Briefly, a transfection mixture was prepared using 97 µl of serum-free RPMI medium with 3 µl of Fugene HD and 2 µg/ml of plasmid DNA, followed by 15 min incubation at room temperature. RAJI cells were plated at a density of $1 \times 10^6$ cells/well in a 24-well plate in 500 µl of serum-free RPMI medium. The cells were transfected by adding the transfection mixture on top of the cells as per manufacturer's instructions and incubated for 48 hours to allow expression of the transfected GLuc cDNA lacking the signal peptide. At the end of 48 hours, RAJI cells transiently expressing GLuc were plated at a density of 100K cells/well in 30 µl medium in a white 384-well plate either alone or in the presence of the indicated effector cells (T cells uninfected, or T cells infected with a lentiviral encoding the FMC63-BBz CAR directed against CD19). After 4 hours, the release of GLuc from dead and dying cells was measured by a luminometer that directly injected native coelenterazine into the 384 well plates in well mode. As shown in FIG. 16, co-culture of RAJI cells transiently transfected with the non-secretory form of GLuc cDNA with T cells expressing FMC63-BBz chimeric antigen receptor resulted in increase in GLuc activity as compared to uninfected T cells, indicative of cell death.

Example 18

Figure 17A:
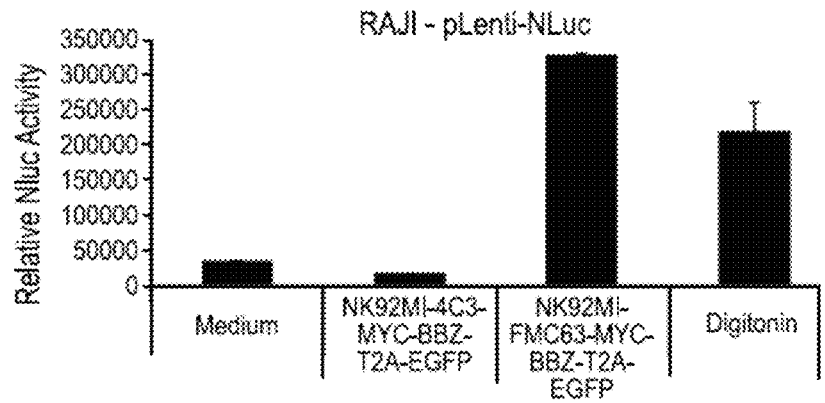
FIG. 17A-FIG. 17B depicts in accordance with various embodiments of the invention.
Figure 17B:
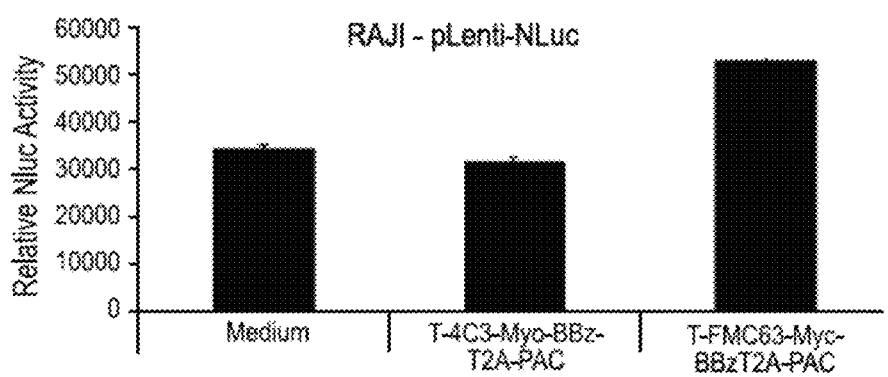

Use of Matador Assay to Measure Cell Mediated Cytotoxicity by CAR-Modified NK and T Cells The pLENTI-NLuc-AcV5-Blast virus was used to infect RAJI cells followed by selection with blasticidin to generate stably transduced cells. RAJI-NLuc cells were plated in a 384 well plate at 30K/well in 30 µl of medium. NK92MI cells were infected with a lentiviral CAR construct targeting CD19 (FMC63-Myc-BBz-T2A-EGFP; SEQ ID NO: 79) or a control CAR (4C3-Myc-BBz-T2A-EGFP) and CAR-expressing cells sorted based on EGFP expression. Primary human T cells were infected with a lentiviral CAR construct targeting CD19 (FMC63-Myc-BBz-T2A-PAC; SEQ ID NO: 80) and CAR-expressing cells selected by puromycin selection. Where indicated, parental and CAR-expressing NK92MI effector cells were added at 15K/well in 30 µl of media to give an E:T ratio 0.5:1. Where indicated, parental and FMC63 CAR-expressing T cells were added at 300K/well in 30 µl to give an E:T ratio of 10:1. After approximately 4 hours of co-culture, NLuc activity was measured using BioTek synergy plate reader after injection of 15 µl of 0.125×CTZ assay buffer in well mode. As shown in FIG. 17A, co-culture of RAJI-NLuc cells with NK92MI cells expressing FMC63-BBZ chimeric antigen receptor resulted in significant increase in NLuc activity as compared to co-culture with NK92MI cells expressing a control (4C3-BBZ) chimeric antigen receptor or culture without NK92MI cells (medium alone). FIG. 17B shows that RAJI cells expressing NLuc also showed a significant increase in NLuc activity upon co-culture with T cells expressing FMC63-BBZ chimeric antigen receptor as compared to those expressing the control (4C3-BBZ) chimeric antigen receptor.

Example 19

Use of Matador Assay for Measuring Drug Induced Cytotoxicity

Figure 18:
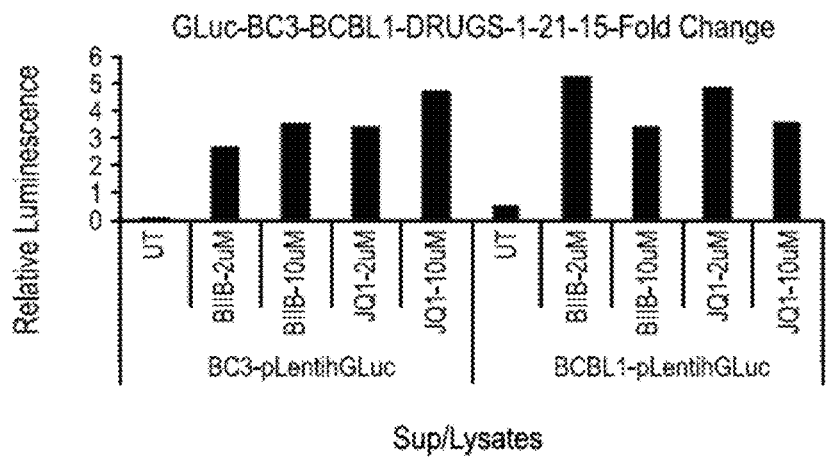
FIG. 18 depicts in accordance with various embodiments of the invention, that treatment of BC3-pLenti-GLuc and BCBL1-pLenti-GLuc cells with drugs BIIB021 and JQ1 results in significant increase in GLuc activity present in the supernatant when normalized for the difference in the GLuc-expressing cells (as measured by GLuc activity in the cell lysates).

To test whether the Matador assay can be used to measure drug induced cell death, BC-3-pLenti-GLuc and BCBL-1-pLenti-GLuc cells that were stably transduced with a lentiviral vector expressing GLuc were treated with different doses of BIIB021 (Hsp90 inhibitor; Selleck chemicals) and JQ1 (BRD4 inhibitor) for 96 hours. Since the duration of drug treatment was relatively long in this experiment, the untreated cells would have continued to proliferate as compared to the drug treated cells. As a result, at the time of GLuc assay, the number of GLuc-expressing cells in the wells that were left untreated was significantly higher as compared to the wells that were drug-treated. To control for the varying number of GLuc-expressing cells in different wells, which could have confounded the results of GLuc cytotoxicity assay due to varying level of spontaneous GLuc release, cells were centrifuged at the end of drug treatments and cellular supernatants were separated from cell pellets. The cell pellets were lysed in 1× Renilla Luciferase Assay Lysis Buffer by diluting one volume of 5× Renilla Luciferase Assay Lysis Buffer (Promega, Cat #E2820) into four volumes of distilled water. GLuc activity was measured in the cellular supernatants and cell lysates fractions separately in triplicate by addition of 0.25× coelenterazine assay buffer (15 µl of assay buffer added to 15 µl of sample in a 384 well plate) to each fraction. For each sample, the average GLuc activity in the cellular supernatant was divided by the average GLuc activity in the cell lysates to normalize for difference in the number of GLuc expressing cells. FIG. 18 shows that treatment of BC-3-pLenti-GLuc and BCBL-1-pLenti-GLuc cells with BIIB021 and JQ1 results in a significant increase in GLuc activity in the supernatant when normalized for the difference in the GLuc-expressing cells as measured by GLuc activity in the cell lysates. As the BC-3 and BCBL-1 cell lines are infected with Kaposi's sarcoma associated herpes virus, the above results demonstrate the utility of the Matador assay to detect cytotoxicity of virally infected cells.

Example 20

Use of Matador Assay for Measuring Cellular Cytotoxicity Induced by an Antibody

Figure 19:
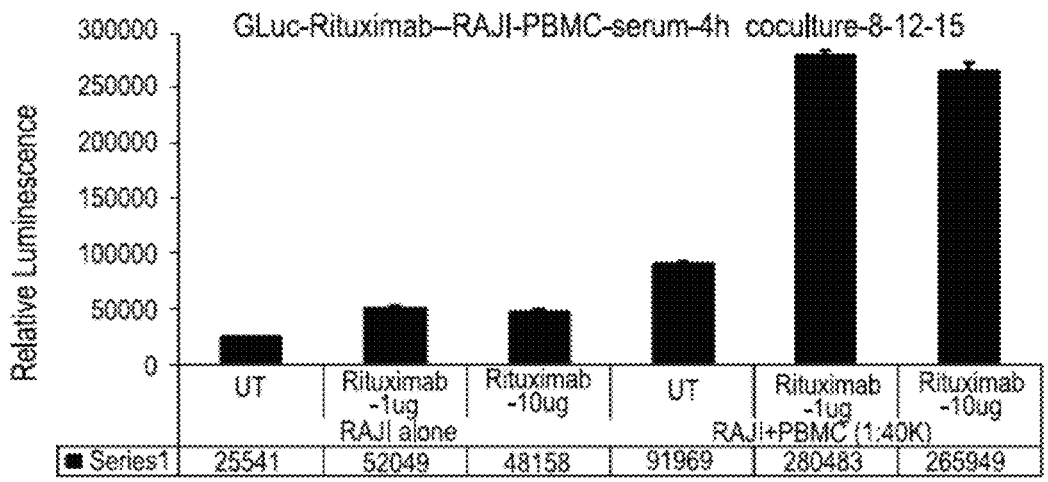
FIG. 19 depicts in accordance with various embodiments of the invention, that treatment of RAJI-GLuc cells with peripheral blood mononuclear cells in the presence of rituximab at both 1 μg/ml and 10 μg/ml concentrations resulted in increase in luciferase activity as compared to untreated cells, suggesting that the Matador assay can be used to monitor rituximab-induced cell death.

Antibody-dependent cellular cytotoxicity (ADCC) assay was performed essentially as described earlier (Teeling, French et al. 2004). To determine the cytotoxicity of Rituximab monoclonal antibody, the cell death was assessed using Matador assay. Peripheral Blood Mononuclear Cells (PBMC) were isolated by Ficoll-Hypaque gradient centrifugation from buffy coat cells obtained from a de-identified healthy donor as a source of natural effector. Briefly, $1 \times 10^5$ RAJI cells expressing GLuc were plated either alone in a 30µl volume per well in a white 384 well plates or plated in the presence of $4 \times 10^6$ PBMC. The cells were either left untreated, or treated with 1 µg/ml or 10 µg/ml of Rituximab. The plates were incubated at 37° C. for 4 hours in a $CO_2$ incubator. After incubation for 4 hours, the cell death was assessed by luciferase assay by addition of CTZ assay buffer containing native coelenterazine to the wells as described earlier. FIG. 19 shows that treatment with rituximab at both 1 µg/ml and 10 µg/ml concentrations resulted in increase in luciferase activity as compared to untreated cells, suggesting mild increase in cell death by treatment with rituximab alone. Addition of PBMC alone also resulted in a modest (approximately 3.5 fold) increase in GLuc luciferase activity. However, addition of rituximab in the presence of PBMC resulted in greater than 10-fold increase in GLuc activity as compared to the untreated cells. The result shows that the Matador cytotoxicity assay can be used to measure antibody dependent cellular toxicity in a rapid and sensitive manner. Essentially similar results were obtained when RAJI cells stably expressing NLuc were used.

Example 21

Use of Matador Assay to Measure Cytotoxicity Induced by a Bispecific Antibody

Figure 20A:
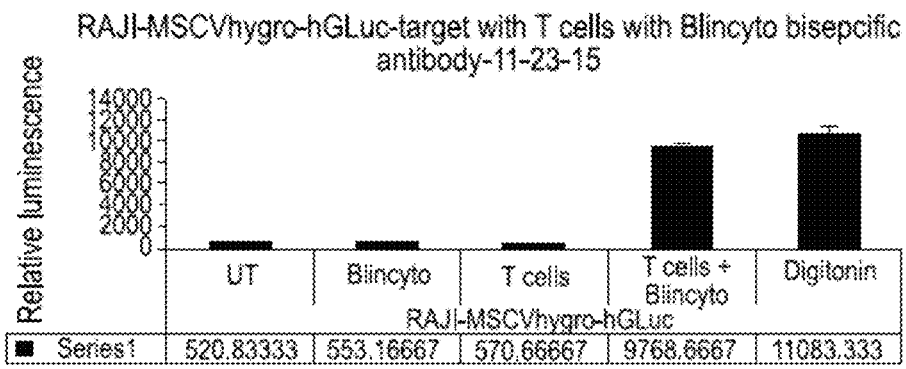
FIG. 20A-FIG. 20D depicts in accordance with various embodiments of the invention.
Figure 20B:
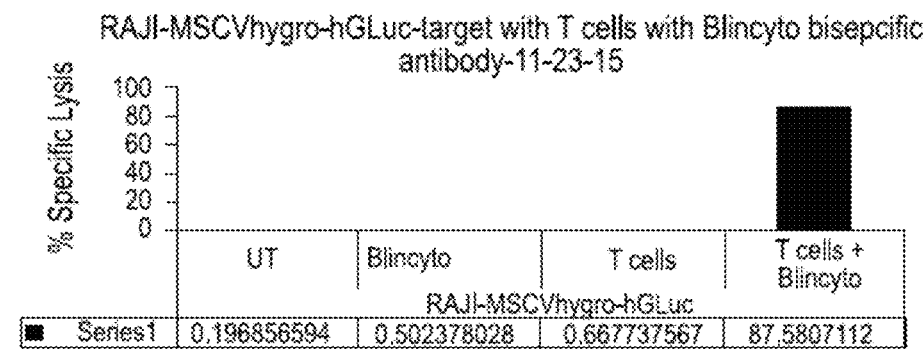
Figure 20C:
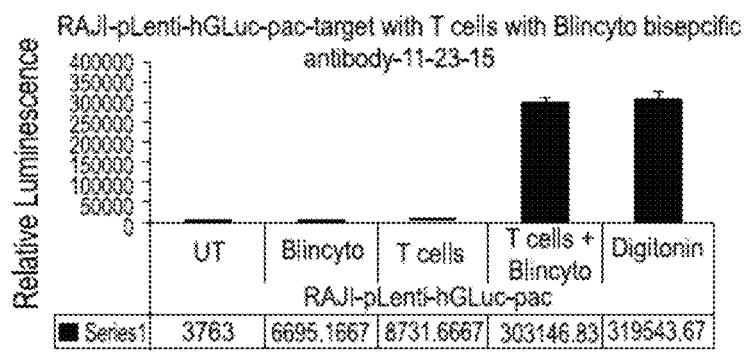
Figure 20D:
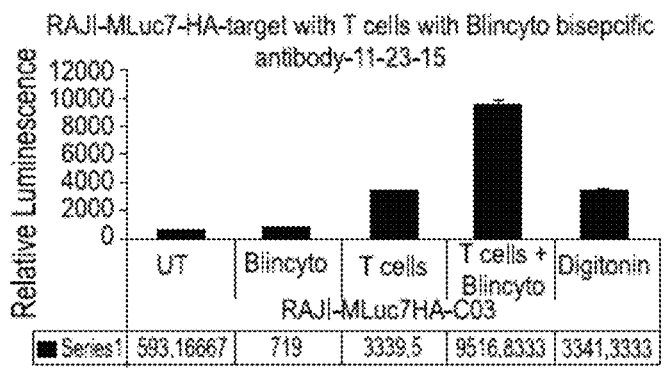

RAJI-MSCVhygro-hGLuc (FIG. 20A and FIG. 20B), RAJI-pLenti-Pac-T2A-hGLuc (FIG. 20C) and Plenti-MLuc7-MM-LL-HA (FIG. 20D) target cells were incubated with a bispecific antibody (Blinatumomab or BLINCYTO; AMGEN) at 100 ng/$10^6$ cells for 30 min at 37° C. in PBS/2% FBS. Next, antibody-treated cells were washed three times in PBS, re-suspended in XVIVO medium and 100 µl (100K) cells were plated per well of a 96-well U-bottom plate. Effector cells (T-cells isolated by CD3 microbeads from Miltenyi Biotech) were washed twice in XVIVO medium and added to wells at an E:T ratio of 20:1. Total volume in each well was adjusted to 200 µl with medium. Plates were quickly centrifuged to settle cells, and incubated at 37° C. in a 5% $CO_2$ incubator for 4 hours. For maximum cell death, one hour prior to doing luciferase-based cell death assay, a total volume of 6 µl of Digitonin (stock 1 mg/ml) was added to wells containing target cells alone to achieve a final concentration of 30 µg/ml of Digitonin. The plates were centrifuge at 1,000 rpm for 5 min and 50 µl of supernatants were transferred to a Greiner 384-well flat bottom white opaque plate. The luciferase activity was measured by BioTek synergy plate reader by directly injecting 0.5×CTZ assay buffer containing native coelenterazine into the 384 well plates in a well mode. As shown in FIG. 20A, and FIG. 20C, treatment of GLuc expressing RAJI cells with T cells that had been incubated with Blinatumomab (BLINCYTO), resulted in significant increase in GLuc activity as compared to treatment with Blinatumomab or T cells alone. Essentially similar results were obtained when the experiment was repeated with RAJI cells expressing MLuc7-MM-LL-HA (FIG. 20D). The % specific lysis (FIG. 20B) was calculated by taking Digitonin-induced cell death as 100% and untreated cells as 0%. % specific lysis was calculated by using formula: % Specific lysis=100×((experimental data)–(spontaneous cell death))/((maximum cell death)–spontaneous cell death)).

Example 22

Figure 21:
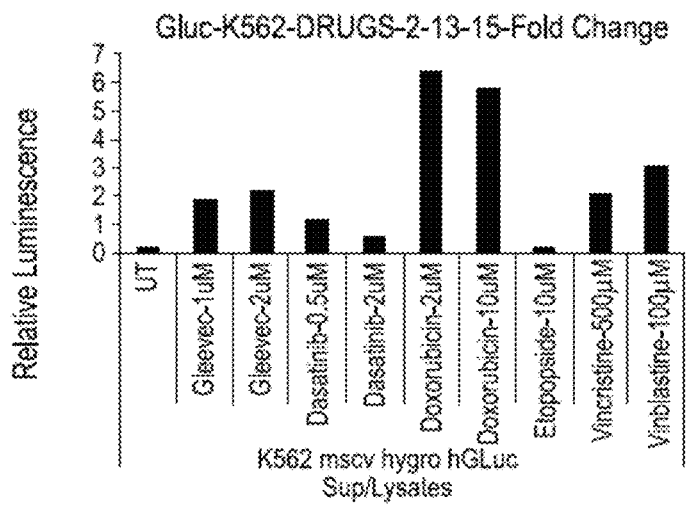
FIG. 21 depicts in accordance with various embodiments of the invention, GLuc-based Matador assay can be used to measure cytotoxicity of targeted agents (e.g. Imatinib (or Gleevec) and Dasatinib) as well as conventional chemotherapy drugs (e.g. doxorubicin, vincristine and vinblastine).

Use of Matador Assay for Measuring Cytotoxicity Induced by Targeted Agents and Chemotherapy Drugs K562-MSCVhygro-GLuc cells were plated at a concentration of 100K cells/500 µl/well in a flat-bottom 24 well plate in phenol-red-free RPMI medium and treated with the indicated chemotherapeutic drugs. After 5 days of drug treatment, the cells were mixed well, collected in 1.5 ml microfuge tubes and divided into 3 groups of 166 µl each. For the first group, the cells with cell supernatant were directly assayed for luciferase activity by plating 50 µl of cells/well in a white 384 well plate in triplicate. For the second group, 166 µl of cells were centrifuged and only cell supernatants were collected in new tubes and plated at 50 µl/well in a white 384 well plate in triplicate. For the third group, samples were centrifuged, supernatant was discarded, cells were re-suspended in PBS, and 50 µl of re-suspended cells were plated per well in a white 384-well plate in triplicate. The luciferase activity in was precisely measured by BioTek synergy plate reader that directly injecting 0.5× CTZ assay buffer containing native coelenterazine into each well of the 384 well plates in a well mode. Drug-induced cell death was measured by calculating fold-change by dividing mean luciferase values in cell supernatant (Group 2) by mean luciferase values in cell pellets (Group 3). Results are shown in FIG. 21 and demonstrate that GLuc assay can be used to measure cytotoxicity of targeted agents (e.g. Imatinib (or Gleevec) and Dasatinib) as well as conventional chemotherapy drugs (e.g. doxorubicin, vincristine and vinblastine).

Example 23

Figure 22:
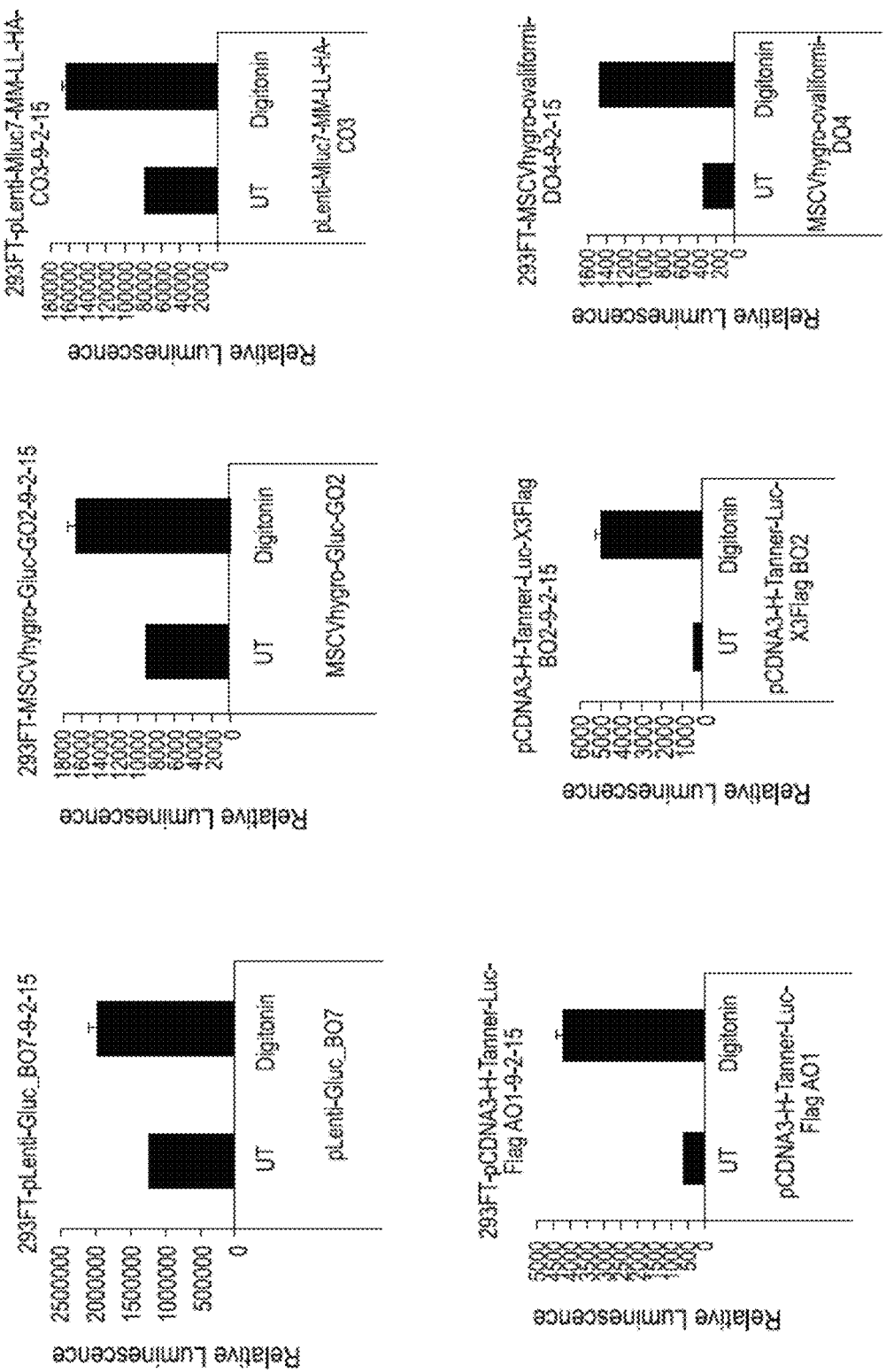
FIG. 22 depicts in accordance with various embodiments of the invention, treatment with Digitonin resulted in increase in luciferase activity in Digitonin-treated samples of 293FT cells that had been transiently transfected with non-secretory forms of luciferases from different copepods. The results demonstrate that similar to GLuc non-secretory forms of luciferases from other copepods can be used in Matador assay.

Development of Matador Assay Based on Transient Transfection of MLuc7, HT Luc, and Lucitia Luc In addition to GLuc, a number of luciferases from the copepods, such as *Pleuromamma abdominalis*, *Metridia pacifica*, *Metridia curticauda*, *Metridia asymmetrica*, *Metridia okhotensis*, *Metridia longa*, *Lucicutia ovaliformis*, *Heterorhabdus tanneri*, and *Pleuromamma scutullata* have been described. To test if the other copepod luciferases can be used similarly to GLuc for development of an assay for cellular cytotoxicity, we cloned the cDNAs encoding the non-secretory (lacking the signal peptide) forms of *Heterorhabdus tanneri* luciferase (HtLuc; SEQ ID NO: 6), *Lucicutia ovaliformis* luciferase (LoLuc; SEQ ID NO: 5), and *Metridia longa* luciferase 7 (MLuc7; SEQ ID NO: 4) into mammalian expression vectors. The MLuc7 cDNA also carried M43L and M110L substitutions. The corresponding substitutions in GLuc have been previously shown to result in Glow type luminescence (Welsh, Patel et al. 2009). The mammalian expression vectors encoding the non-secretory forms of the above luciferase cDNAs were transiently transfected into 293FT cells by calcium phosphate co-precipitation method. Approximately 24 hours post-transfection, cells from each transfection were split into 12 wells of 384 well plates. 6 wells were treated with Digitonin and 6 wells were left untreated. Luciferase activity was measured by addition of containing assay buffer directly to each well. As shown in FIG. 22, treatment with Digitonin coelenterazine resulted in increase in luciferase activity in Digitonin-treated samples of 293FT cells transfected with all luciferases tested. These results demonstrate that, similar to GLuc, non-secretory forms of luciferases from other copepods can be used to develop assay for measurement of cell toxicity.

Example 24

Development of Matador Assay Based on Transient Transfection of GLuc, TurboLuc16, NLuc, Renilla, PaLuc1, HTluc1, LoLuc, Lucia Luc and MLuc7 in 293FT Cells The indicated luciferase constructs in either retroviral or lentiviral vectors were transiently transfected into 293FT cells by calcium phosphate co-precipitation method. Approximately 18 hours post-transfection, cells were treated with Digitonin for 90 minutes or left untreated (control).

Figure 23:
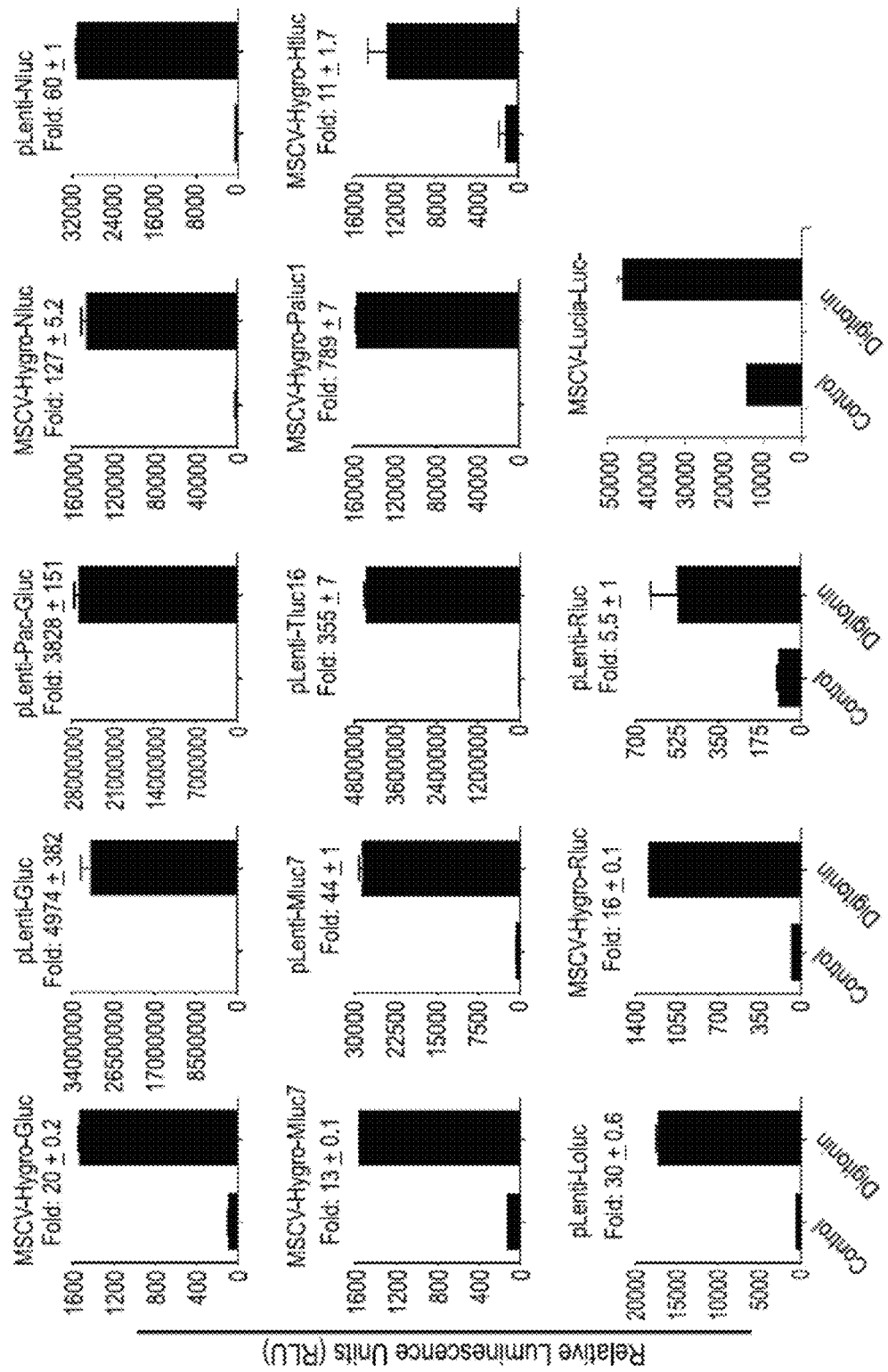
FIG. 23 depicts in accordance with various embodiments of the invention, induction of cell death by treatment with Digitonin resulted in increase in luciferase activity in case of 293FT cells transiently transfected with GLuc, TurboLuc16, NLuc, Renilla (RLuc), PaLuc1, HTluc1, LoLuc, Lucia Luc and MLuc7.

Cell-free supernatants (25 µl) were assayed for luminescence by addition of coelenterazine containing assay buffer (25 µl) directly to each well in a 384-well lumitrac plate for GLuc, NLuc, MLuc7, TLuc16, Paluc1, Htluc1, Loluc and Renilla luc (RLuc). Essentially a similar procedure was used with a construct encoding Lucia-Luc. As shown in FIG. 23, treatment with Digitonin resulted in increase in luciferase activity in the cell-free supernatants of 293FT cells transiently transfected with all the luciferase constructs tested. Essentially similar results are obtained when the experiment is repeated using other marine luciferases listed in Table 1.

Example 25

Use of Matador Assay when GLuc is Targeted to Cell Membrane

Figure 24:
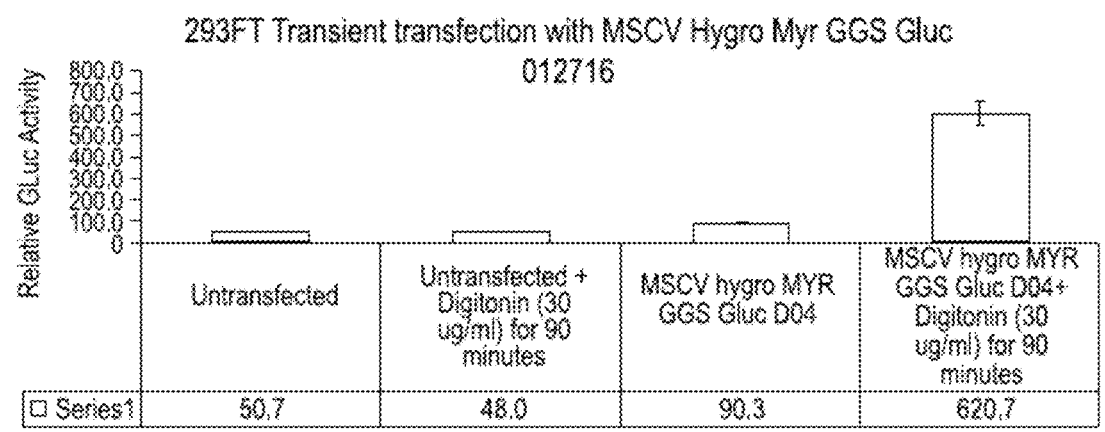
FIG. 24 depicts in accordance with various embodiments of the invention, that treatment with Digitonin resulted in increase in Luciferase activity in case of 293FT cells transiently transfected with the MYR-GGS-GLuc construct.

In the preceding examples, GLuc was expressed in the cytosol. To examine if the assay would work if GLuc is targeted to a specific cellular compartment, a construct (MSCV-hygro-MYR-GGS-GLuc-D04) was created in which GLuc encoding its amino acids 18 to 185 is expressed with an N-terminal Myristoylation sequence through an intervening Glycine-Glycine-Serine linker. The GLuc cDNA in this construct also carried M60L and M127L mutations that have been previously shown to result in Glow type luminescence (Welsh, Patel et al. 2009). The sequence of the MYR-GGS-GLuc fragment is provided in SEQ ID NO: 30. 293FT cells were transiently transfected with the above construct or left untransfected. Approximately 18 hours post-transfection, cells were treated for 90 min with Digitonin (final concentration 30 µg/ml) or left untreated. After the 90 minute incubation, 200 µl supernatant was collected from each well in a 1.5 ml tubes. The tubes were spun down at 1500 RPM for 5 minutes. Then, 25 µl supernatant was collected from the top and plated in a 384 well plate in triplicate (25 µl/well). Luciferase activity was measured by addition of 0.5×CTZ assay buffer (25 l) directly to each well in well mode. FIG. 24 shows that treatment with Digitonin resulted in increase in Luc activity in case of 293FT cells transiently transfected with the MYR-GGS-GLuc construct. The fold increase in GLuc activity was however lower as compared to the experiments where GLuc was not targeted to the cell membrane through the myristoylation signal. Treatment with Digitonin also resulted in increase in GLuc activity in case of 293FT cells transiently transfected with the MYR-GGS-GLuc construct when measured in the cell plus supernatant fraction.

Example 26

Figure 25:
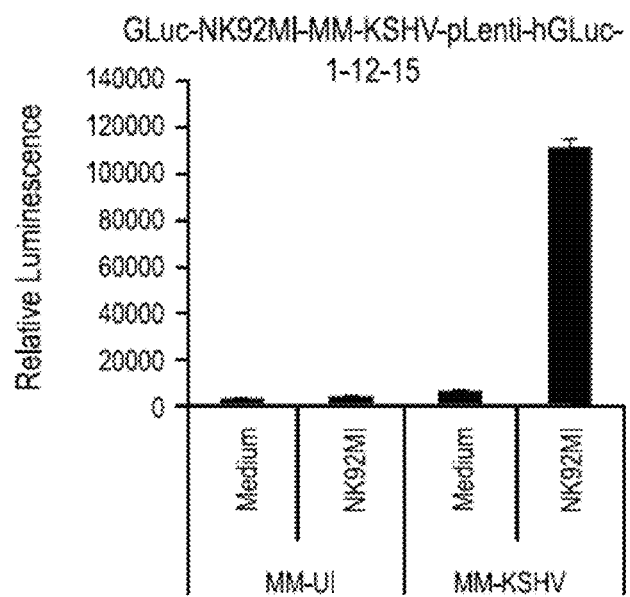
FIG. 25 depicts in accordance with various embodiments of the invention, increase in GLuc activity upon co-culture of KSHV-infected MM cells stably expressing GLuc with NK92MI suggesting that Matador assay can be used to monitor death of virally infected cells.

Matador Cytotoxicity Assay can be Used to Measure Cytotoxicity Against Virally-Infected Cells To determine if the reporter release assay can be used to measure cytotoxicity against virally infected cells, we tested the effector function of NK92MI cells against KSHV-transformed primary rat embryonic metanephric mesenchymal precursor (MM; a gift from Dr. S. J. Gao, University of Southern California) cells. MM-Parental and MM-KSHV cells were engineered to express GLuc by infection with pLenti-EF1a-Pac-T2A-Gluc-B07 (SEQ ID NO: 94) lentiviral vector and selection with puromycin. NK92MI effector cells were co-cultured with Gluc-expressing target cells at an E:T ratio of 05:1co-culture for 4 hours in a 96-well flat bottom plate. The luciferase activity was precisely measured after directly injecting 0.5×CTZ assay buffer containing native coelenterazine in the 96-well plate in well mode. FIG. 25 shows increase in GLuc activity upon co-culture of MM-KSHV-GLuc cells with NK92MI cells, indicating specific cytotoxicity. Thus, the Matador assay can be used to monitor cytotoxicity against virally infected cells. The above results also provide yet another example of the use of method of the Matador assay to measure cytotoxicity in solid-tumor derived adherent cells. They also demonstrate that the utility of the assay is not limited to human cells since MM cells are of rat origin.

Example 27

Uses of Matador Cytotoxicity Assay to Measure Cell Death Induced by Antibody Drug Conjugate Brentuximab Vedotin (Adcetris)

Figure 26:
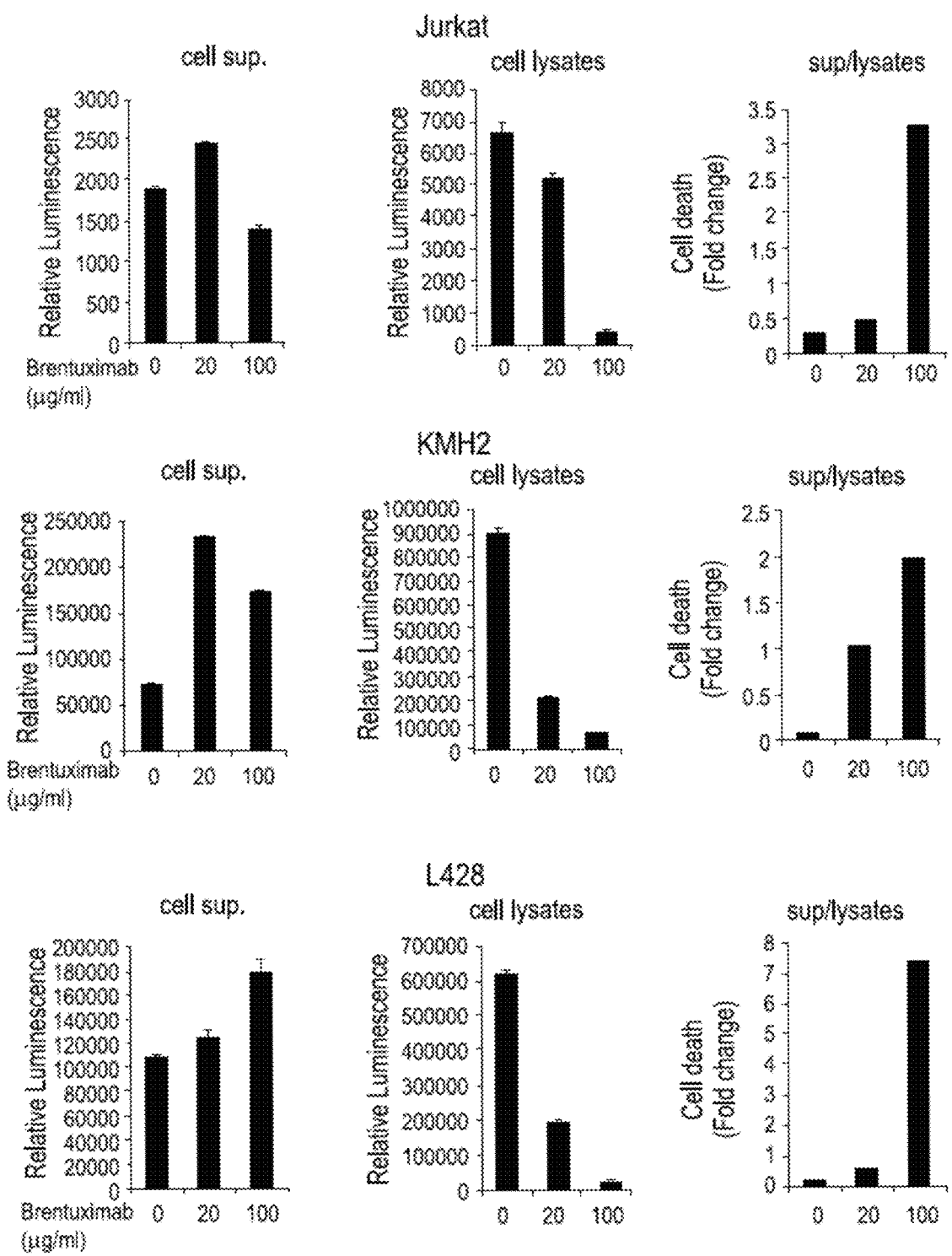
FIG. 26 depicts in accordance with various embodiments of the invention, Brentuximab vedotin treatment of GLuc-expressing Jurkat, KMH2, L428 cells led to a significant increase in GLuc activity in cell supernatant when normalized for the GLuc activity in cell lysates, demonstrating the utility of Matador assay for monitoring cytotoxicity induced by an antibody drug conjugate.

We next used the Matador cytotoxicity assay to measure cell death induced by CD30-directed antibody-drug-conjugate (ADC), Brentuximab vedotin (Adcetris). The CD30-positive Hodgkin lymphoma cells (L428 and KMH2) were engineered to express GLuc luciferase cDNA lacking the signal peptide by infecting these cells with pLenti-EF1 a-Pac-T2A-Gluc-B07 (SEQ ID NO: 94) viral supernatant, followed by selection with puromycin to make stably transduced L428-GLuc, and KMH2-GLuc cells, respectively. Similarly, Jurkat cells were transduced with MSCVhygro-GLuc-HA-G02 (SEQ ID NO: 95) retroviral vector and selected with hygromycin to generate Jurkat-GLuc stable cell line. These GLuc-expressing target cells were plated at a concentration of $10 \times 10^5$ cells/well in a flat-bottom 24 well plate in 500 µl of phenol-red-free RPMI medium with 10% FBS and treated with the indicated dose of Brentuximab vedotin. After 5 days of drug treatment, the cells were mixed well, collected in 1.5 ml microfuge tubes and divided into 3 groups of 166 µl each. For the first group, the cells with cell supernatant were directly assayed for luciferase activity by plating 30 µl of cells/well in a white 384 well plate in triplicate. For the second group, 166 µl of cells were centrifuged and only cell supernatants were collected in a new tube and plated at 30 µl/well in triplicate in a white 384 well plate. For the third group, samples were centrifuged, supernatant was removed, cells were lysed in Renilla lysis buffer (Promega) and 30 µl of cell lysates were plated per well in a 384-well plate in triplicate. The luciferase activity was precisely measured by BioTek synergy plate reader by injecting 0.5×CTZ assay buffer containing native coelenterazine into each well of the 384 well plate in a well mode. As shown in FIG. 26, there was an increase in GLuc activity in the supernatant of Brentuximab vedotin-treated cells. However, in contrast to the cell-mediated cytotoxicity which occurs over a relatively short time (e.g., over 4-5 hour), Brentuximab vedotin-induced cell death is a slow process and takes 4-5 days to manifest. Since the duration of Brentuximab vedotin treatment was relatively long, the untreated cells had continued to proliferate as compared to the drug treated cells. As a result, at the time of GLuc assay, the number of GLuc-expressing cells in the wells that were left untreated was significantly higher as compared to the wells that were Brentuximab vedotin-treated. To control for the varying number of GLuc-expressing cells in different wells, which could have confounded the results of the Matador assay due to varying level of spontaneous GLuc-release, Brentuximab vedotin-induced cell death was measured by dividing mean GLuc values in the cell supernatant (Group 2) by mean luciferase values in cell lysates (Group 3). As shown in FIG. 26, Brentuximab vedotin treatment led

Example 28

Use of Matador Assay to Measure Activation Induced Cell Death

Figure 27:
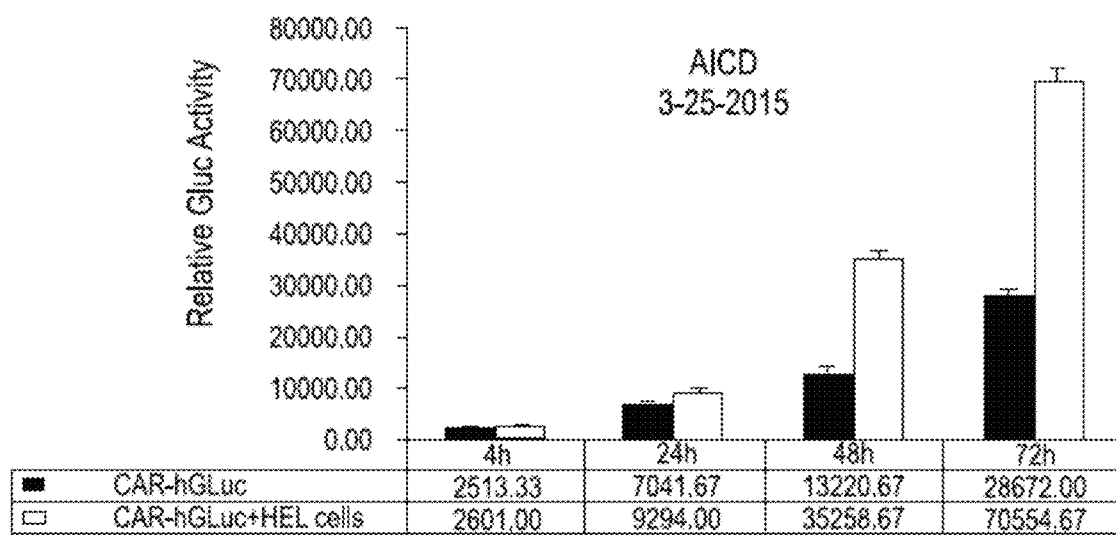
FIG. 27 depicts in accordance with various embodiments of the invention, that co-culture of peripheral blood mononuclear cells infected with a chimeric antigen receptor (CAR) targeting MPL and co-expressing GLuc with HEL cells expressing the MPL protein results in increase in GLuc activity, thereby demonstrating the utility of the Matador assay for monitoring activation-induced cell death.

To determine the Activation Induced Cell death (AICD) in CAR-expressing primary cells, peripheral blood mononuclear cells (PBMCs) were obtained from healthy de-identified adult donors. PBMC were isolated from buffy coats by Ficoll-Hypaque gradient centrifugation and re-suspended in XVIVO medium (Lonza) supplanted with 10ng/ml soluble anti-CD3, 10 ng/ml soluble anti-CD28 and 100IU recombinant human-IL2. PBMCs were engineered to express a $2^{nd}$ generation chimeric antigen receptor (CAR) targeting a protein expressed on HEL.92.1.7 cells. The CAR construct consisted of human CD8 signal peptide, followed by codon-optimized sequences of a scFv derived from a monoclonal antibody directed against the extracellular domain of the target protein expressed on HEL.92.1.7 cells, a MYC epitope tag, the hinge, transmembrane and cytosolic signaling domains from human CD28 molecule, the cytoplasmic domain of human CD3C molecule, T2A ribosomal skip sequence and a Gaussia princeps luciferase cDNA sequence without the secretory signal. PBMC were transduced with CAR expressing lentiviral supernatant to make PBMC-CAR-GLuc effector cells. Specific activation-induced cell death of these GLuc expressing effector cells by HEL.92.1.7 cells was assayed after effector and target cells were co-cultured for 4 to 72 hours at an E:T ratio of 2:1 in a 384-well flat bottom plate. The luciferase activity was precisely measured by BioTek synergy plate reader that directly injected 15 μl of the 0.5×CTZ assay buffer into the 384 well plates in a well mode. As shown FIG. 27, there was a significant increase in GLuc activity when GLuc expressing CAR-T cells were co-cultured with the HEL target cells for 24 hours, 48 hours and 72 hours as compared to CAR-T cells that had been cultured alone without the target cells.

Example 29

Figure 28C:
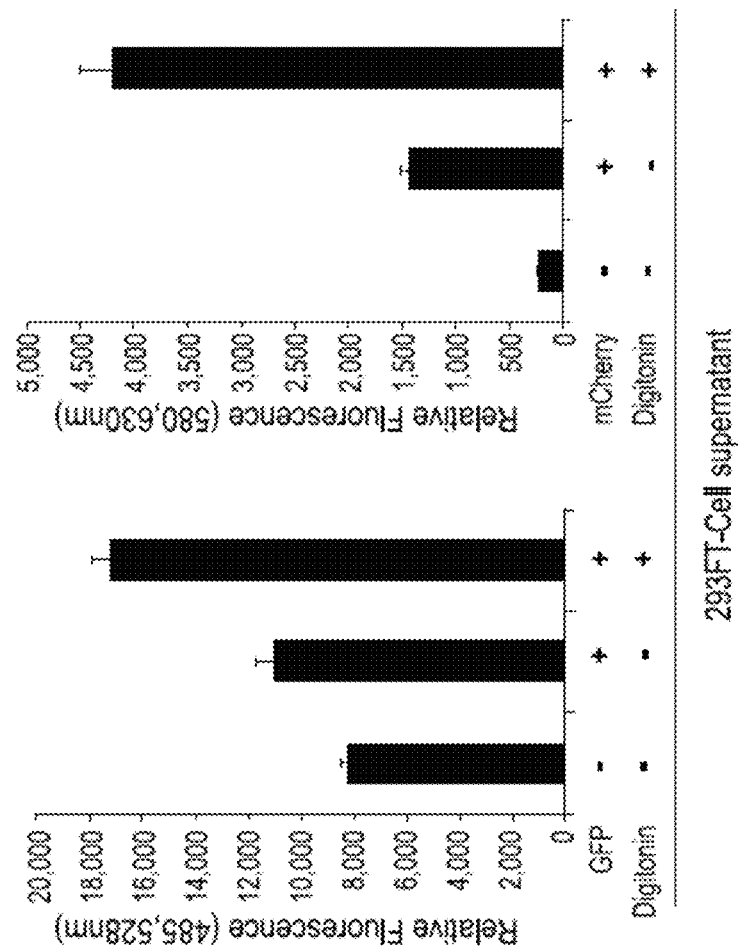
FIG. 28A-C depicts in accordance with various embodiments of the invention.
Figure 28A:
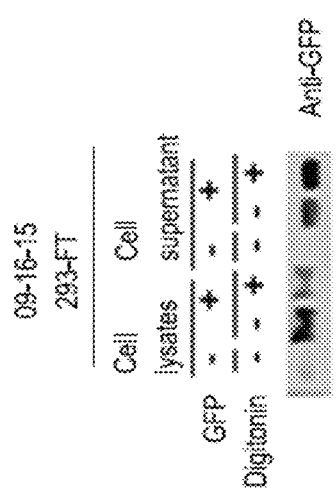
Figure 28B:
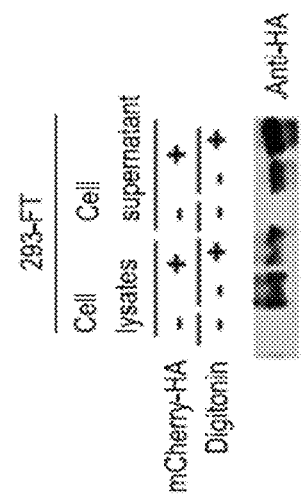

Development of Matador Assay Based on the Release of Enhanced Green Fluorescent Protein (EGFP) and mCherry We next examined if the Matador cytotoxicity assay developed by us is limited to only luciferase proteins or can be adapted to any other protein that is not endogenously expressed by the target cells. For this purpose, we transiently transfected 293FT cells by calcium phosphate co-precipitation method with an expression plasmid encoding enhanced green fluorescent protein (GFP) or HA-epitope tagged-mCherry. Approximately 24 post-transfection, the transfected cells were either left untreated or treated with Digitonin to induce cell death. The cells were collected in tubes and centrifuged at 2,000 rpm for 5 min. Cell supernatant was collected in a new set of tubes and cell pellet were washed with cold phosphate-buffered saline twice and lysed in lysis buffer containing 20 mM Tris-HCl, pH 8.0, 500 mM NaCl, 0.25% Triton X-100, 1 mM EDTA, 10 mM P-glycophosphate, 10 mMNaF, 1 mM DTT, 1x protease inhibitor mixture (Roche Molecular Biochemicals) at 4° C. for 30 min. After incubation, the mixture was pipetted five or six times to disperse the cells followed by centrifugation at 14,000 rpm at 4° C. for 10 min. The cell lysates were collected as whole cell extracts, and protein concentration was determined by using Bio-Rad protein assay reagent. 30 l of cell supernatant or 30 μg of whole cell extracts were heated in the presence of SDS-PAGE sample buffer and loaded on 10% SDS-PAGE gel followed by transferring to nitrocellulose membranes. These membranes were incubated with primary antibodies against specified proteins in Tris-buffered-saline with Tween 20 followed by incubation with secondary antibody (IRDye 800CW conjugates of goat anti-rabbit IgG; Li-Cor) and development with Odyssey Infrared Imaging System CLx (Li-Cor Biosciences). The secondary antibody was used at a 1:10,000 dilution. The blots were scanned and analyzed using an Odyssey Infrared scanner using Odyssey imaging software, version 2.0. The primary antibodies used in these experiments were anti-GFP or anti-HA polyclonal antibodies from Santa Cruz Biotechnology at 1:2,000 or 1:10,000 dilutions, respectively. As shown in FIG. 28A Digitonin-induced cell death of GFP transfected 293FT cells resulted in increase in GFP release in the supernatant fraction as measured by Western blotting with an antibody against GFP. There was a corresponding decrease in GFP expression in cell lysate fraction upon treatment with Digitonin. Similarly, Digitonin-induced cell death of HA-mCherry transfected 293FT cells resulted in increase in mCherry release in the supernatant fraction as measured by Western blotting with an antibody against HA tag (FIG. 28B). There was a corresponding decrease in mCherry expression in cell lysate fraction upon treatment with Digitonin. The above results demonstrate that any protein or peptide that can be expressed intracellularly and against which a suitable antibody or an antibody like binding-fragment is available can be used to develop an assay for cellular cytotoxicity. In addition, the results with mCherry-HA experiment demonstrate that an epitope tagged version of the protein can be used to develop an assay for cellular cytotoxicity. In addition to Western blotting, we used fluorescence measurement to detect release of GFP and mCherry in the supernatant fractions upon induction of cell death with Digitonin. Fluorescence signal from GFP (excitation=488 nm, emission=528 nm) and mCherry (excitation=580 nm, emission=630 nm) was measured using BioTek synergy plate reader. As shown in FIG. 28C, there was significant increase in fluorescence in cell supernatant collected from cells that had been transfected with GFP and mCherry-HA, respectively, and then treated with Digitonin as compared to untreated cells.

Taken collectively, these results demonstrate that a cytotoxicity assay can be developed using any molecule (e.g. protein, peptide, DNA, or RNA) that is 1) not expressed endogenously in the target cells; 2) can be ectopically expressed intracellularly; 3) is leaked extracellularly upon loss of cell membrane integrity; 4) can be measured in the extracellular compartment. The presence of protein/peptide can be detected by ELISA, mass-spectroscopy, Western blotting, or by measuring the activity of the protein by functional assays, such as luciferase reporter assay for luciferases or by measuring fluorescence as in case of a fluorescent protein, or combination thereof. In the case of DNA and RNA, various methods for measurement can be used, including PCR amplification, hybridization, mass spectroscopy, sequencing (including next generation sequencing) or combination thereof.

Finally, in another embodiment, it is possible to develop a cytotoxicity assay using 1) any molecule (e.g. protein, peptide, DNA, or RNA) that is not expressed endogenously in the cells; 2) can be ectopically expressed intracellularly; 3) whose detection requires the presence of factor or factors that are not cell membrane permeable or are cell membrane permeable to only limited extent and therefore are excluded from the intracellular compartment; 4) where the above factor or factors gain increased entrance to the intracellular compartment upon loss of cell membrane integrity which results in enhanced detection of the molecule described in step 1 that is ectopically expressed intracellularly. In the case of DNA and RNA, various methods for measurement can be used, including PCR amplification, hybridization, sequencing (including next generation sequencing) or combination thereof.

Example 30

Use of Matador Assay Based on Calculation of % Specific Lysis

We constructed two lentiviral vectors encoding second generation CD19-specific CARs designated FMC63-Myc-BBz-T2A-Pac (SEQ ID NO: 80) and FMC63-Myc-28z-T2A-PAC (SEQ ID NO: 81), respectively, and a control CAR designated 4C3-Myc-BBz-T2A-PAC (SEQ ID NO: 83). To generate T cells expressing CD19-specific CAR, T cells were transduced by CAR lentiviral supernatant by spinfection at 2,800 rpm at 32° C. for 90 min. The spinfection steps were repeated for three consecutive days and cells selected in puromycin and expanded. The target (RAJI-NLuc) cells were plated a concentration of $5 \times 10^4$ cells/well in a white 384-cell plate and either left untreated or treated with T cells expressing the CARs FMC63-Myc-BBZ-T2A-PAC, FMC63-Myc-CD28z-T2A-PAC or 4C3-Myc-BBz-T2A-PAC at an E:T ratio of 10:1 for 4 h. For measurement of maximum cell death, cells were treated with 30 μl of Digitonin dissolved in DMSO for approximately 90 min prior to measurement of NLuc activity. The cell death was assayed by luciferase-based cytotoxicity assay as discussed earlier by addition of 0.5×CTZ assay (15p/well) buffer containing native coelenterazine using an automatic injector. The % specific lysis was calculated by taking Digitonin-induced cell death as 100% and untreated cells as 0%. % specific lysis was calculated by using formula: % Specific lysis=100×((experimental data)−(spontaneous cell death))/((maximum cell death)-spontaneous cell death)). FIG. 29 shows increase in % specific lysis of RAJI-NLuc cells when co-cultured with CD19-directed FMC63-Myc-BBZ and FMC63-Myc-CD28z CAR constructs.

Example 31

Figure 30B:
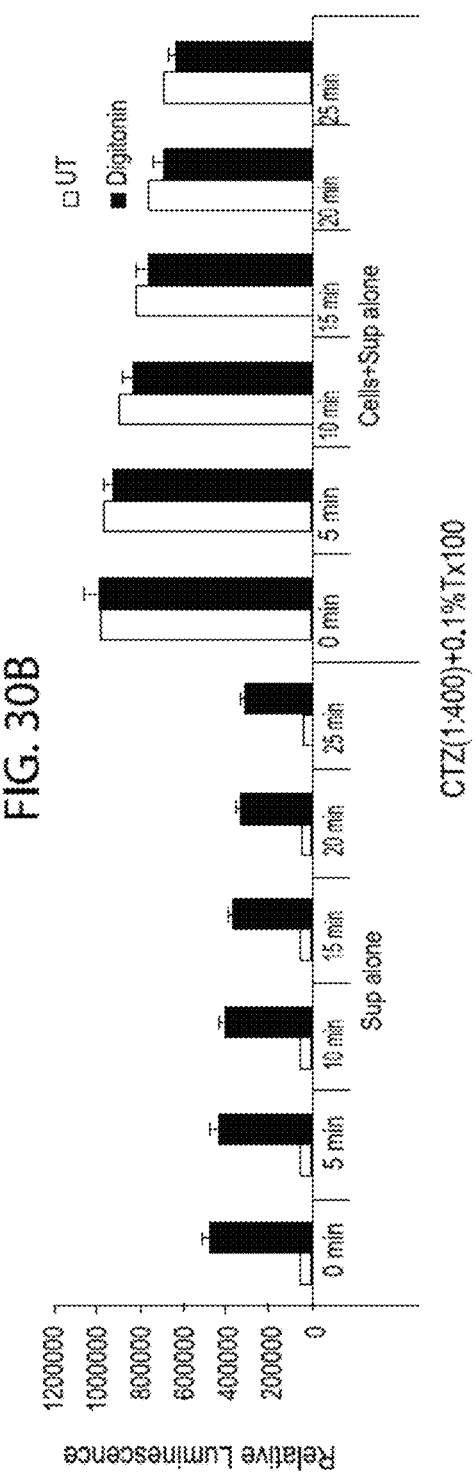
Figure 30C:
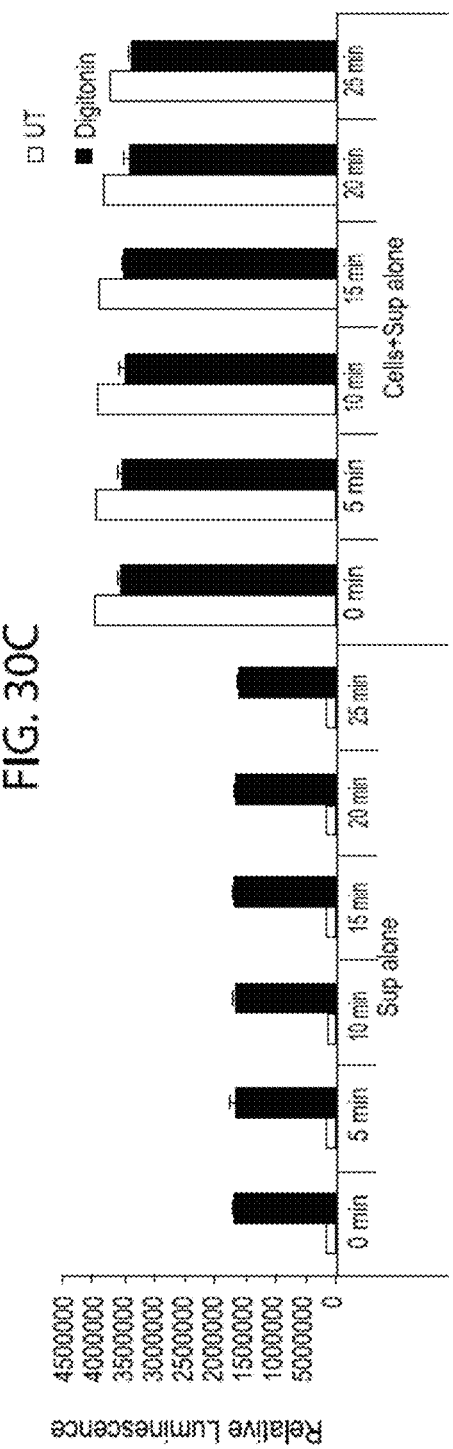

Effect of Different Assay Buffers on Glow-Type Luminescence by NLuc when Used in Matador Assay NLuc is known to result in glow-type luminescence which makes it an attractive candidate for inclusion in assays that are high-throughput compatible without the need for an automatic injector. To examine if NLuc would also result in glow-type luminescence when used in a cytotoxicity assay, K562-NLuc cells (1 million cells/ml) in XVIVO medium were aliquoted into 4 tubes. Cells in tubes 1 and 3 were left untreated while those in the tubes 2 and 4 were treated with Digitonin (30 μg/ml) for 1 h at 37° C. in duplicate. Tubes 1 and 2 were centrifuged to collect supernatant which were transferred into new tubes. Tubes 3 and 4 were designated as cells plus supernatant samples. All samples were diluted 1:2 in XVIVO medium and assayed in 384-well white plates. 25 μl of each sample was plated in each well and assayed using three assay buffers: A) CTZ diluted 1:400 in PBS; B) CTZ diluted 1:400 in PBS with 0.1% Triton 100; C) Nano-Glo® luciferase assay system (Promega) where Nano-Glo® assay substrate was diluted (1:400) in 1× Nano-Glo® assay buffer provided with the kit. 25 μl of assay buffer (A, B or C) was added in each well (n=5 for each sample) manually. Luminescence was read in a kinetic mode after 0, 5, 10, 15, 20 and 25 minutes. FIG. 30 shows that there is increase in luminescence upon Digitonin treatment when measured in the supernatant using all three assay buffers. However, while the luminescence value was stable in samples for over 25 minutes after addition of buffer C, it started declining within 5 minutes after addition of buffers A and B. These results demonstrate that the NLuc cytotoxicity assay results in a glow-type luminescence when performed on the cell supernatants using buffer C (i.e. Nano-Glo® assay reagent; Promega), making the assay high-throughput compatible without the need for an automatic injector. FIG. 30 further shows that there is increase in luminescence upon Digitonin treatment in the cells plus supernatant samples only in the buffer A (i.e. CTZ diluted 1:400 in PBS). No increase in luminescence upon Digitonin treatment in the cells+supernatant samples was observed in assay buffers B and C as the luminescence value was very high even in wells without Digitonin treatment. This is probably due to induction of cell death by 0.1% Triton X in case of buffer B. The exact composition of Nano-Glo® Luciferase Assay Buffer is proprietary but it could contain a cell death-inducing substance similar to Triton X. These results demonstrate that the Nano-Glo® assay reagent is not ideally suited for use in the Matador cytotoxicity when the assay is performed in a homogenous manner (i.e. performed on cells plus supernatant). It is, however, possible to use the Nano-Glo® assay reagent in the Matador assay when the assay is performed on cell supernatants that are freed from the cells. As it was suspected that the Nano-Glo® Luciferase assay buffer contains a cell death inducing agent, it was next examined if the Nano-Glo® substrate (Promega) could be diluted in Phosphate Buffer Saline (PBS) for use in the Matador assay. The experiment was repeated with RAJI-NLuc cells using Nano-Glo® substrate diluted 1:400 in PBS. It was observed that Nano-Glo® substrate in PBS led to glow-type luminescence with signal that was stable for 20-25 minutes. Additionally, in contrast to the situation with Nano-Glo® reagent (i.e. Nano-Glo® substrate dissolved in the Nano-Glo® Luciferase assay buffer), there was a clear difference in the signal between the untreated and digitonin treated cell samples when Nano-Glo® substrate suspended in PBS was used in the assay. These results demonstrate that Matador assay can be performed in homogeneous manner with NLuc expressing cells using Nano-Glo® substrate suspended in PBS. It was also noted that addition of Nano-Glo® reagent to K562-NLuc cells using an autoinjector followed immediately (i.e. without any time delay) by the measurement of luminescence still resulted in an increase in NLuc activity as compared to untreated cells. This result suggested that the exposure of the target cells to the cell death inducing agent present in the Nano-Glo® can instantly lead to induction of cell death, which can be measured by the Matador assay. Hence, depending on the agent that is being tested, the Matador assay can be performed even when the duration of exposure of the target cells to the test agent is very short (e.g., a second or less).

Example 32

Figure 31:
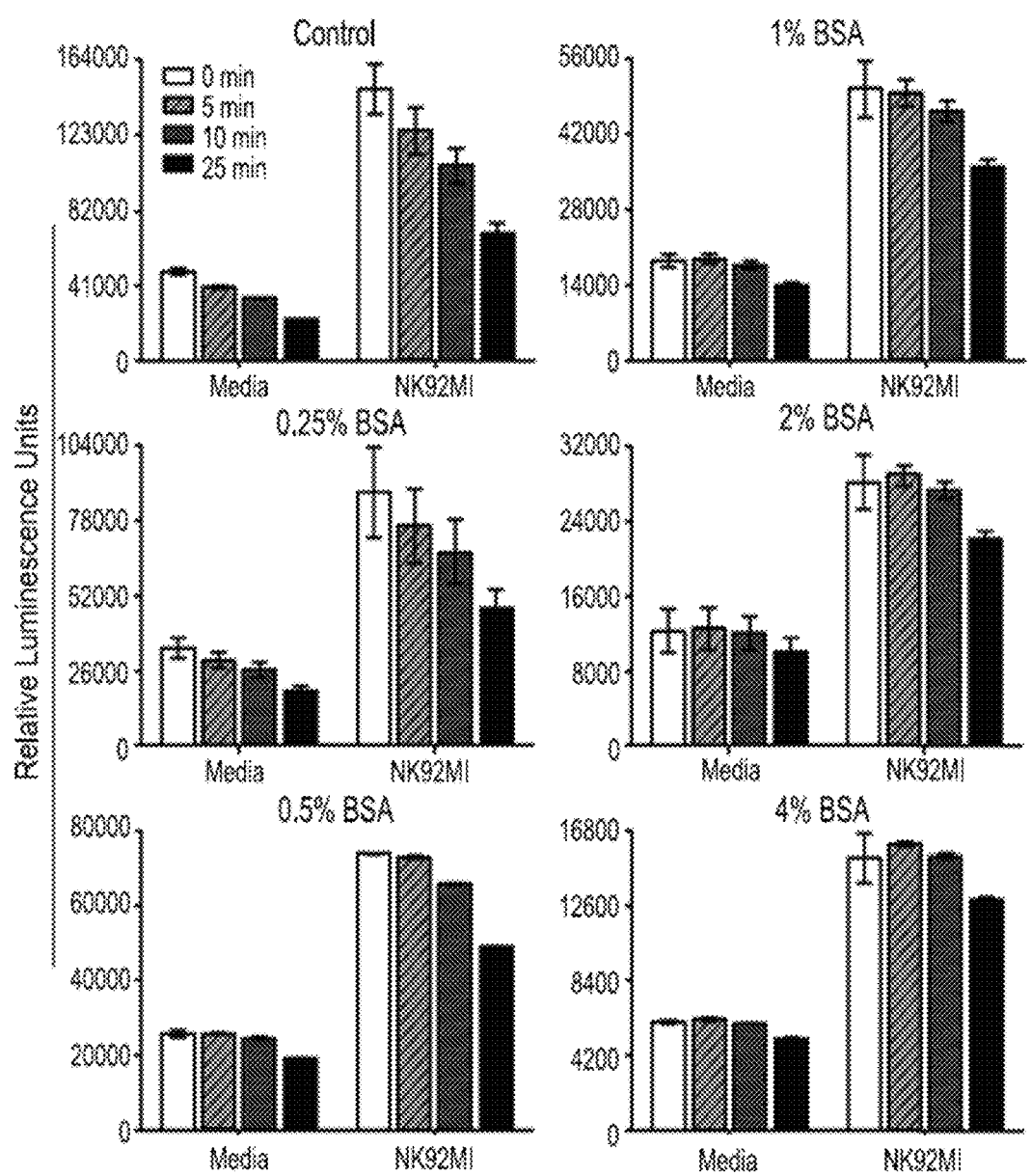
FIG. 31 depicts in accordance with various embodiments of the invention, the effect of addition of bovine serum albumin on production of glow-type luminescence by NLuc when used in Matador cytotoxicity assay.

Effect of Bovine Serum Albumin on Generation of Glow-Type Luminescence in Matador Cytotoxicity Assay As addition of bovine serum albumin (BSA) has been reported to stabilize the luminescence, various concentrations of bovine serum albumin (BSA) were added in the assay buffer in order to make the assay high-throughput compatible in a homogeneous setting (i.e. when performed on cells +supernatant). K562 cells stably expressing NLuc were plated in a 384-well plate (15000 cells/15 µL) and treated with media alone or co-cultured with NK92MI at Effector:Target (E:T) ratio of 1:1 for 4 hours. After the incubation, the luminescence was measured from whole homogeneous mixture by manually adding CTZ containing assay buffer with indicated concentrations of BSA using a multi-channel pipette, read immediately (0 min) and at the indicated time points. The values shown are mean±SE of a representative experiment performed in duplicate for at least two times. FIG. 31 shows that addition of BSA to the CTZ assay buffer produced glow-type luminescence with stabilization of NLuc luminescence signal starting at a BSA concentration of >0.5%. These results demonstrate that by modifying the assay buffer with appropriate stabilizing agents the Matador cytotoxicity assay can be made high-throughput compatible in homogeneous setting when the assay buffer is added manually thus obviating the need of a luminometer equipped with an auto-injector.

Example 33

Matador Assay can be Used to Monitor Cell Toxicity In Vivo

Figure 32:
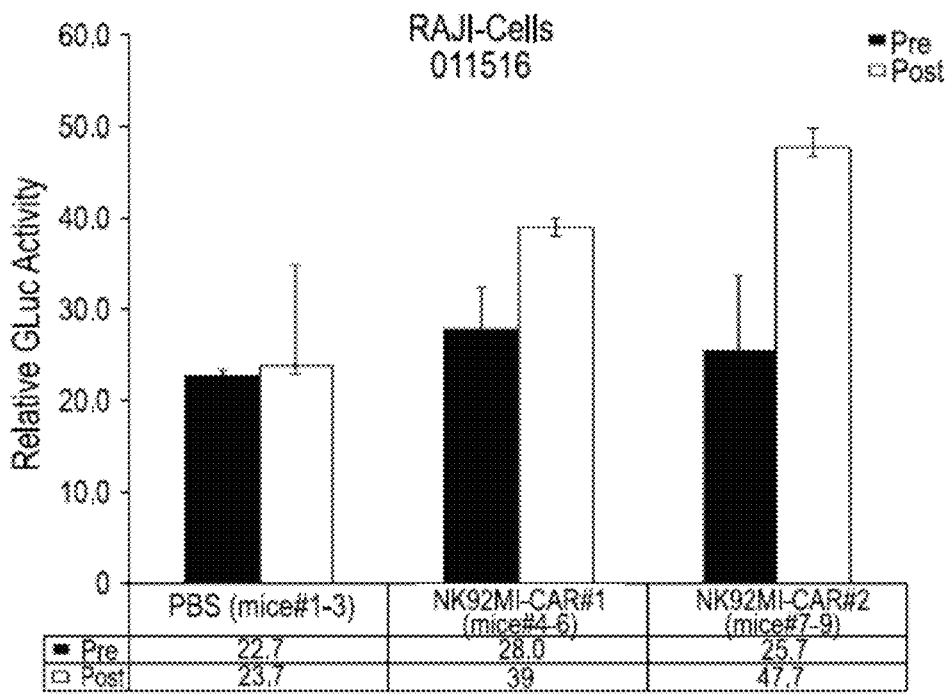
FIG. 32 depicts in accordance with various embodiments of the invention, that there was a significant increase in GLuc activity between the pre- and post-treatment serum samples of mice injected with RAJI-GLuc cells and then treated with NK92MI cells expressing chimeric antigen receptors targeting CD19. These results demonstrate that the Matador assay can be used to monitor cytotoxicity in vivo.

Raji cells were engineered to co-express GLuc and FfLuc (firefly luciferase) by sequential infection with lentiviral vectors (pLenti-EF1a-Pac-T2A-GLuc-B07 and pLENTI-EF1-pGL3-FfLuc-blasticidin-A07) expressing the two luciferases and selection with Puromycin and Blasticidin, respectively. However, only the GLuc activity was measured in this assay. Approximately 8 weeks old male NSG mice (n=9; Jackson Lab) were numbered 1 through 9 and injected with approximately 2 million Raji-GLuc/FfLuc cells in 100 µl PBS. Three additional mice (#10-12) were not injected with Raji cells and served as blanks. Approximately 30 minutes later, 50-100 µl of blood (pre-treatment sample) was collected from retro-orbital plexus of all animals (including blank animals) and immediately placed on ice. Approximately 1 hour post-injection of Raji cells, animals #1-3 were injected with 100 µl of PBS while animals #4-6 and #7-9 were injected with 100 µl of PBS containing 2 million of NK92MI cells expressing CAR #1 (chimeric antigen receptor #1) and CAR #2 (chimeric antigen receptor #2). 4 hours post NK92MI cells injection, 50-100 µl of blood (post-treatment sample) was collected from retro-orbital plexus of the mice and immediately placed on ice. The samples were spun at 4000 g for 10 min at 4° C. to separate serum. The serum was diluted 5 fold (i.e. 6 µl serum+24 µl PBS). GLuc activity in the diluted samples (25 l) was assayed using BioTek synergy plate reader that directly injected 25 µl of the 0.5×CTZ assay buffer into the samples plated in a 384 well plate as described earlier. The averaged value of blanked samples was subtracted from all test values to control for non-specific background reading. FIG. 32 shows that there was no significant increase in GLuc activity between the pre- and post-treatment samples of mice that had been treated with PBS. However, there was a significant increase in GLuc activity between the pre- and post-treatment samples of mice that had been treated with NK92MI cells expressing the two different chimeric antigen receptors. These results demonstrate that the Matador assay described in this invention can be used to monitor cytotoxicity in vivo.

Example 34

Figure 33:
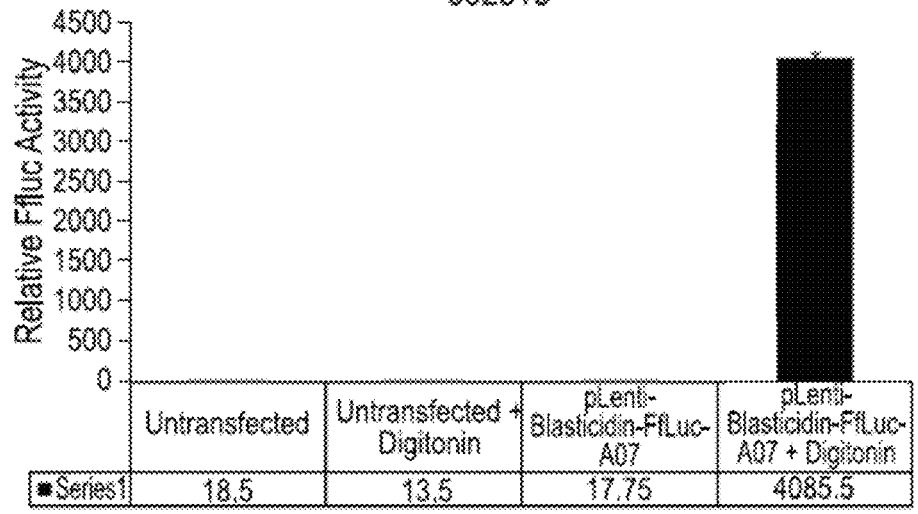
FIG. 33 depicts in accordance with various embodiments of the invention, treatment with Digitonin resulted in increase in luciferase activity in case of 293FT cells transiently transfected with the FfLuc construct.

Development of Matador Assay Based on Transient Transfection of FfLuc in 293FT Cells The mammalian expression vectors encoding Firefly luciferase cDNA (pLENTI-Blasticidin-FfLuc-A07; SEQ ID NO: 99) was transiently transfected into 293FT cells by calcium phosphate co-precipitation method. Approximately 18 hours post-transfection, one well for each transfection was treated for 90 min with Digitonin (final concentration 30 µg/ml) and the other well was left untreated. After the 90 minute incubation, 200 µl of supernatant was collected from each well in 1.5 ml tubes. The tubes were spun down at 1500 RPM for 5 minutes. Then, 25 µl of supernatant was collected and plated in a 384 well plate in triplicate (25 µl/well). Luciferase activity was measured in well mode using BioTek synergy plate reader by addition to each well of 25 µl Luciferase assay buffer described in FfLuc Assay, which consisted per 1.0 ml of 885.5 µl assay buffer+1 µl DTT (1M stock)±100 µl of 10× Luciferin stock solution+13.5 µl ATP (100 mM stock). As shown in FIG. 33, treatment with Digitonin resulted in increase in luciferase activity in case of 293FT cells transiently transfected with the FfLuc construct.

Example 35

Development of Dual Reporter Based Matador Assay Utilizing a Beetle Luciferase (e.g. FfLuc) and a Marine Luciferase (e.g. GLuc)

Figure 34:
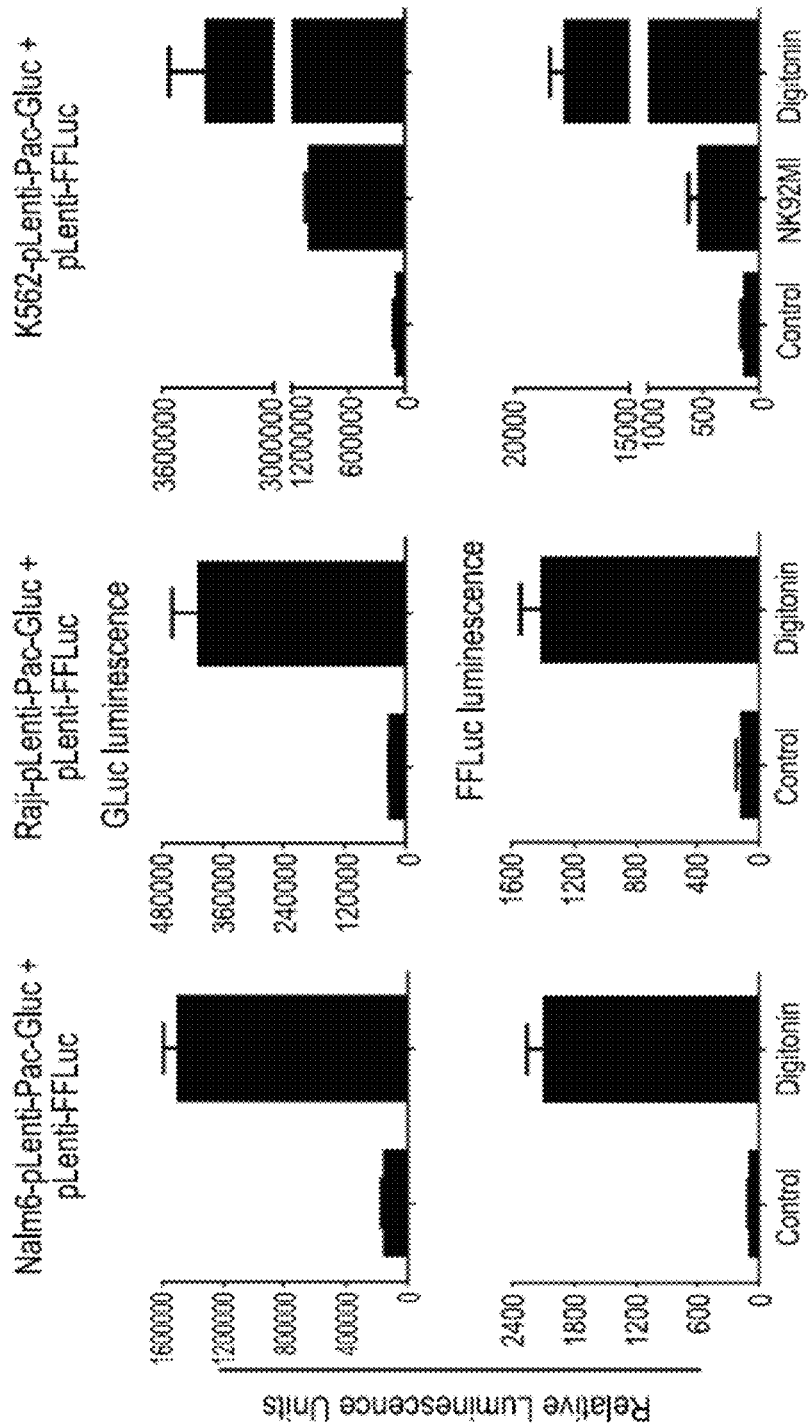
FIG. 34 depicts in accordance with various embodiments of the invention, treatment with Digitonin resulted in increase in both FfLuc and GLuc activities in cell lines coexpressing both FfLuc and GLuc.

FfLuc and GLuc utilize different substrates (i.e., D-luciferin and coelenterazine) for light production. It was therefore next checked if increase in the activity of both GLuc and FfLuc can be measured from cells expressing both luciferases as a measure of cytotoxicity. For this purpose, Nalm6, Raji and K562 cells were engineered to stably express both GLuc and FfLuc by sequential infection with lentiviral vectors encoding the respective luciferases followed by selection with appropriate Puromycin and Blasticidin. Briefly, 20000 cells in 20 µl media were plated in each well of a 384 well plate followed by addition of 20 µl of Digitonin (final concentration 30 µg/ml) or media alone (20 l) and incubated for 90 minutes. In the case of K562 cells, cell death was also induced by coincubation with NK92MI cells for 4 hours at an E:T ratio of 1:1. After the incubation, the firefly and GLuc activities were sequentially measured from the sample using the Dual-Luciferase® Reporter (DLR™) Assay System (Promega) and following the manufacturer's recommendations. As shown in the FIG. 34, treatment with Digitonin resulted in increase in both FfLuc and GLuc activities. Co-culture of K562 cells with NK92Mi cells also resulted in increase in both FfLuc and GLuc activities. Essentially, similar results are obtained when the assay is repeated using cells expressing other beetle luciferases in combination with different marine luciferases (e.g. NLuc). Thus, surprisingly and in contrast to a previous report (Fu, Tao et al. 2010), we were able to successfully detect significant increase in FfLuc activity upon induction of cell death from cells stably expressing this reporter in the cytosol, suggesting that FfLuc and other beetle luciferases can be potentially used in Matador cytotoxicity assay. It is possible that the success of our assay is in part due to use of optimized vectors, such as lentiviral vectors, and use of strong promoters (e.g., CMV and EF1α promoters) that result in higher levels of FfLuc expression.

Example 36

Stability of Different Luciferases Under the Conditions of Matador Assay

Figure 35:
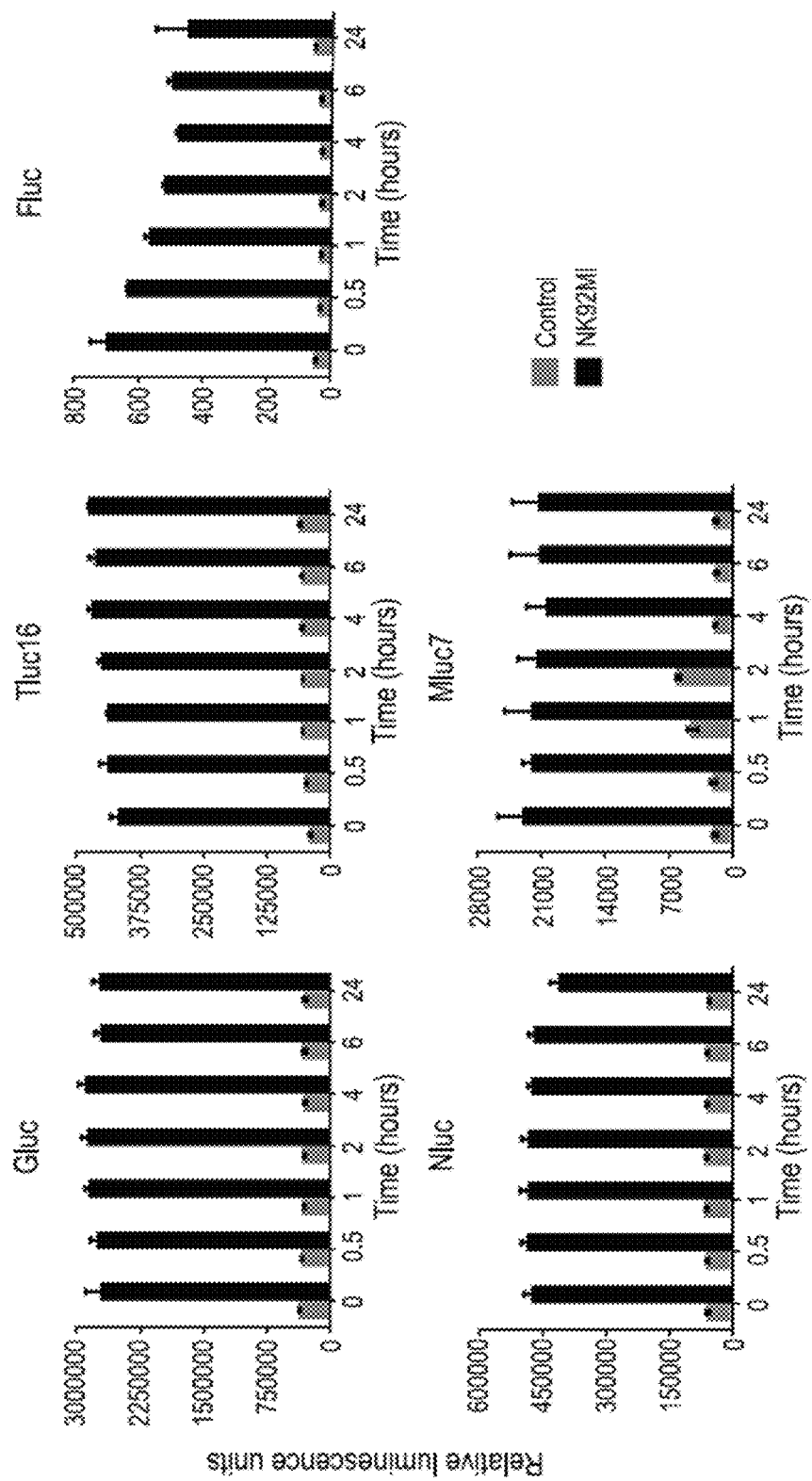
FIG. 35 depicts in accordance with various embodiments of the invention, stability of the exemplary luciferases at 37° C. that can be used in the Matador cytotoxicity assay. The results confirm that FfLuc has short half-life at 37° C. when used in the Matador cytotoxicity assay.

The shorter half-life (<30 minutes) of firefly luciferase (FLuc or FfLuc) in tissue culture medium has been reported to make it impractical to use it in a standard 4 hours co-culture cytotoxicity assay (Thompson, Hayes et al. 1991, Schafer, Schafer et al. 1997). Although the marine luciferases used in this study have been reported to have longer half-life (>24 hours) in tissue culture medium, we wanted to confirm that they would retain their stability under the assay conditions as the cell death proteases released during cell death could lead to their degradation. Therefore, to demonstrate that the marine luciferases are suitable for the Matador cytotoxicity assay, K562 cells stably expressing GLuc, NLuc, TLuc16, Mluc7 and Fluc, were plated in a 24-well plate and treated with media alone or with NK92MI cells at an Effector:Target (E:T) ratio of 1:1 for 6 hours. Post-incubation, the cell-free supernatants were divided into 7 different tubes and frozen immediately at −80° C. The tubes were then incubated at 37° C. for 0, 0.5, 1, 2, 4, 6, and 24 hours. After incubation, supernatants were transferred to a 384-well plate, and luminescence was measured by adding CTZ-containing assay buffer (for GLuc, NLuc, TLuc16, and Mluc7), and D-luciferin-containing assay buffer (for Fluc), respectively. As shown in FIG. 35, luminescence of GLuc, NLuc, TLuc16, and Mluc7 was stable for 24 hours at 37° C. in cell culture supernatants thereby demonstrating the suitability of these luciferases for the cytotoxicity assay. In contrast, luminescence of Fluc started decaying as early as 0.5 hours after incubation at 37° C. in cell culture supernatants, confirming that Fluc may not be ideal for the Matador cytotoxicity assay.

Example 37

Use of Thermostable Luciferase LucPPe-146-1H2 from *Photuris pennsylvanica* in Cytotoxicity Assay It was conceivable that short half-life of FLuc under the conditions of Matador assay is due to its poor thermostability. Thermostable luciferases from *Photuris pennsylvanica* and *Pyrophorus plagiothalamus* have been described (PCT/US99/30925). To examine whether thermostable luciferases are suitable for Matador cytotoxicity assay, K562 cells stably expressing LucPPe-146-1H2 mutant (SEQ ID NO: 21) were plated in triplicate at approximately 20,000 cells/well in a Greiner 384-well flat bottom white opaque plate. The cells were cultured alone or with NK92MI cells at an E:T ratio of 1:1 for 4 hours in 40 µl total volume. For measurement of maximum cell death, cells in three wells were treated with Digitonin (final concentration 30 µg/ml). At the end of co-culture period, the luminescence was measured by adding D-luciferin containing assay buffer (40 l) to the cell-culture medium containing the cells at 1:1 (v/v) ratio. FIG. 36A shows that induction of cell death of K562 cells stably expressing the LucPPe-146-1H2 by Digitonin or by co-culture with NK92MI cells results in increase in LucPPe-146-1H2 activity. FIG. 36B shows that transient transfection of LucPPe-146-1H2 in 293FT cells also resulted in increase in LucPPe luciferase activity in Digitonin treated cells as compared to cells that had not been treated with Digitonin. The above results demonstrate that the activity of the thermostable beetle luciferases, such as LucPPe-146-1H2, is increased upon induction of cell death and therefore they are suitable candidates for inclusion in the Matador cytotoxicity assay.

Example 38

Stability of Thermostable Luciferase LucPPe-146-1H2 from *Photuris Pennsylvanica* Under Conditions of Cytotoxicity Assay Although thermostable luciferases are stable at 37° C., it was not obvious whether thermostability is the only criteria for stability of a reporter under the conditions used in the cytotoxicity assays. Thus, a thermostable luciferase could be degraded under the culture conditions of the cytotoxicity assay due to the activity of proteases that are present in the serum or are released during the process of cell death. Therefore, to examine whether thermostable luciferases are suitable for inclusion in the Matador cytotoxicity assay, K562 cells stably expressing LucPPe-146-1H2 mutant were plated in a 6-well plate, treated with media alone (control) or co-cultured with NK92MI at Effector:Target (E:T) ratio of 1:1 for 4 hours. After incubation, cell-free supernatants were transferred into 7 different tubes and frozen immediately at −80° C. The tubes were directly transferred to 37° C. (from −80° C.) and were incubated for indicated time periods (0 to 24 hours). The luminescence was measured by adding D-luciferin containing assay buffer directly to each well in well mode. FIG. 37 shows increase in LucPPe-146-1H2 luminescence in the supernatants collected from cells that had been co-culture with NK92MI cells. Furthermore, the luminescence signal was stable in the cell culture medium for nearly 4-6 hours. These results demonstrate that thermosstability is a key determinant of stability of reporters under the conditions of use in the cytotoxicity assays. As most cytotoxicity assays are carried out at 37° C., these results demonstrate that thermostable reporters are the preferred reporters to be used in the cytotoxicity assay described in this invention. In addition to LucPPe-146-1H2, GLuc, NLuc and TLuc, a number of other thermostable reporters have been described in the art (e.g., PCT/US99/30925) and are the preferred reporters for use in the cytotoxicity assay of the present invention.

Example 39

Figure 38A:
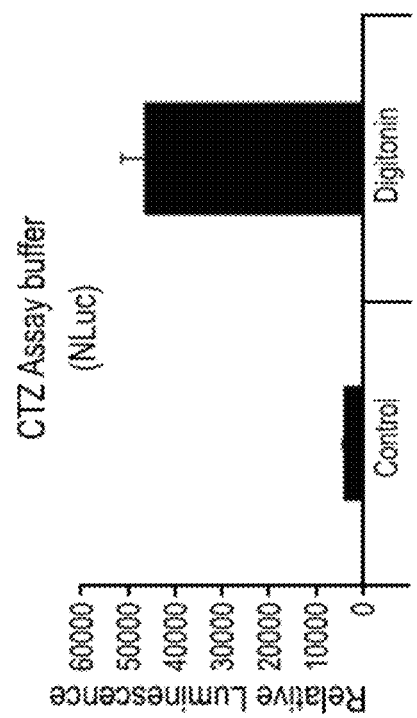
FIG. 38A-D depicts in accordance with various embodiments of the invention, that LucPPe-146-1H2 and NLuc can be combined to develop a dual luciferase based Matador cytotoxicity assay.
Figure 38B:
Figure 38C:
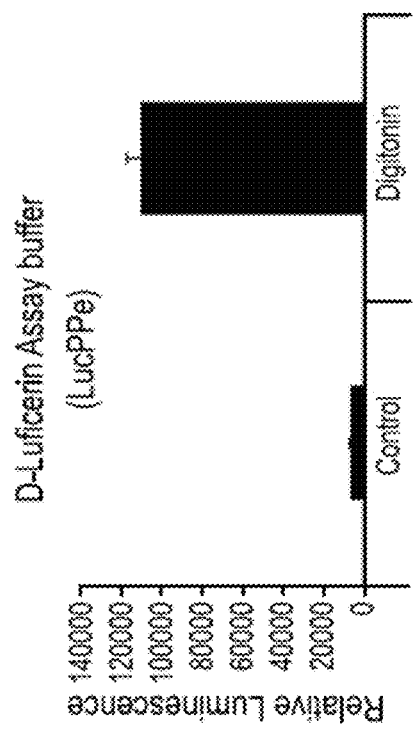
Figure 38D:
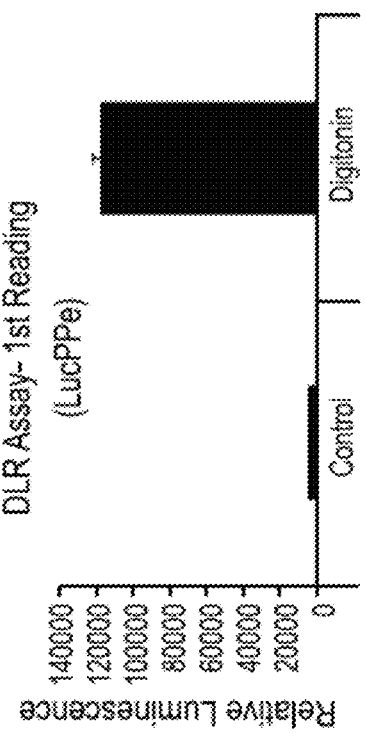

Development of Dual Luciferase Based Matador Assay Using LucPPe-146-1H2 and NLuc It was next checked if increase in the activity of both NLuc and LucPPe-146-1H2 can be measured from cells expressing both luciferases as a measure of cytotoxicity. For this purpose, K562 cells were engineered to stably express both NLuc and LucPPe-146-1H2 by sequential infection with lentiviral vectors (pLENTI-NLuc-AcV5-Blasticidin-Pa08, SEQ ID NO: 92 and pLenti-EF1-LucPPe-146-1H2-Flag-Pac-R01; SEQ ID NO: 100) encoding the respective luciferases followed by selection with Blasticidin and Puromycin, respectively. Briefly, 20000 cells in 20 µl media were plated in each well of a 384 well plate followed by addition of 20 µl of Digitonin (final concentration 30 µg/ml) or media alone (20 l) and incubated for 90 minutes. After incubation, the LucPPe-146-1H2 and NLuc activities were sequentially measured from the sample using the Dual-Luciferase® Reporter (DLR™) Assay System (Promega) and following the manufacturer's recommendations. Essentially, 20 µl of FFluc luciferase assay buffer was first added and the resulting luminescence detected for LucPPe-146-1H2. Then 20 µl of Stop and Glo assay buffer was added to the same wells and the resulting luminescence was measured for NLuc. FIG. 38A-B show that treatment with Digitonin resulted in increase in both LucPPe-146-1H2 and NLuc luminescence in cells co-expressing both luciferases when measured using the Dual-Luciferase® Reporter (DLR™) Assay System. The LucPPe-146-1H2 and NLuc activities were also measured from the samples that had been added to different wells. For this purpose, LucPPe-146-1H2 was measured by addition of 40 µl of D-luciferin assay buffer to three wells containing supernatant from untreated cells and three wells containing supernatant from Digitonin-treated cells, respectively. Similarly, NLuc activity was measured by addition of 40 µl of CTZ assay buffer to three wells containing supernatant from untreated cells and three wells containing supernatant from Digitonin-treated cells, respectively. FIG. 38C-D show that treatment with Digitonin resulted in increase in both LucPPe-146-1H2 and NLuc activities in cells co-expressing both luciferases. While in the above examples, a single cell co-expressed both beetle (i.e. LucPPe-146-1H2) and marine (NLuc) luciferases, it is possible to conduct the assay in which one target cell expresses one luciferase (e.g. LucPPe-146-1H2) and the other target cell expresses the other luciferase (e.g. NLuc). The two cells are mixed together in the same well and exposed to the cytotoxic agent. Digitonin-treated cells are used as a measure of maximum cell death for both cell types. Subsequently, the relative effect of the cytotoxicity agent on the two cell types is measured by assaying for the LucPPe-146-1H2 and NLuc activities, respectively.

In the above examples, the experiment is conducted with LucPPe-146-1H2 and NLuc. Essentially similar results are obtained when the assay is repeated using cells expressing other thermostable beetle luciferases in combination with different marine luciferases (e.g. GLuc) or RLuc.

Example 40

Use of Thermostable Luciferases from *Photuris pennsylvanica* and *Pyrophorus plagiothalamus* in Matador Cytotoxicity Assay Many thermostable luciferases from *Photuris pennsylvanica* and *Pyrophorus plagiothalamus* have been described (PCT/US99/30925). To examine whether other thermostable luciferases are suitable for cytotoxicity assay, K562 cells stably expressing Luc49-7C6A, Luc78-0B10, Luc133-IB2 and LucPpL-81-6G1 are plated in triplicate at approximately 20,000 cells/well in a Greiner 384-well flat bottom white opaque plate. The cells are cultured alone or with NK92MI cells at an E:T ratio of 1:1 for 4 hours in 40 µl total volume. For measurement of maximum cell death, cells in three wells are treated with Digitonin (final concentration 30 µg/ml). At the end of co-culture period, the luminescence is measured by adding D-luciferin containing assay buffer (40 l) to the cell-culture medium at 1:1 (v/v) ratio in well mode. Induction of cell death by Digitonin and NK92MI cells is shown to result in increase in Luc49-7C6A, Luc78-0B10, Luc133-IB2 and LucPpL-81-6G1 activities as compared to the activities measured in untreated samples.

Example 41

Figure 39:
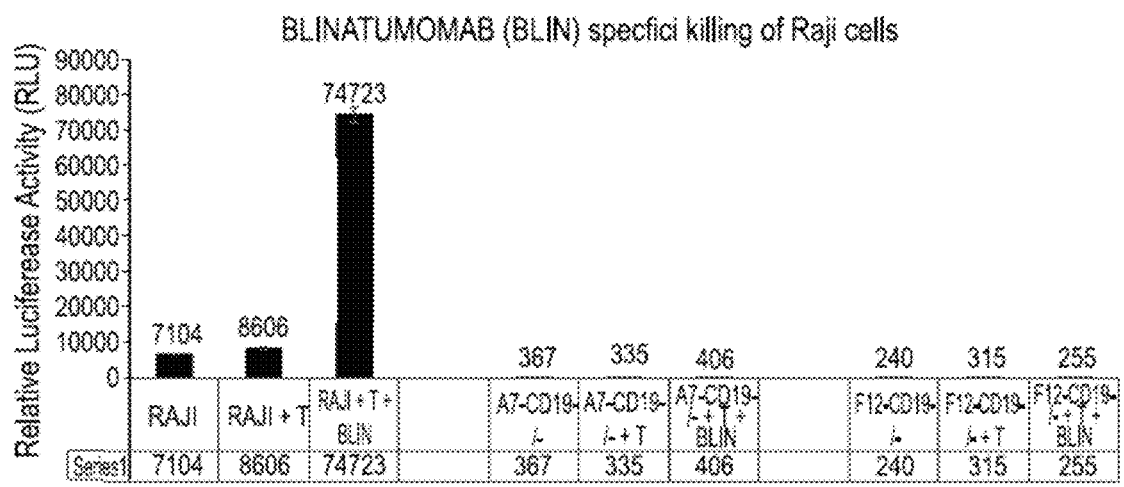
FIG. 39 depicts in accordance with various embodiments of the invention, co-culture of CD19$^{-/-}$ clones of RAJI cells expressing NLuc with Blinatumomab in the presence of T cells fails to result in increase in NLuc activity thereby demonstrating that the Matador cytotoxicity assay can be used to rule out off-target cytotoxicity of an agent.

Utility of the Matador Cytotoxicity Assay to Demonstrate Specificity of a Targeting Agent and to Rule Out Non-Specific Toxicity The off-target toxicity of immune-oncology agents, such as bispecific antibodies and CAR-T cells, is a major concern during their research and development. To demonstrate that the Matador assay can be used to rule out off-target toxicity, RAJI cells were stably infected with a retroviral vector encoding a Cas9 targeting human CD19. Two clones of RAJI cells lacking CD19 expression (A7/CD19$^{-/-}$ and F12/CD19$^{-/-}$) as determined by immunofluorescence staining with a CD19 antibody were selected by flow cytometry and were subsequently stably transduced with a vector encoding NLuc. Primary T cells were incubated with (Blinatumomab BLIN) at a final concentration of (100 ng/1 million T cells) for 30 mins at 4° C. RAJI/NLuc, A7/CD19$^{-/-}$/NLuc and F12/CD19$^{-/-}$/NLuc (5×10$^4$ cells/30 µl) were incubated with T cells or with T cells that had been pre-incubated with-Blinatumomab (3×10$^5$ cells/30 µl) or with medium for 4 hours (37° C. at 5% CO$_2$) in white 384 well plates. Cell death was assessed by injecting 30 µl of CTZ-containing assay buffer using an auto-injector to measure luminescence. FIG. 39 shows that co-culture of RAJI/NLuc cells with T cells plus Blinatumomab results in significant increase in NLuc activity as compared to co-culture with unmodified T cells while co-culture of T cells plus Blinatumomab with A7/CD19$^{-/-}$/NLuc and F12/CD19$^{-/-}$/NLuc cells failed to do so. These results show that cytotoxicity of Blinatumomab is specific for CD19-expressing cells, thereby demonstrating that the Matador cytotoxicity assay can be used to rule out off-target toxicity of an agent.

Example: 42

Utility of the Matador Cytotoxicity Assay to Demonstrate Specificity of a Targeting Agent and to Rule Out Non-Specific Toxicity It is next examined if the positive and negative control target cell lines can be combined in a single well for the performance of the Matador cytotoxicity assay, which would result in reduced cost and improved efficiency. Approximately 1×10$^5$ RAJI/NLuc and A7/CD19$^{-/-}$/NLuc cells are mixed separately with equal number of RAJI/LucPPe-146-1H2 cells. To demonstrate the specificity of the assay, 1×10$^4$ RAJI/NLuc cells plus 1×10$^4$ RAJI/LucPPe-146-1H2 cells or 1×10$^4$ A7/CD19$^{-/-}$/NLuc plus 1×10$^4$ RAJI/LucPPe-146-1H2 cells are co-cultured in triplicate with unmodified T cells or T cells expressing a CD19-CAR at an E:T ratio of 10:1 in a 384 well plate. After 4 hour, cultures are assayed for NLuc and LucPPe-146-1H2 activities using CTZ and D-Luciferin assay buffers respectively or using the Nano-Glo® Dual-Luciferase® Reporter (NanoDLR™) assay (Promega) and following the instructions of the manufacturer. Co-culture with CD19-CAR-T cells is shown to result in increase in both NLuc and LucPPe-146-1H2 activities in the wells containing a mixture of RAJI/NLuc plus RAJI/LucPPe-146-1H2 cells as compared with co-culture with unmodified T cells. However, co-culture with CD19-CAR-T cells is shown to result in an increase in only LucPPe-146-1H2 activity in the wells containing a mixture of RAJI/CD19$^{-/-}$/NLuc plus A7/LucPPe-146-1H2 cells as compared with co-culture with unmodified T cells. Essentially a similar approach is used to generate NLuc-expressing RAJI/CD20$^{-/-}$, RAJI/CD22$^{-/-}$, NALM6/CD20$^{-/-}$, NALM6/CD22$^{-/-}$, U266/BCMA$^{-/-}$, L363/BCMA-/, BV173/CD123$^{-/-}$, MV:411/CD123$^{-/-}$, HL60/CD33$^{-/-}$, MG-63/IL13RA2$^{-/-}$, Jurkat/CD30$^{-/-}$, and HEL-92.1.7/MPL$^{-/-}$ cell lines. The resulting gene knock out cells expressing NLuc and their wild-type counterparts expressing LucPPe-146-1H2 are used to determine the on-target and off-target cytotoxicity of chimeric antigen receptors and bispecific antibodies targeting the corresponding target antigens. In another exemplary embodiment, expression of p2 microglobulin (B2M) is knocked-down by Cas9 approach in the HLA-A2+ BV173 cell line. As B2M is needed for HLA-A2 expression, this results in the loss of HLA-A2 expression. The BV173/B2M$^{-/-}$/NLuc cells are used to monitor the on-target and off-target cytotoxicity of T cells expressing a TCR or a CAR targeting the WT1/HLA-A2+ complex. In another exemplary embodiment, a panel of primary cells and established cell lines of different tissue origins are engineered to stably express NLuc or LucPPe-146-1H2 or other suitable luciferases described in this invention. The primary cells or cell lines could be further genetically modified to lose the expression of specific genes and proteins. The panel is then used to monitor the on-target and off-target toxicities of candidate agents (e.g. CAR-T cells, TCR-T cells or bispecific antibodies) against different cells, tissues and target antigens to select the best candidate for further clinical development.

Example 43

Utility of the Matador Cytotoxicity Assay to Demonstrate Cytotoxicity of a Number of Candidate CAR Constructs T cells were engineered to express CARs, including chimeric TCRs, targeting more than 100 antigens. The target antigens of the CARs included cell surface proteins as well as intracellular proteins. The target antigens of the CARs also included viral proteins, such as HIV1 cell surface glycoprotein. To test the cytotoxic activity of these CAR-T cells, a panel of hematopoietic- and solid tumor-derived cell lines, (Table 3), were engineered to stably express intracellularly luciferase reporters, such as GLuc, NLuc, PaLuc or TLuc. The CAR-T cells were co-cultured with the cell line(s) expressing their cognate target antigen(s) for 4 hours to 96 hours at E:T ratios of 1:1 to 1:10 and the cytotoxicity assay conducted as described in the previous examples by addition of CTZ containing assay buffers using an autoinjector. CAR-T cells were shown to result in increase in luciferase activity when co-cultured with the target cell lines as compared to T cells that had not been infected with any CAR-encoding lentivirus or T cells that were engineered to express a non-specific control CAR. Some of the detailed results are included in PCT/US2017/024843 which is incorporated herein by reference. Collectively, these results demonstrate the broad utility of the Matador cytotoxicity assay described here to detect the cytotoxicity of T cells directed against a diverse group of cell surface and intracellular antigens. The results also demonstrate that the Matador cytotoxicity assay can be used to detect the cytotoxicity of a large number of healthy and diseased cells derived from different organs, tissues and infected with different infectious agents. Although in the above examples, CAR-modified T cells were used as the cytotoxic agents, the utility of this assay, however, is not limited to CAR-T cells and the assay can be used to detect the cytotoxic activity of any agent, including but not limited to unmodified T cells, synthetic TCR-expressing T cells and antibodies (including bispecific antibodies, DARTs and antibody drug conjugates etc.).

TABLE 3

Cell lines engineered to express luciferases for measuring cytotoxicity of different CAR constructs targeting cell surface and intracellular antigens.

| Cell line | Culture Conditions | CAR-Antigen |
| --- | --- | --- |
| BC-1 | RPMI, 20% FCS | BCMA, GPRC, CD138 |
| BC-3 | RPMI, 20% FCS | BCMA, GPRC, CD138 |
| BCBL-1 | RPMI, 20% FCS | GPRC, CD138 |
| JSC-1 | RPMI, 20% FCS | GPRC, CD138 |
| MM1S | RPMI, 10% FCS | CD38, GPRC, CD44, CD200R |
| U266 | RPMI, 10% FCS | BCMA, WT1/HLA-A2+, CS1, CLL1, CD138, c-MET, IL6R, CD179b, NY-ESO/HLA-A2, NYBR, LAMP1 |
| L363 | RPMI, 10% FCS | BCMA, GPRC, WT1/HLA-A2+, CS1, CLL1, CD138, NY-ESO/HLA-A2, NYBR, LAMP1 |
| K562 | RPMI, 10% FCS | CD33, IL1Ra, TnAg |
| BV173 | RPMI, 10% FCS | CD123, CD179b, IL1Ra, WT1/HLA-A2+,CXCR4, FLT3 |
| Nalm6 | RPMI, 10% FCS | CD19, CD20, CD22, CD179b |
| HL60 | RPMI, 10% FCS | CD33, CD34, CLL1, IL6R, CD32, CD179 |
| U937 | RPMI, 10% FCS | CD4, CLL1 |
| RS:411 | RPMI, 20% FCS | CD19, Folate Receptor beta (FRbeta), TGFbeta, CD179b, NKGD2, FLT3 |
| MV:411 | RPMI, 10% FCS | FLT3,CD123, FRbeta |
| Raji | RPMI, 10% FCS | CD19, CD20, CD22, BCMA, CD38, CD70, CD79, Folate Receptor beta, CLL1 |
| HEL-92.1.7 | RPMI, 10% FCS | MPL, CD33, CD32, CD200R |
| Jurkat | RPMI, 10% FCS | TnAg, TSLRP, TSHR, CD4, CD38 |
| Daudi | RPMI, 10% FCS | BCMA, FRbeta |
| REC-1 | RPMI, 10% FCS | NKGD2, ROR1 |
| KG-1 | RPMI, 20% FCS | CD33, CD34, CD123, TSLRP |
| CEM | RPMI, 10% FCS | CD5 |
| U937 | RPMI, 10% FCS | CD4, CLL1 |
| LAMA5 | RPMI, 10% FCS | WT1/HLA-A2 |
| A549 | DMEM, 10% FCS | ROR1, CD22, TIM1, CDH17 |
| HT29 | DMEM, 10% FCS | EGFR, SLEA, c-MET |
| Molm-13 | RPMI, 20% FCS | FLT3, IL6R, LAMP1, TSLRP, CD4, CSF2RA,CXCR4, IL6R, CSF2RA, GPC3 |
| A431 | DMEM, 10% FCS | EGFR, Folate Receptor Alpha, Her3 |
| P19 | DMEM, 10% FCS | SSEA |
| THP-1 | RPMI, 10% FCS | CD32, CD33,CXCR4, CD123, CD44, IL6R, Folate Receptor beta, CD70, LAMP1, FLT3, CSF2RA |
| U87MG | DMEM, 10% FCS | CD276, gpNMB, IL13RA2 |
| LoVo | DMEM, 10% FCS | Tissue Factor, CDH17, EGFR |
| SKOV-3 | DMEM, 10% FCS | Folate Receptor alpha (FR1), FSHR, Her2, Her3, LHR, MSLN, TIM1, EPCAM |

TABLE 3-continued

Cell lines engineered to express luciferases for measuring cytotoxicity of different CAR constructs targeting cell surface and intracellular antigens.

| Cell line | Culture Conditions | CAR-Antigen |
|---|---|---|
| NCI-H1993 | DMEM, 10% FCS | EGFR |
| Kasumi-1 | RPMI, 20% FCS | CLEC5A, PR1/HLA-A2, TGFbeta, |
| Jeko-1 | RPMI, 20% FCS | BCMA, ROR1 |
| PC-3 | DMEM, 10% FCS | CGH, TROP2, PSCA, PSMA. EPCAM, FSHR |
| HeLa | DMEM, 10% FCS | EGFR, FR1, MSLN, TSHR |
| LnCap | DMEM, 10% FCS | EGFR, FSHR, PSCA, PSMA, CD22, Her3, CD22, LHR |
| OVCAR-3 | DMEM, 10% FCS | B7H4, CDH6, DLL3, FR1, FSH, LHR, MSLN, PTK7, TnAg, TSHR, L1CAM |
| MEL-624 | DMEM, 10% FCS | CDH19, GD2, GD3, gp100/HLA-A2, gpNMB, HMWMAA, NYESO/HLA-A2, MART1/HLA-A2 |
| LS174-T | DMEM, 10% FCS | CEA |
| MEL-526 | DMEM, 10% FCS | GD2 |
| MDA-MB231 | DMEM, 10% FCS | CD324, Muc1 |
| L1236 | RPMI, 20% FCS | CD30, CD23, PDL1 |
| L428 | RPMI, 20% FCS | CD30, CD123, CCR4, PDL1 |
| L540 | RPMI, 20% FCS | CD30, CCR4, PDL1 |
| Molt-16 | RPMI, 20% FCS | IL1ra, NKGD2 |
| CEM | RPMI, 10% FCS | CD5 |
| MG-63 | DMEM, 10% FCS | IL13RA2 |
| Karpass-299 | RPMI, 20% FCS | Alk, GPRC, PDL1 |
| MCF7 | DMEM, 10% FCS | B7D4, CD276, TROP2, Her3, Mud, LewisY, LHR |
| AA-2 | RPMI, 10% FCS | HIV1 env glycoprotein (gp120) |
| HL2/3 | DMEM, 10% FCS | HIV1 env glycoprotein (gp120) |
| TF228.1.16 | DMEM, 10% FCS | HIV1 env glycoprotein (gp120), CCR4 |
| TT | DMEM, 10% FCS | TGF-Beta, TSHR, GFRalpha4 |
| DMS79 | RPMI, 10% FCS | Fucosyl-GM1, Slea (CA19.9; Sialyl Lewis Antigen) |
| LAN-5 | DMEM, 10% FCS | ALK, DLL3, GFRalpha4, GM1 |
| PEER1 | RPMI, 10% FCS | TSHR |
| SK-MEL-37 | DMEM, 10% FCS | DLL3, GD2 |
| F9 | DMEM, 10% FCS | SSEA |
| HepG2 | DMEM, 10% FBS | GPC3, AFP/HLA-A2 |

Example 44

Figure 40:
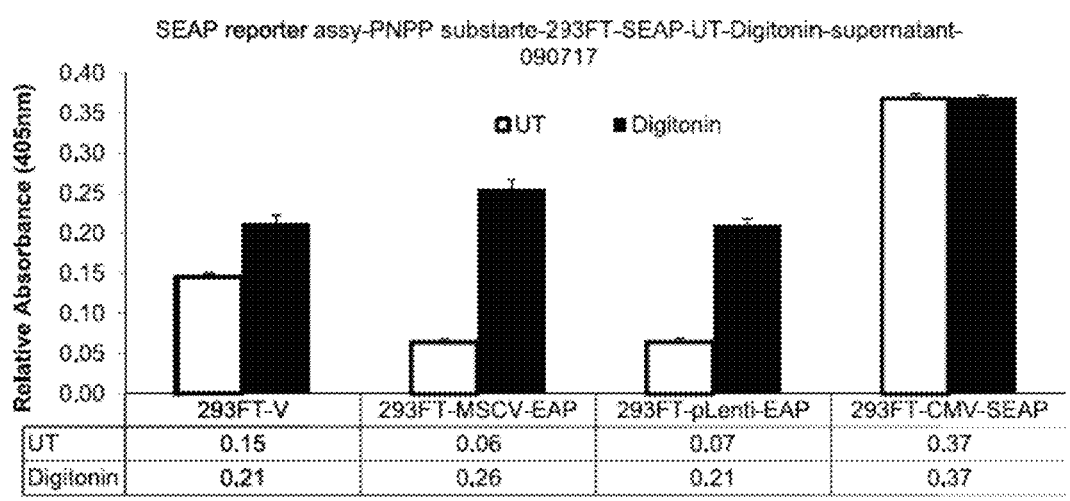
FIG. 40 depicts in accordance with various embodiments of the invention, treatment with Digitonin resulted in increase in embryonic alkaline phosphatase (EAP) activity in case of 293FT cells transiently transfected with an EAP expression construct.

Use of Non-Secretory Form of Human Placental Alkaline Phosphatase in Matador Cytotoxicity Assay A gene fragment encoding human embryonal alkaline phosphatase lacking its secretory sequence was codon optimized (SEQ ID NO: 27) and cloned into MSCV and lentiviral vectors. 293FT cells were transfected in 24-well plates with 1) a control plasmid (pCDNA3), 2) a retroviral vector (MSCV) encoding human embryonal alkaline phosphatase lacking its secretory sequence; 3) a lentiviral vector encoding human embryonal alkaline phosphatase lacking its secretory sequence; 4) pCMV-SEAP vector encoding secretory form of human embryonal alkaline phosphatase. Each construct was transfected in 6 wells at 500ng/well. The culture medium was changed from DMEM 10% FCS to XVIVO medium before transfection due to the concern that phenol red in the DMEM medium could interfere with subsequent performance of the assay to detect alkaline phosphatase. 18 hours post transfection, 3 well were left untreated and three wells were treated with Digitonin for 90 min. Cells were scraped and collected in 1.5 ml tubes. An aliquot was centrifuged to collect supernatant only fraction. 10 µl of the supernatant fraction was plated in triplicate in a 384 well plate. A PNPP tablet ((p-nitrophenyl phosphate; Sigma-Aldrich) was dissolved in 20 ml of water as directed by manufacturer and used as substrate to measure alkaline phosphatase activity. 50 µl of substrate was added to each well containing the supernatant. Plates were mixed and incubated at room temp to develop the reaction. Absorbance was measured at 405 nm using a BioTek synergy plate reader. FIG. 40 shows greater than 3-fold increase in alkaline phosphatase activity in the cell supernatants upon induction of cell death by Digitonin in cells that had been transfected with the constructs encoding human embryonal alkaline phosphatase lacking the secretory signal while there was little or no increase in the alkaline phosphatase activity upon Digitonin treatment in cells that had been transfected with an empty vector or a plasmid encoding the secretory form of human embryonal alkaline phosphatase.

Example 45

Use of In Vitro Transcribed (IVT) RNA for Expression of GLuc in Matador Assay

IVT to generate GLuc encoding RNAs is performed essentially as described (Zhao Y, et al, MOLECULAR THERAPY Vol. 13, No. 1, 2006). The mMESSAGE mMACHINE High Yield Capped RNA Transcription Kit (Invitrogen) is utilized to generate IVT RNA using GLuc cDNA cloned in the pCDNA3 vector as a template. The IVT RNA is purified using an RNeasy Mini Kit (Qiagen, Inc., Valencia, CA, USA) and purified RNA is eluted in RNase-free water at 1-0.5 µg/ml. For the electroporation, RAJI cells (0.1 ml) are electroporated with 5 µg of RNA encoding GLuc. Cells and cuvettes are pre-chilled by putting them on ice for 5 min before electroporation. Subsequently, approximately 0.1 ml of the cells ($10^6$ cells) are mixed with RNA and electroporated in a 2-mm cuvette (Harvard Apparatus BTX, Holliston, MA, USA), using an ECM830 Electro Square Wave Porator (Harvard Apparatus BTX). Immediately after electroporation, the cells are transferred to fresh media and incubated at 37° C. After 48 hours, the cells transfected with IVT RNA encoding GLuc are used in Matador assay after co-culture with T cells expressing a CAR directed against CD19 (SEQ ID NO: 80) at an E:T ratio of 10:1 in a 384 well plate. At the end of the co-culture period, GLuc luminescence is measured by adding CTZ-containing assay buffer. Co-culture of RAJI cells transfected with Gluc IVT RNA with CD19 CAR-T cells is shown to result in increase in GLuc activity as compared to cells that are co-cultured with a control CAR-expressing T cells or T cells that do not express any CAR.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

REFERENCES

1. Bovenberg, M. S., M. H. Degeling and B. A. Tannous (2012). "Enhanced *Gaussia* luciferase blood assay for monitoring of in vivo biological processes." Anal Chem 84(2): 1189-1192.
2. Brown, C. E., C. L. Wright, A. Naranjo, R. P. Vishwanath, W. C. Chang, S. Olivares, J. R. Wagner, L. Bruins, A. Raubitschek, L. J. Cooper and M. C. Jensen (2005). "Biophotonic cytotoxicity assay for high-throughput screening of cytolytic killing." J Immunol Methods 297 (1-2): 39-52.
3. Degeling, M. H., M. S. Bovenberg, G. K. Lewandrowski, M. C. de Gooijer, C. L. Vleggeert-Lankamp, M. Tannous, C. A. Maguire and B. A. Tannous (2013). "Directed molecular evolution reveals *Gaussia* luciferase variants with enhanced light output stability." Anal Chem 85(5): 3006-3012.
4. Eshhar, Z., T. Waks, G. Gross and D. G. Schindler (1993). "Specific activation and targeting of cytotoxic lymphocytes through chimeric single chains consisting of antibody-binding domains and the gamma or zeta subunits of the immunoglobulin and T-cell receptors." Proc Natl Acad Sci USA 90(2): 720-724.
5. Fu, X., L. Tao, A. Rivera, S. Williamson, X. T. Song, N. Ahmed and X. Zhang (2010). "A simple and sensitive method for measuring tumor-specific T cell cytotoxicity." PLoS One 5(7): e11867.
6. Gross, G., Z. Eshhar, G. S and J. CH (2016). "Therapeutic Potential of T Cell Chimeric Antigen Receptors (CARs) in Cancer Treatment: Counteracting Off-Tumor Toxicities for Safe CAR T Cell Therapy
7. Going viral: chimeric antigen receptor T-cell therapy for hematological malignancies." Annual Review of Pharmacology and Toxicology 56(1): 59-83.
8. Gross, G., T. Waks and Z. Eshhar (1989). "Expression of immunoglobulin-T-cell receptor chimeric molecules as functional receptors with antibody-type specificity." Proc Natl Acad Sci USA 86(24): 10024-10028.
9. Hall, M. P., J. Unch, B. F. Binkowski, M. P. Valley, B. L. Butler, M. G. Wood, P. Otto, K. Zimmerman, G. Vidugiris, T. Machleidt, M. B. Robers, H. A. Benink, C. T. Eggers, M. R. Slater, P. L. Meisenheimer, D. H. Klaubert, F. Fan, L. P. Encell and K. V. Wood (2012). "Engineered luciferase reporter from a deep sea shrimp utilizing a novel imidazopyrazinone substrate." ACS Chem Biol 7(11): 1848-1857.
10. Inouye, S. and Y. Sahara (2008). "Identification of two catalytic domains in a luciferase secreted by the copepod Gaussia princeps." Biochem Biophys Res Commun 365 (1): 96-101.
11. Matta, H., B. Hozayev, R. Tomar, P. Chugh and P. M. Chaudhary (2003). "Use of lentiviral vectors for delivery of small interfering RNA." Cancer Biol Ther 2(2): 206-210.
12. Roybal, K. T., L. J. Rupp, L. Morsut, W. J. Walker, K. A. McNally, J. S. Park and W. A. Lim (2016). "Precision Tumor Recognition by T Cells With Combinatorial Antigen-Sensing Circuits." Cell 164(4): 770-779.
13. Schafer, H., A. Schafer, A. F. Kiderlen, K. N. Masihi and R. Burger (1997). "A highly sensitive cytotoxicity assay based on the release of reporter enzymes, from stably transfected cell lines." J Immunol Methods 204(1): 89-98.
14. Sharel, A., A. Adamo, R. Langer and K. F. Jansen Intracellular delivery. W. I. Property, Massachusetts Institute of Technology: 1-126.
15. Takenaka, Y., A. Yamaguchi, N. Tsuruoka, M. Torimura, T. Gojobori and Y. Shigeri (2012). "Evolution of bioluminescence in marine planktonic copepods." Mol Biol Evol 29(6): 1669-1681.
16. Teeling, J. L., R. R. French, M. S. Cragg, J. van den Brakel, M. Pluyter, H. Huang, C. Chan, P. W. Parren, C. E. Hack, M. Dechant, T. Valerius, J. G. van de Winkel and M. J. Glennie (2004). "Characterization of new human CD20 monoclonal antibodies with potent cytolytic activity against non-Hodgkin lymphomas." Blood 104(6): 1793-1800.
17. Thompson, J. F., L. S. Hayes and D. B. Lloyd (1991). "Modulation of firefly luciferase stability and impact on studies of gene regulation." Gene 103(2): 171-177.
18. Thorne, N., J. Inglese and D. S. Auld (2010). "Illuminating insights into firefly luciferase and other bioluminescent reporters used in chemical biology." Chem Biol 17(6): 646-657.
19. van Rijn, S., J. Nilsson, D. P. Noske, W. P. Vandertop, B. A. Tannous and T. Wurdinger (2013). "Functional multiplex reporter assay using tagged Gaussia luciferase." Sci Rep 3: 1046.
20. van Rijn, S., T. Wurdinger and J. Nilsson (2014). "Multiplex functional bioluminescent reporters using Gaussia luciferase fused to epitope tags in an immunobinding assay." Methods Mol Biol 1098: 231-247.
21. Welsh, J. P., K. G. Patel, K. Manthiram and J. R. Swartz (2009). "Multiply mutated Gaussia luciferases provide prolonged and intense bioluminescence." Biochem Biophys Res Commun 389(4): 563-568.

What is claimed is:

1. A method for assessing cytotoxicity of an agent comprising:
   i) exposing a target cell engineered to express an intracellular non-secretory thermostable reporter to an agent capable of modulating cytotoxicity;
   ii) measuring the level of the reporter; and
   wherein the reporter is a thermostable beetle luciferase.

2. The method of claim 1, wherein the reporter is stable under assay conditions of 37° C. for more than 15 min.

3. The method of claim 1, wherein the beetle luciferase has the amino acid sequence of SEQ ID NO: 50-56 or a sequence with 85-99% identity thereto.

4. The method of claim 1, where the beetle luciferase has the amino acid sequence of SEQ ID NO: 50-56 or a functionally active homolog, ortholog, mutant, variant or derivative thereof.

5. The method of claim 1, wherein the beetle luciferase is obtained from *Photinus pyralis, Photuris pennsylvanica* or *Pyrophorus plagiothalamus*.

6. The method of claim 1, wherein the beetle luciferase is any one or more of
   Firefly luciferase (FfLuc or Fluc), *Photuris pennsylvanica* luciferase LucPPe-146-1H2, LucPPe-133-1B2, LucPPe-78-OB10, or LucPPe49-7C6A, *Pyrophorus plagiothalamus* luciferase LucPpL-81-6G1, or CBGRluc, or functionally active homologs or orthologs or mutants or variants or derivatives thereof.

7. The method of claim 1, wherein the target cells are present in a cell media wherein the reporter is assayed in a) the cell media containing the target cells; or b) a cell supernatant that is free of the target cells.

8. The method of claim 1, where the reporter activity is assayed using a substrate; and wherein optionally the substrate is D-luciferin or a synthetic analog thereof with which the luciferase can interact to generate light.

9. The method of claim 1, wherein the target cell expresses a second reporter.

10. The method of claim 9, wherein the activity of the first reporter and the second reporter is measured independently, simultaneously or sequentially.

11. The method of claim 9, where the second reporter is selected from the group consisting of a) a non-secretory luciferase derived from a copepod, a deep-sea shrimp, or a functional variant thereof; and b) alkaline phosphatase or a functional variant thereof.

12. The method of claim 9, where the second reporter is *Guassia princeps* luciferase (GLuc), NanoLuc (NLuc), *Metrida longa* luciferase-7 (MLuc7), *Heterorhabdus tanneri* luciferase (HTLuc), *Pleuromamma abdominalis* luciferase-1 (PaLuc1), *Pleuromamma abdominalis* luciferase-2 (PaLuc2), *Metridia pacifica* luciferase-1 (MpLuc1), *Metridia curticauda* luciferase-1 (McLuc1), *Metridia asymmetrica* luciferase-1 (MaLuc1), *Metridia okhotensis* luciferase-1 (MoLuc1), *Metridia okhotensis* luciferase-2 (MoLuc2), *Metridia longa* luciferase-39 (MLuc39), *Pleuromamma scutullata* luciferase-1 (PsLuc1), *Lucicutia ovaliformis* luciferase 1-3 (LoLuc1-3), *Heterorhabdus tanneri* luciferase-2 (HtLuc2), TurboLuc16 (TLuc), Lucia Luc, Renilla Luc, or a functionally active homologs or orthologs or mutants or variants or derivatives thereof.

13. The method of claim 9, wherein
   i) the substrate for one of the two reporters is D-luciferin or a synthetic analog thereof, with which the luciferase can interact to generate light and the substrate for the other of the two reporters is coelenterazine or an imidazopyrazinone or a synthetic analog thereof, with which the luciferase can interact to generate light; or
   ii) the substrate for a one of the two reporters is pNNP and the substrate for the other of the two reporters is coelenterazine or an imidazopyrazinone or a synthetic analog thereof, with which the luciferase can interact to generate light; or iii) the substrate for one of the two reporters is D-luciferin or a synthetic analog thereof with which the luciferase can interact to generate light and the substrate for the other of the two reporters is pNNP.

14. The method of claim 1, wherein the target cell expresses two or more reporters and the target cell expressing two or more reporters are mixed together prior to the assay.

15. The method of claim 1, wherein the agent capable of modulating cytotoxicity is any one or more of an antibody, small molecule, chemical compound, radiation agent, cytotoxic cells, biologics or combinations thereof.

16. The method of claim 15, where the agent capable of modulating cytotoxicity targets an antigen selected from the group consisting of: Cluster of Differentiation (CD)-19 (CD19); CD-1-91 CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRviii); ganglioside G2 (GD2); ganglioside GD3 (aNeu5Ac(2-8)aNeu5Ac(2-3)bDGalp(1-4)bDGlcp(1-1) Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); FmsLike Tyrosine Kinase 3 (FLT3); Tumor-associated glycoprotein 72 (TAG72); CD38; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-llRa); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gpl00); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3; transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ES0-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family Member 1A (XAGE-1A); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCT A-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); lymphocyte-specific protein tyrosine kinase (LCK); A kinase anchor protein 4 (AKAP-4); synovial sarcoma X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); immunoglobulin lambda-like polypeptide 1 (IGLL1), MPL, Biotin, c-MYC epitope Tag, CD34, LAMP1, TROP2, GFRalpha4, CDH17, CDH6, NYBR1, CDH19, CD200R, Slea (CA19.9; Sialyl Lewis Antigen) Fucosyl-GM1, PTK7, gpNMB, CDH1, DLL3, CD276/B7H3, IL11Ra, IL13Ra2, CD179b, ALK, TCR gamma-delta, NKG2D, CD32 (FCGR2A), Tim1, CSF2RA (GM-CSFR-alpha), TGFbetaR2, VEGFR2/KDR, Lewis Ag, TCR-betal chain, TCR-beta2 chain, TCR-gamma chain, TCR-delta chain, FITC, Luteinizing hormone receptor (LHR), Follicle stimulating hormone receptor (FSHR), Chorionic Gonadotropin Hormone receptor (CGHR), CCR4, GD3, SLAMF6, SLAMF4, HIV1 envelope glycoprotein, HTLV1-Tax, CMV pp65, EBV-EBNA3c, influenza A hemagglutinin (HA), GAD, PDL1, Guanylyl cyclase C (GCC), KSHV-K8.1 protein, KSHV-gH protein, HLA, HLA-A, HLA-A2, HLA-B, HLA-C, HLA-DP, HLA-DM, HLA-DOA, HLA-DOB, HLA-DQ, HLA-DR or HLA-G.

17. The method of claim 1, wherein the target cell is exposed to the agent a) in vitro; and/or b) in vivo.

18. The method of claim 1, wherein the assay is performed a) in vitro and/or b) in vivo.

19. The method of claim 1, which is practiced using a kit containing one or more components of claim 1.

* * * * *